US012709758B2

(12) United States Patent
Cuero Rengifo

(10) Patent No.: US 12,709,758 B2
(45) **Date of Patent: *Aug. 18, 2026**

(54) POLYACTIVE CARBOHYDRATES AND METHODS OF USE THEREOF

(71) Applicant: Bio Capital Holdings, LLC, Houston, TX (US)

(72) Inventor: Raul Cuero Rengifo, Cypress, TX (US)

(73) Assignee: Bio Capital Holdings, LLC, Houston, TX (US)

( * ) Notice: Subject to any disclaimer, the term of this patent is extended or adjusted under 35 U.S.C. 154(b) by 781 days.

This patent is subject to a terminal disclaimer.

(21) Appl. No.: 17/754,506

(22) PCT Filed: Oct. 6, 2020

(86) PCT No.: PCT/US2020/054424

§ 371 (c)(1),
(2) Date: Apr. 4, 2022

(87) PCT Pub. No.: WO2021/071851

PCT Pub. Date: Apr. 15, 2021

(65) Prior Publication Data

US 2024/0102036 A1 Mar. 28, 2024

Related U.S. Application Data

(60) Provisional application No. 62/911,421, filed on Oct. 7, 2019.

(51) Int. Cl.

| | |
|---|---|
| ***C12N 15/82*** | (2006.01) |
| ***C12N 9/10*** | (2006.01) |
| ***C12N 9/24*** | (2006.01) |
| ***C12N 9/80*** | (2006.01) |
| ***C12N 15/81*** | (2006.01) |

(52) U.S. Cl.

CPC ....... *C12N 15/8261* (2013.01); *C12N 9/1051* (2013.01); *C12N 9/2402* (2013.01); *C12N 9/80* (2013.01); *C12N 15/81* (2013.01); *C12Y 204/01016* (2013.01); *C12Y 204/01034* (2013.01); *C12Y 302/01132* (2013.01); *C12Y 305/01041* (2013.01)

(58) Field of Classification Search

None

See application file for complete search history.

(56) References Cited

U.S. PATENT DOCUMENTS

| | | | | |
|---|---|---|---|---|
| 10,995,353 | B2 * | 5/2021 | Cuero Rengifo ........ | C12N 9/16 |
| 2005/0042735 | A1 | 2/2005 | Deng et al. | |
| 2013/0337541 | A1 | 12/2013 | Brzezinski et al. | |
| 2016/0168311 | A1 | 6/2016 | Cuero Rengifo et al. | |
| 2017/0035600 | A1 | 2/2017 | Preciado | |
| 2017/0356002 | A1 | 12/2017 | Thompson et al. | |
| 2021/0261997 | A1 | 8/2021 | Cuero Rengifo et al. | |

FOREIGN PATENT DOCUMENTS

| | | |
|---|---|---|
| WO | 2000009729 | 2/2000 |
| WO | 2019055456 | 3/2019 |
| WO | 2004092391 | 2/2020 |

OTHER PUBLICATIONS

Saporta, Rubén, et al. "A method for a fast evaluation of the biostimulant potential of different natural extracts for promoting growth or tolerance against abiotic stress." Agronomy 9.3 (2019): 143. (Year: 2019).*

Sharp, Russell G. "A review of the applications of chitin and its derivatives in agriculture to modify plant-microbial interactions and improve crop yields." Agronomy 3.4 (2013): 757-793. (Year: 2013).*

U.S. Appl. No. 17/245,416, US-2021-0261997-A1.

U.S. Appl. No. 16/646,218, U.S. Pat. No. 10,995,353-A1.

Nagahashi et al.; Characterization of Chitin Synthase 2 of *Saccharomyces cerevisiae*; The Journal of Biological Chemistry; vol. 270 , No. 23, pp. 13961-13967, published Jun. 9, 1995 (Year: 1995).

Shimosaka et al.; Analysis of Essential Carboxylic Amino Acid Residues for Catalytic Activity of Fungal Chitosanases by Site-Directed Mutagenesis; Journal of Bioscience and Bioengineering; vol. 100, No. 5, pp. 545-550 (2005) (Year: 2005).

Arakane et al. Chitin-Related Enzymes in Agro-Biosciences, Current Drug Targets, 13, 00-00, 2012.

International Search Report and Written Opinion issued for PCT/US2018/050571, mailed Jan. 15, 2019.

International Search Report and Written Opinion or PCT/US2020/54424 mailed Mar. 25, 2021.

* cited by examiner

*Primary Examiner* — Charles Logsdon

(74) *Attorney, Agent, or Firm* — Thomas | Horstemeyer, LLP

(57) ABSTRACT

Described herein are biological devices and methods for using the same to produce a polyactive carbohydrate. The biological devices include microbial cells transformed with a DNA construct containing genes for producing a chitin synthase, a chitosanase, 5 and a chitin deacetylase, and, optionally, lipase, regulatory sequence CHR1, transglycosylase, dehydrogenase, and/or (1→3), (1→4)-β-glucan synthase. Methods for using the polyactive carbohydrate are also provided herein including, but not limited to, increasing plant hormone production and improving the appearance and root strength of plants and production of polyurethane biofoams.

37 Claims, 16 Drawing Sheets

Specification includes a Sequence Listing.

POLYACTIVE CARBOHYDRATES AND METHODS OF USE THEREOF

CROSS REFERENCE TO RELATED APPLICATIONS

This application is a National Stage of International Application No. PCT/US2020/054424, filed Oct. 6, 2020, which claims the benefit of U.S. Provisional Application No. 62/911,421, filed on Oct. 7, 2019, which is incorporated herein by reference in its entirety.

CROSS REFERENCE TO SEQUENCE LISTING

The genetic components described herein are referred to by sequence identifier numbers (SEQ ID NO). The SEQ ID NOs correspond numerically to the sequence identifiers <400>1, <400>2, etc. The Sequence Listing, in written computer readable format (CRF), is incorporated by reference in its entirety.

BACKGROUND

Plants with strong root systems are more robust; more tolerant to drought as well as damage from insects and/or fungi; better able to hold soil in place and withstand erosion forces; more productive of desired fibers, fruits, vegetables, grains, nuts and seeds, woods, and the like, in the case of agricultural or other commercial products; and more aesthetically pleasing, in the case of ornamental species, golf course and sports field grasses, and the like. Plant hormones such as, for example, cytokinins, auxins, salicylic acid, and jasmonic acid play key roles in root development. Increasing the production of these hormones can lead to an increase in both root length and root strength.

Chitosan is a linear polysaccharide derived from chitin, a polymer found in the shells of shrimp and other crustaceans as well as in some fungal cell walls. Chitosan is composed of D-glucosamine and N-acetyl-D-glucosamine units, which are $\beta$-(1→4) linked and randomly distributed.

Chitosan has been employed for a wide variety of commercial uses. However, several drawbacks to the widespread use of chitosan exist. Few facilities worldwide are able to process chitosan, and the separation of chitosan from crustacean shells is laborious. Separation methods are inefficient as the necessary reagents cannot easily access the polymer due to the crystalline nature of chitin. Existing methods for producing chitosan are destructive and wasteful in addition to being expensive, and they employ corrosive chemicals and hazardous solvents. Further, since chitosan is typically extracted from shellfish, individuals with shellfish allergies, vegans and vegetarians, and people with religious prohibitions against consuming shellfish may want to avoid products containing chitosan extracted from shrimp, crabs, and the like.

What is needed is a polyactive carbohydrate and a process for making the same that shares the properties of chitosan. Purification would not require the use of harsh chemicals or solvents, thus reducing materials costs and the production of hazardous waste. Further, the polyactive carbohydrate would be suitable for use in all of the industrial applications traditionally associated with chitosan as well as in new uses such as increasing the production of plant hormones, production of polyurethane biofoams, and the like. The present invention addresses these needs.

SUMMARY

Described herein are biological devices and methods for using the same to produce a polyactive carbohydrate. The biological devices include microbial cells transformed with a DNA construct containing genes for producing a chitin synthase, a chitosanase, and a chitin deacetylase, and, optionally, lipase, regulatory sequence CHR1, transglycosylase, dehydrogenase, and/or (1→3),(1→4)-$\beta$-glucan synthase. Methods for using the polyactive carbohydrate are also provided herein including, but not limited to, increasing plant hormone production and improving the appearance and root strength of plants and production of polyurethane biofoams.

The advantages to the invention will be set forth in part in the description that follows, and in part will be obvious from the description, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

BRIEF DESCRIPTION OF THE DRAWINGS

The accompanying drawings, which are incorporated in and constitute a part of this specification, illustrate several aspects described below.

DETAILED DESCRIPTION

Figure 1A:
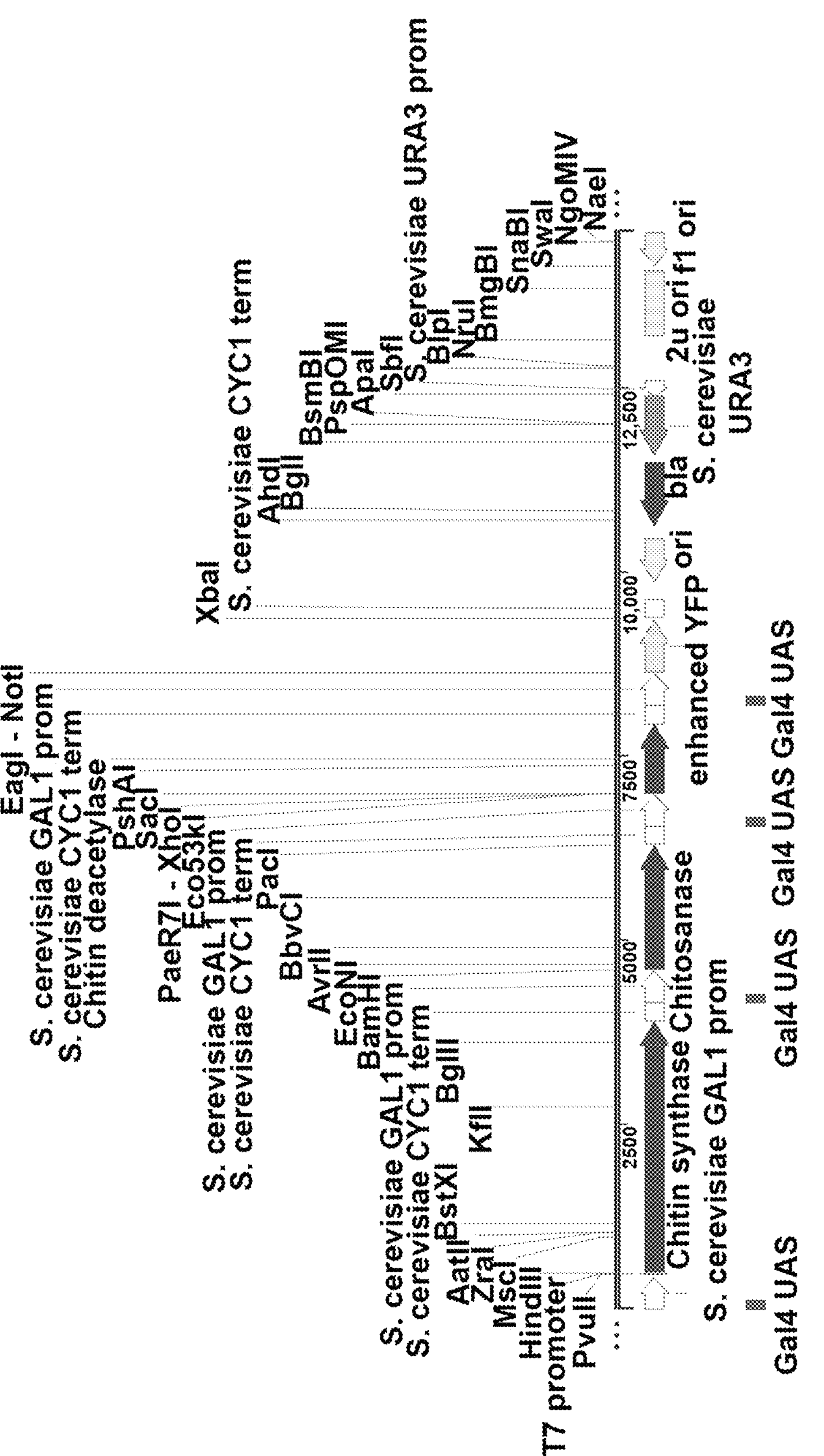
FIGS. 1A and 1B show, respectively, a linear and a circular schematic of a constructed pYES2 plasmid showing the direction, placement, and size of genetic parts of an exemplary DNA device disclosed herein.

Before the present compounds, compositions, articles, devices, and/or methods are disclosed and described, it is to be understood that the aspects described below are not limited to specific compounds, synthetic methods, or uses, as such may, of course, vary. It is also to be understood that the terminology used herein is for the purpose of describing particular aspects only and is not intended to be limiting.

In this specification and in the claims that follow, reference will be made to a number of terms that shall be defined to have the following meanings:

It must be noted that, as used in the specification and the appended claims, the singular forms "a," "an," and "the" include plural referents unless the context clearly dictates otherwise. Thus, for example, reference to "a plasmid" includes mixtures of two or more such plasmids, and the like.

"Optional" or "optionally" means that the subsequently described event or circumstance can or cannot occur, and that the description includes instances where the event or circumstance occurs and instances where it does not. For example, the phrase "optionally includes a reporter protein" means that the reporter protein may or may not be present.

Ranges may be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

"Admixing" or "admixture" refers to a combination of two or more components together wherein there is no chemical reaction or physical interaction. The terms "admixing" and "admixture" can also include the chemical reaction or physical interaction between any of the components described herein upon mixing to produce the composition. The components can be admixed alone, in water, in another solvent, or in a combination of solvents.

As used herein, a "polyactive carbohydrate" is a compound produced by the biological devices disclosed herein. In one aspect, the polyactive carbohydrate is partially or fully acetylated. In another aspect, an enzymatic or chemical deacetylation process can be used on the polyactive carbohydrate or any precursors to alter the degree of acetylation. In still another aspect, the polyactive carbohydrate can be chemically or enzymatically fully or partially hydrolyzed prior to use in order to fine tune the properties of the polyactive carbohydrate as they relate to molecular weight. Example applications of the polyactive carbohydrate are discussed in detail below.

As used herein, a "plant hormone" is a promoter or stimulator for plant growth and/or development. Different plant hormones have different features. In some aspects, application of the extracts disclosed herein stimulates endogenous production of plant hormones, in turn enhancing root growth.

"Cytokinins" are responsible for growth of roots and for anchoring the plant in the soil. Cytokinins are typically classified into two groups: cis- and trans zeatin, as well as cis- and trans-zeatin riboside. Cytokinin production is promoted by the presence of auxins. These hormones are often found in different concentrations and/or different parts of the plant. In one aspect, disclosed herein is a method for increasing cytokinin production.

"Salicylic acid" is a plant hormone that promotes or enhances photosynthesis, transpiration, and mineral uptake. In one aspect, salicylic acid promotes the vigor or plants as well as protecting the plant against pathogenic microorganisms. In another aspect, salicylic acid can make a plant more resistant to disease. In a further aspect, the benefits of salicylic acid are particularly important for plants such as grasses that may spend a long time growing in locations such as, for example, lawns and golf courses. In one aspect, disclosed herein is a method for increasing salicylic acid production.

As used herein, "auxins" are plant hormones involved in numerous developmental processes in plants including, but not limited to, cell division and cellular expansion (i.e., axial elongation in shoots, swelling in roots, fruit growth, and the like). In one aspect, auxin to cytokinin ratio in plant tissues is implicated in development of roots versus development in shoots. In one aspect, disclosed herein is a method for increasing auxin production.

"Jasmonic acid" as used herein is a plant hormone that is useful in protecting plants against environmental damage, microbial pathogens, and insects. In one aspect, jasmonic acid can prevent early senescence of a plant. In another aspect, jasmonic acid can be found in plants in several forms including a jasmonic acid-isoleucine conjugate and unconjugated jasmonic acid. In one aspect, disclosed herein is a method for increasing jasmonic acid production. In one aspect, jasmonic acid is particularly important for field grasses (e.g., on golf courses) since the grasses are kept green for most of the year.

Disclosed are materials and components that can be used for, can be used in conjunction with, can be used in preparation for, or are products of the disclosed compositions and methods. These and other materials are disclosed herein, and it is understood that when combinations, subsets, interactions, groups, etc., of these materials are disclosed that while specific reference to each various individual and collective combination and permutation of these compounds may not be explicitly disclosed, each is specifically contemplated and described herein. For example, if a bacterium is disclosed and discussed and a number of different compatible bacterial plasmids are discussed, each and every combination and permutation of bacterium and bacterial plasmid that is possible is specifically contemplated unless specifically indicated to the contrary. For example, if a class of molecules A, B, and C are disclosed as well as a class of molecules D, E, and F, and an example of a combination molecule, A-D, is disclosed, then even if each is not individually recited, each is individually and collectively contemplated. Thus, in this example, each of the combinations A-E, A-F, B-D, B-E, B-F, C-D, C-E, and C-F are specifically contemplated and should be considered disclosed from disclosure of A, B, and C; D, E, and F; and the example combination A-D. Likewise, any subset or combination of these is also specifically contemplated and disclosed. Thus, for example, the subgroup of A-E, B-F, and C-E is specifically contemplated and should be considered disclosed from disclosure of A, B, and C; D, E, and F; and the example combination A-D. This concept applies to all aspects of this disclosure including, but not limited to, steps in methods of making and using the disclosed compositions. Thus, if there are a variety of additional steps that can be performed, it is understood that each of these additional steps can be performed with any specific embodiment or combination of embodiments of the disclosed methods, and that each such combination is specifically contemplated and should be considered disclosed.

References in the specification and concluding claims to parts by weight, of a particular element or component in a composition or article, denote the weight relationship between the element or component and any other elements or components in the composition or article for which a part by weight is expressed. Thus, in a compound containing 2 parts by weight of component X and 5 parts by weight of component Y, X and Y are present at a weight ratio of 2:5, and are present in such ratio regardless of whether additional components are contained in the compound.

A weight percent of a component, unless specifically stated to the contrary, is based on the total weight of the formulation or composition in which the component is included.

I. DNA Constructs

DNA constructs are provided herein for the production of polyactive carbohydrates. It is understood that one way to define the variants and derivatives of the genetic components and DNA constructs described herein is in terms of homology/identity to specific known sequences. Those of skill in the art readily understand how to determine the homology of two nucleic acids. For example, the homology can be calculated after aligning two sequences so that the homology is at its highest level. Another way of calculating homology can be performed according to published algorithms (see Zuker, M., Science, 244:48-52, 1989; Jaeger et al, *Proc. Natl. Acad. Sci. USA,* 86:7706-7710, 1989; Jaeger et al, *Methods Enzymol.,* 183:281-306, 1989, which are herein incorporated by reference for at least material related to nucleic acid alignment).

As used herein, "conservative" mutations are mutations that result in an amino acid change in the protein produced from a sequence of DNA. When a conservative mutation occurs, the new amino acid has similar properties as the wild type amino acid and generally does not drastically change the function or folding of the protein (e.g., switching isoleucine for valine is a conservative mutation since both are small, branched, hydrophobic amino acids). "Silent mutations," meanwhile, change the nucleic acid sequence of a gene encoding a protein but do not change the amino acid sequence of the protein.

It is understood that the description of mutations and homology can be combined together in any combination, such as embodiments that have at least 70%, 75%, 80%, 85%, 90%, 95%, or 99% homology to a particular sequence wherein the variants are conservative or silent mutations. It is understood that any of the sequences described herein can be a variant or derivative having the homology values listed above.

In one aspect, a database such as, for example, GenBank, can be used to determine the sequences of genes and/or regulatory regions of interest, the species from which these elements originate, and related homologous sequences.

In one aspect, provided herein is a DNA construct including the following genetic components:

a) a gene that expresses chitin synthase;
b) a gene that expresses chitosanase; and
c) a gene that expresses chitin deacetylase.

In another aspect, provided herein is a DNA construct including the following genetic components:

a) a gene that expresses chitin synthase;
b) a gene that expresses chitosanase;
c) a gene that expresses chitin deacetylase; and
d) a gene that expresses lipase.

In still another aspect, provided herein is a DNA construct including the following components:

a) a gene that expresses chitin synthase;
b) a gene that expresses chitosanase;
c) a gene that expresses chitin deacetylase;
d) optionally, a gene that expresses lipase;
e) optionally, a gene that expresses chitin synthase regulatory factor CHR1;
f) optionally, a gene that expresses transglycosylase; and/or
g) optionally, a gene that expresses dehydrogenase.

In one aspect, provided herein is a DNA construct including the following components:

a) a gene that expresses lipase;
b) a gene that expresses chitin synthase;
c) a gene that expresses chitosanase;
d) a gene that expresses chitin deacetylase; and
e) a gene that expresses (1→3),(1→4)-β-glucan synthase.

In one aspect, provided herein is a DNA construct including the following components:

a) a gene that expresses chitin synthase;
b) a gene that expresses chitosanase;
c) a gene that expresses chitin deacetylase; and
d) a gene that expresses (1→3),(1→4)-β-glucan synthase.

In one aspect, provided herein is a supplemental DNA construct including the following genetic components:

a) a gene that expresses transglycosylase; and
b) a gene that expresses chitin synthase regulatory factor CHR1.

In one aspect, the nucleic acids (e.g., genes that express lipase, chitin synthase, chitosanase, chitin deacetylase, chitin synthase regulatory factor CHR1, gene that expresses transglycosylase, dehydrogenase, and/or gene that expresses (1→3),(1→4)-β-glucan synthase) used in the DNA constructs described herein can be amplified using polymerase chain reaction (PCR) prior to being ligated into a plasmid or other vector. Typically, PCR-amplification techniques make use of primers, or short, chemically-synthesized oligonucleotides that are complementary to regions on each respective strand flanking the DNA or nucleotide sequence to be amplified. A person having ordinary skill in the art will be able to design or choose primers based on the desired experimental conditions. In general, primers should be designed to provide for both efficient and faithful replication of the target nucleic acids. Two primers are required for the amplification of each gene, one for the sense strand (that is, the strand containing the gene of interest) and one for the antisense strand (that is, the strand complementary to the gene of interest). Pairs of primers should have similar melting temperatures that are close to the PCR reaction's annealing temperature. In order to facilitate the PCR reaction, the following features should be avoided in primers: mononucleotide repeats, complementarity with other primers in the mixture, self-complementarity, and internal hairpins and/or loops. Methods of primer design are known in the art; additionally, computer programs exist that can assist the skilled practitioner with primer design. Primers can optionally incorporate restriction enzyme recognition sites at their 5' ends to assist in later ligation into plasmids or other vectors.

PCR can be carried out using purified DNA, unpurified DNA that is integrated into a vector, or unpurified genomic DNA. The process for amplifying target DNA using PCR consists of introducing an excess of two primers having the characteristics described above to a mixture containing the sequence to be amplified, followed by a series of thermal cycles in the presence of a heat-tolerant or thermophilic DNA polymerase, such as, for example, any of Taq, Pfu, Pwo, Tfl, rTth, Tli, or Tma polymerases. A PCR "cycle" involves denaturation of the DNA through heating, followed by annealing of the primers to the target DNA, followed by extension of the primers using the thermophilic DNA polymerase and a supply of deoxynucleotide triphosphates (i.e., dCTP, dATP, dGTP, and TTP), along with buffers, salts, and other reagents as needed. In one aspect, the DNA segments created by primer extension during the PCR process can serve as templates for additional PCR cycles. Many PCR cycles can be performed to generate a large concentration of target DNA or genes. PCR can optionally be performed in a device or machine with programmable temperature cycles for denaturation, annealing, and extension steps. Further, PCR can be performed on multiple genes simultaneously in the same reaction vessel or microcentrifuge tube since the primers chosen will be specific to selected genes. PCR products can be purified by techniques known in the art such as, for example, gel electrophoresis followed by extraction from the gel using commercial kits and reagents.

In a further aspect, the plasmid can include an origin of replication, allowing it to use the host cell's replication machinery to create copies of itself.

As used herein, "operably linked" refers to the association of nucleic acid sequences on a single nucleic acid fragment so that the function of one affects the function of another. For example, if sequences for multiple genes are inserted into a single plasmid, their expression may be operably linked. Alternatively, a promoter is said to be operably linked with a coding sequence when it is capable of affecting the expression of that coding sequence.

As used herein, "expression" refers to transcription and/or accumulation of an mRNA derived from a gene or DNA fragment. Expression may also be used to refer to translation of mRNA into a peptide, polypeptide, or protein.

A lipase is an esterase that catalyzes the hydrolysis of fats, oils, and lipids. In one aspect, the gene that expresses lipase is isolated from a bacterium. In a further aspect, the bacterium is a *Micrococcus* species, a *Pseudomonas* species, a *Moraxella* species, or an *Acinetobacter* species. In a further aspect, the gene that expresses lipase has SEQ ID NO. 1 or at least 70% homology thereof, at least 75% homology thereof, at least 80% homology thereof, at least 85% homology thereof, at least 90% homology thereof, or at least 95% homology thereof. In one aspect, the gene that expresses lipase can be positioned anywhere in the DNA construct disclosed herein. In one aspect, the gene that expresses lipase is positioned 5' (i.e., prior) to the gene that expresses chitin synthase.

Other sequences expressing lipase or related or homologous genes can be identified in a database such as, for example, GenBank. In one aspect, sequences useful herein include those with the GI numbers listed in Table 1:

TABLE 1

Lipase Genes

| Source Organism | Sequence Description | GI Number |
|---|---|---|
| *Micrococcus* sp. HL-2003 | lipase gene | AY268069.1 |
| *Pseudomonas* sp. | esterase gene | M68491.1 |
| *Moraxella* L1 | lipase 1 | X53053.1 |
| *A. calcoaceticus* | carboxylesterase and peptidyl prolyl-cis-trans-isomerase | X74839.1 |
| *Acinetobacter* sp. ADP1 | genomic DNA | CR543861.1 |
| *A. calcoaceticus* | esterase | X71598.1 |
| *Pseudomonas trivialis* | genomic DNA | CP011507.1 |
| *Pseudomonas azotoformans* | genomic DNA | CP019856.1 |
| *Pseudomonas extremaustralis* | genomic DNA | LT629689.1 |
| *Pseudomonas fluorescens* | genomic DNA | CP005975.1 |
| *Pseudomonas fluorescens* | genomic DNA | CP010896.1 |
| *Pseudomonas fluorescens* | genomic DNA | AF228666.1 |
| *Pseudomonas simiae* | genomic DNA | CP007637.1 |
| *Pseudomonas fluorescens* | genomic DNA | AM181176.4 |
| *Pseudomonas Antarctica* | genomic DNA | CP015600.1 |
| *Pseudomonas fluorescens* | genomic DNA | CP015639.1 |
| *Pseudomonas fluorescens* | genomic DNA | LT907842.1 |
| *Pseudomonas* sp. NS1 | genomic DNA | CP022960.1 |
| *Pseudomonas poae* | genomic DNA | LT629706.1 |
| *Pseudomonas poae* | genomic DNA | CP004045.1 |
| *Pseudomonas rhodesiae* | genomic DNA | LT629801.1 |
| *Pseudomonas trivialis* | genomic DNA | LT629760.1 |
| *Pseudomonas azotoformans* | genomic DNA | LT629702.1 |
| *Pseudomonas Antarctica* | genomic DNA | LT629704.1 |
| *Pseudomonas fluorescens* | genomic DNA | CP012400.1 |
| *Pseudomonas azotoformans* | genomic DNA | CP014546.1 |
| *Pseudomonas yamanorum* | genomic DNA | LT629793.1 |
| *Pseudomonas prosekii* | genomic DNA | LT629762.1 |
| *Pseudomonas koreensis* | genomic DNA | CP014947.1 |
| *Pseudomonas libanensis* | genomic DNA | LT629699.1 |
| *Pseudomonas* sp. GR 6-02 | genomic DNA | CP011567.1 |
| *Pseudomonas fluorescens* | genomic DNA | CP014868.1 |
| *Pseudomonas fluorescens* | genomic DNA | CP011117.1 |
| *Pseudomonas fluorescens* | genomic DNA | S69066.1 |
| *Pseudomonas cedrina* | genomic DNA | LT629753.1 |
| *Pseudomonas* sp. bs2935 | genomic DNA | LT629744.1 |
| *Pseudomonas fluorescens* | genomic DNA | CP017296.1 |
| *Pseudomonas* sp. WCS374 | genomic DNA | CP007638.1 |
| *Pseudomonas fluorescens* | genomic DNA | CP003041.1 |
| *Pseudomonas corrugate* | genomic DNA | LT629798.1 |
| *Pseudomonas corrugate* | genomic DNA | CP014262.1 |
| *Pseudomonas mediterranea* | genomic DNA | LT629790.1 |
| *Pseudomonas tolaasii* | genomic DNA | CP020369.1 |
| *Pseudomonas fluorescens* | genomic DNA | CP015638.1 |
| *Pseudomonas fluorescens* | genomic DNA | CP015637.1 |
| *Pseudomonas* sp. TKP | genomic DNA | CP006852.1 |
| Synthetic construct | carboxylesterase | HM212419.1 |
| Synthetic construct | carboxylesterase | FJ213454.1 |
| *Pseudomonas* sp. FDAARGOS 380 | genomic DNA | CP023969.1 |
| *Pseudomonas synxantha* | genomic DNA | LT629786.1 |
| *Pseudomonas orientalis* | genomic DNA | LT629782.1 |
| *Pseudomonas* sp. URMO17WK12:I11 | genomic DNA | LN854573.1 |

Chitin synthase is a glycosyltransferase enzyme that catalyzes the following reaction:

$$\text{UDP-N-acetyl-D-glucosamine+[1,4-(N-acetyl-}\beta\text{-D-glucosaminyl)]}_n \rightarrow \text{UDP+[1,4-(N-acetyl-}\beta\text{-D-glucosaminyl)]}_{n+1}$$

where UDP is uridine diphosphate and N-acetyl-D-glucosamine units are added to the growing chitin chain one residue at a time.

In one aspect, the gene that expresses chitin synthase is isolated from yeast. In a further aspect, the yeast can be *Saccharomyces cerevisiae*. In a still further aspect, the *S. cerevisiae* strain that is the source of chitin synthase can be strain S288c, BSPX042, ySR127, DBVPG6765, YJM1526, YJM972, YJM969, YJM470, YJM248, YJM1478, YJM996, YJM244, YJM1477, YJM1387, YJM993, YJM1332, YJM1242, YJM990, T63, T52, or any other commonly cultured experimental strain of yeast. In another aspect, the *S. cerevisiae* is a wild type strain. In a further aspect, the gene that expresses chitin synthase has SEQ ID NO. 2 or at least 70% homology thereto, at least 75% homology thereto, at least 80% homology thereto, at least 85% homology thereto, at least 90% homology thereto, or at least 95% homology thereto. In one aspect, the gene that expresses chitin synthase is isolated from *Saccharomyces cerevisiae* and can be found in GenBank with GI number NC_001146.8.

Other sequences expressing chitin synthase or related or homologous genes can be identified in a database such as, for example, GenBank. In one aspect, sequences useful herein include those with the GI numbers listed in Table 2.

TABLE 2

| Chitin Synthase Genes | | |
|---|---|---|
| Source Organism | Sequence Description | GI Number |
| *Saccharomyces cerevisiae* | synthetic construct | DQ331902.1 |
| *Saccharomyces cerevisiae* | chromosome XIV sequence | CP020136.1 |
| *Saccharomyces cerevisiae* | chromosome XIV sequence | CP014729.1 |
| *Saccharomyces cerevisiae* | chromosome XIV sequence | CP011560.1 |
| *Saccharomyces cerevisiae* | chromosome XIV sequence | BK006947.3 |
| *Saccharomyces cerevisiae* | chitin synthase | NM_001183030.2 |
| *Saccharomyces cerevisiae* | chromosome XIV sequence | Z71468.1 |
| *Saccharomyces cerevisiae* | chitin synthase | M14045.1 |
| *Saccharomyces cerevisiae* | chromosome XIV sequence | CP020170.1 |
| *Saccharomyces cerevisiae* | chromosome XIV sequence | CP005579.2 |
| *Saccharomyces cerevisiae* | chromosome XIV sequence | CP005519.2 |
| *Saccharomyces cerevisiae* | chromosome XIV sequence | CP005518.2 |
| *Saccharomyces cerevisiae* | chromosome XIV sequence | CP005508.2 |
| *Saccharomyces cerevisiae* | chromosome XIV sequence | CP005498.2 |
| *Saccharomyces cerevisiae* | chromosome XIV sequence | CP005577.2 |
| *Saccharomyces cerevisiae* | chromosome XIV sequence | CP005527.2 |
| *Saccharomyces cerevisiae* | chromosome XIV sequence | CP005497.2 |
| *Saccharomyces cerevisiae* | chromosome XIV sequence | CP005576.2 |
| *Saccharomyces cerevisiae* | chromosome XIV sequence | CP005556.2 |
| *Saccharomyces cerevisiae* | chromosome XIV sequence | CP005526.2 |
| *Saccharomyces cerevisiae* | chromosome XIV sequence | CP005545.2 |
| *Saccharomyces cerevisiae* | chromosome XIV sequence | CP005535.2 |
| *Saccharomyces cerevisiae* | chromosome XIV sequence | CP005525.2 |
| *Saccharomyces cerevisiae* | chromosome XIV sequence | CP008334.1 |
| *Saccharomyces cerevisiae* | chromosome XIV sequence | CP008317.1 |
| *Saccharomyces cerevisiae* | chromosome XIV sequence | CP008351.1 |
| *Saccharomyces cerevisiae* | chromosome XIV sequence | CP008470.1 |
| *Saccharomyces cerevisiae* | chromosome XIV sequence | CP008572.1 |
| *Saccharomyces cerevisiae* | chromosome XIV sequence | CP008674.1 |
| *Saccharomyces cerevisiae* | chromosome XIV sequence | CP008657.1 |
| *Saccharomyces cerevisiae* | chromosome XIV sequence | CP008623.1 |
| *Saccharomyces cerevisiae* | chromosome XIV sequence | CP008181.1 |
| *Saccharomyces cerevisiae* | chromosome XIV sequence | CP008147.1 |
| *Saccharomyces cerevisiae* | chromosome XIV sequence | CP008045.1 |
| *Saccharomyces cerevisiae* | chromosome XIV sequence | CP008028.1 |
| *Saccharomyces cerevisiae* | chromosome XIV sequence | CP008011.1 |
| *Saccharomyces cerevisiae* | chromosome XIV sequence | CP007926.1 |
| *Saccharomyces cerevisiae* | chromosome XIV sequence | CP007892.1 |
| *Saccharomyces cerevisiae* | chromosome XIV sequence | CP007875.1 |
| *Saccharomyces cerevisiae* | chromosome XIV sequence | CP007858.1 |
| *Saccharomyces cerevisiae* | chromosome XIV sequence | CP007824.1 |
| *Saccharomyces cerevisiae* | chromosome XIV sequence | CP005494.2 |
| *Saccharomyces cerevisiae* | chromosome XIV sequence | CP005583.2 |
| *Saccharomyces cerevisiae* | chromosome XIV sequence | CP005573.2 |
| *Saccharomyces cerevisiae* | chromosome XIV sequence | CP005533.2 |
| *Saccharomyces cerevisiae* | chromosome XIV sequence | CP005523.2 |
| *Saccharomyces cerevisiae* | chromosome XIV sequence | CP005503.2 |
| *Saccharomyces cerevisiae* | chromosome XIV sequence | CP005552.2 |
| *Saccharomyces cerevisiae* | chromosome XIV sequence | CP005542.2 |
| *Saccharomyces cerevisiae* | chromosome XIV sequence | CP005532.2 |
| *Saccharomyces cerevisiae* | chromosome XIV sequence | CP005522.2 |
| *Saccharomyces cerevisiae* | chromosome XIV sequence | CP005521.2 |
| *Saccharomyces cerevisiae* | chromosome XIV sequence | CP005550.2 |
| *Saccharomyces cerevisiae* | chromosome XIV sequence | CP005520.2 |
| *Saccharomyces cerevisiae* | chromosome XIV sequence | CP005500.2 |
| *Saccharomyces cerevisiae* | chromosome XIV sequence | CP005524.1 |
| *Saccharomyces cerevisiae* | chromosome XIV sequence | CP005516.1 |
| *Saccharomyces cerevisiae* | chromosome XIV sequence | CP004112.1 |
| *Saccharomyces cerevisiae* | chromosome XIV sequence | CP008266.1 |
| *Saccharomyces cerevisiae* | chromosome XIV sequence | CP008453.1 |
| *Saccharomyces cerevisiae* | chromosome XIV sequence | CP008521.1 |
| *Saccharomyces cerevisiae* | chromosome XIV sequence | CP008640.1 |
| *Saccharomyces cerevisiae* | chromosome XIV sequence | CP008079.1 |
| *Saccharomyces cerevisiae* | chromosome XIV sequence | CP005529.2 |
| *Saccharomyces cerevisiae* | chromosome XIV sequence | CP005499.2 |
| *Saccharomyces cerevisiae* | chromosome XIV sequence | CP005548.2 |
| *Saccharomyces cerevisiae* | chromosome XIV sequence | CP005547.2 |
| *Saccharomyces cerevisiae* | chromosome XIV sequence | CP005546.2 |
| *Saccharomyces cerevisiae* | chromosome XIV sequence | CP005536.2 |
| *Saccharomyces cerevisiae* | chromosome XIV sequence | CP005506.2 |
| *Saccharomyces cerevisiae* | chromosome XIV sequence | CP008283.1 |
| *Saccharomyces cerevisiae* | chromosome XIV sequence | CP008232.1 |
| *Saccharomyces cerevisiae* | chromosome XIV sequence | CP008487.1 |

TABLE 2-continued

| Chitin Synthase Genes | | |
|---|---|---|
| Source Organism | Sequence Description | GI Number |
| *Saccharomyces cerevisiae* | chromosome XIV sequence | CP008436.1 |
| *Saccharomyces cerevisiae* | chromosome XIV sequence | CP008589.1 |
| *Saccharomyces cerevisiae* | chromosome XIV sequence | CP008555.1 |
| *Saccharomyces cerevisiae* | chromosome XIV sequence | CP008538.1 |
| *Saccharomyces cerevisiae* | chromosome XIV sequence | CP008606.1 |
| *Saccharomyces cerevisiae* | chromosome XIV sequence | CP008198.1 |
| *Saccharomyces cerevisiae* | chromosome XIV sequence | CP008164.1 |
| *Saccharomyces cerevisiae* | chromosome XIV sequence | CP008691.1 |
| *Saccharomyces cerevisiae* | chromosome XIV sequence | CP008130.1 |
| *Saccharomyces cerevisiae* | chromosome XIV sequence | CP008113.1 |
| *Saccharomyces cerevisiae* | chromosome XIV sequence | CP008096.1 |
| *Saccharomyces cerevisiae* | chromosome XIV sequence | CP007977.1 |
| *Saccharomyces cerevisiae* | chromosome XIV sequence | CP007960.1 |
| *Saccharomyces cerevisiae* | chromosome XIV sequence | CP005564.2 |
| *Saccharomyces cerevisiae* | chromosome XIV sequence | CP005544.2 |
| *Saccharomyces cerevisiae* | chromosome XIV sequence | CP005563.2 |
| *Saccharomyces cerevisiae* | chromosome XIV sequence | CP005581.2 |
| *Saccharomyces cerevisiae* | chromosome XIV sequence | CP005551.2 |
| *Saccharomyces cerevisiae* | chromosome XIV sequence | CP005531.2 |
| *Saccharomyces cerevisiae* | chromosome XIV sequence | CP005580.2 |
| *Saccharomyces cerevisiae* | chromosome XIV sequence | CP005530.2 |
| *Saccharomyces cerevisiae* | chromosome XIV sequence | CP005510.2 |
| *Saccharomyces cerevisiae* | chromosome XIV sequence | FN393086.1 |
| *Saccharomyces cerevisiae* | chromosome XIV sequence | CP008504.1 |
| *Saccharomyces cerevisiae* | chromosome XIV sequence | CP007909.1 |
| *Saccharomyces cerevisiae* | chromosome XIV sequence | CP005549.2 |
| *Saccharomyces cerevisiae* | chromosome XIV sequence | CP005539.2 |

Chitosanase is any one of a class of enzymes that perform hydrolysis of β-(1→4)-linkages between D-glucosamine residues in a partially acetylated chitosan molecule. The hydrolysis carried out by chitosanase typically occurs in the middle of the chitosan rather than at the ends.

In one aspect, the gene that expresses chitosanase is isolated from yeast. In a further aspect, the yeast can be *Saccharomyces cerevisiae*. In another aspect, the *S. cerevisiae* strain can be S288c, BSPX042, ySR127, YJM683, YJM682, YJM554, YJM541, YJM456, YJM326, YJM1615, YJM1208, YJM1133, NCIM3107, NCIM3186, T52, T63, YJM1573, YJM1402, YJM1401, another commonly cultured experimental strain, or can be a wild type strain. In a further aspect, the gene that expresses chitosanase has SEQ ID NO. 3 or at least 70% homology thereto, at least 75% homology thereto, at least 80% homology thereto, at least 85% homology thereto, at least 90% homology thereto, or at least 95% homology thereto. In one aspect, the gene that expresses chitosanase is isolated from *Saccharomyces cerevisiae* and can be found in GenBank with GI number AAB67331.1.

Other sequences expressing chitosanase or related or homologous genes can be identified in a database such as, for example, GenBank. In one aspect, sequences useful herein include those with the GI numbers listed in Table 3.

TABLE 3

| Chitosanase Genes | | |
|---|---|---|
| Source Organism | Sequence Description | GI Number |
| *Saccharomyces cerevisiae* | chromosome XII sequence | CP020134.1 |
| *Saccharomyces cerevisiae* | chromosome XII sequence | CP014727.1 |
| *Saccharomyces cerevisiae* | chromosome XII sequence | CP011558.1 |
| *Saccharomyces cerevisiae* | chromosome XII sequence | CP006456.1 |
| *Saccharomyces cerevisiae* | chromosome XII sequence | CP006455.1 |
| *Saccharomyces cerevisiae* | chromosome XII sequence | CP006451.1 |
| *Saccharomyces cerevisiae* | chromosome XII sequence | CP006450.1 |
| *Saccharomyces cerevisiae* | chromosome XII sequence | CP006448.1 |
| *Saccharomyces cerevisiae* | chromosome XII sequence | CP006443.1 |
| *Saccharomyces cerevisiae* | chromosome XII sequence | CP006434.1 |
| *Saccharomyces cerevisiae* | chromosome XII sequence | CP006383.1 |
| *Saccharomyces cerevisiae* | chromosome XII sequence | CP006379.1 |
| *Saccharomyces cerevisiae* | chromosome XII sequence | BK006945.2 |
| *Saccharomyces cerevisiae* | genomic DNA | NM_001182173.1 |
| *Saccharomyces cerevisiae* | chromosome XII sequence | U17243.1 |
| *Saccharomyces cerevisiae* | endochitinase | M74070.1 |
| *Saccharomyces cerevisiae* | chromosome XII sequence | CP009950.1 |
| *Saccharomyces cerevisiae* | chromosome XII sequence | CP011821.1 |
| *Saccharomyces cerevisiae* | chromosome XII sequence | CP008196.1 |
| *Saccharomyces cerevisiae* | chromosome XII sequence | CP008553.1 |
| *Saccharomyces cerevisiae* | chromosome XII sequence | CP008536.1 |
| *Saccharomyces cerevisiae* | chromosome XII sequence | CP008519.1 |
| *Saccharomyces cerevisiae* | chromosome XII sequence | CP008655.1 |

TABLE 3-continued

| Chitosanase Genes | | |
|---|---|---|
| Source Organism | Sequence Description | GI Number |
| *Saccharomyces cerevisiae* | chromosome XII sequence | CP008213.1 |
| *Saccharomyces cerevisiae* | chromosome XII sequence | CP008315.1 |
| *Saccharomyces cerevisiae* | chromosome XII sequence | CP008264.1 |
| *Saccharomyces cerevisiae* | chromosome XII sequence | CP008145.1 |
| *Saccharomyces cerevisiae* | chromosome XII sequence | CP006431.1 |
| *Saccharomyces cerevisiae* | chromosome XII sequence | CP006411.1 |
| *Saccharomyces cerevisiae* | chromosome XII sequence | CP006410.1 |
| *Saccharomyces cerevisiae* | chromosome XII sequence | CP008247.1 |
| *Saccharomyces cerevisiae* | chromosome XII sequence | CP008366.1 |
| *Saccharomyces cerevisiae* | chromosome XII sequence | CP008349.1 |
| *Saccharomyces cerevisiae* | chromosome XII sequence | CP008485.1 |
| *Saccharomyces cerevisiae* | chromosome XII sequence | CP008604.1 |
| *Saccharomyces cerevisiae* | chromosome XII sequence | CP008179.1 |
| *Saccharomyces cerevisiae* | chromosome XII sequence | CP008162.1 |
| *Saccharomyces cerevisiae* | chromosome XII sequence | CP008128.1 |
| *Saccharomyces cerevisiae* | chromosome XII sequence | CP008026.1 |
| *Saccharomyces cerevisiae* | chromosome XII sequence | CP007975.1 |
| *Saccharomyces cerevisiae* | chromosome XII sequence | CP007958.1 |
| *Saccharomyces cerevisiae* | chromosome XII sequence | CP007941.1 |
| *Saccharomyces cerevisiae* | chromosome XII sequence | CP007873.1 |
| *Saccharomyces cerevisiae* | chromosome XII sequence | CP007856.1 |
| *Saccharomyces cerevisiae* | chromosome XII sequence | CP007839.1 |
| *Saccharomyces cerevisiae* | chromosome XII sequence | CP008400.1 |
| *Saccharomyces cerevisiae* | chromosome XII sequence | CP020219.1 |
| *Saccharomyces cerevisiae* | chromosome XII sequence | CP008451.1 |
| *Saccharomyces cerevisiae* | chromosome XII sequence | CP006417.1 |
| *Saccharomyces cerevisiae* | chromosome XII sequence | CP006398.1 |
| *Saccharomyces cerevisiae* | chromosome XII sequence | CP006389.1 |
| *Saccharomyces cerevisiae* | chromosome XII sequence | CP008332.1 |
| *Saccharomyces cerevisiae* | chromosome XII sequence | CP008298.1 |
| *Saccharomyces cerevisiae* | chromosome XII sequence | CP008417.1 |
| *Saccharomyces cerevisiae* | chromosome XII sequence | CP008434.1 |
| *Saccharomyces cerevisiae* | chromosome XII sequence | CP008587.1 |
| *Saccharomyces cerevisiae* | chromosome XII sequence | CP008638.1 |
| *Saccharomyces cerevisiae* | chromosome XII sequence | CP008689.1 |
| *Saccharomyces cerevisiae* | chromosome XII sequence | CP008111.1 |
| *Saccharomyces cerevisiae* | chromosome XII sequence | CP008094.1 |
| *Saccharomyces cerevisiae* | chromosome XII sequence | CP008077.1 |
| *Saccharomyces cerevisiae* | chromosome XII sequence | CP008043.1 |
| *Saccharomyces cerevisiae* | chromosome XII sequence | CP007924.1 |
| *Saccharomyces cerevisiae* | chromosome XII sequence | CP007907.1 |
| *Saccharomyces cerevisiae* | chromosome XII sequence | CP007890.1 |
| *Saccharomyces cerevisiae* | chromosome XII sequence | CP007822.1 |
| *Saccharomyces cerevisiae* | chromosome XII sequence | CP008281.1 |
| *Saccharomyces cerevisiae* | chromosome XII sequence | CP006429.1 |
| *Saccharomyces cerevisiae* | chromosome XII sequence | CP006419.1 |
| *Saccharomyces cerevisiae* | chromosome XII sequence | CP008230.1 |
| *Saccharomyces cerevisiae* | chromosome XII sequence | CP008468.1 |
| *Saccharomyces cerevisiae* | chromosome XII sequence | CP008672.1 |
| *Saccharomyces cerevisiae* | chromosome XII sequence | CP008502.1 |
| *Saccharomyces cerevisiae* | chromosome XII sequence | CP006454.1 |
| *Saccharomyces cerevisiae* | chromosome XII sequence | CP006445.1 |
| *Saccharomyces cerevisiae* | chromosome XII sequence | CP006427.1 |
| *Saccharomyces cerevisiae* | chromosome XII sequence | CP006420.1 |
| *Saccharomyces cerevisiae* | chromosome XII sequence | CP006409.1 |
| *Saccharomyces cerevisiae* | chromosome XII sequence | CP006390.1 |
| *Saccharomyces cerevisiae* | chromosome XII sequence | CP008621.1 |
| *Saccharomyces cerevisiae* | chromosome XII sequence | CP008009.1 |
| *Saccharomyces cerevisiae* | chromosome XII sequence | CP006452.1 |
| *Saccharomyces cerevisiae* | chromosome XII sequence | CP006430.1 |
| *Saccharomyces cerevisiae* | chromosome XII sequence | CP006401.1 |
| *Saccharomyces cerevisiae* | chromosome XII sequence | CP006393.1 |
| *Saccharomyces cerevisiae* | chromosome XII sequence | CP007992.1 |
| *Saccharomyces cerevisiae* | chromosome XII sequence | CP006414.1 |
| *Saccharomyces cerevisiae* | chromosome XII sequence | CP008570.1 |
| *Saccharomyces cerevisiae* | chromosome XII sequence | CP008383.1 |
| *Saccharomyces cerevisiae* | chromosome XII sequence | CP020236.1 |
| *Saccharomyces cerevisiae* | chromosome XII sequence | CP006421.1 |
| *Saccharomyces cerevisiae* | chromosome XII sequence | CP008060.1 |
| *Saccharomyces cerevisiae* | chromosome XII sequence | CP020151.1 |
| *Saccharomyces cerevisiae* | chromosome XII sequence | CP006453.1 |
| *Saccharomyces cerevisiae* | chromosome XII sequence | CP006418.1 |
| *Saccharomyces cerevisiae* | chromosome XII sequence | CP006386.1 |
| *Saccharomyces cerevisiae* | chromosome XII sequence | CP006449.1 |

TABLE 3-continued

| Chitosanase Genes | | |
|---|---|---|
| Source Organism | Sequence Description | GI Number |
| *Saccharomyces cerevisiae* | chromosome XII sequence | CP006404.1 |
| *Saccharomyces cerevisiae* | chromosome XII sequence | LN907795.1 |
| *Saccharomyces cerevisiae* | chromosome XII sequence | CP006387.1 |

Chitin deacetylase is an enzyme that catalyzes the hydrolysis of chitin to chitosan and acetate. In one aspect, the chitin deacetylase reaction can proceed to completion. In an alternative aspect, the hydrolysis is incomplete, leaving some acetate groups attached to glucosamine residues in the polymer backbone.

In one aspect, the gene that expresses chitin deacetylase is isolated from yeast. In a further aspect, the yeast can be *Saccharomyces cerevisiae*. In another aspect, the *S. cerevisiae* strain can be Y12, S288c, BSPX042, N85, YJM470, YJM456, YJM1615, YJM1592, YJM1549, YJM1460, YJM1389, YJM1388, YJM1387, YJM1304, YJM1208, YJM689, YJM1202, YJM1199, YJM1133, YJM1381, YPS128, another commonly cultured experimental strain, or can be a wild type strain. In a further aspect, the gene that expresses chitin deacetylase has SEQ ID NO. 4 or at least 70% homology thereto, at least 75% homology thereto, at least 80% homology thereto, at least 85% homology thereto, at least 90% homology thereto, or at least 95% homology thereto. In one aspect, the gene that expresses chitin deacetylase is isolated from *Saccharomyces cerevisiae* and can be found in GenBank with accession number NM_001182196.

Other sequences expressing chitin deacetylase or related or homologous genes can be identified in a database such as, for example, GenBank. In one aspect, sequences useful herein include those with the GI numbers listed in Table 4.

TABLE 4

| Chitin Deacetylase Genes | | |
|---|---|---|
| Source Organism | Sequence Description | GI Number |
| *Saccharomyces cerevisiae* | chromosome XII sequence | CP020202.1 |
| *Saccharomyces cerevisiae* | chromosome XII sequence | CP020134.1 |
| *Saccharomyces cerevisiae* | chromosome XII sequence | CP014727.1 |
| *Saccharomyces cerevisiae* | chromosome XII sequence | LN907795.1 |
| *Saccharomyces cerevisiae* | chromosome XII sequence | CP006449.1 |
| *Saccharomyces cerevisiae* | chromosome XII sequence | CP006448.1 |
| *Saccharomyces cerevisiae* | chromosome XII sequence | CP006434.1 |
| *Saccharomyces cerevisiae* | chromosome XII sequence | CP006433.1 |
| *Saccharomyces cerevisiae* | chromosome XII sequence | CP006430.1 |
| *Saccharomyces cerevisiae* | chromosome XII sequence | CP006423.1 |
| *Saccharomyces cerevisiae* | chromosome XII sequence | CP006407.1 |
| *Saccharomyces cerevisiae* | chromosome XII sequence | CP006406.1 |
| *Saccharomyces cerevisiae* | chromosome XII sequence | CP006405.1 |
| *Saccharomyces cerevisiae* | chromosome XII sequence | CP006390.1 |
| *Saccharomyces cerevisiae* | chromosome XII sequence | CP006383.1 |
| *Saccharomyces cerevisiae* | chromosome XII sequence | BK006945.2 |
| *Saccharomyces cerevisiae* | chitin deacetylase | NM_001182196.1 |
| *Saccharomyces cerevisiae* | chromosome XII sequence | U17247.1 |
| *Saccharomyces cerevisiae* | chromosome XII sequence | CP006457.1 |
| *Saccharomyces cerevisiae* | chromosome XII sequence | CP006382.1 |
| *Saccharomyces cerevisiae* | chromosome XII sequence | CP006381.1 |
| *Saccharomyces cerevisiae* | chromosome XII sequence | CP006379.1 |
| *Saccharomyces cerevisiae* | chromosome XII sequence | CP006401.1 |
| *Saccharomyces cerevisiae* | chromosome XII sequence | CP020219.1 |
| *Saccharomyces cerevisiae* | chromosome XII sequence | CP006427.1 |
| *Saccharomyces cerevisiae* | chromosome XII sequence | CP006426.1 |
| *Saccharomyces cerevisiae* | chromosome XII sequence | CP006422.1 |
| *Saccharomyces cerevisiae* | chromosome XII sequence | CP006419.1 |
| *Saccharomyces cerevisiae* | chromosome XII sequence | CP006417.1 |
| *Saccharomyces cerevisiae* | chromosome XII sequence | CP006409.1 |
| *Saccharomyces cerevisiae* | chromosome XII sequence | CP006389.1 |
| *Saccharomyces cerevisiae* | chromosome XII sequence | CP006377.1 |
| *Saccharomyces cerevisiae* | chromosome XII sequence | CP020236.1 |
| *Saccharomyces cerevisiae* | chromosome XII sequence | CP006429.1 |
| *Saccharomyces cerevisiae* | chromosome XII sequence | CP006421.1 |
| *Saccharomyces cerevisiae* | chromosome XII sequence | CP006420.1 |
| *Saccharomyces cerevisiae* | chromosome XII sequence | CP006414.1 |
| *Saccharomyces cerevisiae* | chromosome XII sequence | CP006410.1 |
| *Saccharomyces cerevisiae* | chromosome XII sequence | CP011821.1 |
| *Saccharomyces cerevisiae* | chromosome XII sequence | CP006458.1 |
| *Saccharomyces cerevisiae* | chromosome XII sequence | CP006456.1 |
| *Saccharomyces cerevisiae* | chromosome XII sequence | CP006455.1 |
| *Saccharomyces cerevisiae* | chromosome XII sequence | CP006451.1 |
| *Saccharomyces cerevisiae* | chromosome XII sequence | CP006450.1 |
| *Saccharomyces cerevisiae* | chromosome XII sequence | CP006446.1 |
| *Saccharomyces cerevisiae* | chromosome XII sequence | CP006445.1 |
| *Saccharomyces cerevisiae* | chromosome XII sequence | CP006443.1 |

TABLE 4-continued

| Chitin Deacetylase Genes | | |
|---|---|---|
| Source Organism | Sequence Description | GI Number |
| *Saccharomyces cerevisiae* | chromosome XII sequence | CP006442.1 |
| *Saccharomyces cerevisiae* | chromosome XII sequence | CP006404.1 |
| *Saccharomyces cerevisiae* | chromosome XII sequence | CP006436.1 |
| *Saccharomyces cerevisiae* | chromosome XII sequence | CP006431.1 |
| *Saccharomyces cerevisiae* | chromosome XII sequence | CP006415.1 |
| *Saccharomyces cerevisiae* | chromosome XII sequence | CP006411.1 |
| *Saccharomyces cerevisiae* | chromosome XII sequence | CP006408.1 |
| *Saccharomyces cerevisiae* | chromosome XII sequence | CP009950.1 |
| *Saccharomyces cerevisiae* | chromosome XII sequence | CP008196.1 |
| *Saccharomyces cerevisiae* | chromosome XII sequence | CP020151.1 |
| *Saccharomyces cerevisiae* | chromosome XII sequence | CP008247.1 |
| *Saccharomyces cerevisiae* | chromosome XII sequence | CP008332.1 |
| *Saccharomyces cerevisiae* | chromosome XII sequence | CP008315.1 |
| *Saccharomyces cerevisiae* | chromosome XII sequence | CP008298.1 |
| *Saccharomyces cerevisiae* | chromosome XII sequence | CP008281.1 |
| *Saccharomyces cerevisiae* | chromosome XII sequence | CP008264.1 |
| *Saccharomyces cerevisiae* | chromosome XII sequence | CP008230.1 |
| *Saccharomyces cerevisiae* | chromosome XII sequence | CP008417.1 |
| *Saccharomyces cerevisiae* | chromosome XII sequence | CP008383.1 |
| *Saccharomyces cerevisiae* | chromosome XII sequence | CP008366.1 |
| *Saccharomyces cerevisiae* | chromosome XII sequence | CP008349.1 |
| *Saccharomyces cerevisiae* | chromosome XII sequence | CP008502.1 |
| *Saccharomyces cerevisiae* | chromosome XII sequence | CP008485.1 |
| *Saccharomyces cerevisiae* | chromosome XII sequence | CP008468.1 |
| *Saccharomyces cerevisiae* | chromosome XII sequence | CP008451.1 |
| *Saccharomyces cerevisiae* | chromosome XII sequence | CP008434.1 |
| *Saccharomyces cerevisiae* | chromosome XII sequence | CP008587.1 |
| *Saccharomyces cerevisiae* | chromosome XII sequence | CP008570.1 |
| *Saccharomyces cerevisiae* | chromosome XII sequence | CP008553.1 |
| *Saccharomyces cerevisiae* | chromosome XII sequence | CP008536.1 |
| *Saccharomyces cerevisiae* | chromosome XII sequence | CP008519.1 |
| *Saccharomyces cerevisiae* | chromosome XII sequence | CP008672.1 |
| *Saccharomyces cerevisiae* | chromosome XII sequence | CP008655.1 |
| *Saccharomyces cerevisiae* | chromosome XII sequence | CP008638.1 |
| *Saccharomyces cerevisiae* | chromosome XII sequence | CP008621.1 |
| *Saccharomyces cerevisiae* | chromosome XII sequence | CP008604.1 |
| *Saccharomyces cerevisiae* | chromosome XII sequence | CP008213.1 |
| *Saccharomyces cerevisiae* | chromosome XII sequence | CP008179.1 |
| *Saccharomyces cerevisiae* | chromosome XII sequence | CP008162.1 |
| *Saccharomyces cerevisiae* | chromosome XII sequence | CP008689.1 |
| *Saccharomyces cerevisiae* | chromosome XII sequence | CP008145.1 |
| *Saccharomyces cerevisiae* | chromosome XII sequence | CP008128.1 |
| *Saccharomyces cerevisiae* | chromosome XII sequence | CP008111.1 |
| *Saccharomyces cerevisiae* | chromosome XII sequence | CP008094.1 |
| *Saccharomyces cerevisiae* | chromosome XII sequence | CP008077.1 |
| *Saccharomyces cerevisiae* | chromosome XII sequence | CP008060.1 |
| *Saccharomyces cerevisiae* | chromosome XII sequence | CP008043.1 |
| *Saccharomyces cerevisiae* | chromosome XII sequence | CP008026.1 |
| *Saccharomyces cerevisiae* | chromosome XII sequence | CP008009.1 |
| *Saccharomyces cerevisiae* | chromosome XII sequence | CP007975.1 |
| *Saccharomyces cerevisiae* | chromosome XII sequence | CP007958.1 |
| *Saccharomyces cerevisiae* | chromosome XII sequence | CP007941.1 |
| *Saccharomyces cerevisiae* | chromosome XII sequence | CP007924.1 |

A (1→3),(1→4)-β-glucan synthase is a glucosyltransferase that catalyzes the synthesis of (1→3),(1→4)-β-glucan synthase, a mixed-linkage polysaccharide found in the cell wall of grasses and related species. In one aspect, the gene that expresses (1→3),(1→4)-β-glucan synthase is isolated from a plant. In a further aspect, the plant is a grass species such as, for example, corn (maize), sorghum, foxtail millet, Hall's panicgrass, barley, common wheat, rice (*Japonica* or *Indica* subspecies), oats, purple false brome, goat grass, a wild rice, or the like. In a further aspect, the gene that expresses (1→3),(1→4)-β-glucan synthase has SEQ ID NO. 6 or at least 70% homology thereof, at least 75% homology thereof, at least 80% homology thereof, at least 85% homology thereof, at least 90% homology thereof, or at least 95% homology thereof. In one aspect, the gene that expresses (1→3),(1→4)-β-glucan synthase is positioned 3' (i.e., after) to the gene that expresses chitin deacetylase.

Other sequences expressing (1→3),(1→4)-β-glucan synthase or related or homologous genes can be identified in a database such as, for example, GenBank. In one aspect, the gene that expresses (1→3),(1→4)-β-glucan synthase is isolated from corn (maize) and can be found in GenBank with accession number NM_001154454.2.

In one aspect, sequences useful herein include those with the GI numbers listed in Table 5:

TABLE 5

| (1→3),(1→4)-β-Glucan Synthase Genes | | |
|---|---|---|
| Source Organism | Sequence Description | GI Number |
| *Zea mays* | Cellulose synthase-like family F | NM_001154454.2 |
| *Zea mays* | (1→3),(1→4)-β-glucan synthase | EU957031.1 |
| *Zea mays* | cDNA clone | BT085572.1 |
| *Sorghum bicolor* | mixed-linked glucan synthase 3 | XM_021452421.1 |
| *Sorghum bicolor* | mixed-linked glucan synthase 3 | XM_002462954.2 |
| *Setaria italica* | mixed-linked glucan synthase 3 | XM_004957913.2 |
| *Panicum hallii* | mixed-linked glucan synthase 3 | XM_025946171.1 |
| *Hordeum vulgare* | predicted protein | AK356498.1 |
| *Hordeum vulgare* | cellulose synthase like CslF3 | EU267179.1 |
| *Triticum aestivum* | mRNA | AK451350.1 |
| *Aegilops tauschii* | mixed-linked glucan synthase 3 | XM_020314348.1 |
| *Brachypodium distachyon* | mixed-linked glucan synthase 3 | XM_003562892.4 |
| *Sorghum bicolor* | mixed-linked glucan synthase 3 | XM_021452870.1 |
| *Oryza sativa Japonica* | mixed-linked glucan synthase 3 | XM_015789971.2 |
| *Avena sativa* | cellulose synthase-like CslF3 | MG543996.1 |
| *Oryza sativa Indica* | chromosome 7 sequence | CP018163.1 |
| *Oryza sativa Japonica* | chromosome 7 sequence | AP014963.1 |
| *Oryza sativa Indica* | chromosome 7 sequence | CP012615.1 |
| *Oryza sativa* | cellulose synthase-like protein OsCslF3 | AF432504.1 |
| *Oryza sativa Japonica* | chromosome 7 DNA | AP004261.3 |
| *Zea mays* | mixed-linked glucan synthase 3 | XM_008673567.2 |
| *Brachypodium distachyon* | mixed-linked glucan synthase 2 | XM_010238892.3 |
| *Aegilops tauschii* | mixed-linked glucan synthase 2-like | XM_020314347.1 |
| *Sorghum bicolor* | mixed-linked glucan synthase 1 | XM_002462951.2 |
| *Triticum aestivum* | cDNA | AK335012.1 |
| *Oryza sativa Japonica* | mixed-linked glucan synthase 4 | XM_015790203.2 |
| *Zea mays* | mixed-linked glucan synthase 2 | XM_008654984.3 |
| *Oryza sativa Japonica* | mixed-linked glucan synthase 2-like | XM_015789850.2 |
| *Oryza sativa* | cellulose synthase-like protein OsCslF2 | AF432503.1 |
| *Oryza sativa Japonica* | cDNA | AK100523.1 |
| *Oryza sativa Japonica* | chromosome 7 sequence | AP005126.3 |
| *Aegilops tauschii* | mixed-linked glucan synthase 8 | XM_020307285.1 |
| *Oryza brachyantha* | mixed-linked glucan synthase 4-like | XM_006658618.1 |
| *Avena sativa* | cellulose synthase-like CSlF4 | MG543997.1 |
| *Oryza brachyantha* | mixed-linked glucan synthase 2 | XM_015839192.1 |
| *Sorghum bicolor* | mixed-linked glucan synthase 3 | XM_021452426.1 |
| *Oryza sativa Japonica* | mixed-linked glucan synthase 1 | XM_015789553.2 |
| *Oryza sativa* | cellulose synthase-like protein OsCslF1 | AF432502.1 |
| *Sorghum bicolor* | mixed-linked glucan synthase 9 | XM_021452834.1 |
| *Avena sativa* | cellulose synthase-like DslF9 | MG544000.1 |
| *Aegilops tauschii* | mixed-linked glucan synthase 6 | XM_020331793.1 |
| *Triticum aestivum* | CslF6 mRNA | KP260638.1 |
| *Avena sativa* | CslF6 mRNA | KP260640.1 |
| *Oryza sativa Japonica* | mixed-linked glucan synthase 6 | XM_015794846.2 |
| *Oryza sativa Indica* | chromosome 8 sequence | CP018164.1 |
| *Oryza sativa Japonica* | chromosome 8 sequence | AP014964.1 |
| *Oryza sativa Indica* | chromosome 8 sequence | CP012616.1 |
| *Oryza sativa* | CslF6 mRNA | KP260643.1 |
| *Oryza sativa Indica* | cDNA | CT832977.1 |
| *Oryza sativa Japonica* | chromosome 8 sequence | AP005504.3 |
| *Oryza sativa Japonica* | cDNA | AK106763.1 |
| *Oryza sativa Japonica* | cDNA | AK065259.1 |
| *Oryza sativa Japonica* | chromosome 8 sequence | AP004635.3 |
| *Avena sativa* | cellulose synthase-like CslF6 | MG543998.1 |
| *Avena sativa* | cellulose synthase-like protein | GQ379900.1 |
| *Brachypodium distachyon* | mixed-linked glucan synthase 6 | XM_003573406.4 |
| *Brachypodium distachyon* | CslF6 mRNA | KP260637.1 |
| *Triticum aestivum* | mRNA | AK447706.1 |
| *Setaria italica* | cellulose synthase-like protein D3 | XM_022827744.1 |
| *Sorghum bicolor* | cellulose synthase-like protein D3 | XM_002444124.2 |
| *Panicum hallii* | mixed-linked glucan synthase 6 | XM_025964637.1 |
| *Panicum hallii* | cellulose synthase-like protein D3 | XM_025966560.1 |
| *Oryza brachyantha* | mixed-linked glucan synthase 6 | XM_006659795.2 |
| *Setaria italica* | mixed-linked glucan synthase 6 | XM_004972717.4 |
| *Oryza sativa Japonica* | cellulose synthase-like protein D3 | XM_015793777.2 |
| *Zea mays* | cellulose synthase-like protein D3 | XM_008666514.2 |
| *Oryza sativa* | cellulose synthase-like D3 | BK000093.1 |
| *Oryza sativa Japonica* | chromosome 8 sequence | AP004459.2 |
| *Aegilops tauschii* | cellulose synthase-like protein D3 | XM_020332159.1 |

TABLE 5-continued

| (1→3),(1→4)-β-Glucan Synthase Genes | | |
|---|---|---|
| Source Organism | Sequence Description | GI Number |
| *Oryza brachyantha* | cellulose synthase-like protein D3 | XM_006660006.2 |
| *Guillardia theta* | hypothetical protein mRNA | XM_005822290.1 |

Chitin synthase regulatory factor CHR1 is a regulatory factor for chitin synthase and is involved in chitin biosynthesis. In one aspect, the gene that expresses CHR1 or a homolog thereof is isolated from a yeast such as, for example, *Schizosaccharomyces pombe*. In another aspect, the gene that expresses CHR1 or a homolog thereof is isolated from almond, chickpea, gilt-head bream, common grape, peanut, zebrafish, morning glory, red clover, common fruit fly, brown trout, tire track eel, cacao, adzuki bean, common carp, whitefish, Nile tilapia, blue lupin, mouse, *Cannabis saliva*, muskmelon, equlne roundworm, human, rice blast fungus, rove beetle, crab-eating macaque, Southern pig-tailed macaque, bighorn sheep, a cotton species, Indian glassy fish, large yellow croaker, climbing perch, thornfish, peregrine falcon, saker falcon, barber's pole worm, water beetle (*Acillus*), wasp (*Gasteruption*), or threadworm. In another aspect, the gene that expresses CHR1 or a homolog thereof is isolated from a microbial species such as, for example, another *Schizosaccharomyces* species not already mentioned, *Talaromyces pinophilus, Hemiselmis andersenii, Staphylococcus hominis, Trichomonas vaginalis, Buchnera aphidicola, Plasmodium reichenowi*, a *Polaribacter* species, a *Clostridium* species, *Paramecium tetraurelia*, an *Arcobacter* species, *Cyberlindnera fabianii, Methanocaldococcus vulcanis*, a *Candidatus erwinia* species, or a *Neocallimastigales* species. In still another aspect, the gene that expresses CHR1 or a homolog thereof is isolated from a phage, a virus, or a synthetic construct. In a further aspect, the gene that expresses CHR1 has SEQ ID NO. 11 or at least 70% homology thereof, at least 75% homology thereof, at least 80% homology thereof, at least 85% homology thereof, at least 90% homology thereof, or at least 95% homology thereof. In another aspect, the gene that expresses CHR1 has SEQ ID NO. 16 or at least 70% homology thereof, at least 75% homology thereof, at least 80% homology thereof, at least 85% homology thereof, at least 90% homology thereof, or at least 95% homology thereof. In one aspect, the gene that expresses CHR1 can be positioned anywhere in the DNA construct disclosed herein. In a further aspect, the gene that expresses CHR1 is positioned directly before or directly after the gene that expresses chitin synthase.

Other sequences expressing CHR1 or related or homologous genes can be identified in a database such as, for example, GenBank. In one aspect, the gene that expresses CHR1 is isolated from *Schizosaccharomyces pombe* and can be found in GenBank with accession number NM_001022015.2.

In one aspect, sequences useful herein include those with the GI numbers listed in Table 6:

TABLE 6

| CHR1 Genes | | |
|---|---|---|
| Source Organism | Sequence Description | GI Number |
| *Schizosaccharomyces pombe* | putative chitin synthase regulatory factor CHR1 | NM_001022015.2 |
| *Schizosaccharomyces pombe* | chromosome II sequence | CU329671.1 |
| *Schizosaccharomyces octosporus* | CHR1 partial mRNA | XM_013161771.1 |
| *Schizosaccharomyces cryophilus* | CHR1 partial mRNA | XM_013165559.1 |
| *Schizosaccharomyces pombe* | SYF2 family spicing factor | NM_001022016.2 |
| *Vitis vinifera* | genomic DNA | AM476062.2 |
| Edafosvirus species | genomic DNA | MK072072.1 |
| *Arachis hypogaea* | chromosomal DNA | CP030984.1 |
| *Clostridium taeniosporum* | chromosomal DNA | CP017253.2 |
| *Clostridium botulinum* | genomic DNA | CP010521.1 |
| *Clostridium botulinum* | genomic DNA | CP010520.1 |
| *Clostridium botulinum* | genomic DNA | CP001078.1 |
| *Danio rerio* | genomic DNA | BX276105.6 |
| *Ipomoea trifida* | chromosome 4 sequence | CP025647.1 |
| *Talaromyces pinophilus* | chromosome 4 sequence | CP017347.1 |
| *Trifolium pretense* | chr3 | LN846351.1 |
| *Drosophila melanogaster* | chromosome 3 sequence | AE014297.3 |
| *Drosophila melanogaster* | genomic DNA | AC246343.1 |
| *Hemiselmis andersenii* | genomic DNA | CP000882.1 |
| *Drosophila melanogaster* | genomic DNA | CP000207.2 |
| *Staphylococcus hominis* | chromosomal DNA | CP031277.1 |
| *Salmo trutta* | uncharacterized mRNA transcript variant | XR_003877870.1 |
| *Salmo trutta* | uncharacterized mRNA transcript variant | XR_003877869.1 |
| *Salmo trutta* | chromosome 4 DNA | LR584420.1 |
| *Mastacembelus armatus* | chromosome 18 DNA | LR535850.1 |
| *Staphylococcus hominis* | genomic DNA | CP014107.1 |
| *Theobroma cacao* | chromosome I DNA | LT594788.1 |

TABLE 6-continued

| CHR1 Genes | | |
|---|---|---|
| Source Organism | Sequence Description | GI Number |
| *Vigna angularis* | chromosome 6 DNA | AP015039.1 |
| *Cyprinus carpio* | chromosome 7 DNA | LN590677.1 |
| *Trichomonas vaginalis* | hypothetical protein partial mRNA | XM_001302772.1 |
| *Coregonus* sp. “balchen” | chromosome 1 DNA | LR664344.1 |
| *Buchnera aphidicola* | chromosomal DNA | CP034876.1 |
| *Parambassis ranga* | chromosome 14 DNA | LR131964.1 |
| *Larimichthys crocea* | chromosome IX DNA | LT972198.1 |
| *Cyberlindnera fabianii* | genomic DNA | LK052908.1 |
| *Methanocaldococcus vulcanius* | genomic DNA | CP001787.1 |
| Vibrio phage 5 | genomic DNA | MK358448.1 |
| Vibrio phage USC-1 | genomic DNA | MK905543.1 |
| *Candidatus erwinia* species | chromosome 1 DNA | LR217713.1 |
| *Anabas testudineus* | chromosome 18 DNA | LR132042.1 |
| *Cottoperca gobio* | chromosome 18 DNA | LR131925.1 |
| *Larimichthys crocea* | up-regulator of cell proliferation | XM_027287996.1 |
| *Ipomoea triloba* | chromosome 4 DNA | CP025663.1 |
| Eukaryotic synthetic construct | chromosome 18 DNA | CP034496.1 |
| *Medon piceus* | genomic DNA | KX087313.1 |
| *Macaca fascicularis* | histamine receptor H2 | XM_015452258.1 |
| *Ovis canadensis* | chromosome 23 sequence | CP011908.1 |
| *Macaca nemestrina* | histamine receptor H2 | XM_011740119.1 |
| *Cucumis melo* | chromosome 6 DNA | LN713260.1 |
| *Cucumis melo* | chromosome 3 DNA | LN713257.1 |
| *Cucumis melo* | genomic DNA | LN681857.1 |
| *Cucumis melo* | genomic DNA | LN681816.1 |
| *Clostridium botulinum* | chromosomal DNA | FR745875.1 |
| *Clostridium botulinum* | genomic DNA | CP001056.1 |
| *Paramecium tetraurelia* | hypothetical protein partial mRNA | XM_001426786.1 |
| *Homo sapiens* | chromosome 18 DNA | AC091135.9 |
| *Parascaris equorum* | genomic DNA | LM474297.1 |
| *Gossypium tumeri* | chromosomal DNA | CP032577.1 |
| *Sparus aurata* | chromosome 12 DNA | LR537132.1 |
| *Sphaeramia orbicularis* | chromosome 8 DNA | LR597465.1 |
| *Gossypium raimondii* | chromosomal DNA | CP032564.1 |
| *Buchnera aphidicola* | genomic DNA | CP034858.1 |
| *Pyricularia oryzae* | chromosome 6 DNA | CP034209.1 |
| *Ipomoea triloba* | chromosome 7 DNA | CP025666.1 |
| *Arcobacter ellisii* | chromosomal DNA | CP032097.1 |
| *Haemonchus contortus* | chromosome 5 DNA | LS997566.1 |
| *Falco cherrug* | nucleoprotein 2 transcript variant | XM_027807545.1 |
| *Falco cherrug* | nucleoprotein 2 transcript variant | XM_027807544.1 |
| *Falco cherrug* | nucleoprotein 2 transcript variant | XM_027807543.1 |
| *Falco cherrug* | nucleoprotein 2 transcript variant | XM_027807542.1 |
| *Falco peregrinus* | nucleoprotein 2 | XM_027779372.1 |
| *Oreochromis niloticus* | non-compact myelin associated protein | XM_019349126.2 |
| *Plasmodium reichenowi* | chromosome 11 DNA | LT969574.1 |
| *Lupinus angustifolius* | chromosomal DNA | CP023125.1 |
| *Lupinus angustifolius* | chromosomal DNA | CP023117.1 |
| *Lupinus angustifolius* | chromosomal DNA | CP023115.1 |
| *Plasmodium reichenowi* | alpha/beta hydrolase | XM_012908292.2 |
| *Polaribacter* sp. Hell 33 78 | chromosome I DNA | LT629794.1 |
| *Acillus sulcatus* | mitochondrial DNA | KT876878.1 |
| *Bacillus* phage AR9 | genomic DNA | KU878088.1 |
| *Ovis canadensis* | chromosome 8 DNA | CP011893.1 |
| *Gasteruption* sp. M19 | mitochondrial DNA | KJ619460.1 |
| *Strongyloides stercoralis* | genomic DNA | LL999127.1 |
| *Cyprinus carpio* | chromosome 20 DNA | LN590713.1 |
| Neocallimastigales clone | internal transcribed spacer 1 partial sequence | GQ587965.1 |
| *Vitis vinifera* | genomic DNA | AM438193.2 |
| *Paramecium tetraurelia* | hypothetical protein partial mRNA | XM_001449370.1 |
| *Mus musculus* | chromosome 10 DNA | AC118198.7 |
| *Mus musculus* | genomic DNA | AC159327.8 |
| *Danio rerio* | genomic DNA | CR392357.6 |
| *Mus musculus* | genomic DNA | AC153829.7 |
| *Cannabis sativa* | pentatricopeptide repeat-containing protein | XM_030650612.1 |

TABLE 6-continued

| CHR1 Genes | | |
|---|---|---|
| Source Organism | Sequence Description | GI Number |
| *Cannabis sativa* | pentatricopeptide repeat-containing protein | XM_030650611.1 |
| *Arcobacter canalis* | genomic DNA | CP042812.1 |
| *Sparus aurata* | chromosome 23 DNA | LR537143.1 |
| *Arcobacter anaerophilus* | genomic DNA | CP041070.1 |
| *Prunus dulcis* | pseudomolecule Pd04 | AP019300.1 |
| *Cicer arietinum* | chromosomal DNA | CP039334.1 |
| *Ovis canadensis* | chromosome 9 DNA | CP011894.1 |

Transglycosylase is a glycoside hydrolase family enzyme that catalyzes the transformation of one glycoside to another. In one aspect, the gene that expresses transglycosylase is isolated from a yeast such as, for example, *Saccharomyces cerevisiae*. In another aspect, the *S. cerevisiae* is a strain such as, for example, ySR128, Y169, X55, SY14, BY4742, CEN.PK113-7D, S288c, YJM1419, Soil7-1, Sol7-2, BSPX042, ySR127, YGR189c, FLH149013.01X, YJM1479, YJM1338, YJM451, YJM1573, YJM1402, YJM1527, YJM1443, YJM1400, YJM1199, N85, YJM1342, YPS128, YJM1434, YJM1389, YJM195, YJM1202, YJM1307, UJM1444, YJM555, YJM320, YJM1273, NCIM3186, YJM1592, NCIM3107, KSD-Yc, Y12, YJM1341, YJM1386, YJM470, YJM1388, MARA-Rsf_A10, HCNTHsf_F8, YJM1450, YJM693, HB_C_O-MARUNUI 14, HPRMTsf_H7, YJM428, YJM1190, YJM1385, T16, T8, HB_S_BILANCHER_12, HB_S_GIM-BLETTROAD_22, HB_C_TUKITUKI2_10, WI_S_JASA 5, T78, HB_C_KOROKIPO 12, WA_C_MATES_13, WSERCsf_G4, WSETAwf_B1, NSERVsf_F8, T.52_3A, NSEBRsf_A9, T.52_2H, HB_C_TUKITUKI2_4, HB_S_GIMBLETTROAD_16, HB_S-BILANCHER_6, HB_C_OMARUNUI_7, T52, HB_C_OMARUNUI_6, WA_C_CODDINGTON_2, WA_C_MATES_10, HB_S_GIMBLETTROAD_5, HCNKIsf_G7, HB_S_GIM-BLETTROAD 9, TNPLST-4-S-2, HCNTHsf_C5, HPR-MAwf_D10, T63, WA_C_KINGSMILL_10, WI_S_JASA_13, HB_C_KOROKIPO_3, WI_C_MBSP_15, WI_C_MBSP_4, MTKSKsf E2, WI_S_OAKURA_4, HB_C_TUIKITUKI1_16, T.52_5A, WI_C_MB95MBMZ_4, CDRDR_sf_H, WA_C_WAITAK-EREROAD 7, HB_S_GIMBLETTROAD 14, CRIRIwf_A11, or another *S. cerevisiae* strain. In a further aspect, the gene that expresses transglycosylase has SEQ ID NO. 12 or at least 70% homology thereof, at least 75% homology thereof, at least 80% homology thereof, at least 85% homology thereof, at least 90% homology thereof, or at least 95% homology thereof. In another aspect, the gene that expresses transgosylase has SEQ ID NO. 15 or at least 70% homology thereof, at least 75% homology thereof, at least 80% homology thereof, at least 85% homology thereof, at least 90% homology thereof, or at least 95% homology thereof. In one aspect, the gene that expresses transglycosylase can be positioned anywhere in the DNA construct disclosed herein.

Other sequences expressing transglycosylase or related or homologous genes can be identified in a database such as, for example, GenBank. In one aspect, the gene that expresses CHR1 is isolated from *Saccharomyces cerevisiae* and can be found in GenBank with accession number NM_001181318.1. In an alternative aspect, the gene that expresses transglycosylase is isolated from *Saccharomyces cerevisiae* and can be found in GenBank with accession number CP008344.1.

In one aspect, sequences useful herein include those with the GI numbers listed in Table 7:

TABLE 7

| Transglycosylase Genes | | |
|---|---|---|
| Source Organism | Sequence Description | GI Number |
| *Saccharomyces cerevisiae* | chromosome 7 sequence | CP036485.1 |
| *Saccharomyces cerevisiae* | chromosome 7 sequence | CP033477.1 |
| *Saccharomyces cerevisiae* | chromosome 7 sequence | CP033494.1 |
| *Saccharomyces cerevisiae* | chromosome 1 sequence | CP029160.1 |
| *Saccharomyces cerevisiae* | chromosome 7 sequence | CP026294.1 |
| *Saccharomyces cerevisiae* | chromosome 7 sequence | CP022972.1 |
| *Saccharomyces cerevisiae* | chromosome 7 sequence | CP020129.1 |
| *Saccharomyces cerevisiae* | chromosome 7 sequence | CP005266.2 |
| *Saccharomyces cerevisiae* | chromosome 7 sequence | CP008021.1 |
| *Saccharomyces cerevisiae* | chromosome 7 sequence | CP007868.1 |
| *Saccharomyces cerevisiae* | chromosome 7 sequence | CP014738.1 |
| *Saccharomyces cerevisiae* | chromosome 7 sequence | CP011553.1 |
| *Saccharomyces cerevisiae* | chromosome 7 sequence | BK006941.2 |
| *Saccharomyces cerevisiae* | transglycosylase | NM_001181318.1 |
| *Saccharomyces cerevisiae* | chromosome 7 sequence | X99074.1 |
| *Saccharomyces cerevisiae* | chromosome 7 sequence | Z72974.1 |
| *Saccharomyces cerevisiae* | transglycosylase | DQ331860.1 |
| *Saccharomyces cerevisiae* | chromosome 7 sequence | CP005278.2 |
| *Saccharomyces cerevisiae* | chromosome 7 sequence | CP005247.2 |
| *Saccharomyces cerevisiae* | chromosome 7 sequence | CP005205.2 |
| *Saccharomyces cerevisiae* | chromosome 7 sequence | CP005282.2 |
| *Saccharomyces cerevisiae* | chromosome 7 sequence | CP005262.2 |
| *Saccharomyces cerevisiae* | chromosome 7 sequence | CP005280.2 |

TABLE 7-continued

| Transglycosylase Genes | | |
|---|---|---|
| Source Organism | Sequence Description | GI Number |
| *Saccharomyces cerevisiae* | chromosome 7 sequence | CP005270.2 |
| *Saccharomyces cerevisiae* | chromosome 7 sequence | CP005260.2 |
| *Saccharomyces cerevisiae* | chromosome 7 sequence | CP005232.2 |
| *Saccharomyces cerevisiae* | chromosome 7 sequence | LN907790.1 |
| *Saccharomyces cerevisiae* | chromosome 7 sequence | CP005249.1 |
| *Saccharomyces cerevisiae* | chromosome 7 sequence | CP020214.1 |
| *Saccharomyces cerevisiae* | chromosome 7 sequence | CP005268.2 |
| *Saccharomyces cerevisiae* | chromosome 7 sequence | CP005258.2 |
| *Saccharomyces cerevisiae* | chromosome 7 sequence | CP005196.2 |
| *Saccharomyces cerevisiae* | chromosome 7 sequence | CP005233.2 |
| *Saccharomyces cerevisiae* | chromosome 7 sequence | CP005242.2 |
| *Saccharomyces cerevisiae* | chromosome 7 sequence | CP005271.2 |
| *Saccharomyces cerevisiae* | chromosome 7 sequence | CP005211.2 |
| *Saccharomyces cerevisiae* | chromosome 7 sequence | CP005201.2 |
| *Saccharomyces cerevisiae* | chromosome 7 sequence | CP005240.2 |
| *Saccharomyces cerevisiae* | chromosome 7 sequence | CP011816.1 |
| *Saccharomyces cerevisiae* | chromosome 7 sequence | CP005284.1 |
| *Saccharomyces cerevisiae* | chromosome 7 sequence | CP009948.1 |
| *Saccharomyces cerevisiae* | chromosome 7 sequence | CP024001.1 |
| *Saccharomyces cerevisiae* | chromosome 7 sequence | CP020197.1 |
| *Saccharomyces cerevisiae* | chromosome 7 sequence | CP005248.2 |
| *Saccharomyces cerevisiae* | chromosome 7 sequence | CP005255.2 |
| *Saccharomyces cerevisiae* | chromosome 7 sequence | CP005208.2 |
| *Saccharomyces cerevisiae* | chromosome 7 sequence | CP005257.2 |
| *Saccharomyces cerevisiae* | chromosome 7 sequence | CP008140.1 |
| *Saccharomyces cerevisiae* | chromosome 7 sequence | CP007936.1 |
| *Saccharomyces cerevisiae* | chromosome 7 sequence | CP005273.2 |
| *Saccharomyces cerevisiae* | chromosome 7 sequence | CP005217.2 |
| *Saccharomyces cerevisiae* | chromosome 7 sequence | CP008446.1 |
| *Saccharomyces cerevisiae* | chromosome 7 sequence | CP008157.1 |
| *Saccharomyces cerevisiae* | chromosome 7 sequence | CP005203.2 |
| *Saccharomyces cerevisiae* | chromosome 7 sequence | CP005231.2 |
| *Saccharomyces cerevisiae* | chromosome 7 sequence | CP005254.1 |
| *Saccharomyces cerevisiae* | chromosome 7 sequence | CP008293.1 |
| *Saccharomyces cerevisiae* | chromosome 7 sequence | CP008225.1 |
| *Saccharomyces cerevisiae* | chromosome 7 sequence | CP008378.1 |
| *Saccharomyces cerevisiae* | chromosome 7 sequence | CP008344.1 |
| *Saccharomyces cerevisiae* | chromosome 7 sequence | CP008480.1 |
| *Saccharomyces cerevisiae* | chromosome 7 sequence | CP008582.1 |
| *Saccharomyces cerevisiae* | chromosome 7 sequence | CP008208.1 |
| *Saccharomyces cerevisiae* | chromosome 7 sequence | CP008684.1 |
| *Saccharomyces cerevisiae* | chromosome 7 sequence | CP008089.1 |
| *Saccharomyces cerevisiae* | chromosome 7 sequence | CP008072.1 |
| *Saccharomyces cerevisiae* | chromosome 7 sequence | CP007953.1 |
| *Saccharomyces cerevisiae* | chromosome 7 sequence | CP007902.1 |
| *Saccharomyces cerevisiae* | chromosome 7 sequence | CP007834.1 |
| *Saccharomyces cerevisiae* | chromosome 7 sequence | CP008106.1 |
| *Saccharomyces cerevisiae* | chromosome 7 sequence | CP007851.1 |
| *Saccharomyces cerevisiae* | chromosome 7 sequence | CP007885.1 |
| *Saccharomyces cerevisiae* | chromosome 7 sequence | CP008242.1 |
| *Saccharomyces cerevisiae* | chromosome 7 sequence | CP008276.1 |
| *Saccharomyces cerevisiae* | chromosome 7 sequence | CP008412.1 |
| *Saccharomyces cerevisiae* | chromosome 7 sequence | CP008497.1 |
| *Saccharomyces cerevisiae* | chromosome 7 sequence | CP008429.1 |
| *Saccharomyces cerevisiae* | chromosome 7 sequence | CP008633.1 |
| *Saccharomyces cerevisiae* | chromosome 7 sequence | CP008599.1 |
| *Saccharomyces cerevisiae* | chromosome 7 sequence | CP008191.1 |
| *Saccharomyces cerevisiae* | chromosome 7 sequence | CP008174.1 |
| *Saccharomyces cerevisiae* | chromosome 7 sequence | CP008055.1 |
| *Saccharomyces cerevisiae* | chromosome 7 sequence | CP008038.1 |
| *Saccharomyces cerevisiae* | chromosome 7 sequence | CP007970.1 |
| *Saccharomyces cerevisiae* | chromosome 7 sequence | CP007919.1 |
| *Saccharomyces cerevisiae* | chromosome 7 sequence | CP008310.1 |
| *Saccharomyces cerevisiae* | chromosome 7 sequence | CP008616.1 |
| *Saccharomyces cerevisiae* | chromosome 7 sequence | CP008361.1 |
| *Saccharomyces cerevisiae* | chromosome 7 sequence | CP008463.1 |
| *Saccharomyces cerevisiae* | chromosome 7 sequence | CP008531.1 |
| *Saccharomyces cerevisiae* | chromosome 7 sequence | CP008514.1 |
| *Saccharomyces cerevisiae* | chromosome 7 sequence | CP008123.1 |
| *Saccharomyces cerevisiae* | chromosome 7 sequence | CP008327.1 |
| *Saccharomyces cerevisiae* | chromosome 7 sequence | CP008395.1 |
| *Saccharomyces cerevisiae* | chromosome 7 sequence | CP008667.1 |
| *Saccharomyces cerevisiae* | chromosome 7 sequence | CP008548.1 |
| *Saccharomyces cerevisiae* | chromosome 7 sequence | CP008004.1 |

TABLE 7-continued

| Transglycosylase Genes | | |
|---|---|---|
| Source Organism | Sequence Description | GI Number |
| *Saccharomyces cerevisiae* | chromosome 7 sequence | CP008565.1 |
| *Saccharomyces cerevisiae* | chromosome 7 sequence | CP008259.1 |
| *Saccharomyces cerevisiae* | chromosome 7 sequence | CP007987.1 |

In one aspect, the DNA constructs disclosed herein optionally include a gene that expresses dehydrogenase. The gene that expresses hydrogenase can be positioned before or after any of the genetic components used to produce the constructs described herein. In another aspect, a dehydrogenase catalyzes the removal of hydrogen atoms from a particular molecule, including, but not limited to, molecules involved in the electron transport chain reactions of cellular respiration or in anaerobic and other non-standard energy-generation metabolisms, particularly in conjunction with coenzymes such as, for example, nicotinamide adenine dinucleotide (NAD), flavin adenine dinucleotide (FAD), or flavin mononucleotide (FMN). In a further aspect, dehydrogenases are classified as oxidoreductases. In some aspects, the dehydrogenases disclosed herein are quinoproteins that use pyrrolo-quinoline quinone (also known as methoxatin) as a redox cofactor. In a further aspect, the dehydrogenases disclosed herein can stimulate bacterial growth. In a still further aspect, a dehydrogenase oxidizes its substrate by transferring a hydrogen to an electron acceptor.

In one aspect, the gene that expresses dehydrogenase is isolated from a bacterium such as, for example, *Acidithiobacillus ferrooxidans* or another *Acidithiobacillus* species. In another aspect, the bacterium can be a *Chloroflexi* species, a *Dehalococcoidia* species, a *Microbispora* species, a *Spirochaetes* species, an *Acidobacteria* species, a *Deltaproteobacteria* species, an *Ardenticatena* species, an *Anaerolina* species, an *Arthospira* species, a *Methanothermobacter* species, or another bacterium. In another aspect, the gene that expresses dehydrogenase is isolated from an archaeon. In a further aspect, the archaeon is a *Halorubrum* species, a *Natronorubrum* species, a *Natronobacterium* species, a *Natronolimnobius* species, a *Halopiger* species, a *Thermoplasmata* species, a *Bathyarchaeota* species, a *Halorhabdus* species, a *Halonotius* species, a *Methanolinea* species, a *Thermococcus* species, a *Hadesarchaea* species, a *Halostella* species, a *Salinarchaeum* species, or another archaeon. In one aspect, the bacterium or archaeon is an extremophile such as an acidophile, halophile, or thermophile, or a combination thereof. In another aspect, the bacterium or archaeon is autotrophic (such as, for example, a cyanobacterium) or has a non-standard metabolism such as, for example, a methanogenic, organohalide respiration, a sulfate- and/or sulfur-reducing metabolism, or the like. In a further aspect, the gene that expresses dehydrogenase produces a protein that has SEQ ID NO. 13 or at least 70% homology thereto, at least 75% homology thereto, at least 80% homology thereto, at least 85% homology thereto, at least 90% homology thereto, at least 95% homology thereto, or at least 99% homology thereto.

Other sequences expressing dehydrogenase or related or homologous sequences can be identified in a database such as, for example, GenBank. In one aspect, the gene that expresses dehydrogenase is isolated from *A. ferrooxidans* and the dehydrogenase protein can be identified in the GenBank database by the GI number RBM01490.1. In one aspect, sequences useful herein include those with the GI numbers listed in Table 8:

TABLE 8

| Dehydrogenase Genes | | |
|---|---|---|
| Source Organism | Sequence Description | GI Number |
| *Acidithiobacillus ferrooxidans* | Pyrrolo-quinoline quinone binding-like beta-propeller repeat protein | WP_113526602.1 |
| *Acidithiobacillus ferridurans* | Pyrrolo-quinoline quinone binding-like beta-propeller repeat protein | WP_126604264.1 |
| *Acidithiobacillus ferrooxidans* | Pyrrolo-quinoline quinone binding-like beta-propeller repeat protein | WP_012537081.1 |
| *Acidithiobacillus* sp. GGI-221 | Pyrrolo-quinoline quinone enzyme repeat domain protein | EGQ62845.1 |
| *Chloroflexi bacterium* | Pyrrolo-quinoline quinone (quinoprotein) | TME01430.1 |
| *Chloroflexi bacterium* | Pyrrolo-quinoline quinone (quinoprotein) | TMC20498.1 |
| *Ktedonobacter* sp. 13_1_20CM_4_53_11 | Hypothetical protein | OLE05215.1 |
| *Chloroflexi bacterium* | Pyrrolo-quinoline quinone | TMB88389.1 |
| *Dictyobacter kobayashii* | Pyrrolo-quinoline quinone binding-like beta-propeller repeat protein | WP_126554454.1 |
| *Chloroflexi bacterium* | Pyrrolo-quinoline quinone (quinoprotein) | TMF49748.1 |
| *Candidatus Bathyarchaeota archaeon* | Pyrrolo-quinoline quinone binding-like beta-propeller repeat protein | WP_116594670.1 |

TABLE 8-continued

| Dehydrogenase Genes | | |
|---|---|---|
| Source Organism | Sequence Description | GI Number |
| *Chloroflexi bacterium* | Pyrrolo-quinoline quinone (quinoprotein) | TMC92340.1 |
| *Chloroflexi bacterium* | Pyrrolo-quinoline quinone (quinoprotein) | TMC88966.1 |
| *Cyanobacteria bacterium* 13_1_40CM_2_61_4 | Hypothetical protein | OLE29789.1 |
| *Streptomyces* sp. LaPpAH-108 | Pyrrolo-quinoline quinone binding-like beta-propeller repeat protein | WP_018546935.1 |
| *Nonomuraea* sp. CH32 | Pyrrolo-quinoline quinone binding-like beta-propeller repeat protein | WP_132612293.1 |
| *Candidatus Bathyarchaeota archaeon* | Pyrrolo-quinoline quinone binding-like beta-propeller repeat protein | WP_119818840.1 |
| *Thermococci archaeon* | Serine/threonine protein kinase | RLF96159.1 |
| *Chloroflexi bacterium* | Protein kinase | RLC80707.1 |
| *Halorhabdus rudnickae* | Pyrrolo-quinoline quinone binding-like beta-propeller repeat protein | WP_135665469.1 |
| *Halonotius* sp. J07HN4 | WD40 repeat protein | ERH07843.1 |
| *Methanolinea tarda* | Pyrrolo-quinoline quinone binding-like beta-propeller repeat protein | WP_084559896.1 |
| *Spirosoma pollinicola* | Pyrrolo-quinoline quinone binding-like beta-propeller repeat protein | WP_100986943.1 |
| *Bacteriodetes bacterium* | Hypothetical protein | RUA29684.1 |
| *Methanoregulaceae archaeon* PtaB.Bin009 | Outer membrane biogenesis protein BamB | OPX66753.1 |
| *Dehalococcoidia bacterium* SM23_28_2 | Hypothetical protein | KPK47637.1 |
| *Microbispora* sp. CSR-4 | Pyrrolo-quinoline quinone binding-like beta-propeller repeat protein | WP_147943314.1 |
| *Salinarchaeum* sp. Harcht-Bsk1 | Pyrrolo-quinoline quinone binding-like beta-propeller repeat protein | WP_081638694.1 |
| *Salinarchaeum* sp. Harcht-Bsk1 | Pyrrolo-quinoline quinone | AGN01927.1 |
| *Spirochaetes bacterium* GWF1_49_6 | Hypothetical protein | OHD58634.1 |
| *Ktedonobacter* sp. 13_2_20CM_53_11 | Hypothetical protein | OLB38658.1 |
| *Euryarchaeota archaeon* RBG_13_31_8 | Hypothetical protein | OGS40133.1 |
| *Candidatus Bathyarchaeota archaeon* | Pyrrolo-quinoline quinone binding-like beta-propeller repeat protein | WP_116594637.1 |
| *Chloroflexi bacterium* | Pyrrolo-quinoline quinone (quinoprotein) | TMC41243.1 |
| *Halonotius* sp. F9-27 | Pyrrolo-quinoline quinone binding-like beta-propeller repeat protein | WP_142444077.1 |
| *Bacteriodetes bacterium* | Serine/threonine protein kinase | RLD44544.1 |
| *Halophilic archaeon* J07HX64 | WD40 repeat protein | ERH08977.1 |
| *Ktedonobacter racemifer* | Pyrrolo-quinoline quinone binding-like beta-propeller repeat protein | WP_007918006.1 |
| *Euryarchaeota archaeon* | Hypothetical protein | RMF91487.1 |
| *Dictyobacter alpinus* | Pyrrolo-quinoline quinone binding-like beta-propeller repeat protein | WP_126625726.1 |
| *Spirosoma* sp. HMF3257 | Pyrrolo-quinoline quinone like beta-propeller repeat protein | WP_111347059.1 |
| *Chloroflexi bacterium* | TPA protein kinase | HBY98375.1 |
| *Halonotius* sp. F13-13 | Pyrrolo-quinoline quinone binding-like beta-propeller repeat protein | WP_120102800.1 |
| *Bacteriodetes bacterium* 4572_112 | Serine/threonine protein kinase | OYT12356.1 |
| *Chloroflexi bacterium* B3 Chlor | Protein kinase | TKJ31615.1 |
| *Methanoregulaceae archaeon* PtaB.Bin108 | Outer membrane biogenesis protein BamB | OPX73454.1 |

TABLE 8-continued

| Dehydrogenase Genes | | |
|---|---|---|
| Source Organism | Sequence Description | GI Number |
| *Chloroflexi bacterium* | Serine/threonine protein kinase | TMD26707.1 |
| *Halorubrum lipolyticum* DSM 21995 | Pyrrolo-quinoline quinone | EMA58759.1 |
| *Acidobacteria bacterium* | Hypothetical protein | PYX04504.1 |
| *Bacteriodetes bacterium* | Hypothetical protein | RLD67800.1 |
| *Thermoplasmata archaeon* | TP A hypothetical protein | DAC72728.1 |
| *Chloroflexi bacterium* | Hypothetical protein | TME01351.1 |
| *Natronorubrum bangense* | Pyrrolo-quinoline quinone binding-like beta-propeller repeat protein | WP_006065827.1 |
| *Natronobacterium texcoconense* | Pyrrolo-quinoline quinone binding-like beta-propeller repeat protein | WP_090386185.1 |
| *Deltaproteobacteria bacterium* RBG_19FT_COMBO_58_16 | Hypothetical protein | OGQ06516.1 |
| *Chloroflexi bacterium* | Protein kinase | RLC69094.1 |
| *Halorubrum lipolyticum* | Pyrrolo-quinoline quinone binding-like beta-propeller repeat protein | WP_082230144.1 |
| *Ardenticatenia bacterium* | Protein kinase | PWH16755.1 |
| *Halorubrum* sp. T3 | Pyrrolo-quinoline quinone like beta-propeller repeat protein | WP_082224198.1 |
| *Methanoregulaceae archaeon* PtaB.Bin108 | Outer membrane biogenesis protein BamB | OPX68859.1 |
| *Natronorubrum bangense* | Pyrrolo-quinoline quinone binding-like beta-propeller repeat protein | WP_136350941.1 |
| *Anaerolinea bacterium* SM23_63 | protein kinase | KPK95498.1 |
| *Streptomyces viridochromogenes* | Pyrrolo-quinoline quinone binding-like beta-propeller repeat protein | WP_053084635.1 |
| *Halostella* sp. DL-M4 | Pyrrolo-quinoline quinone binding-like beta-propeller repeat protein | WP_138798004.1 |
| *Chloroflexi bacterium* | TPA: pyrrolo-quinoline quinone | HAL61700.1 |
| *Halobacteriaceae bacterium* SHR40 | Pyrrolo-quinoline quinone binding-like beta-propeller repeat protein | WP_128226427.1 |
| *Natronolimnobius* sp. XQ-INN 246 | Pyrrolo-quinoline quinone binding-like beta-propeller repeat protein | WP_141465618.1 |
| *Armatimonadetes bacterium* CG07_land_8_20_14_0_80_40_9 | Hypothetical protein | PIU68144.1 |
| *Spirosoma* sp. TY50 | Pyrrolo-quinoline quinone binding-like beta-propeller repeat protein | WP_129601008.1 |
| *Haloarcula* sp. Atlit-7R | Pyrrolo-quinoline quinone binding-like beta-propeller repeat protein | WP_121513686.1 |
| *Methanoregulaceae archaeon* PtaB.Bin108 | Outer membrane biogenesis protein BamB | OPX68846.1 |
| *Ktedonobacter racemifer* | Pyrrolo-quinoline quinone binding-like beta-propeller repeat protein | WP_007921914.1 |
| *Candidatus Promineofilum breve* | Serine/threonine protein kinase | WP_095043790.1 |
| *Natrarchaeobius chitinivorans* | Pyrrolo-quinoline quinone binding-like beta-propeller repeat protein | WP_124193682.1 |
| *Haloarcula* (multiple species) | Pyrrolo-quinoline quinone binding-like beta-propeller repeat protein | WP_079980887.1 |
| *Arthospira* sp. PLM2.Bin9 | Hypothetical protein | TVU55373.1 |
| *Spirosoma* sp. 209 | Pyrrolo-quinoline quinone binding-like beta-propeller repeat protein | WP_077920679.1 |
| *Anaerolineales bacterium* | Pyrrolo-quinoline quinone (quinoprotein) | TEU15797.1 |
| *Halopenitus persicus* | Pyrrolo-quinoline quinone binding-like beta-propeller repeat protein | WP_092735151.1 |

TABLE 8-continued

| Dehydrogenase Genes | | |
|---|---|---|
| Source Organism | Sequence Description | GI Number |
| *Runella limosa* | Pyrrolo-quinoline quinone binding-like beta-propeller repeat protein | WP_051397871.1 |
| *Natronobacterium texcoconense* | Pyrrolo-quinoline quinone binding-like beta-propeller repeat protein | WP_090386230.1 |
| *Halorubrum* sp. Atlit_26R | Pyrrolo-quinoline quinone binding-like beta-propeller repeat protein | WP_121595873.1 |
| *Halobacteriales archaeon* SW_7_65_23 | Pyrrolo-quinoline quinone (quinoprotein) | PSQ50321.1 |
| *Methanoregulaceae archaeon* PtaB.Bin056 | Outer membrane biogenesis protein BamB | OPX67114.1 |
| *Halopiger djelfimassiliensis* | Pyrrolo-quinoline quinone binding-like beta-propeller repeat protein | WP_049921122.1 |
| *Anaerolineales bacterium* | Hypothetical protein | TEU11756.1 |
| *Chloroflexi bacterium* | Serine/threonine protein kinase | TMC21583.1 |
| *Halomicrobium zhouii* | Pyrrolo-quinoline quinone binding-like beta-propeller repeat protein | WP_089812696.1 |
| *Bacterium* HR22 | DNA damage responsive serine/threonine protein kinase | GBD09898.1 |
| *Euhalothece natronophila* | Pyrrolo-quinoline quinone binding-like beta-propeller repeat protein | WP_146297369.1 |
| *Arthrospira platensis* | Pyrrolo-quinoline quinone binding-like beta-propeller repeat protein | WP_051659755.1 |
| *Hadesarchaea archaeon* B3 Hades | Hypothetical protein | TKJ25118.1 |
| *Natronobacterium gregoryi* | Pyrrolo-quinoline quinone binding-like beta-propeller repeat protein | WP_005579994.1 |
| SAR202 cluster *bacterium* Io17_Chloro-G4 | Hypothetical protein | PKB68728.1 |
| *Spirochaetes bacterium* GFW1_51_8 | Hypothetical protein | OHD57547.1 |
| *Halobacteriaceae bacterium* SHR40 | Pyrrolo-quinoline quinone binding-like beta-propeller repeat protein | WP_128224037.1 |
| *Arthrospira platensis* | Pyrrolo-quinoline quinone binding-like beta-propeller repeat protein | WP_014277203.1 |
| *Methanothermobacter marburgensis* str. Marburg | Conserved hypothetical protein | ADL57678.1 |
| *Methanothermobacter marburgensis* | Pyrrolo-quinoline quinone binding-like beta-propeller repeat protein | WP_148215518.1 |
| *Halofilum ochraceum* | Pyrrolo-quinoline quinone binding-like beta-propeller repeat protein | WP_083330933.1 |

In one aspect, the DNA construct has the following genetic components: a) a gene that expresses chitin synthase, b) a gene that expresses chitosanase, and c) a gene that expresses chitin deacetylase.

In an alternative aspect, the DNA construct has the following genetic components: a) a gene that expresses lipase, b) a gene that expresses chitin synthase, c) a gene that expresses chitosanase, and d) a gene that expresses chitin deacetylase.

In still another aspect, the DNA construct has the following genetic components: a) optionally, a gene that expresses lipase, b) a gene that expresses chitin synthase, c) a gene that expresses chitosanase, d) a gene that expresses chitin deacetylase, e) optionally, a gene that expresses CHR1 regulatory sequence, f) optionally, a gene that expresses transglycosylase, and g) optionally, a gene that expresses dehydrogenase.

In still another aspect, the DNA construct has the following genetic components: a) a gene that expresses lipase, b) a gene that expresses chitin synthase, c) a gene that expresses chitosanase, d) a gene that expresses chitin deacetylase, and e) a gene that expresses (1→3),(1→4)-β-glucan synthase.

In still another aspect, the DNA construct has the following genetic components: a) a gene that expresses chitin synthase, b) a gene that expresses chitosanase, c) a gene that expresses chitin deacetylase, d) a gene that expresses (1→3),(1→4)-β-glucan synthase, e) a gene that expresses CHR1 regulatory sequence, and f) a gene that expresses transglycosylase.

In still another aspect, the DNA construct has the following genetic components: a) a gene that expresses chitin synthase, b) a gene that expresses chitosanase, c) a gene that expresses chitin deacetylase, d) a gene that expresses (1→3),(1→4)-β-glucan synthase, e) a gene that expresses CHR1 regulatory sequence, f) a gene that expresses transglycosylase, and g) a gene that expresses dehydrogenase.

In still another aspect, the DNA construct has the following genetic components: a) a gene that expresses chitin synthase, b) a gene that expresses chitosanase, c) a gene that expresses chitin deacetylase, and d) a gene that expresses (1→3),(1→4)-β-glucan synthase.

In still another aspect, the supplemental DNA construct has the following genetic components: a) a gene that expresses transglycosylase and b) a gene that expresses chitin synthase regulatory factor CHR1.

In another aspect, said construct further includes a) a promoter, b) a terminator or stop sequence, c) a gene that confers resistance to an antibiotic (a "selective marker"), d) a reporter protein, or a combination thereof.

In one aspect, the construct includes a regulatory sequence. In a further aspect, the regulatory sequence is already incorporated into a vector such as, for example, a plasmid, prior to genetic manipulation of the vector. In another aspect, the regulatory sequence can be incorporated into the vector through the use of restriction enzymes or any other technique known in the art.

In one aspect, the regulatory sequence is an operon such as, for example, the LAC operon. As used herein, an "operon" is a segment of DNA containing a group of genes wherein the group is controlled by a single promoter. Genes included in an operon are all transcribed together. In a further aspect, the operon is a LAC operon and can be induced when lactose crosses the cell membrane of the biological device.

In one aspect, the regulatory sequence is a promoter. The term "promoter" refers to a DNA sequence capable of controlling the expression of a coding sequence. In another aspect, the coding sequence to be controlled is located 3' to the promoter. In still another aspect, the promoter is derived from a native gene. In an alternative aspect, the promoter is composed of multiple elements derived from different genes and/or promoters. A promoter can be assembled from elements found in nature, from artificial and/or synthetic elements, or from a combination thereof. It is understood by those skilled in the art that different promoters can direct the expression of a gene in different tissues or cell types, at different stages of development, in response to different environmental or physiological conditions, and/or in different species. In one aspect, the promoter functions as a switch to activate the expression of a gene.

In one aspect, the promoter is "constitutive." A constitutive promoter is a promoter that causes a gene to be expressed in most cell types at most times. In another aspect, the promoter is "regulated." A regulated promoter is a promoter that becomes active in response to a specific stimulus. A promoter may be regulated chemically, such as, for example, in response to the presence or absence of a particular metabolite (e.g., lactose or tryptophan), a metal ion, a molecule secreted by a pathogen, or the like. A promoter also may be regulated physically, such as, for example, in response to heat, cold, water stress, salt stress, oxygen concentration, illumination, wounding, or the like.

Promoters that are useful to drive expression of the nucleotide sequences described herein are numerous and familiar to those skilled in the art. Suitable promoters include, but are not limited to, the following: T3 promoter, T7 promoter, an iron promoter, and GAL1 promoter. In a further aspect, the promoter is a native part of the vector used herein. Variants of these promoters are also contemplated. The skilled artisan will be able to use site-directed mutagenesis and/or other mutagenesis techniques to modify the promoters to promote more efficient function. The promoter may be positioned, for example, from 10-100 nucleotides from a ribosomal binding site. In another aspect, the promoter is positioned before the gene that expresses lipase (when used), chitin synthase, the gene that expresses chitosanase, the gene that expresses chitin deacetylase, the gene that expresses the CHR1 regulatory element (when used), the gene that expresses transglycosylase (when used), or any combination thereof.

In one aspect, the promoter is a GAL1 promoter. In another aspect, the GAL1 promoter is native to the plasmid used to create the vector. In another aspect, a GAL1 promoter is positioned before the gene that expresses chitin synthase, the gene that expresses chitosanase, the gene that expresses chitin deacetylase, the gene that expresses lipase (when used), the gene that expresses the CHR1 regulatory element (when used), the gene that expresses transglycosylase (when used), or any combination thereof. In another aspect, the promoter is a GAL1 promoter obtained from or native to the pYES2 plasmid.

In another aspect, the promoter is a T7 promoter. In a further aspect, the T7 promoter is native to the plasmid used to create the vector. In still another aspect, the GAL1 promoter is positioned before any or all of the genes in the construct, or is positioned before the LAC operon. In yet another aspect, the promoter is a T7 promoter obtained from or native to the pETDuet-1 plasmid.

In another aspect, the regulatory sequence is a terminator or stop sequence. As used herein, a terminator is a sequence of DNA that marks the end of a gene or operon to be transcribed. In a further aspect, the terminator is an intrinsic terminator or a Rho-dependent transcription terminator. As used herein, an intrinsic terminator is a sequence wherein a hairpin structure can form in the nascent transcript that disrupts the mRNA/DNA/RNA polymerase complex. As used herein, a Rho-dependent transcription terminator requires a Rho factor protein complex to disrupt the mRNA/DNA/RNA polymerase complex. In one aspect, the terminator is a T7 terminator. In an alternative aspect, the terminator is a CYC1 terminator obtained from or native to the pYES2 plasmid.

In a further aspect, the regulatory sequence includes both a promoter and a terminator or stop sequence. In a still further aspect, the regulatory sequence can include multiple promoters or terminators. Other regulatory elements, such as enhancers, are also contemplated. Enhancers may be located from about 1 to about 2000 nucleotides in the 5' direction from the start codon of the DNA to be transcribed, or may be located 3' to the DNA to be transcribed. Enhancers may be "cis-acting," that is, located on the same molecule of DNA as the gene whose expression they affect.

In another aspect, the vector contains one or more ribosomal binding sites. As used herein, a "ribosomal binding site" is a sequence of nucleotides located 5' to the start codon of an mRNA that recruits a ribosome to initiate protein translation. In one aspect, the ribosomal binding site can be positioned before one or more or of all genes in the DNA construct, or a before a subset of genes in a DNA construct.

In one aspect, when the vector is a plasmid, the plasmid can also contain a multiple cloning site or polylinker. In a further aspect, the polylinker contains recognition sites for multiple restriction enzymes. The polylinker can contain up to 2, 3, 4, 5, 6, 7, 8, 9, 10, 11, 12, 13, 14, 15, 16, 17, 18, 19, 20, or more than 20 recognition sites for restriction enzymes. Further, restriction sites may be added, disabled, or removed as required, using techniques known in the art. In one aspect, the plasmid contains restriction sites for any known restriction enzyme such as, for example, HindIII, KpnI, SacI, BamHI, BstXI, EcoRI, BasBI, NotI, XhoI, XphI, XbaI, ApaI, SalI, ClaI, EcoRV, PstI, SmaI, XmaI, SpeI, EagI, SacII, or any combination thereof. In a further aspect, the plasmid contains more than one recognition site for the same restriction enzyme.

In one aspect, the restriction enzyme can cleave DNA at a palindromic or an asymmetrical restriction site. In a further aspect, the restriction enzyme cleaves DNA to leave blunt ends; in an alternative aspect, the restriction enzyme cleaves DNA to leave "sticky" or overhanging ends. In another aspect, the enzyme can cleave DNA at a distance of from 20 bases to over 1000 bases away from the restriction site. A variety of restriction enzymes are commercially available and their recognition sequences, as well as instructions for use (e.g., amount of DNA needed, precise volumes of reagents, purification techniques, as well as information about salt concentration, pH, optimum temperature, incubation time, and the like) are provided by enzyme manufacturers.

In one aspect, a plasmid with a polylinker containing one or more restriction sites can be digested with one restriction enzyme and a nucleotide sequence of interest can be ligated into the plasmid using a commercially-available DNA ligase enzyme. Several such enzymes are available, often as kits containing all reagents and instructions required for use. In another aspect, a plasmid with a polylinker containing two or more restriction sites can be simultaneously digested with two restriction enzymes and a nucleotide sequence of interest can be ligated into the plasmid using a DNA ligase enzyme. Using two restriction enzymes provides an asymmetric cut in the DNA, allowing for insertion of a nucleotide sequence of interest in a particular direction and/or on a particular strand of the double-stranded plasmid. Since RNA synthesis from a DNA template proceeds from 5' to 3', usually starting just after a promoter, the order and direction of elements inserted into a plasmid can be especially important. If a plasmid is to be simultaneously digested with multiple restriction enzymes, these enzymes must be compatible in terms of buffer, salt concentration, and other incubation parameters.

In some aspects, prior to ligation using a ligase enzyme, a plasmid that has been digested with a restriction enzyme is treated with an alkaline phosphatase enzyme to remove 5' terminal phosphate groups. This prevents self-ligation of the plasmid and thus facilitates ligation of heterologous nucleotide fragments into the plasmid.

In one aspect, different genes can be ligated into a plasmid in one pot. In this aspect, the genes will first be digested with restriction enzymes. In certain aspects, the digestion of genes with restriction enzymes provides multiple pairs of matching 5' and 3' overhangs that will spontaneously assemble the genes in the desired order. In another aspect, the genes and components to be incorporated into a plasmid can be assembled into a single insert sequence prior to insertion into the plasmid. In a further aspect, a DNA ligase enzyme can be used to assist in the ligation process.

In another aspect, the ligation mix may be incubated in an electromagnetic chamber. In one aspect, the incubation lasts for about 1 minute, about 2 minutes, about 5 minutes, about 10 minutes, about 15 minutes, about 20 minutes, about 30 minutes, or about 1 hour.

The DNA construct described herein can be part of a vector. In general, plasmid vectors containing replicon and control sequences that are derived from species compatible with the host cell are used in connection with the hosts. The vector ordinarily carries a replication site as well as marking sequences that are capable of performing phenotypic selection in transformed cells. Plasmid vectors are well known and commercially available. Such vectors include, but are not limited to, pWLneo, pSV2cat, pOG44, pXT1, pSG, pSVK3, pBSK, pYES, pYES2, pBSKII, pUC, pUC19, and pETDuet-1 vectors.

Plasmids are double-stranded, autonomously-replicating, genetic elements that are not integrated into host cell chromosomes. Further, these genetic elements are usually not part of the host cell's central metabolism. In bacteria, plasmids may range from 1 kilobase (kb) to over 200 kb. Plasmids can be engineered to encode a number of useful traits including the production of secondary metabolites, antibiotic resistance, the production of useful proteins, degradation of complex molecules and/or environmental toxins, and others. Plasmids have been the subject of much research in the field of genetic engineering, as plasmids are convenient expression vectors for foreign DNA in, for example, microorganisms. Plasmids generally contain regulatory elements such as promoters and terminators and also usually have independent replication origins. Ideally, plasmids will be present in multiple copier per host cell and will contain selectable markers (such as genes for antibiotic resistance) to show the skilled artisan to select host eels that have been successfully transfected with the plasmids (for example, by growing the host cells in a medium containing the antibiotic).

In one aspect, the vector encodes a selection marker. In a further aspect, the selection marker is a gene that confers resistance to an antibiotic. In certain aspects, during fermentation of host cells transformed with the vector, the cells are contacted with the antibiotic. For example, the antibiotic may be included in the culture medium. Cells that have not been successfully transformed cannot survive in the presence of the antibiotic; only cells containing the vector, which confers antibiotic resistance, can survive. Optimally, only cells containing the vector to be expressed will be cultured, as this will result in the highest production efficiency of the desired gene products (e.g., peptides). Cells that do not contain the vector would otherwise compete with transformed cells for resources. In one aspect, the antibiotic is tetracycline, neomycin, kanamycin, ampicillin, hygromycin, chloramphenicol, amphotericin B, bacitracin, carbapenem, cephalosporin, ethambutol, fluoroquinolones, isoniazid, methicillin, oxacillin, vancomycin, streptomycin, quinolines, rifampin, rifampicin, sulfonamides, cephalothin, erythromycin, streptomycin, gentamycin, penicillin, other commonly-used antibiotics, or a combination thereof.

In certain aspects, the DNA construct can include a gene that expresses a reporter protein. The selection of the reporter protein can vary. For example, the reporter protein can be a yellow fluorescent protein, a red fluorescent protein, a green fluorescent protein, or a cyan fluorescent protein. In one aspect, the reporter protein is a yellow fluorescent protein and the gene that expresses the reporter protein has SEQ ID NO. 5 or at least 70% homology thereto. The amount of fluorescence that is produced can be correlated to the amount of DNA incorporated into the transfected cells. The fluorescence produced can be detected and quantified using techniques known in the art. For example, spectrofluorometers are typically used to measure fluorescence.

The DNA construct described herein can be part of a vector. In one aspect, the vector is a plasmid, a phagemid, a cosmid, a yeast artificial chromosome, a bacterial artificial chromosome, a virus, a phage, or a transposon.

Exemplary methods for producing the DNA constructs described herein are provided in the Examples. Restriction enzymes and purification techniques known in the art can be used to assemble the DNA constructs. Backbone plasmids and synthetic inserts can be mixed together for ligation purposes at different ratios ranging from 1:1, 1:2, 1:3, 1:4, and up to 1:5. In one aspect, the ratio of backbone plasmid to synthetic insert is 1:4. After the vector including the DNA construct has been produced, the resulting vector can be incorporated into the host cells using the methods described below.

In one aspect the construct includes from 5' to 3' the following genetic components in the following order: (1) a gene that expresses chitin synthase, (2) a gene that expresses chitosanase, and (3) a gene that expresses chitin deacetylase.

In one aspect the construct includes from 5' to 3' the following genetic components in the following order: a gene that expresses chitin synthase having SEQ ID NO. 2 or at least 70% homology thereto, a gene that expresses chitosanase having SEQ ID NO. 3 or at least 70% homology thereto, and a gene that expresses chitin deacetylase having SEQ ID NO. 4 or at least 70% homology thereto.

In another aspect the construct includes from 5' to 3' the following genetic components in the following order: (1) a GAL1 promoter, (2) a gene that expresses chitin synthase, (3) a CYC1 terminator, (4) a GAL1 promoter, (5) a gene that expresses chitosanase, (6) a CYC1 terminator, (7) a GAL1 promoter, (8) a gene that expresses chitin deacetylase, and (9) a CYC1 terminator.

In another aspect the construct includes from 5' to 3' the following genetic components in the following order: a GAL1 promoter, a gene that expresses chitin synthase having SEQ ID NO. 2 or at least 90% homology thereto, a GAL1 promoter, a gene that expresses chitosanase having SEQ ID NO. 3 or at least 90% homology thereto, a GAL1 promoter, and a gene that expresses chitin deacetylase having SEQ ID NO. 4 or at least 90% homology thereto.

In another aspect, the construct is a pYES2 plasmid having from 5' to 3' the following genetic components in the following order: a) a gene that expresses chitin synthase having SEQ ID NO. 2 or at least 70% homology thereto, b) a CYC1 terminator, c) a GAL1 promoter, d) a gene that expresses chitosanase having SEQ ID NO. 3 or at least 70% homology thereto, e) a CYC1 terminator, f) a GAL1 promoter, g) a gene that expresses chitin deacetylase having SEQ ID NO. 4 or at least 70% homology thereto, h) a CYC1 terminator, i) a GAL1 promoter, and j) a yellow fluorescent reporter protein having SEQ ID NO. 5 or at least 70% homology thereto. In another aspect, the construct is a pYES2 plasmid having SEQ ID NO. 7 or at least 70% homology thereto, at least 75% homology thereto, at least 80% homology thereto, at least 85% homology thereto, at least 90% homology thereto, or at least 95% homology thereto.

In another aspect the construct includes from 5' to 3' the following genetic components in the following order: (1) a gene that expresses lipase, (2) a gene that expresses chitin synthase, (3) a gene that expresses chitosanase, and (4) a gene that expresses chitin deacetylase.

In one aspect the construct includes from 5' to 3' the following genetic components in the following order: (1) a gene that expresses lipase having SEQ ID NO. 1 or at least 70% homology thereto, (2) a gene that expresses chitin synthase having SEQ ID NO. 2 or at least 70% homology thereto, (3) a gene that expresses chitosanase having SEQ ID NO. 3 or at least 70% homology thereto, and (4) a gene that expresses chitin deacetylase having SEQ ID NO. 4 or at least 70% homology thereto.

In one aspect the construct includes from 5' to 3' the following genetic components in the following order: a gene that expresses chitin synthase having SEQ ID NO. 2 or at least 90% homology thereto, a gene that expresses chitosanase having SEQ ID NO. 3 or at least 90% homology thereto, and a gene that expresses chitin deacetylase having SEQ ID NO. 4 or at least 90% homology thereto.

In one aspect the construct includes from 5' to 3' the following genetic components in the following order: a gene that expresses lipase having SEQ ID NO. 1 or at least 90% homology thereto, a gene that expresses chitin synthase having SEQ ID NO. 2 or at least 90% homology thereto, a gene that expresses chitosanase having SEQ ID NO. 3 or at least 90% homology thereto, and a gene that expresses chitin deacetylase having SEQ ID NO. 4 or at least 90% homology thereto.

In another aspect the construct includes from 5' to 3' the following genetic components in the following order: a gene that expresses lipase having SEQ ID NO. 1 or at least 90% homology thereto, a GAL1 promoter, a gene that expresses chitin synthase having SEQ ID NO. 2 or at least 90% homology thereto, a GAL1 promoter, a gene that expresses chitosanase having SEQ ID NO. 3 or at least 90% homology thereto, a GAL1 promoter, and a gene that expresses chitin deacetylase having SEQ ID NO. 4 or at least 90% homology thereto.

In another aspect the construct includes from 5' to 3' the following genetic components in the following order: (1) a GAL1 promoter, (2) a gene that expresses lipase, (3) a GAL1 promoter, (4) a gene that expresses chitin synthase, (5) a CYC1 terminator, (6) a GAL1 promoter, (7) a gene that expresses chitosanase, (8) a CYC1 terminator, (9) a GAL1 promoter, (10) a gene that expresses chitin deacetylase, and (11) a CYC1 terminator.

In another aspect, the construct is a pYES2 plasmid having from 5' to 3' the following genetic components in the following order: a) a gene that expresses lipase having SEQ ID NO. 1 or at least 70% homology thereto, b) a CYC1 terminator, c) a GAL1 promoter, d) a gene that expresses chitin synthase having SEQ ID NO.2 or at least 70% homology thereto, e) a CYC1 terminator, f) a GAL1 promoter, g) a gene that expresses chitosanase having SEQ ID NO. 3 or at least 70% homology thereto, h) a CYC1 terminator, i) a GAL1 promoter, j) a gene that expresses chitin deacetylase having SEQ ID NO. 4 or at least 70% homology thereto, k) a CYC1 terminator, l) a GAL1 promoter, and m) a yellow fluorescent reporter protein having SEQ ID NO. 5 or at least 70% homology thereto. In one aspect, the construct is a pYES2 plasmid having SEQ ID NO. 8 or at least 70% homology thereto, at least 75% homology thereto, at least 80% homology thereto, at least 85% homology thereto, at least 90% homology thereto, or at least 95% homology thereto.

In another aspect the construct includes from 5' to 3' the following genetic components in the following order: (1) a gene that expresses lipase, (2) a gene that expresses chitosanase, (3) a gene that expresses chitin synthase, and (4) a gene that expresses chitin deacetylase.

In another aspect, the construct includes from 5' to 3' the following genetic components in the following order: (1) a gene that expresses lipase having SEQ ID NO. 1 or at least 70% homology thereto, (2) a gene that expresses chitosanase having SEQ ID NO. 3 or at least 70% homology thereto, (3) a gene that expresses chitin synthase having SEQ ID NO. 2 or at least 70% homology thereto, and (4) a gene that expresses chitin deacetylase having SEQ ID NO. 4 or at least 70% homology thereto.

In another aspect, the construct includes from 5' to 3' the following genetic components in the following order: (1) a ribosomal binding site, (2) a gene that expresses lipase, (3) a ribosomal binding site, (4) a gene that expresses chitosanase, (5) a T7 promoter, (6) a ribosomal binding site, (7) a gene that expresses chitin synthase, (8) a ribosomal binding site, and (9) a gene that expresses chitin deacetylase.

In another aspect, the construct includes from 5' to 3' the following genetic components in the following order: a gene that expresses lipase having SEQ ID NO. 1 or at least 90% homology thereto, a ribosomal binding site, a gene that expresses chitosanase having SEQ ID NO. 3 or at least 90% homology thereto, a T7 promoter, a LAC operon, a ribosomal binding site, a gene that expresses chitin synthase having SEQ ID NO. 2 or at least 90% homology thereto, a ribosomal binding site, and a gene that expresses chitin deacetylase having SEQ ID NO. 4 or at least 90% homology thereto.

In still another aspect, the construct is a pETDuet-1 plasmid having from 5' to 3' the following genetic components in the following order: a gene that expresses lipase having SEQ ID NO. 1 or at least 70% homology thereto, b) a ribosomal binding site, c) a gene that expresses chitosanase having SEQ ID NO. 3 or at least 70% homology thereto, d) a T7 promoter, e) a LAC operon, f) a ribosomal binding site, g) a gene that expresses chitin synthase having SEQ ID NO. 2 or at least 70% homology thereto, h) a ribosomal binding site, and i) a gene that expresses chitin deacetylase having SEQ ID NO. 4 or at least 70% homology thereto. In one aspect, the DNA construct is a pETDuet-1 plasmid having SEQ ID NO. 9 or at least 70% homology thereto, at least 75% homology thereto, at least 80% homology thereto, at least 85% homology thereto, at least 90% homology thereto, or at least 95% homology thereto.

In another aspect the construct includes from 5' to 3' the following genetic components in the following order: (1) a gene that expresses lipase, (2) a gene that expresses chitin synthase, (3) a gene that expresses chitosanase, (4) a gene that expresses chitin deacetylase, and (5) a gene that expresses (1→3),(1→4)-β-glucan synthase.

In another aspect the construct includes from 5' to 3' the following genetic components in the following order: (1) a gene that expresses lipase having SEQ ID NO. 1 or at least 70% homology thereto, (2) a gene that expresses chitin synthase having SEQ ID NO. 2 or at least 70% homology thereto, (3) a gene that expresses chitosanase having SEQ ID NO. 3 or at least 70% homology thereto, (4) a gene that expresses chitin deacetylase having SEQ ID NO. 4 or at least 70% homology thereto, and (5) a gene that expresses (1→3),(1→4)-β-glucan synthase having SEQ ID NO. 6 or at least 70% homology thereto.

In another aspect, the construct includes from 5' to 3' the following genetic components in the following order: (1) a ribosomal binding site, (2) a gene that expresses lipase, (3) a ribosomal binding site, (4) a gene that expresses chitin synthase, (5) a ribosomal binding site, (6) a gene that expresses chitosanase, (7) a ribosomal binding site, (8) a gene that expresses chitin deacetylase, (9) a ribosomal binding site, and (10) a gene that expresses (1→3),(1→4)-β-glucan synthase.

In one aspect, the construct includes from 5' to 3' the following genetic components in the following order: a gene that expresses lipase having SEQ ID NO. 1 or at least 90% homology thereto, a CYC1 terminator, a GAL1 promoter, a gene that expresses chitin synthase having SEQ ID NO. 2 or at least 90% homology thereto, a CYC1 terminator, a GAL1 promoter, a gene that expresses chitosanase having SEQ ID NO. 3 or at least 90% homology thereto, a CYC1 terminator, a GAL1 promoter, a gene that expresses chitin deacetylase having SEQ ID NO. 4 or at least 90% homology thereto, a CYC1 terminator, a GAL1 promoter, and a gene that expresses (1→3),(1→4)-β-glucan synthase having SEQ ID NO. 6 or at least 90% homology thereto.

In still another aspect, the construct is a pYES2 plasmid having from 5' to 3' the following genetic components in the following order: a) a gene that expresses lipase having SEQ ID NO. 1 or at least 70% homology thereto, b) a CYC1 terminator, c) a GAL1 promoter, d) a gene that expresses chitin synthase having SEQ ID NO. 2 or at least 70% homology thereto, e) a CYC1 terminator, f) a GAL1 promoter, g) a gene that expresses chitosanase having SEQ ID NO. 3 or at least 70% homology thereto, h) a CYC1 terminator, i) a GAL1 promoter, j) a gene that expresses chitin deacetylase having SEQ ID NO. 4 or at least 70% homology thereto, k) a CYC1 terminator, l) a GAL1 promoter, and m) a gene that expresses (1→3),(1→4)-β-glucan synthase having SEQ ID NO. 6 or at least 70% homology thereto. In one aspect, the construct is a pYES2 plasmid having SEQ ID NO. 10 or at least 70% homology thereto, at least 75% homology thereto, at least 80% homology thereto, at least 85% homology thereto, at least 90% homology thereto, or at least 95% homology thereto.

In another aspect the construct includes from 5' to 3' the following genetic components in the following order: (1) a gene that expresses chitin synthase, (2) a gene that expresses chitosanase, (3) a gene that expresses chitin deacetylase, and (4) a gene that expresses (1→3),(1→4)-β-glucan synthase.

In another aspect the construct includes from 5' to 3' the following genetic components in the following order: (1) a gene that expresses chitin synthase having SEQ ID NO. 2 or at least 70% homology thereto, (2) a gene that expresses chitosanase having SEQ ID NO. 3 or at least 70% homology thereto, (3) a gene that expresses chitin deacetylase having SEQ ID NO. 4 or at least 70% homology thereto, and (4) a gene that expresses (1→3),(1→4)-β-glucan synthase having SEQ ID NO. 6 or at least 70% homology thereto.

In one aspect, the construct includes from 5' to 3' the following genetic components in the following order: a gene that expresses chitin synthase having SEQ ID NO. 2 or at least 90% homology thereto, a CYC1 terminator, a GAL1 promoter, a gene that expresses chitosanase having SEQ ID NO. 3 or at least 90% homology thereto, a CYC1 terminator, a GAL1 promoter, a gene that expresses chitin deacetylase having SEQ ID NO. 4 or at least 90% homology thereto, a CYC1 terminator, a GAL1 promoter, and a gene that expresses (1→3),(1→4)-β-glucan synthase having SEQ ID NO. 6 or at least 90% homology thereto.

In still another aspect, the construct is a pYES2 plasmid having from 5' to 3' the following genetic components in the following order: a) a gene that expresses chitin synthase having SEQ ID NO. 2 or at least 70% homology thereto, b) a CYC1 terminator, c) a GAL1 promoter, d) a gene that expresses chitosanase having SEQ ID NO. 3 or at least 70% homology thereto, e) a CYC1 terminator, f) a GAL1 promoter, g) a gene that expresses chitin deacetylase having SEQ ID NO. 4 or at least 70% homology thereto, h) a CYC1 terminator, i) a GAL1 promoter, and j) a gene that expresses (1→3),(1→4)-β-glucan synthase having SEQ ID NO. 6 or at least 70% homology thereto. In one aspect, the construct is a pYES2 plasmid having SEQ ID NO. 14 or at least 70% homology thereto, at least 75% homology thereto, at least 80% homology thereto, at least 85% homology thereto, at least 90% homology thereto, or at least 95% homology thereto.

Figure 1B:
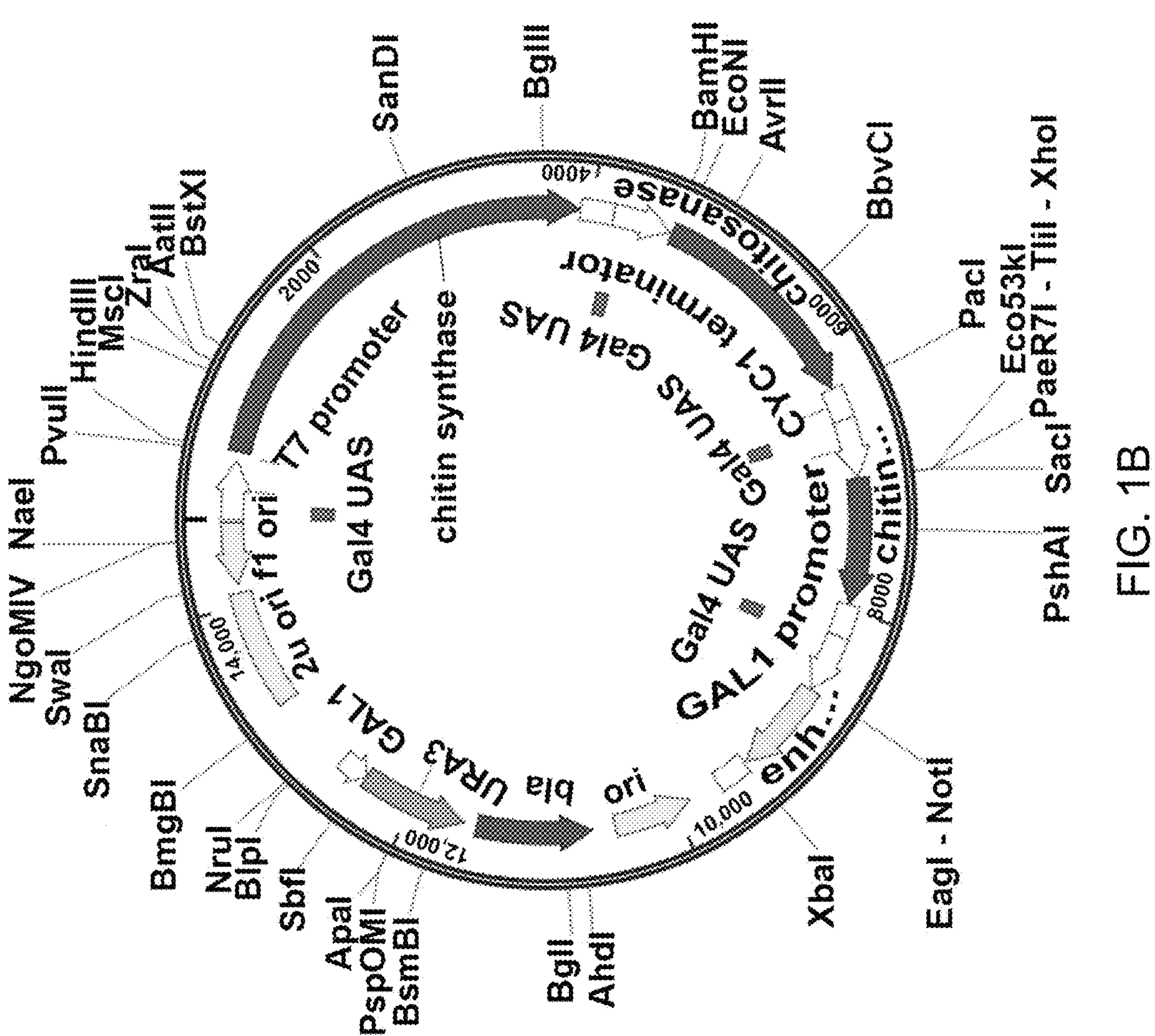
Figure 2A:
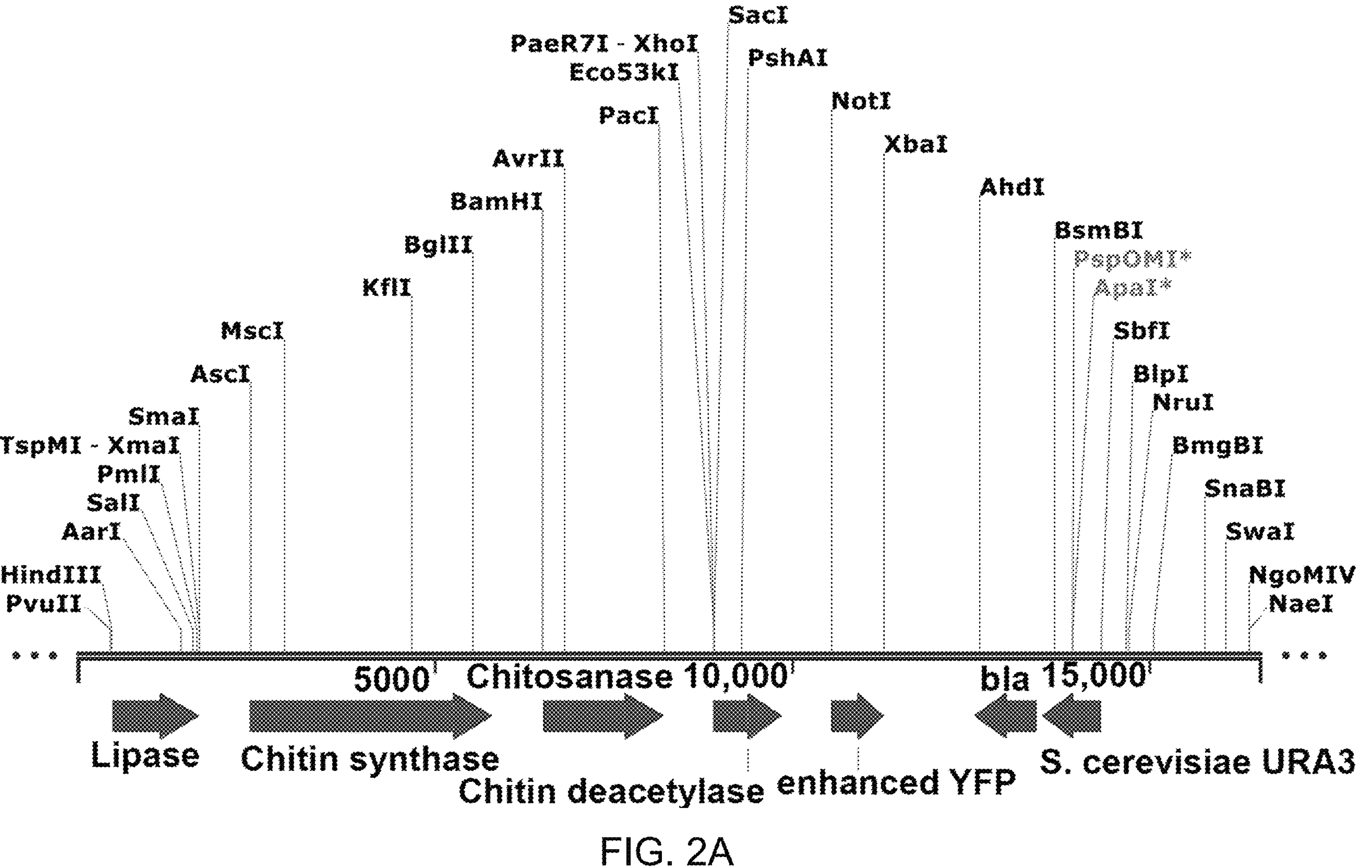
FIGS. 2A and 2B show, respectively, a linear and a circular schematic of a constructed pYES2 plasmid showing the direction, placement, and size of genetic parts of an exemplary DNA device disclosed herein.
Figure 2B:
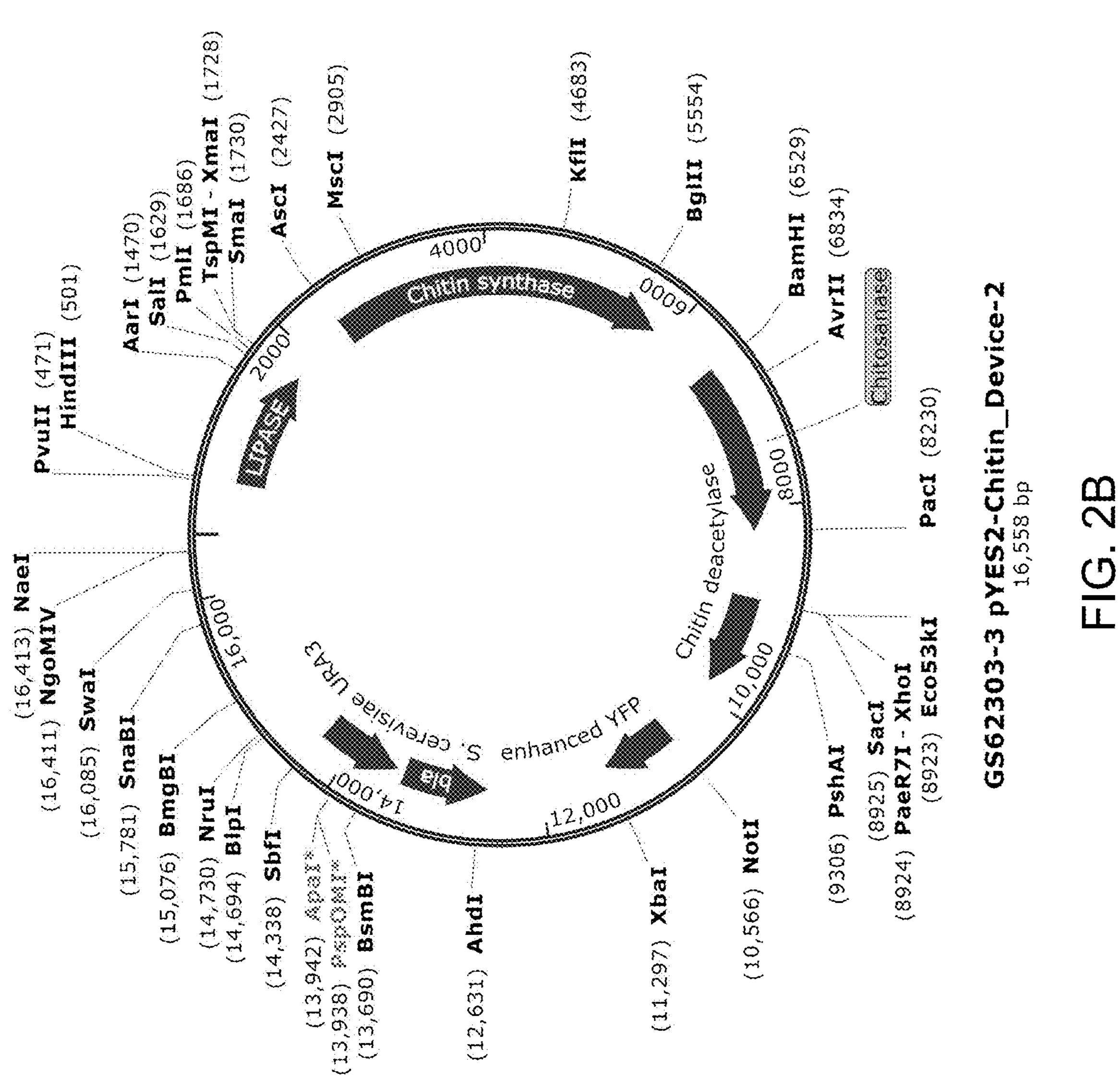
Figure 3A:
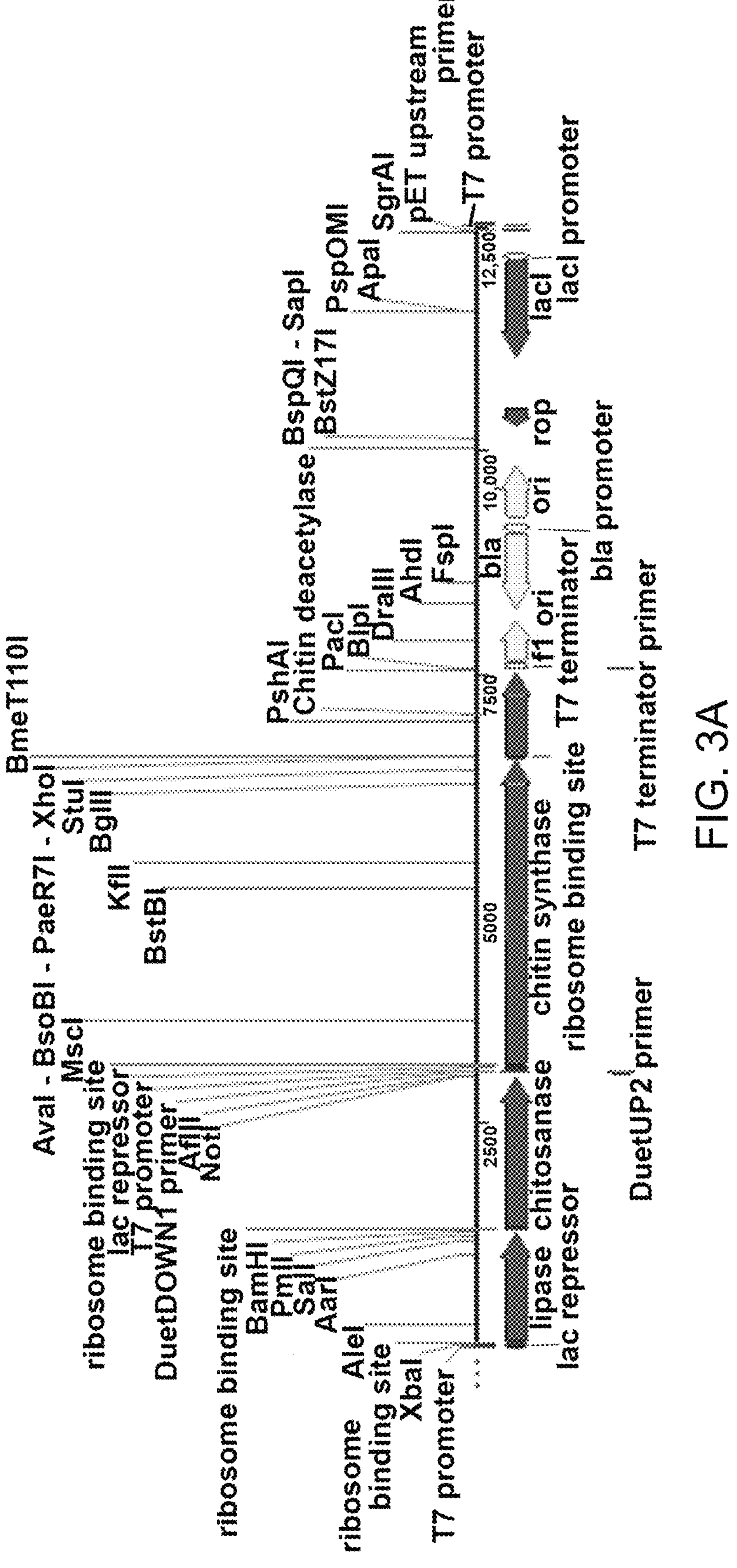
FIGS. 3A and 3B show, respectively, a linear and a circular schematic of a constructed pETDuet-1 plasmid showing the direction, placement, and size of genetic parts of an exemplary DNA device disclosed herein.
Figure 3B:
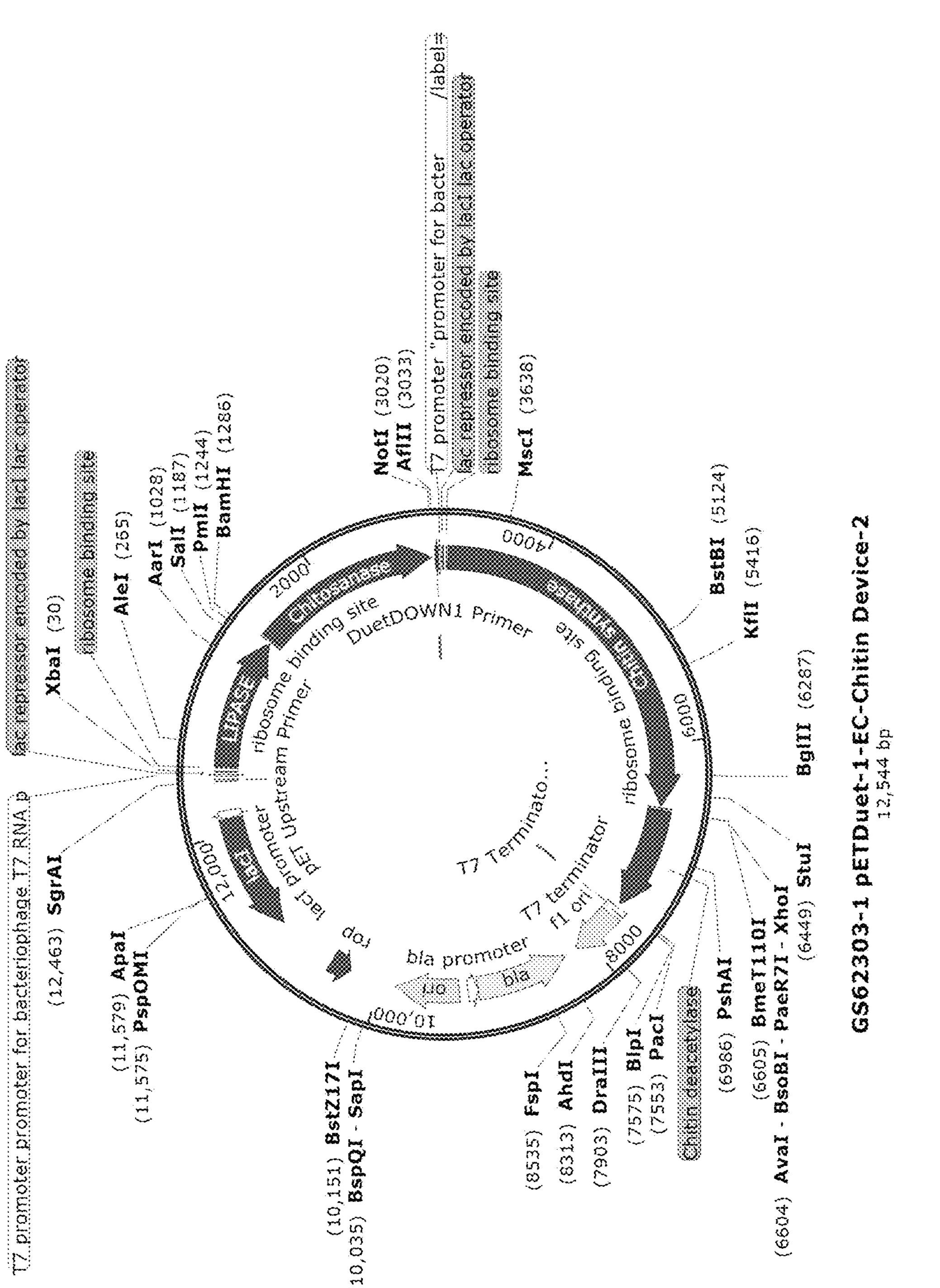
Figure 4A:
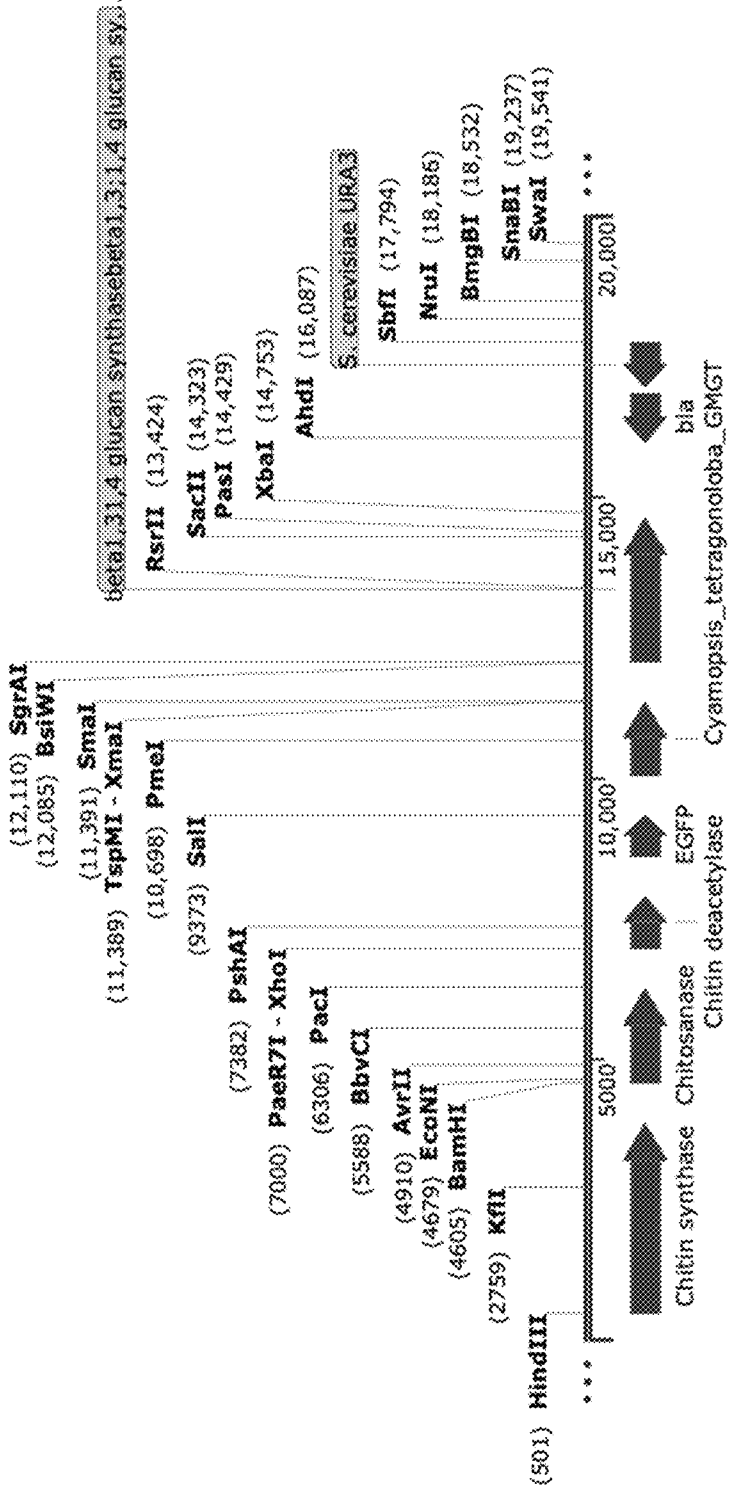
FIGS. 4A and 4B show, respectively, a linear and a circular schematic of a constructed pYES2 plasmid showing the direction, placement, and size of genetic parts of an exemplary DNA device disclosed herein.
Figure 4B:
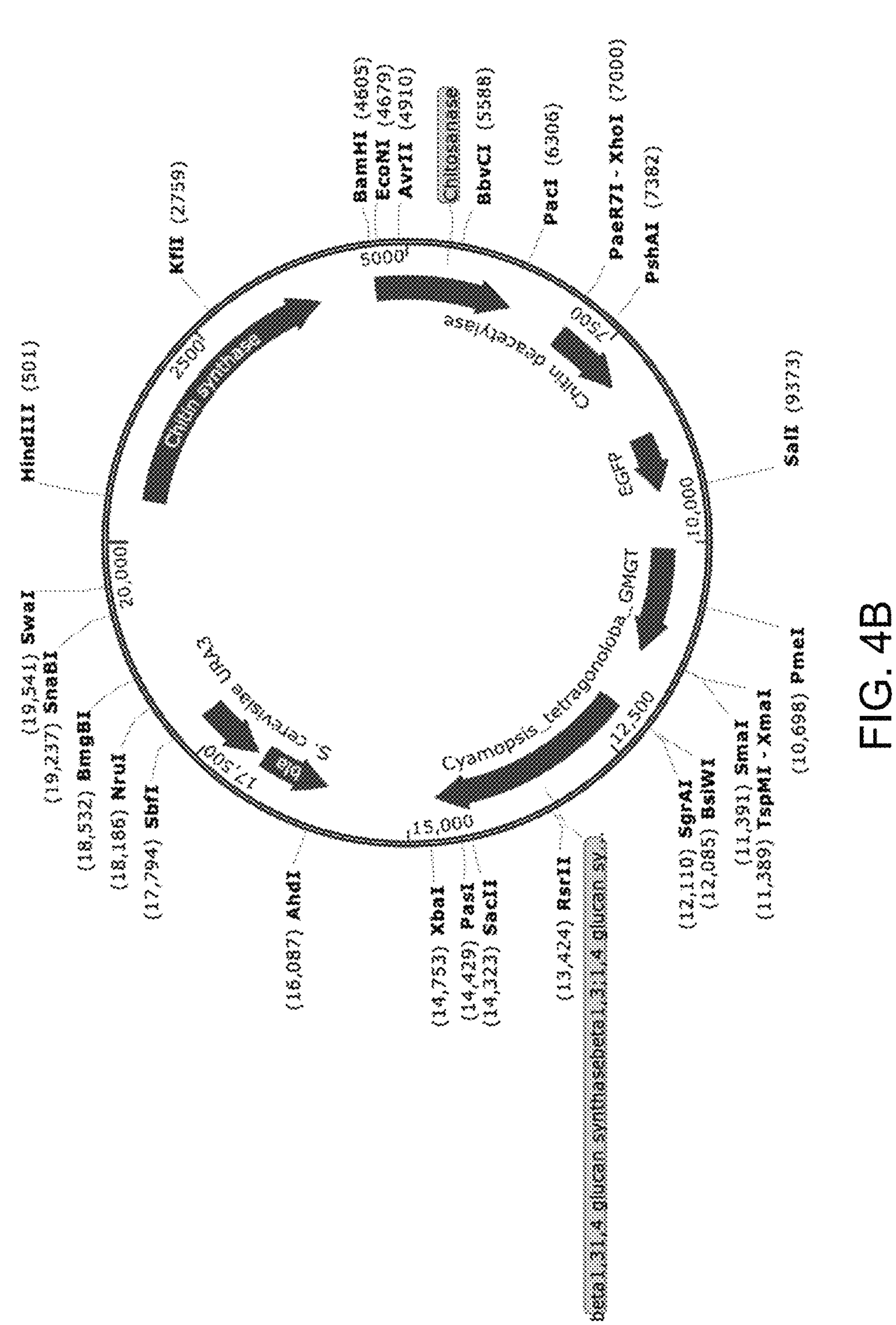
Figure 9A:
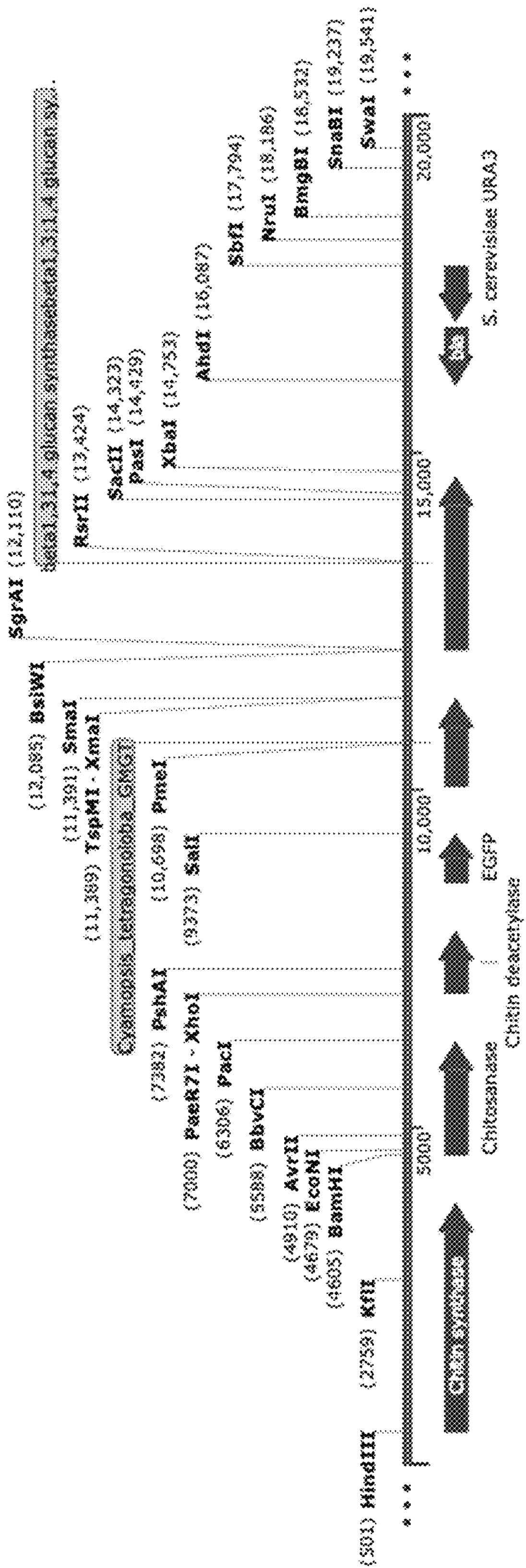
FIGS. 9A and 9B show, respectively, a linear and a circular schematic of a constructed pYES2 plasmid showing the direction, placement, and size of genetic parts of an exemplary DNA device disclosed herein.
Figure 9B:
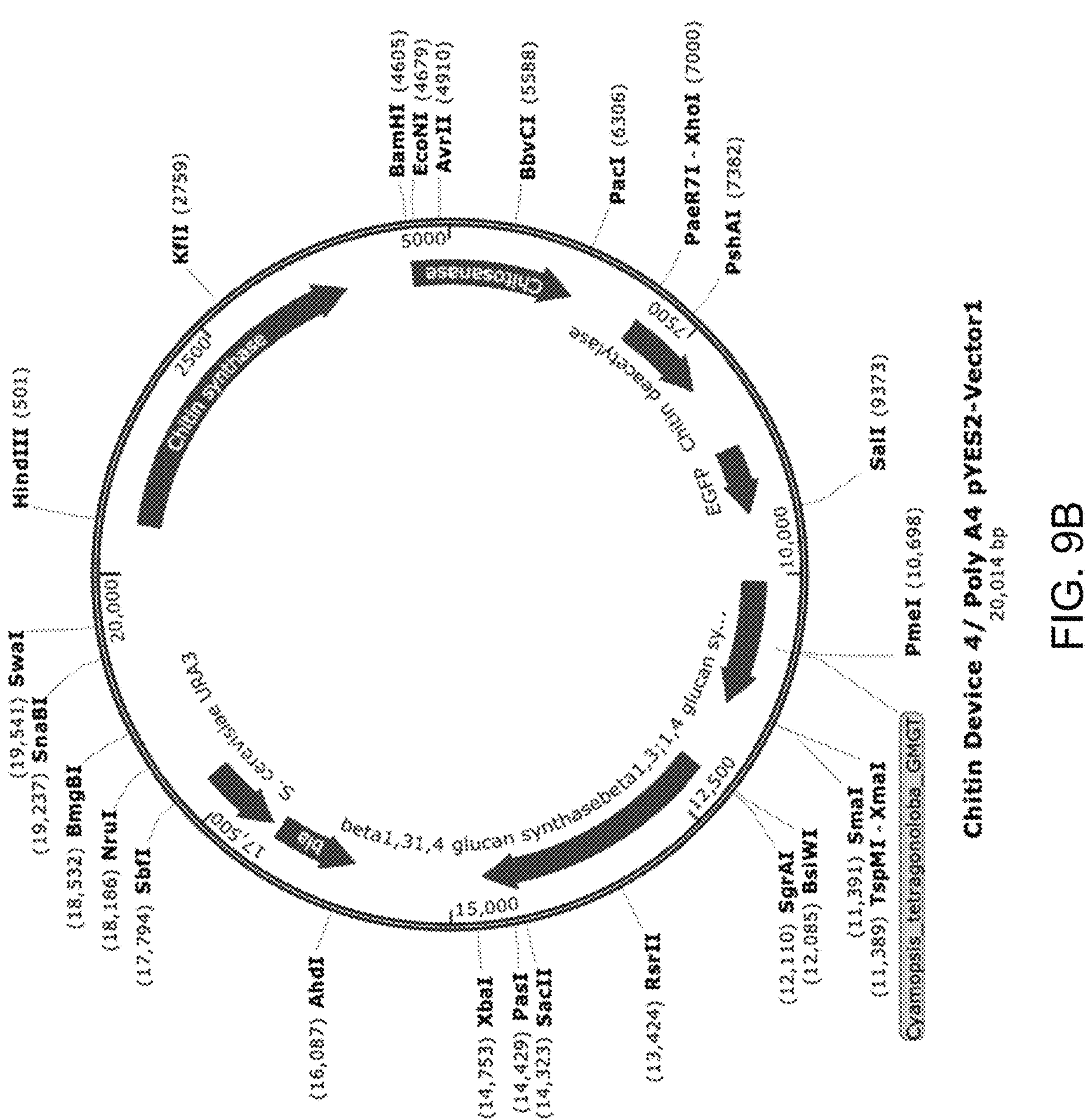

In another aspect, the DNA construct is SEQ ID NO. 7 or at least 90% homology thereof as depicted in FIGS. 1A and 1B. In another aspect, the DNA construct is SEQ ID NO. 8 or at least 90% homology thereof as depicted in FIGS. 2A and 2B. In yet another aspect, the DNA construct is SEQ ID NO. 9 or at least 90% homology thereof as depicted in FIGS. 3A and 3B. In still another aspect, the DNA construct is SEQ ID NO. 10 or at least 90% homology thereof as depicted in FIGS. 4A and 4B. In one aspect, the DNA construct is SEQ ID NO. 14 or at least 90% homology thereof as depicted in FIGS. 9A and 9B.

In some aspects, provided herein is a supplemental DNA construct. In one aspect, the supplemental DNA construct includes from 5' to 3' the following genetic components in the following order: (1) a gene that expresses transglycosylase and (2) a gene that expresses chitin synthase regulatory factor CHR1.

In another aspect the supplemental DNA construct includes from 5' to 3' the following genetic components in the following order: (1) a gene that expresses transglycosylase having SEQ ID NO. 15 or at least 70% homology thereto and (2) a gene that expresses chitin synthase regulatory factor CHR1 having SEQ ID NO. 16 or at least 70% homology thereto.

In one aspect, the supplemental DNA construct includes from 5' to 3' the following genetic components in the following order: a gene that expresses transglycosylase having SEQ ID NO. 15 or at least 90% homology thereto, a CYC1 terminator, a GAL1 promoter, and a gene that expresses chitin synthase regulatory factor CHR1 having SEQ ID NO. 16 or at least 90% homology thereto.

In still another aspect, the supplemental DNA construct is a pYES2 plasmid having from 5' to 3' the following genetic components in the following order: a) a gene that expresses transglycosylase having SEQ ID NO. 15 or at least 70% homology thereto, b) a CYC1 terminator, c) a GAL1 promoter, and d) a gene that expresses chitin synthase regulatory factor CHR1 having SEQ ID NO. 16 or at least 70% homology thereto. In one aspect, the supplemental DNA construct is a pYES2 plasmid having SEQ ID NO. 17 or at least 70% homology thereto, at least 75% homology thereto, at least 80% homology thereto, at least 85% homology thereto, at least 90% homology thereto, or at least 95% homology thereto.

II. Biological Devices

In one aspect, a "biological device" is formed when a microbial cell is transfected with the DNA construct or supplemental DNA construct described herein. The biological devices are generally composed of microbial host cells, where the host cells are transformed with a DNA construct described herein.

In one aspect, the DNA construct is carried by the expression vector into the cell and is separate from the host cell's genome. In another aspect, the DNA construct is incorporated into the host cell's genome. In still another aspect, incorporation of the DNA construct into the host cell enables the host cell to produce a polyactive carbohydrate. "Heterologous" genes and proteins are genes and proteins that have been experimentally inserted into a cell that are not normally expressed by the cell. A heterologous gene may be cloned or derived from a different cell type or species than the recipient cell or organism. Heterologous genes may be introduced into cells by transduction or transformation.

An "isolated" nucleic acid is one that has been separated from other nucleic acid molecules and/or cellular material (peptides, proteins, lipids, saccharides, and the like) normally present in the natural source of the nucleic acid. An "isolated" nucleic acid may optionally be free of the flanking sequences found on either side of the nucleic acid as it naturally occurs. An isolated nucleic acid can be naturally occurring, can be chemically synthesized, or can be a cDNA molecule (i.e., is synthesized from an mRNA template using reverse transcriptase and DNA polymerase enzymes).

"Transformation" or "transfection" as used herein refers to a process for introducing heterologous DNA into a host cell. Transformation can occur under natural conditions or may be induced using various methods known in the art. Many methods for transformation are known in the art and the skilled practitioner will know how to choose the best transformation method based on the type of cells being transformed. Methods for transformation include, for example, viral infection, electroporation, lipofection, chemical transformation, and particle bombardment. Cells may be stably transformed (i.e., the heterologous DNA is capable of replicating as an autonomous plasmid or as part of the host chromosome) or may be transiently transformed (i.e., the heterologous DNA is expressed only for a limited period of time).

"Competent cells" refers to microbial cells capable of taking up heterologous DNA. Competent cells can be purchased from a commercial source, or cells can be made competent using procedures known in the art. Exemplary procedures for producing competent cells are provided in the Examples.

The host cells as referred to herein include their progeny, which are any and all subsequent generations formed by cell division. It is understood that not all progeny may be identical due to deliberate or inadvertent mutations. A host cell may be "transfected" or "transformed," which refers to a process by which an exogenous nucleic acid is transferred or introduced into the host cell.

A transformed cell includes the primary subject cell and its progeny. The host cells can be naturally-occurring cells or "recombinant" cells. Recombinant cells are distinguishable from naturally-occurring cells in that naturally-occurring cells do not contain heterologous DNA introduced through molecular cloning procedures. In one aspect, the host cell is a prokaryotic cell such as, for example, *Escherichia coli*. In other aspects, the host cell is a eukaryotic cell such as, for example, the yeast *Saccharomyces cerevisiae*. Host cells transformed with the DNA construct described herein are referred to as "biological devices."

The DNA construct is first delivered into the host cell. In one aspect, the host cells are naturally competent (i.e., able to take up exogenous DNA from the surrounding environment). In another aspect, cells must be treated to induce artificial competence. This delivery may be accomplished in vitro, using well-developed laboratory procedures for transforming cell lines. Transformation of bacterial cell lines can be achieved using a variety of techniques. One method involves calcium chloride. The exposure to the calcium ions renders the cells able to take up the DNA construct. Another method is electroporation. In this technique, a high-voltage electric field is applied briefly to cells, producing transient holes in the membranes of the cells through which the vector containing the DNA construct enters. Another method involves exposing intact yeast cells to alkali cations such as, for example, lithium. In one aspect, this method includes exposing yeast to lithium acetate, polyethylene glycol, and single-stranded DNA such as, for example, salmon sperm DNA. Without wishing to be bound by theory, the single-stranded DNA is thought to bind to the cell wall of the yeast, thereby blocking plasmids from binding. The plasmids are then free to enter the yeast cell. Enzymatic and/or electromagnetic techniques can also be used alone, or in combination with other methods, to transform microbial cells. Exemplary procedures for transforming yeast and bacteria with specific DNA constructs are provided in the Examples. In certain aspects, two or more types of DNA can be incorporated into the host cells. Thus, different metabolites can be produced from the same host cells at enhanced rates.

In one aspect, a biological device that includes a DNA construct as disclosed herein and a second biological device that includes a supplemental DNA construct as disclosed herein can initially be cultured separately. Further in this aspect, after an initial period of culturing the biological device and second biological device separately, the cultures can be admixed to form a mixed culture. In a still further aspect, co-metabolism of the proteins produced by the DNA construct and the supplemental DNA construct can occur. In a still further aspect, a mixed extract can be prepared according to the procedures disclosed herein and the mixed extract can then be employed in the methods disclosed herein.

III. Preparation of Polyactive Carbohydrates

The biological devices described herein are useful in the production of polyactive carbohydrates. In a further aspect, the polyactive carbohydrates can be applied to plants to enhance the physiological properties of the plants. In a still further aspect, the polyactive carbohydrates increase the production of important plant hormones such as, for example, cytokinins, salicylic acid, auxins, and jasmonic acid. Once the DNA construct has been incorporated into the host cell, the cells are cultured such that the cells multiply. A satisfactory microbiological culture contains available sources of hydrogen donors and acceptors, carbon, nitrogen, sulfur, phosphorus, inorganic salts, and, in certain cases, vitamins or other growth-promoting substances. For example, the addition of peptone provides a readily-available source of nitrogen and carbon. Furthermore, the use of different types of media results in different growth rates and different stationary phase densities; stationary phase is where secondary metabolite production occurs most frequently. A rich media results in a short doubling time and higher cell density at stationary phase. Minimal media results in slow growth and low final cell densities. Efficient agitation and aeration increase final cell densities.

In one aspect, host cells can be cultured or fermented by any method known in the art. The skilled practitioner will be able to select a culture medium based on the species and/or strain of host cell selected. In certain aspects, the culture medium will contain a carbon source. A variety of carbon sources are contemplated, including, but not limited to: monosaccharides such as glucose and fructose, disaccharides such as lactose or sucrose, oligosaccharides, polysaccharides such as starch, or mixtures thereof. Unpurified mixtures extracted from feedstocks are also contemplated and include molasses, barley malt, and related compounds and compositions. Other glycolytic and tricarboxylic acid cycle intermediates are also contemplated as carbon sources, as are one-carbon substrates such as carbon dioxide and/or methanol in the cases of compatible organisms. The carbon source utilized is limited only by the particular organism being cultured.

Culturing or fermenting of host cells can be accomplished by any technique known in the art. In one aspect, batch fermentation can be conducted. In batch fermentation, the composition of the culture medium is set at the beginning and the system is closed to future alterations. In some aspects, a limited form of batch fermentation may be carried out, wherein factors such as oxygen concentration and pH are manipulated, but additional carbon is not added. Continuous fermentation methods are also contemplated. In continuous fermentation, equal amounts of a defined medium are continuously added to and removed from a bioreactor. In other aspects, microbial host cells are immobilized on a substrate. Fermentation may be carried out on any scale and may include methods in which literal "fermentation" is carried out as well as other culture methods that are non-fermentative.

In one aspect, the method involves growing the biological devices described herein for a sufficient time to produce a polyactive carbohydrate. The ordinary artisan will be able to choose a culture medium and optimum culture conditions based on the biological identity of the host cells.

IV. Methods for Increasing the Production of Plant Hormones

Methods for Increasing Root Growth

In one aspect, disclosed herein are methods for increasing root growth of a plant. In one aspect, the methods disclosed herein involve contacting a plant with an extract produced by the biological devices disclosed herein. In a further aspect, the biological devices include host cells transformed with the DNA constructs disclosed herein. In one aspect, the DNA constructs include the following genetic components: (a) a gene that expresses chitin synthase, (b) a gene that expresses chitosanase, and (c) a gene that expresses chitin deacetylase. In one aspect, the extracts produced herein can increase root growth compared to a control (i.e., no extract) by about 50%, about 75%, about 100%, about 150%, about 200%, about 250%, about 300%, about 350%, about 400%, about 450%, about 500%, about 600%, about 650%, or about 700%, where any value can be a lower or upper endpoint of a range (e.g., about 100% to about 300%). In another aspect, the extracts produced herein can increase root strength compared to a control (i.e., no extract) by about 50%, about 75%, about 100%, about 150%, about 200%, about 250%, about 300%, about 350%, about 400%, about 450%, about 500%, about 600%, about 650%, or about 700%, where any value can be a lower or upper endpoint of a range (e.g., about 100% to about 300%) as measured by a tension meter.

In one aspect, increased root growth has numerous advantages. In one aspect, plants with longer roots can access water deeper in the soil and thereby require less watering or irrigation to grow and survive. In another aspect, increased root growth can fortify soil and may help to prevent landslides. In still another aspect, increased root growth can prevent sod, sections of sod, or individual grass plants from being uprooted when exposed to contact with heavy or moving objects such as, for example, swinging golf clubs, balls and mallets for yard games, falling or sliding individuals, shoes and cleats, and the like.

Methods for Increasing the Production of Plant Hormones

In one aspect, the polyactive carbohydrates and biological devices and extracts disclosed herein are useful for promoting the production of plant hormones. In a further aspect, plant hormone concentration correlates with the earlier appearance of roots in plants as well as the plants having roots that are, overall, longer and stronger.

In one aspect, disclosed herein is a method for increasing hormone production in a plant. In a further aspect, the method includes contacting the plant with an extract produced by a biological device as disclosed herein. In a further aspect, the biological devices include host cells transformed with the DNA constructs disclosed herein. In one aspect, the DNA constructs include the following genetic components: (a) a gene that expresses chitin synthase, (b) a gene that expresses chitosanase, and (c) a gene that expresses chitin deacetylase. In another aspect, the DNA constructs can optionally include (d) a gene that expresses lipase, (e) a gene that expresses regulatory sequence CHR1, (f) a gene that expresses transglycosylase, and/or (g) a gene that expresses (1→3),(1→4)-β-glucan synthase. In a further aspect, the plant hormone includes cytokinins, auxins, salicylic acid, jasmonic acid, or any combination thereof.

Without wishing to be bound by theory, the polyactive carbohydrate disclosed herein is thought to relate to its chemical makeup including glucosamine units. In one aspect, it is hypothesized that glucosamine acts as a ligand with an auxin-protein complex and is thus able to trigger the functions of the complex such as, for example, promoting the rate of cell division and elongation in roots.

In one aspect, disclosed herein is a method for increasing resistance of a plant to drought or other conditions involving water stress. In a further aspect, the method involves contacting the plant with an extract produced by the biological devices disclosed herein. In a further aspect, the biological devices include host cells transformed with the DNA constructs disclosed herein. In one aspect, the DNA constructs include the following genetic components: (a) a gene that expresses chitin synthase, (b) a gene that expresses chitosanase, and (c) a gene that expresses chitin deacetylase. In another aspect, the DNA constructs can optionally include (d) a gene that expresses lipase, (e) a gene that expresses regulatory sequence CHR1, (f) a gene that expresses transglycosylase, (g) a gene that expresses dehydrogenase, and/or (h) a gene that expresses (1→3),(1→4)-β-glucan synthase.

Methods for Improving the Physical Appearance of a Plant

In still another aspect, disclosed herein is a method for improving the physical appearance of a plant. In a further aspect, the method involves contacting the plant with an extract produced by the biological devices disclosed herein. In a further aspect, the biological devices include host cells transformed with the DNA constructs disclosed herein. In one aspect, the DNA constructs include the following genetic components: (a) a gene that expresses chitin synthase, (b) a gene that expresses chitosanase, and (c) a gene that expresses chitin deacetylase. In another aspect, the DNA constructs can optionally include (d) a gene that expresses lipase, (e) a gene that expresses regulatory sequence CHR1, (f) a gene that expresses transglycosylase, (g) a gene that expresses dehydrogenase, and/or (h) a gene that expresses (1→3),(1→4)-β-glucan synthase. In one aspect, the method can cause stressed, yellow or brown grass to lush, green grass. In a further aspect, the method can be used on golf courses, sports fields, lawns, parks, or anywhere grass is commonly grown.

In one aspect, the plant is an angiosperm or gymnosperm. In another aspect, the plant can be a vegetable, a fruit, grass, a tree, a shrub, a vine, a flower, or any other plant that is grown for horticultural or agricultural purposes. In one aspect, the vegetable can be a nightshade vegetable such as, for example, an eggplant, tomato, potato, bell pepper, or hot pepper. In another aspect, the vegetable can be from the onion family such as, for example, chives, garlic, leeks, scallions, onions, or shallots. In still another aspect, the vegetable can be a cruciferous vegetable such as, for example, broccoli, cauliflower, kale, kohlrabi, or Brussels sprouts. In still another aspect, the vegetable can be a root vegetable such as, for example, beet, carrot, celeriac, parsnip, rutabaga, radish, jicama, sweet potato, turnip, or yam. In one aspect, the vegetable can be a squash including, but not limited to, acorn squash, butternut squash, zucchini, cucumber, delicate squash, spaghetti squash, yellow squash, kabocha squash, or pumpkin. In still another aspect, the vegetable can be a green, leafy vegetable such as, for example, lettuce, watercress, arugula, turnip greens, mustard greens, collard greens, chard, spinach, escarole, bok choy, cabbage, endive, or the like. In yet another aspect, the vegetable can be a legume such as, for example, alfalfa sprouts, black beans, black eyed peas, peanuts, chickpeas, green beans, kidney beans, lentils, lima beans, mung beans, navy beans, pinto beans, split peas, peas, soybeans, or snap peas. In still another aspect, the vegetable can be any vegetable not already mentioned such as, for example, avocado, artichoke, asparagus, celery, fennel, okra, or sweet corn.

In another aspect, the fruit can be a citrus fruit such as, for example, an orange, clementine, mandarin, tangerine, tangelo, kumquat, grapefruit, ugli fruit, pomelo, lemon, lime, or citron. In another aspect, the fruit can be a berry such as, for example, a cranberry, gooseberry, mulberry, strawberry, blueberry, raspberry, blackberry, goji berry, acai berry, elderberry, or the like. In still another aspect, the fruit can be a stone fruit such as, for example, a plum, peach, nectarine, plumcot, pluot, apricot, cherry, or hybrid thereof. In another aspect, the fruit can be a grape, currant, date, fig, apple, watermelon, cantaloupe, pear or Asian pear, kiwifruit, quince, or the like. In yet another aspect, the fruit can be an exotic or tropical fruit such as, for example, pineapple, coconut, guava, papaya, tamarind, mango, jackfruit, dragonfruit, durian, lychee, star fruit, or the like.

In still another aspect, the grass can be a lawn grass such as, for example, Bahia grass, Bermuda grass, Buffalo grass, Carpet grass, Centipede grass, St. Augustine grass, zoysia grass, annual or perennial ryegrass, Kentucky bluegrass, or a fescue variety. In another aspect, the grass can be an ornamental grass such as a reedgrass, pampas grass, an ornamental fescue, an oat grass, switchgrass, or a decorative sedge. In yet another aspect, the grass can be a cereal grass such as, for example, maize (corn), rice, wild rice, bread wheat or durum wheat, barley, sorghum, millet, oats, rye, triticale, farro, kamut, or the like. In still another aspect, the plant can be a plant commonly called a grain but not part of the grass family such as, for example, buckwheat, quinoa, amaranth, or teff.

In one aspect, the tree can be a fruit tree including any tree that produces a fruit already discussed above (e.g., apple, pear, peach, orange). In another aspect, the tree can be a nut tree that produces almonds, Brazil nuts, cashews, chestnuts, filberts or hazelnuts, hickory nuts, macadamia nuts, pecans, pine nuts, pistachios, walnuts, or the like. In another aspect, the tree can be a tree used as a source of wood including a softwood (i.e., cedar, fir, pine, redwood, and the like) or a hardwood (i.e., ash, birch, cherry, mahogany, maple, oak, poplar, teak, black walnut, and the like) or a soft hardwood (i.e., soft maples, soft birches, soft ashes, magnolia, sweetgum, cottonwood, aspen, soft cherries, willow, elm, or the like). In yet another aspect, the tree can be an ornamental tree including an ornamental cherry, a crabapple tree, a dogwood, a magnolia, a Japanese maple or other ornamental maple, redbud, or the like.

In another aspect, the shrub can be aloe, sagebrush, barberry, angel's trumpet, butterfly bush, heather, camellia, hawthorn, forsythia, fuchsia, huckleberry, broom, witch hazel, hibiscus, sea buckthorn, hydrangea, Rose of Sharon, hyssop, holly, star anise, indigo, jasmine, juniper, lavender, privet, honeysuckle, peony, sumac, rose, rue, rosemary, lilac, yew, gorse, thyme, bilberry, vervain, mistletoe, periwinkle, yucca, or a shrub growth form of any of the trees previously listed.

In one aspect, the flower can be a buttercup, daisy, lily, sweet alyssum, amaryllis, anemone, snapdragon, milkweed, columbine, baby's breath, bachelor's button, begonia, black-eyed Susan, bleeding heart, hyacinth, morning glory, nightshade, calendula, poppy, primrose, carnation, chrysanthemum, clematis, clover, Echinacea, coreopsis, cosmos, geranium, phlox, crocus, cyclamen, daffodil, dahlia, daylily, iris, bluebell, flax, forget-me-not, foxglove, freesia, marigold, fuchsia, gardenia, jasmine, gladiolus, grape hyacinth, heather, heliotrope, hibiscus, hydrangea, impatiens, jonquil, orchid, lavender, lilac, lily of the valley, lotus, lupin, marigold, narcissus, nasturtiums, pansy, petunia, poinsettia, poppy anemone, snowdrop, sweet pea, tea rose, tulip, tuberose, trumpet vine, periwinkle, viola, violet, or any other common ornamental or medicinal flower.

In another aspect, the plant is vine, flower, bark, leaf, stem, seed, or the like, used as an herb or spice, included, but not limited to: allspice, anise, bay leaf, basil, cumin, mustard, black pepper, caraway, cardamom, cassia or cinnamon, catnip, cayenne pepper, celery seed, chervil, cilantro or coriander, clove, dill, ginger, horseradish, lemon balm, lemongrass, lemon verbena, licorice, mace, marjoram, nutmeg, oregano, paprika, parsley, peppermint, poppy seed, rosemary, saffron, sage, savory, sesame, star anise, spearmint, tarragon, thyme, turmeric, vanilla, or any other commonly used herb or spice.

In another aspect, the vine can be any common vine plant including vine forms of plants already listed, as well as hemp, silvervine, ivy, a Bougainvillea species, or another vine. In one aspect, the plant is a plant grown for fibers or canes such as, for example, flax (for linen), jute, rattan, cotton, bamboo, sisal, or the like. In still another aspect, the plant can be a herbaceous plant such as, for example, cannabis.

Methods of Applying the Polyactive Carbohydrate to Plants

In one aspect, the extracts disclosed herein are applied to the soil where the plant is growing. In another aspect, the plants can be further contacted with chitosan. Chitosan is generally composed of glucosamine units and N-acetylglucosamine units and can be chemically or enzymatically extracted from chitin, which is a component of arthropod exoskeletons and fungal and microbial cell walls. In certain aspects, the chitosan can be acetylated to a specific degree of acetylation. In one aspect, the chitosan is from 60% to about 100%, 80% to 90%, 75% to 85%, or about 80% acetylated. The molecular weight of the chitosan can vary, as well. For example, the chitosan can have about 3, 4, 5, 6, 7, 8, 9, 10, 11, 12, 13, 14, 15, 16, 17, 18, 19, or 20 glucosamine units and/or N-acetylglucosamine units. In another aspect, the chitosan includes 5 to 7 glucosamine units and/or N-acetylglucosamine units. In one aspect, the plant is contacted with chitosan before being contacted with the extracts disclosed herein, after being contacted with the extracts, or simultaneously with the extracts.

In one aspect, application of the compounds or extracts disclosed herein increases root tension (i.e., how difficult it is to pull up a plant or section of sod to which the compounds or extracts have been applied) and/or root length. In another aspect, applications of the compounds or extracts disclosed herein leads to a greener appearance of plants such as, for example, field grasses or turf grasses. In one aspect, the compositions and extracts described herein can increase the root force of sod by about 50% to about 200%, or about 50%, about 75%, about 100%, about 125%, about 150%, about 175%, or about 200% compared to sod that has not been treated with the composition or extract, where any value can be a lower and upper endpoint of a range (e.g., about 50% to about 175%, about 75% to about 125%, etc.).

In one aspect, the compositions and extracts described herein can increase the root force of a plant by about 50% to about 200%, or about 50%, about 75%, about 100%, about 125%, about 150%, about 175%, or about 200% compared to a plant that has not been treated with the composition or extract, where any value can be a lower and upper endpoint of a range (e.g., about 50% to about 175%, about 75% to about 125%, etc.).

In one aspect, the compounds and extracts disclosed herein can be applied at a volume of about 50 to about 200 mL per square meter of, for example, turf, or can be applied at about 50 mL, about 75 mL, about 100 mL, about 125 mL, about 150 mL, about 175 mL, or about 200 mL per square meter of turf, or a combination of any of the foregoing values, or a range encompassing any of the foregoing values. In one aspect, the compounds and extracts are applied to turf at a volume of about 75 mL per square meter. In an alternative aspect, the compounds and extracts are applied to turf at a concentration of about 150 mL per square meter.

In one aspect, the compositions and extracts disclosed herein are applied multiple times to the plants of interest. Further in this aspect, the compositions and extracts can be applied once per week, twice per week, or three times per week. In one aspect, the compositions and/or extracts are applied to the plants of interest twice per week.

In another aspect, the compositions and extracts disclosed herein can be applied alone or in combination with another product intended to enhance plant growth. In one aspect, the compositions and extracts disclosed herein are applied in combination with a fertilizer such as, for example, activated sewage sludge including, but not limited to, Hou-actinite, or another commercially-available fertilizer. In one aspect, the compositions and extracts disclosed herein are applied after fertilizer application, or can be applied before fertilizer application, or can be applied at the same time as fertilizer is applied to the plants of interest. In still another aspect, another compound such as, for example, chitosan, can be applied to the plants in addition to the compositions and extracts disclosed herein. In one aspect, the chitosan can be applied as a solution with a concentration of from about 0.01% to about 0.05% (w/v), or can be applied as a solution with a concentration of about 0.01, 0.02, 0.03, 0.04, or about 0.05%. In one aspect, the chitosan is applied as a solution with a concentration of about 0.02%. In another aspect, In one aspect, the chitosan can be applied at a concentration of about 50 to about 200 mL per square meter of, for example, turf, or can be applied at about 50, 75, 100, 125, 150, 175, or about 200 mL per square meter of turf, or a combination of any of the foregoing values, or a range encompassing any of the foregoing values. In one aspect, the chitosan is applied to turf at a concentration of 75 mL per square meter. In an alternative aspect, the chitosan is applied to turf at a concentration of 150 mL per square meter. In another aspect, the chitosan can be applied to the turf once per week, twice per week, or three times per week. In one aspect, the chitosan is applied twice per week. In still another aspect, the chitosan can be applied before the compounds and extracts disclosed herein, or after the compounds and extracts disclosed herein, or simultaneously with the compounds and extracts disclosed herein.

In any of the above aspects, application of the compounds and extracts disclosed herein leads to an increase in plant hormones and, in turn, improvement in properties such as earlier rooting, root anchoring or tension, root strength, root length, green coloration, nutrient availability, reduction of irrigation needs, prevention of erosion, and other desirable properties of plants. These improved features of the plant also provides defense responses in the plant with respect to insects, pathogens, parasites of the roots, and soil-borne diseases.

V. Polyurethanes and Biofoams

In another aspect, the polyactive carbohydrates described herein can be used to produce polyurethane compositions that have numerous applications.

In one aspect, the polyurethane composition is produced by:

a) admixing the polyactive carbohydrate produced herein and a natural oil polyol to produce a first admixture; and b) reacting the first admixture with a polyisocyanate to produce the polyurethane composition.

A "natural oil" as used herein is any oil extracted from a living organism. In one aspect, the living organism is a plant or alga. In a further aspect, the plant is the castor bean or castor oil plant (*Ricinus communis*). In another aspect, the living organism is an animal. In an alternative aspect, the living organism is a fungus. Natural oils can additionally contain triglycerides, fatty acids, fatty acid esters, sterols, isoprenoid or terpenoid compounds, alkaloids, phenols, and other metabolites.

"Natural oil polyols" are compounds that include at least one free hydroxyl group and are derived from or present in natural oils. A natural oil polyol may be naturally occurring, as with the ricinoleic acid in castor oil, or it may be chemically synthesized from an oil or fat containing one or more carbon-carbon double bonds. In one aspect, a natural fatty acid or triglyceride containing a carbon-carbon double bond is subjected to ozonolysis to cleave the double bond, followed by treatment with another molecule such as, for example, ethylene glycol, to form an alcohol. In another aspect, a natural fatty acid or triglyceride containing a carbon-carbon double bond can be epoxidized and treated with a nucleophile to generate an alcohol. In still another aspect, a natural fatty acid or triglyceride containing a carbon-carbon double bond can be formylated in the presence of carbon monoxide and hydrogen gas, followed by hydrogenation to generate a hydroxyl group. Other methods of producing natural oil polyols are also contemplated. Natural oils can be used as extracted or can optionally be purified. In one aspect, the natural oil polyol is or is derived from soy, a chemically-modified vegetable oil, a carbohydrate, lignin, cork, cashew nutshell liquid, *Lesquerella* oil, or a combination thereof. In one aspect, the natural oil polyol is castor oil. In another aspect, the natural oil polyol is ricinoleic acid. In still another aspect, the natural oil polyol is coriolic acid or a chemically-modified fatty acid.

"Castor oil" can optionally be extracted from the seeds of the castor oil plant. The primary component of castor oil is ricinoleic acid; minor components include oleic acid, linoleic acid, linolenic acid, stearic acid, palmitic acid, dihydroxystearic acid, and other trace fatty acids.

In one aspect, the natural oil polyol can include one or more hydroxyl fatty acids, which are defined herein as fatty acids having at least one free hydroxyl group. The hydroxyl fatty acid has the general formula R'C(O)OH, wherein R' is a saturated or unsaturated hydrocarbon chain having from 10 to 25 carbon atoms, and at least one hydroxyl group is covalently attached to a carbon atom of the hydrocarbon chain. The hydrocarbon can be linear or branched. In the case where the hydrocarbon is unsaturated, the hydrocarbon can have one carbon-carbon double bond or multiple carbon-carbon double bonds. Examples of monohydroxy fatty acids (i.e., one hydroxyl group present on the fatty acid) include, but are not limited to, hydroxynervonic acid, cerebronic acid, 10-hydroxy-20-decenoic acid, hydroxy-2-decenoic acid 10-phosphate, strophantus acid, lesquerolic acid, densipolic acid, auricolic acid, a-dimorphecolic acid, kamlolenic acid, 8-hydroxyoctadeca-9,11-diynoic acid, 8-hydroxyoctadeca-17-en-9,11-diynoic acid (isanolic), or 8-hydroxyoctadeca-13,17-dien-9,11-diyonic acid. Examples of polyhydroxy fatty acids (i.e., two or more hydroxyl groups) include, but are not limited to, axillarenic acid, tetrapedic acid, byrsonic acid, 9,10-dihyrdoxyoctadecanoic acid, phaseolic acid, phloionolic acid, Resolvin D1, 10,18S-docosatriene, or Resolvin E1. The hydroxyl fatty acids can be used as is in the natural oil (e.g., castor oil), isolated from a natural oil, or synthesized accordingly.

In certain aspects, a surfactant can be used to produce the polyurethane compositions described herein, where it is admixed with the polyactive carbohydrate and a natural oil polyol to produce a first admixture. A "surfactant" is an organic compound that may be derived from a natural product, or may result from chemical modification of a natural product, or may be completely chemically synthesized. Surfactants typically contain hydrophilic head groups and hydrophobic tails. In one aspect, the head group is anionic, cationic, non-ionic, or zwitterionic. In another aspect, the tail is composed of a hydrocarbon or a glucoside. Surfactants alter the surface tension of liquids and may form micelles or bilayers in aqueous solution. Many applications of surfactants are known in the art. Surfactants are, for example, commonly employed as emulsifiers, detergents, wetting agents, and the like.

Numerous cationic surfactants can be used in the compositions described herein. In one aspect, the cationic surfactant can be a quaternary ammonium salt.

Numerous zwitterionic surfactants can be used in the compositions described herein. In one aspect, the zwitterionic surfactant can be a lecithin such as soy lecithin; in another aspect, the zwitterionic surfactant can be a hydroxysultaine, a betaine, a sulfobetaine, or a mixture thereof. Among betaines, surfactants may be selected from the group that includes high alkyl betaines such as cetyl dimethyl carboxymethyl betaine, cocamidopropyl betaine, cocobetaine, coco dimethyl carboxymethyl betaine, lauryl amidopropyl betaine, lauryl bis-(2-hydroxyethyl) carboxymethyl betaine, lauryl bis-(2-hydroxypropyl)alphacarboxyethyl betaine, lauryl dimethyl alphacarboxyethyl betaine, lauryl dimethyl carboxymethyl betaine, oleyl betaine, oleyl dimethyl gamma-carboxypropyl betaine, stearyl bis-(2-hydroxypropyl) carboxymethyl betaine, and mixtures thereof. Among sulfobetaines, surfactants may be selected from the group that includes coco dimethyl sulfopropyl betaine, lauryl bis-(2-hydroxyethyl) sulfopropyl betaine, lauryl dimethyl sulfoethyl betaine, stearyl dimethyl sulfopropyl betaine, and mixtures thereof. Amidobetaines and amidosulfobetaines are also contemplated.

Numerous nonionic surfactants can be used in the compositions described herein. Nonionic surfactants useful in the compositions described herein include alkoxylated fatty acid esters, alkyl glucosides, alkyl polyglucosides, amine oxides, alcohol ethoxylates, cocoamine oxide, glyceryl monohydroxystearate, glyceryl stearate, hydroxyl stearic acid, lauramine oxide, laureth-2, polyhydroxy fatty acid amides, polyoxyalkylene stearates, propylene glycol stearate, sorbitan monostearate, sucrose cocoate, sucrose esters, sucrose laurate, steareth-2, PEG-40 hydrogenated castor oil, and mixtures thereof. Preferred nonionic surfactants include those based on polyethoxylated sorbitan and oleic acid such as, for example, polysorbate 80 and polysorbate 20, both of which are available under a variety of trade names.

Further nonionic surfactants contemplated include, in one aspect, the condensation products of a higher aliphatic alcohol, such as a fatty alcohol, containing about 8 to 20 carbon atoms, in a straight or branched chain configuration, condensed with about 3 to about 100 moles, preferably about 5 to about 40 moles, most preferably about 5 to about 20 moles of ethylene oxide. Examples of such nonionic ethoxylated fatty alcohol surfactants are the Tergitol™ 15-S series from Union Carbide and Brij™ surfactants from ICI. Tergitol™ 15-S surfactants include $C_{11}$-$C_{13}$ secondary alcohol polyethylene glycol ethers, Brij™97 surfactant is polyoxyethylene(10) oleyl ether; Brij™58 surfactant is polyoxyethylene(20) cetyl ether; and Brij™76 surfactant is polyoxyethylene(10) stearyl ether.

In another aspect, a useful class of nonionic surfactants includes the polyethylene oxide condensates of one mole of alkyl phenol containing from about 6 to 12 carbon atoms in a straight or branched chain configuration, with about 3 to about 100 moles, preferably about 5 to about 40 moles, most preferably about 5 to about 20 moles of ethylene oxide to achieve the above defined HLB. Examples of nonreactive nonionic surfactants are the Igepal™ CO and CA series from Rhone-Poulenc. Igepal™ CO surfactants include nonylphenoxy poly(ethyleneoxy)ethanols. Igepal™ CA surfactants include octylphenoxy poly(ethyleneoxy)ethanols. Still another useful class of hydrocarbon nonionic surfactants includes block copolymers of ethylene oxide and propylene oxide or butylene oxide with HLB values of about 6 to about 19, preferably about 9 to about 18, and most preferably about 10 to about 16. Examples of such nonionic block copolymer surfactants are the Pluronic™ and Tetronic™ series of surfactants from BASF. Pluronic™ surfactants include ethylene oxide-propylene oxide block copolymers. Tetronic™ surfactants include ethylene oxide-propylene oxide block copolymers. In other aspects, the nonionic surfactants include sorbitan fatty acid esters, polyoxyethylene sorbitan fatty acid esters and polyoxyethylene stearates having HLBs of about 6 to about 19, about 9 to about 18, and about 10 to about 16. Examples of such fatty acid ester nonionic surfactants are the Span™, Tween™, and Myj™ surfactants from ICI. Span™ surfactants include $C_{12}$-$C_{18}$ sorbitan monoesters. Tween™ surfactants include poly(ethylene oxide) $C_{12}$-$C_{18}$ sorbitan monoesters. Myj™ surfactants include poly(ethylene oxide) stearates. In one aspect, the nonionic surfactant can include polyoxyethylene alkyl ethers, polyoxyethylene alkyl-phenyl ethers, polyoxyethylene acyl esters, sorbitan fatty acid esters, polyoxyethylene alkylamines, polyoxyethylene alkylamides, polyoxyethylene lauryl ether, polyoxyethylene cetyl ether, polyoxyethylene stearyl ether, polyoxyethylene oleyl ether, polyoxyethylene octylphenyl ether, polyoxyethylene nonylphenyl ether, polyethylene glycol laurate, polyethylene glycol stearate, polyethylene glycol distearate, polyethylene glycol oleate, oxyethylene-oxypropylene block copolymer, sorbitan laurate, sorbitan stearate, sorbitan distearate, sorbitan oleate, sorbitan sesquioleate, sorbitan trioleate, polyoxyethylene sorbitan laurate, polyoxyethylene sorbitan stearate, polyoxyethylene sorbitan oleate, polyoxyethylene laurylamine, polyoxyethylene laurylamide, laurylamine acetate, hard beef tallow propylenediamine dioleate, ethoxylated tetramethyldecynediol, fluoroaliphatic polymeric ester, polyether-polysiloxane copolymer, and the like.

Numerous anionic surfactants can be used herein. In one aspect, the anionic surfactant can be alcohol phosphates and phosphonates, alkyl alkoxy carboxylates, alkyl aryl sulfates, alkyl aryl sulfonates, alkyl carboxylates, alkyl ether carboxylates, alkyl ether sulfates, alkyl ether sulfonates, alkyl phosphates, alkyl polyethoxy carboxylates, alkyl polyglucosides, alkyl polyglucoside sulfates, alkyl polyglucoside sulfonates, alkyl succinamates, alkyl sulfates, alkyl sulfonates, aryl sulfates, aryl sulfonates, fatty taurides, isethionates, N-acyl taurates, nonoxynol phosphates, octoxynol phosphates, sarcosinates, sulfated fatty acid esters, taurates, and mixtures thereof. Useful anionic surfactants include, but are not limited to, alkali metal and (alkyl)ammonium salts of: 1) alkyl sulfates and sulfonates such as sodium dodecyl sulfate, sodium 2-ethylhexyl sulfate, and potassium dodecanesulfonate; 2) sulfates of polyethoxylated derivatives of straight or branched chain aliphatic alcohols and carboxylic acids; 3) alkylbenzene or alkylnaphthalene sulfonates and sulfates such as sodium laurylbenzene-4-sulfonate and ethoxylated and polyethoxylated alkyl and aralkyl alcohol carboxylates; 5) glycinates such as alkyl sarcosinates and alkyl glycinates; 6) sulfosuccinates including dialkyl sulfosuccinates; 7) isothionate derivatives; 8) N-acyltaurine derivatives such as sodium N methyl-N-oleyltaurate); 9) amine oxides including alkyl and alkylamidoalkyldialkylamine oxides; and 10) alkyl phosphate mono or di-esters such as ethoxylated dodecyl alcohol phosphate ester, sodium salt. Representative commercial examples of suitable anionic sulfonate surfactants include, for example, sodium lauryl sulfate, available as TEXAPON™ L-100 from Henkel Inc., Wilmington, Del., or as POLYSTEP™ B-3 from Stepan Chemical Co, Northfield, Ill.; sodium 25 lauryl ether sulfate, available as POLYSTEP™ B-12 from Stepan Chemical Co., Northfield, Ill.; ammonium lauryl sulfate, available as STANDAPOL™ A from Henkel Inc., Wilmington, Del.; and sodium dodecyl benzene sulfonate, available as SIPONATE™ DS-10 from Rhone-Poulenc, Inc., Cranberry, N.J., dialkyl sulfosuccinates, having the trade name AEROSOL™ OT, commercially available from Cytec Industries, West Paterson, N.J.; sodium methyl taurate (available under the trade designation NIKKOL™ CMT30 from Nikko Chemicals Co., Tokyo, Japan); secondary alkane sulfonates such as Hostapur™ SAS which is a Sodium (C14-C17) secondary alkane sulfonates (alpha-olefin sulfonates) available from Clariant Corp., Charlotte, N.C.; methyl-2-sulfoalkyl esters such as sodium methyl-2-sulfo(C12-16)ester and disodium 2-sulfo(C12-C16) fatty acid available from Stepan Company under the trade designation ALPHASTE™ PC48; alkylsulfoacetates and alkylsulfosuccinates available as sodium laurylsulfoacetate (under the trade designation LANTHANOL™ LAL) and disodiumlaurethsulfosuccinate (STEPANMILD™ SL3), both from Stepan Company; alkylsulfates such as ammoniumlauryl sulfate commercially available under the trade designation STEPANOL™ AM from Stepan Company, and/or dodecylbenzenesulfonic acid sold under BIO-SOFT® AS-100 from Stepan Chemical Co. In one aspect, the surfactant can be a disodium alpha olefin sulfonate, which contains a mixture of $C_{12}$ to $C_{16}$ sulfonates. In one aspect, CALSOF™ AOS-40 manufactured by Pilot Corp. can be used herein as the surfactant. In another aspect, the surfactant is DOWFAX 2A1 or 2G manufactured by Dow Chemical, which are alkyl diphenyl oxide disulfonates. Representative commercial examples of suitable anionic phosphate surfactants include a mixture of mono-, di- and tri-(alkyltetraglycolether)-o-phosphoric acid esters generally referred to as trilaureth-4-phosphate commercially available under the trade designation HOSTAPHAT™

340KL from Clariant Corp., as well as PPG-5 cetyl 10 phosphate available under the trade designation CRODAPHOS™ SG from Croda Inc., Parsipanny, N.J. Representative commercial examples of suitable anionic amine oxide surfactants those commercially available under the trade designations AMMONYX™ LO, LMDO, and CO, which are lauryldimethylamine oxide, laurylamidopropyldimethylamine oxide, and cetyl amine oxide, all from Stepan Company.

In one aspect, a surfactant is chosen based on its ability to form a stable emulsion containing an acidic aqueous solution of a polyactive carbohydrate and a natural oil polyol. In a further aspect, the concentration of surfactant can be from 0.001% to 1% (v/v), or can be about 0.001%, 0.005%, 0.01%, 0.05%, 0.1%, 0.35%, 0.5%, or 1% (v/v) with respect to the final emulsion volume. In another aspect, 0.35% of polysorbate 80 is used. In a further aspect, emulsion formation can be evaluated as a function of stirring time (e.g., about 1 minute, about 2 minutes, about 4 minutes, about 6 minutes, about 8 minutes, or about 10 minutes) and/or stirring speed (e.g., about 2000 rpm, about 5000 rpm, about 10,000 rpm, or about 20,000 rpm).

The order in which the polyactive carbohydrate and natural oil polyol can be admixed with one another to produce the first admixture can vary. In one aspect, the natural oil polyol can be added to a solution of the polyactive carbohydrate. In one aspect, the natural oil polyol is added over time (e.g., 2 minutes, 4 minutes, 5 minutes, 6 minutes, 8 minutes, or 10 minutes) with stirring (2000 rpm, 5000 rpm, 10,000 rpm, or 20,000 rpm) to create a final admixture that also incorporates the polyactive carbohydrate. In one aspect, the natural oil polyol is castor oil and stirring is conducted at 10,000 rpm for 5 minutes.

In one aspect, the polyactive carbohydrate is from 0.1 to 1% by weight of the first admixture. In another aspect, the amount of polyactive carbohydrate is 0.1, 0.2, 0.3, 0.4, 0.5, 0.6, 0.7, 0.8, 0.9, or 1 wt % of the first admixture, where any value can be a lower or upper endpoint of a range (2. g., 0.2 to 0.7, etc.). In another aspect, the polyactive carbohydrate can be prepared and used as a solution. In one aspect, the polyactive carbohydrate is an aqueous solution of 1% to 5% (v/v), where the first admixture includes 20% to 80% (v/v) of the aqueous solution of polyactive carbohydrate.

In one aspect, the natural oil polyol is from 20% to 80% (v/v) of the first admixture. In another aspect, the natural oil polyol is about 20%, 25%, 30%, 35%, 40%, 45%, 50%, 55%, 60%, 70%, 75%, or 80% (v/v) of the first admixture, where any value can be a lower or upper endpoint of a range (e.g., 40% to 60%, etc.).

Prior to the addition of the polyisocyanate, additional components can be added to the first admixture of polyactive carbohydrate and natural oil polyol. In one aspect, a catalyst can be added to the first admixture. A "catalyst" as used herein is any substance that can increase the rate of a chemical reaction. In one aspect, the catalyst is not consumed in the reaction. A single molecule of a catalyst can assist with multiple chemical reactions. Catalysts useful herein include, but are not limited to, tertiary amines such as dimethylethanolamine (DMAE), triethylenediamine (DABCO), β-aminopropyldimethylamine (DMAPA), dimethylcyclohexylamine (DMCHA); compounds containing hydroxyl groups or secondary amines such as, for example, propylene glycol; metallic compounds including metal carboxylates such as, for example, dibutyltin dilaurate (DBTDL) as well as mercury, lead, bismuth, and zinc carboxylates; and other alkyl tin carboxylates, oxides, and mercaptides. In one aspect, the catalyst is added to an emulsion containing the polyactive carbohydrate and natural oil polyol at from about 0.05% to about 2% (v/v) with respect to the volume of the emulsion. In another aspect, about 0.05%, 0.1%, 0.15%, 0.2%, 0.25%, 0.4%, 0.6%, 0.7%, 0.8%, 1%, 1.2%, 1.5%, or 2% catalyst is used. In some aspects, a combination of catalysts is used. In one aspect, 0.5% (v/v) dibutyltin dilaurate and 1% (v/v) dimethylethanolamine were used in combination. In a further aspect, stirring is used to incorporate the catalyst throughout an emulsion containing the polyactive carbohydrate and natural oil polyol. In one aspect, different stirring times (e.g., about 1 minute, about 2 minutes, about 3 minutes, about 4 minutes, about 5 minutes, about 8 minutes, or about 10 minutes) and different stirring speeds (about 100 rpm, about 200 rpm, about 300 rpm, about 400 rpm, about 500 rpm, about 600 rpm, or about 700 rpm) are evaluated to determine the minimum stirring time and speed required to fully incorporate the catalyst into the emulsion. In one aspect, the emulsion and added catalyst are stirred at 300 rpm for 3 minutes.

In another aspect, a clay can be added to the first admixture. "Clay" and "clay minerals" as used herein refer to hydrous aluminum phylosilicates. Clays can optionally include oxides and/or chelates of other metals and semimetals such as, for example, silicon, iron, calcium, magnesium, sodium, potassium, and other alkali and alkaline earth metals. "Bentonite" is a category of impure clay that can consist of montmorillonite, kaolinite, and other species; and that can include potassium, sodium, calcium, aluminum, as well as other metals. "Zeolites" are microporous aluminosilicates that can accommodate a variety of cations, including, but not limited to, sodium, potassium, calcium, and magnesium. The cations in zeolites can be exchanged in aqueous solutions. Clays, bentonites, and zeolites can be used as sources of trace oxides and/or ions in the practice of the present invention. An "oxide" as used herein refers to a molecule, a network solid, or an ionic compound containing at least one oxygen atom and one other element. In one aspect, clays, bentonites, and zeolites contain chelated metal and semimetal ions. Not wishing to be bound by theory, the inclusion of the clay can be used to vary the pore size of the final biofoam product produced.

In one aspect, a metal or semimetal oxide or a chelated metal ion can be incorporated into the first admixture. In one aspect, the metal or semimetal oxide includes, for example, $Al_2O_3$, $Fe_2O_3$, MgO, CaO, $Na_2O$, $K_2O$, $SiO_2$, or a combination thereof. In this aspect, the metal or semimetal oxide can be introduced into the polyurethane compositions as a pure compound. In an alternative aspect, ions such as, for example, aluminum, iron (III), magnesium, calcium, sodium, potassium, silicon, and combinations thereof, can be incorporated into the polyurethane compositions described herein through the inclusion of clays or clay minerals. In one aspect, the metal or semimetal oxides or chelated metals are incorporated at concentrations of from about 0.02 nM to about 1.2 mM, or at 0.2 nM, 0.04 nM, 0.06 nM, 0.08 nM, 0.1 nM, 0.15 nM, 0.2 nM, 0.25 nM, 0.3 nM, 0.35 nM, 0.4 nM, 0.45 nM, 0.5 nM, 0.55 nM, 0.2 mM, 0.4 mM, 0.6 mM, 0.8 mM, or 1.2 mM.

In another aspect, one or more water-soluble metal salts can be incorporated into the first admixture. In one aspect, the water-soluble metal salts can include, for example, gallium (III) nitrate hydrate, zinc sulfate, zinc acetate, or a combination thereof. In one aspect, 50 mg/L of gallium (III) nitrate hydrate is incorporated into the emulsion containing the polyactive carbohydrate and natural oil polyol. In another aspect, 100 mg/L of zinc sulfate is incorporated into the emulsion containing the polyactive carbohydrate and natural oil polyol.

After preparation of the first admixture as described above, a polyisocyanate is added to the first admixture. "Polyisocyanates" as used herein are compounds with two or more —N═C═O groups. In one aspect, the polyisocyanate is an aliphatic diisocyanate, a cycloaliphatic diisocyanate, an aromatic diisocyanate, or an isomer thereof. In another aspect, the isocyanate or polyisocyanate is 2,4-toluenediisocyanate, 2,6-toluenediisocyanate, 4,4'-methylene diphenyl diisocyanate (MDI), 4,4'-methylenebis(cyclohexylisocyanate) (H12-MDI), 1-isocyanato-β-isocyanatomethyl-3,5,5-trimethylcyclohexane (isophorone diisocyanate), 2,4,4-trimethylhexamethylenediisocyanate, ethylidenediisocyanate, butylenediisocyanate, hexamethylenediisocyanate, cyclohexylene-1,4-diisocyanate, cyclohexylene-1,2-diisocyanate, xylylene diisocyanate, dichlorohexamethylene diisocyanate, dicyclohexyl-4,4'-diisocyanate, 1-methyl-2,4-diisocyanato-cyclohexane, 1-methyl-2,6-diisocyanato-cyclohexane, naphthalene-1,5-diisocyanate, p-phenylendiisocyanate, tetramethyl-xylylenediisocyanate (TMXDI), or any combination thereof. The isocyanate or polyisocyanate can exist as one or more structural isomers. Alternatively, the isocyanate or polyisocyanate can be a dimer, trimer, or oligomer. In other aspects, the isocyanate or polyisocyanate can exist as one or more positional isomers. For example, the polyisocyanate can be a mixture of 2,4-toluenediisocyanate and 2,6-toluenediisocyanate. In a further aspect, the polyisocyanate can be a 65:35 mixture of 2,4-TDI and 2,6-TDI (i.e., TDI 65). In a different aspect, the polyisocyanate can be an 80:20 mixture of 2,4-TDI and 2,6-TDI (i.e., TDI 80). In an alternative aspect, the polyisocyanate is a modified MDI or polyphenylmethane polyisocyanate such as one of those sold by Yantai Wanhua Polyurethanes Co. under the trade name WANNATE®.

In one aspect, the polyisocyanate is added to the first admixture at different ratios such as, for example, about 1:1, about 1:2, about 1:3, about 1:4, about 1:5, about 1:6, about 1:7, or about 1:8 with respect to the total emulsion volume, or any range thereof (e.g., 1: to 1:8, 1:3 to 1:5, etc.). In this aspect, polymerization reactions can then be carried out. Different reaction times (e.g. 8 minutes, 10 minutes, 12 minutes, 15 minutes, or 20 minutes) and stirring speeds (e.g., 500 rpm, 600 rpm, 700 rpm, 800 rpm, 900 rpm, or 1000 rpm) can be evaluated to determine the optimum reaction time and stirring speed. In one aspect, the first admixture is admixed with the polyisocyanate for 10 minutes at 500 rpm. In another aspect, the reaction is conducted at room temperature.

Upon admixing the components in the first admixture with the polyisocyanate, isocyanate-reactive functional groups present on the polyactive carbohydrate and/or natural oil polyol react with the isocyanate groups on the polyisocyanate to produce a polyurethane. Here, a polymer composed of organic residues joined by urethane linkages is produced. Although the components in the first admixture include hydroxyl groups, other components may be present that include other isocyanate-reactive functional groups such as amine groups, thiol groups, or other nucleophilic groups capable of reacting with isocyanate groups.

The polyurethane compositions described herein can be used to produce biofoams that nave numerous applications. The term "biofoam" as used herein is any substance formed when pockets of gas have been trapped in a solid or liquid. In one aspect, the biofoams produced herein can exist as an emulsion or dispersion at room temperature. In other aspects, the biofoams produced herein are solid materials at room temperature.

The amount of the polyactive carbohydrate present in the final biofoam product can vary. In one aspect, the amount of polyactive carbohydrate present in the biofoam is from 0.005% to 0.1% by weight of the biofoam. In another aspect, the amount of polyactive carbohydrate present in the biofoam is about 0.005%, 0.01%, 0.02%, 0.03%, 0.04%, 0.05%, 0.06%, 0.07%, 0.08%, 0.09%, or 0.1% by weight of the biofoam, where any value can be a lower and/or upper endpoint of a range (e.g., 0.01% to 0.05%). When used to prepare the biofoams, the polyactive carbohydrate can be prepared as a stock solution. For example, the polyactive carbohydrate in powder form (0.05, 0.1, 0.2, 0.3, 0.4, 0.5, 0.6, 0.7, 0.8, 0.9, or Ig) can be added to water (100 mL to 1 L) to produce a stock solution. The pH of the stock solution can be adjusted as necessary.

The selection and amounts of reactants as well as processing conditions will determine the physical state of the biofoams. For example, by varying the amount of the polyactive carbohydrate relative to the amount of castor oil it is possible to produce soft and hard biofoams. In one aspect, when the polyisocyanate is admixed with the first admixture, a solid biofoam is produced. The polyurethane compositions produced herein can be poured into a mold of any desired shape. If necessary, the mold containing the polyurethane composition can be placed in an oven to remove residual solvent and produce the final biofoam.

In other aspects, one or more blowing agents can be incorporated into the polyurethane compositions to produce the biofoams. A blowing agent can be physical or chemical in nature. A "physical blowing agent" is a gas or low boiling point liquid which expands due to heat generated by the polyurethane-forming reaction, thus forming bubbles and creating foam. A "chemical blowing agent" is a compound or substance that reacts to form a gas. In one aspect, the blowing agent is a physical blowing agent. Physical blowing agents include compounds such as, for example, hydrofluorocarbons (HFCs), hydrocarbons (HCs), hydrofluoroolefins, liquid $CO_2$, and other low boiling point liquids. In one aspect, the physical blowing agent is HFC-134a (1,1,1,2-tetrafluoroethane), HFC-245fa (pentafluoropropane), HFC-365mfc (1,1,1,3,3-pentafluorobutane), HFC-152a (1,1-difluoroethane), formic acid, methyl formate, HFO-1234ze (1,3,3,3-tetrafluoropropene), cyclopentane, n-pentane, isopentane, iso-butane, acetone, dichloromethane, or a mixture thereof. In another aspect, the blowing agent is a chemical blowing agent. In one aspect, the chemical blowing agent is carbon dioxide produced by the reaction of isocyanate groups with water. In a further aspect, both chemical and physical blowing agents can be used.

In other aspects, the biofoams include additional additives not already described above such as, for example, flame retardants, color additives, release agents, biocides, other additives, or a combination thereof. The additional components can be admixed with a dispersion or emulsion of polyurethane composition in order incorporate the additives throughout the biofoam. In the alternative, the additives can be applied to the surface of the solid biofoam.

In another aspect, after the preparation of the biofoam, the biofoam can contain residual solvent (e.g., water). In certain aspects, it is desirable to remove all or substantially all (e.g., greater than 70%, greater than 80%, greater than 90%, greater than 95%, greater than 99%, or 100%) of the solvent in the biofoam. In one aspect, drying of the biofoams can be accomplished in an oven at about 20° C., 30° C., 40° C., 50°

C., 60° C., or about 70° C. In one aspect, the biofoams are dried in an oven at 50° C. In a further aspect, the biofoams can be dried for from about 0.5 to about 100 hours, or for about 72 hours. In one aspect, removal of water from biofoams is assessed by periodically removing the biofoams from the oven and weighing them. When the biofoams have the same weight at, for example, at least 2 or 3 successive weighings separated by several hours, the biofoams can be considered to be dry and can be removed from the oven.

The biofoams produced herein have several beneficial properties. In one aspect, the biofoams are resistant to discoloration. In another aspect, discoloration of the biofoams can be assessed by exposing the biofoams to an agent known to cause stains. In a further aspect, the agent known to cause stains is, for example, tea, coffee, or red wine. In one aspect, the biofoams can be submersed in coffee for a period of up to about 24 hours. In this aspect, after 24 hours, the biofoams are removed from the coffee and rinsed with water. Discoloration can then be qualitatively assessed as, for example, weak, medium, or strong.

In another aspect, the biofoams are resistant to acid degradation. For example, the biofoam can be assessed by placing a piece of the foam in an aqueous solution of an acid for 24 or 48 hours. In a further aspect, the acid is present at a 0.1N concentration. In another aspect, the acid is an organic acid such as, for example, acetic acid or formic acid. In an alternative aspect, the acid is an inorganic acid such as, for example, nitric acid, hydrochloric acid, phosphoric acid, or sulfuric acid. Resistance to mixtures of acids can also be tested. In a further aspect, photographs of the foam before and after exposure to acid can be compared to qualitatively assess acid resistance. In another aspect, the foam can be weighed before and after acid exposure to assess whether material has been lost.

In one aspect, it is desirable to know the maximum temperature to which the biofoams can be exposed without decomposition. This is known as temperature resistance. In one aspect, decomposition due to heat exposure can be assessed by placing a piece of the foam in an oven at a temperature of from about 50° C. to about 120° C. In a further aspect, temperature resistance is assessed at about 50° C., at about 80° C., or at about 120° C. In certain aspects, pieces of biofoam can be placed in an oven and the internal temperatures of the biofoam pieces can be measured periodically with, for example, a thermometer or a thermocouple. In a further aspect, temperature resistance can be measured every 10 minutes for up to one hour. In one aspect, the biofoam samples can be weighed prior to assessing temperature resistance, and can be weighed periodically to evaluate the level of decomposition. In this aspect, samples can be weighed every 10 minutes for up to one hour, at about the same time the internal temperature of the biofoam pieces is being measured, with weight loss indicating that decomposition has occurred. In an additional aspect, temperature resistance can be qualitatively assessed by, for example, visually noting any discoloration of the biofoam samples that occurs subsequently to heat treatment. In one aspect, if a sample exhibits less than about 20% weight loss, or less than about 10% weight loss, after exposure to a particular temperature, the sample can be said to be temperature resistant. In another aspect, if a sample does not become visibly discolored after exposure to a particular temperature, the sample can be said to be temperature resistant.

In one aspect, it is desirable to assess the biofoams for recovery from deformation. In this aspect, pressure can be applied to the biofoams, causing deformation. Also in this aspect, when pressure is removed from the biofoams, the biofoams can return to their original shapes and/or sizes. In certain aspects, from about 0.5 bars to about 1 bar of pressure are applied. In other aspects, the time required for the biofoams to recover from deformation is measured. In one aspect, the biofoams take up to about 5 seconds to recover from deformation. In another aspect, the biofoams take from about 1 second to about 3 seconds to recover from deformation.

In one aspect, provided herein are articles composed of or including the biofoams described herein. The biofoams produced herein can be used in any application where soft synthetic polyurethane foams are used. For example, the biofoams can be used in upholstery such as cushions, pillows, furniture, or mattresses, including in automobiles, trains, watercraft and boats, and aircraft. In another aspect, the biofoams can be used to produce equipment for exercise or physical therapy including, for example, yoga mats and other floor mats, padding or upholstery for weight machines and seating for stationary and street bicycles, foam balls for physical therapy, comfort grips for handles for weights, kettlebells, bicycles, and the like, helmet padding and other personal protective equipment, and similar applications. In still another aspect, the biofoams can be used in the construction industry such as for insulation, carpet padding or carpet underlay materials, and materials useful in soundproofing rooms. In another aspect, the biofoams can be used to create packaging materials including anti-static cushioning, case inserts, pads for vibration control, camping pads, and the like.

In another aspect, the biofoams disclosed herein can be used in the medical industry. In one aspect, the biofoam can be used where it is desirable to reduce or minimize blunt force or trauma to a subject. For example, the polyurethane composition can be injected between the skin of the subject and a cast to produce a biofoam that can further prevent any applied force to the broken bone of the subject. In certain aspects, the polyurethane composition can include antimicrobial agents in order to prevent odor.

In other aspects, the polyurethane compositions described herein can be used as adhesives. For example, the polyurethane composition can be in a sufficient amount of solvent so that is can readily be applied to the surface of a substrate (e.g., spray coating, dipping, brushing). Upon removal of the solvent a biofoam is produced, which results in the formation of a strong bond between to substrates. In other aspects, the polyurethane compositions can be used to seal cracks and holes. Here, the polyurethane composition is sprayed in a hole or crack then forms a biofoam.

Aspects

Aspect 1. A method for increasing root growth of a plant, the method comprising contacting the plant with an extract produced from a biological device, wherein the biological device comprises host cells transformed with a DNA construct comprising the following genetic components: (a) a gene that expresses chitin synthase, (b) a gene that expresses chitosanase, and (c) a gene that expresses chitin deacetylase.

Aspect 2. A method for increasing hormone production in a plant, the method comprising contacting the plant with an extract produced from a biological device, wherein the biological device comprises host cells transformed with a DNA construct comprising the following genetic components: (a) a gene that expresses chitin synthase, (b) a gene that expresses chitosanase, and (c) a gene that expresses chitin deacetylase.

Aspect 3. The method of aspect 2, wherein the hormone comprises cytokinins, salicylic acid, jasmonic acid, or any combination thereof.

Aspect 4. A method for increasing the drought-resistance of a plant, the method comprising contacting the plant with an extract produced from a biological device, wherein the biological device comprises host cells transformed with a DNA construct comprising the following genetic components: (a) a gene that expresses chitin synthase, (b) a gene that expresses chitosanase, and (c) a gene that expresses chitin deacetylase.

Aspect 5. A method for improving the physical appearance of a plant, the method comprising contacting the plant with an extract produced from a biological device, wherein the biological device comprises host cells transformed with a DNA construct comprising the following genetic components: (a) a gene that expresses chitin synthase, (b) a gene that expresses chitosanase, and (c) a gene that expresses chitin deacetylase.

Aspect 6. The method according to any one of aspects 1-5, wherein the plant comprises a vegetable, fruit, grass, or tree.

Aspect 7. The method according to any one of aspects 1-6, wherein the extract is further applied to the soil where the plant is growing.

Aspect 8. The method according to any one of aspects 1-7, wherein the plant is further contacted with chitosan.

Aspect 9. The method of aspect 8, wherein the chitosan is from 60% to 100% acetylated and has from 3 to 20 glucosamine units, N-acetylglucosamine units, or a combination thereof.

Aspect 10. The method of aspect 8, wherein the plant is contacted with the chitosan before and/or after the plant is contacted with the extract.

Aspect 11. The method of aspect 8, wherein the plant is contacted with a composition comprising the extract and chitosan.

Aspect 12. The method according to any one of aspects 1-11, wherein the gene that expresses chitin synthase has SEQ ID NO. 2 or at least 70% homology thereof.

Aspect 13. The method according to any one of aspects 1-11, wherein the gene that expresses chitosanase has SEQ ID NO. 3 or at least 70% homology thereof.

Aspect 14. The method according to any one of aspects 1-11, wherein the gene that expresses chitin deacetylase has SEQ ID NO. 4 or at least 70% homology thereof.

Aspect 15. The method according to any one of aspects 1-14, wherein the construct further comprises a gene that expresses lipase.

Aspect 16. The method of aspect 15, wherein the gene that expresses lipase has SEQ ID NO. 1 or at least 70% homology thereof.

Aspect 17. The method according to any one of aspects 1-16, wherein the construct further comprises a gene that expresses (1→3),(1→4)-β-glucan synthase.

Aspect 18. The method of aspect 17, wherein the gene that expresses (1→3),(1→4)-β-glucan synthase has SEQ ID NO. 6 of at least 70% homology thereof.

Aspect 19. The method according to any one of aspects 1-18, wherein the construct further comprises a gene that expresses chitin synthase regulatory factor CHR1.

Aspect 20. The method of aspect 19, wherein the gene that expresses chitin synthase regulatory factor CHR1 has SEQ ID NO. 11 or at least 70% homology thereof.

Aspect 21. The method of aspect 19, wherein the gene that expresses chitin synthase regulatory factor CHR1 has SEQ ID NO. 16 or at least 70% homology thereof.

Aspect 22. The method according to any one of aspects 1-21, wherein the construct further comprises a gene that expresses transglycosylase.

Aspect 23. The method of aspect 22, wherein the gene that expresses transglycosylase has SEQ ID NO. 12 or at least 70% homology thereof.

Aspect 24. The method of aspect 22, wherein the gene that expresses transglycosylase has SEQ ID NO. 15 or at least 70% homology thereof.

Aspect 25. The method according to any one of aspects 1-23, wherein the construct further comprises a gene that expresses a dehydrogenase.

Aspect 26. The method according to aspect 25, wherein the gene that expresses a dehydrogenase expresses a protein having SEQ ID NO. 13 or at least 70% homology thereof.

Aspect 27. The method according to any one of aspects 1-26, wherein the construct further comprises a promoter.

Aspect 28. The method of aspect 27, wherein the promoter comprises a GAL1 promoter, a T7 promoter, or both.

Aspect 29. The method of aspect 27, wherein the promoter is a GAL1 promoter, and wherein the promoter precedes the gene that expresses lipase, the gene that expresses chitin synthase, the gene that expresses chitosanase, the gene that expresses chitin deacetylase, the gene that expresses chitin synthase regulatory factor CRH1, the gene that expresses transglycosylase, or any combination thereof.

Aspect 30. The method of aspect 27, wherein the promoter is a T7 promoter.

Aspect 31. The method according to any one of aspects 1-30, wherein the construct further comprises a terminator.

Aspect 32. The method of aspect 31, wherein the terminator is CYC1 terminator.

Aspect 33. The method according to any one of aspects 1-32, wherein the construct further comprises a LAC operon.

Aspect 34. The method according to any one of aspects 1-33, wherein the construct further comprises one or more ribosomal binding sites preceding the gene that expresses lipase, the gene that expresses chitin synthase, the gene that expresses chitosanase, the gene that expresses chitin deacetylase, the gene that expresses (1→3),(1→4)-β-glucan synthase, the gene that expresses chitin synthase regulatory factor CHR1, the gene that expresses transglycosylase, or any combination thereof.

Aspect 35. The method according to any one of aspects 1-34, wherein the construct further comprises a gene that confers resistance to an antibiotic.

Aspect 36. The method of aspect 35, wherein the antibiotic comprises tetracycline, neomycin, kanamycin, ampicillin, hygromycin, chloramphenicol, amphotericin B, bacitracin, carbapenem, cephalosporin, ethambutol, fluoroquinolones, isoniazid, methicillin, oxacillin, vancomycin, streptomycin, quinolines, rifampin, rifampicin, sulfonamides, cephalothin, erythromycin, gentamicin, penicillin, other commonly-used antibiotics, or a combination thereof.

Aspect 37. The method according to any one of aspects 1-36, wherein the construct further comprises a gene for expressing a reporter protein.

Aspect 38. The method of aspect 37, wherein the gene for expressing the reporter protein expresses a fluorescent protein.

Aspect 39. The method of aspect 37, wherein the reporter protein comprises a red fluorescent protein, a cyan fluorescent protein, a green fluorescent protein, a yellow fluorescent protein, or a combination thereof.

Aspect 40. The method of aspect 37, wherein the reporter protein is a yellow fluorescent protein having SEQ ID NO. 5 or at least 70% homology thereof.

Aspect 41. The method according to any one of aspects 1-40, wherein the construct comprises from 5' to 3' the following genetic components in the following order: (1) a gene that expresses chitin synthase, (2) a gene that expresses chitosanase, and (3) a gene that expresses chitin deacetylase.

Aspect 42. The method according to any one of aspects 1-40, wherein the construct comprises from 5' to 3' the following genetic components in the following order: (1) a gene that expresses chitin synthase having SEQ ID NO. 2 or at least 70% homology thereto, (2) a gene that expresses chitosanase having SEQ ID NO. 3 or at least 70% homology thereto, and (3) a gene that expresses chitin deacetylase having SEQ ID NO. 4 or at least 70% homology thereto.

Aspect 43. The method according to any one of aspects 1-40, wherein the construct comprises from 5' to 3' the following genetic components in the following order: (1) a GAL1 promoter, (2) a gene that expresses chitin synthase, (3) a CYC1 terminator, (4) a GAL1 promoter, (5) a gene that expresses chitosanase, (6) a CYC1 terminator, (7) a GAL1 promoter, (8) a gene that expresses chitin deacetylase, and (9) a CYC1 terminator.

Aspect 44. The method according to any one of aspects 41-43, wherein the construct has SEQ ID NO. 7 or at least 70% homology thereto.

Aspect 45. The method according to any one of aspects 1-40, wherein the construct comprises from 5' to 3' the following genetic components in the following order: (1) a gene that expresses lipase, (2) a gene that expresses chitin synthase, (3) a gene that expresses chitosanase, and (4) a gene that expresses chitin deacetylase.

Aspect 46. The method according to any one of aspects 1-40, wherein the construct comprises from 5' to 3' the following genetic components in the following order: (1) a gene that expresses lipase having SEQ ID NO. 1 or at least 70% homology thereto, (2) a gene that expresses chitin synthase having SEQ ID NO. 2 or at least 70% homology thereto, (3) a gene that expresses chitosanase having SEQ ID NO. 3 or at least 70% homology thereto, and (4) a gene that expresses chitin deacetylase having SEQ ID NO. 4 or at least 70% homology thereto.

Aspect 47. The method according to any one of aspects 1-40, wherein the construct comprises from 5' to 3' the following genetic components in the following order: (1) a GAL1 promoter, (2) a gene that expresses lipase, (3) a GAL1 promoter, (4) a gene that expresses chitin synthase, (5) a CYC1 terminator, (6) a GAL1 promoter, (7) a gene that expresses chitosanase, (8) a CYC1 terminator, (9) a GAL1 promoter, (10) a gene that expresses chitin deacetylase, and (11) a CYC1 terminator.

Aspect 48. The method according to any of aspects 45-47, wherein the construct has SEQ ID NO. 8 or at least 70% homology thereto.

Aspect 49. The method according to any one of aspects 1-40, wherein the construct comprises from 5' to 3' the following genetic components in the following order: (1) a gene that expresses lipase, (2) a gene that expresses chitosanase, (3) a gene that expresses chitin synthase, and (4) a gene that expresses chitin deacetylase.

Aspect 50. The method according to any one of aspects 1-40, wherein the construct comprises from 5' to 3' the following genetic components in the following order: (1) a gene that expresses lipase having SEQ ID NO. 1 or at least 70% homology thereto, (2) a gene that expresses chitosanase having SEQ ID NO. 3 or at least 70% homology thereto, (3) a gene that expresses chitin synthase having SEQ ID NO. 2 or at least 70% homology thereto, and (4) a gene that expresses chitin deacetylase having SEQ ID NO. 4 or at least 70% homology thereto.

Aspect 51. The method according to any one of aspects 1-40, wherein the construct comprises from 5' to 3' the following genetic components in the following order: (1) a ribosomal binding site, (2) a gene that expresses lipase, (3) a ribosomal binding site, (4) a gene that expresses chitosanase, (5) a T7 promoter, (6) a ribosomal binding site, (7) a gene that expresses chitin synthase, (8) a ribosomal binding site, and (9) a gene that expresses chitin deacetylase.

Aspect 52. The method according to any of aspects 49 to 51, wherein the construct has SEQ ID NO. 9 or at least 70% homology thereto.

Aspect 53. The method according to any one of aspects 1-40, wherein the construct comprises from 5' to 3' the following genetic components in the following order: (1) a gene that expresses lipase, (2) a gene that expresses chitin synthase, (3) a gene that expresses chitosanase, (4) a gene that expresses chitin deacetylase, and (5) a gene that expresses (1→3),(1→4)-β-glucan synthase.

Aspect 54. The method according to any one of aspects 1-40, wherein the construct comprises from 5' to 3' the following genetic components in the following order: (1) a gene that expresses lipase having SEQ ID NO. 1 or at least 70% homology thereto, (2) a gene that expresses chitin synthase having SEQ ID NO. 2 or at least 70% homology thereto, (3) a gene that expresses chitosanase having SEQ ID NO. 3 or at least 70% homology thereto, (4) a gene that expresses chitin deacetylase having SEQ ID NO. 4 or at least 70% homology thereto, and (5) a gene that expresses (1→3),(1→4)-β-glucan synthase having SEQ ID NO. 6 or at least 70% homology thereto.

Aspect 55. The method according to any one of aspects 1-40, wherein the construct comprises from 5' to 3' the following genetic components in the following order: (1) a gene that expresses lipase, (2) a CYC1 terminator, (3) a GAL1 promoter, (4) a gene that expresses chitin synthase, (5) a CYC1 terminator, (6) a GAL1 promoter, (7) a gene that expresses chitosanase, (8) a CYC1 terminator, (9) a GAL1 promoter, (10) a gene that expresses chitin deacetylase, (11) a CYC1 terminator, (12) a GAL1 promoter, and (13) a gene that expresses (1→3),(1→4)-β-glucan synthase.

Aspect 56. The method according to any of aspects 53 to 55, wherein the construct has SEQ ID NO. 10 or at least 70% homology thereto.

Aspect 57. The method according to any one of aspects 1-40, wherein the construct comprises from 5' to 3' the following genetic components in the following order: (1) a gene that expresses chitin synthase, (2) a gene that expresses chitosanase, (3) a gene that expresses chitin deacetylase, and (4) a gene that expresses (1→3),(1→4)-β-glucan synthase.

Aspect 58. The method according to any one of aspects 1-40, wherein the construct comprises from 5' to 3' the following genetic components in the following order: (1) a gene that expresses chitin synthase having SEQ ID NO. 2 or at least 70% homology thereto, (2) a gene that expresses chitosanase having SEQ ID NO. 3 or at least 70% homology thereto, (3) a gene that expresses chitin deacetylase having SEQ ID NO. 4 or at least 70% homology thereto, and (4) a gene that expresses (1→3),(1→4)-β-glucan synthase having SEQ ID NO. 6 or at least 70% homology thereto.

Aspect 59. The method according to any one of aspects 1-40, wherein the construct comprises from 5' to 3' the following genetic components in the following order: (1) a gene that expresses chitin synthase, (2) a CYC1 terminator, (3) a GAL1 promoter, (4) a gene that expresses chitosanase, (5) a CYC1 terminator, (6) a GAL1 promoter, (7) a gene that expresses chitin deacetylase, (8) a CYC1 terminator, (9) a GAL1 promoter, and (10) a gene that expresses (1→3),(1→4)-β-glucan synthase.

Aspect 60. The method according to any of aspects 57 to 59, wherein the construct has SEQ ID NO. 10 or at least 70% homology thereto.

Aspect 61. The method according to any one of aspects 1-40, wherein the construct comprises from 5' to 3' the following genetic components in the following order: (1) a gene that expresses chitin synthase, (2) a gene that expresses chitosanase, (3) a gene that expresses chitin deacetylase, (4) a gene that expresses (1→3),(1→4)-β-glucan synthase, (5) a gene that expresses transglycosylase, and (6) a gene that expresses chitin synthase regulatory factor CHR1.

Aspect 62. The method of aspect 61, wherein the construct further comprises a promoter.

Aspect 63. The method of aspect 62, wherein the promoter comprises a GAL1 promoter, a T7 promoter, or both.

Aspect 64. The method of aspect 61, wherein the promoter is a GAL1 promoter, and wherein the promoter precedes the gene that expresses chitin synthase, the gene that expresses chitosanase, the gene that expresses chitin deacetylase, the gene that expresses (1→3),(1→4)-β-glucan synthase, the gene that expresses chitin synthase regulatory factor CRH1, the gene that expresses transglycosylase, or any combination thereof.

Aspect 65. The method of any of aspects 1-64, further comprising contacting the plant with a second extract produced from a second biological device, wherein the second biological device comprises second host cells transformed with a supplemental DNA construct comprising the following genetic components: (a) a gene that expresses transglycosylase and (b) a gene that expresses chitin synthase regulatory factor CRH1.

Aspect 66. The method according to aspect 65, wherein the supplemental DNA construct comprises from 5' to 3' the following genetic components in the following order: (1) a gene that expresses transglycosylase (2) a gene that expresses chitin synthase regulatory factor CRH1.

Aspect 67. The method according to aspect 65, wherein the supplemental DNA construct comprises from 5' to 3' the following genetic components in the following order: (1) a gene that expresses transglycosylase having SEQ ID NO. 15 or at least 70% homology thereto and (2) a gene that expresses chitin synthase regulatory factor CRH1 having SEQ ID NO. 16 or at least 70% homology thereto.

Aspect 68. The method according to aspect 65, wherein the supplemental DNA construct comprises from 5' to 3' the following genetic components in the following order: (1) a gene that expresses transglycosylase, (2) a CYC1 terminator, (3) a GAL1 promoter, and (4) a gene that expresses chitin synthase regulatory factor 1.

Aspect 69. The method according to any of aspects 66-68, wherein the supplemental DNA construct has SEQ ID NO. 10 or at least 70% homology thereto.

Aspect 70. The method of any of aspects 65-69, wherein the biological device and the second biological device are cultured separately.

Aspect 71. The method of aspect 70, further comprising admixing a culture of the biological device and a culture of the second biological device to create a mixed culture prior to performing the method.

Aspect 72. The method of aspect 71, wherein the mixed culture comprises the extract and the second extract.

Aspect 73. The method according to any one of aspects 1-64, wherein the DNA construct comprises a vector.

Aspect 74. The method of aspect 73, wherein the vector is a plasmid.

Aspect 75. The method of aspect 73, wherein the vector is pWLNEO, pSV2CAT, pOG44, pXTI, pSG, pSVK3, pBSK, pBR322, pYES, pYES2, pBSKII, pUC, pUC19, or pET-Duet-1.

Aspect 76. The method of aspect 73, wherein the vector is pYES2.

Aspect 77. The method of aspect 73, wherein the vector is pBSK.

Aspect 78. The method of aspect 73, wherein the vector is pETDuet-1.

Aspect 79. The method according to any one of aspects 1-78, wherein the host cells comprise yeast or bacteria.

Aspect 80. The method of aspect 79, wherein the bacteria comprise *Escherichia coli*.

Aspect 81. The method of aspect 79, wherein the yeast comprise *Saccharomyces cerevisiae*.

Aspect 82. The method according to any one of aspects 65-72, wherein the supplemental DNA construct comprises a second vector.

Aspect 83. The method of aspect 82, wherein the second vector is a second plasmid.

Aspect 84. The method of aspect 82, wherein the second vector is pWLNEO, pSV2CAT, pOG44, pXTI, pSG, pSVK3, pBSK, pBR322, pYES, pYES2, pBSKII, pUC, pUC19, or pETDuet-1.

Aspect 85. The method of aspect 82, wherein the second vector is pYES2.

Aspect 86. The method according to any one of aspects 65-72 or 81-85, wherein the second host cells comprise yeast.

Aspect 87. The method of aspect 86, wherein the yeast comprise *Saccharomyces cerevisiae*.

Aspect 88. A DNA construct comprising the following genetic components: (1) a gene that expresses chitin synthase, (2) a gene that expresses chitosanase, (3) a gene that expresses chitin deacetylase, and (4) a gene that expresses (1→3),(1→4)-β-glucan synthase.

Aspect 89. The DNA construct of aspect 88, wherein the construct further comprises a gene that expresses lipase.

Aspect 90. The DNA construct of aspect 88, wherein the gene that expresses lipase has SEQ ID NO. 1 or at least 70% homology thereto.

Aspect 91. The DNA construct of aspect 88, wherein the gene that expresses chitin synthase has SEQ ID NO. 2 or at least 70% homology thereto.

Aspect 92. The DNA construct of aspect 88, wherein the gene that expresses chitosanase has SEQ ID NO. 3 or at least 70% homology thereto.

Aspect 93. The DNA construct of aspect 88, wherein the gene that expresses chitin deacetylase has SEQ ID NO. 4 or at least 70% homology thereto.

Aspect 94. The DNA construct of aspect 88, wherein the gene that expresses (1→3),(1→4)-β-glucan synthase has SEQ ID NO. 6 or at least 70% homology thereto.

Aspect 95. The DNA construct of any one of aspects 88-94, wherein the construct further comprises a gene that expresses chitin synthase regulatory factor CHR1.

Aspect 96. The DNA construct of aspect 95, wherein the gene that expresses chitin synthase regulatory factor CHR1 has SEQ ID NO. 11 or at least 70% homology thereof.

Aspect 97. The DNA construct of aspect 95, wherein the gene that expresses chitin synthase regulatory factor CHR1 has SEQ ID NO. 16 or at least 70% homology thereof.

Aspect 98. The DNA construct of aspects 88-96, wherein the construct further comprises a gene that expresses transglycosylase.

Aspect 99. The DNA construct of aspect 98, wherein the gene that expresses transglycosylase has SEQ ID NO. 12 or at least 70% homology thereof.

Aspect 100. The DNA construct of aspect 98, wherein the gene that expresses transglycosylase has SEQ ID NO. 15 or at least 70% homology thereof.

Aspect 101. The DNA construct in any one of aspects 88-99, wherein the construct further comprises a gene that expresses a dehydrogenase.

Aspect 102. The DNA construct of aspect 101, wherein the gene that expresses dehydrogenase expresses a protein having SEQ ID NO. 13 or at least 70% homology thereof.

Aspect 103. The DNA construct of aspect 88, wherein the construct further comprises a promoter.

Aspect 104. The DNA construct of aspect 103, wherein the promoter comprises a GAL1 promoter, a T7 promoter, or both.

Aspect 105. The DNA construct of aspect 103, wherein the promoter is a GAL1 promoter and wherein the promoter precedes the gene that expresses lipase, the gene that expresses chitin synthase, the gene that expresses chitosanase, the gene that expresses chitin deacetylase, the gene that expresses (1→3),(1→4)-β-glucan synthase, gene that expresses chitin synthase regulatory factor CHR1, gene that expresses transglycosylase, the gene that expresses dehydrogenase, or any combination thereof.

Aspect 106. The DNA construct of aspect 88, wherein the construct further comprises a terminator.

Aspect 107. The DNA construct of aspect 106, wherein the terminator is a CYC1 terminator.

Aspect 108. The DNA construct of any of aspects 88-107, wherein the DNA construct comprises from 5' to 3' the following genetic components in the following order: (1) a gene that expresses chitin synthase, (2) a gene that expresses chitosanase, and (3) a gene that expresses chitin deacetylase.

Aspect 109. The DNA construct of any one of aspects 88-107, wherein the DNA construct comprises from 5' to 3' the following genetic components in the following order: (1) a gene that expresses chitin synthase having SEQ ID NO. 2 or at least 70% homology thereto, (2) a gene that expresses chitosanase having SEQ ID NO. 3 or at least 70% homology thereto, and (3) a gene that expresses chitin deacetylase having SEQ ID NO. 4 or at least 70% homology thereto.

Aspect 110. The DNA construct of any one of aspects 88-107, wherein the DNA construct comprises from 5' to 3' the following genetic components in the following order: (1) a GAL1 promoter, (2) a gene that expresses chitin synthase, (3) a CYC1 terminator, (4) a GAL1 promoter, (5) a gene that expresses chitosanase, (6) a CYC1 terminator, (7) a GAL1 promoter, (8) a gene that expresses chitin deacetylase, and (9) a CYC1 terminator.

Aspect 111. The DNA construct of any one of aspects 108-110, wherein the DNA construct has SEQ ID NO. 7 or at least 70% homology thereto.

Aspect 112. The DNA construct of any one of aspects 88-107, wherein the DNA construct comprises from 5' to 3' the following genetic components in the following order: (1) a gene that expresses lipase, (2) a gene that expresses chitin synthase, (3) a gene that expresses chitosanase, and (4) a gene that expresses chitin deacetylase.

Aspect 113. The DNA construct of any one of aspects 88-107, wherein the DNA construct comprises from 5' to 3' the following genetic components in the following order: (1) a gene that expresses lipase having SEQ ID NO. 1 or at least 70% homology thereto, (2) a gene that expresses chitin synthase having SEQ ID NO. 2 or at least 70% homology thereto, (3) a gene that expresses chitosanase having SEQ ID NO. 3 or at least 70% homology thereto, and (4) a gene that expresses chitin deacetylase having SEQ ID NO. 4 or at least 70% homology thereto.

Aspect 114. The DNA construct of any one of aspects 88-107, wherein the DNA construct comprises from 5' to 3' the following genetic components in the following order: (1) a GAL1 promoter, (2) a gene that expresses lipase, (3) a GAL1 promoter, (4) a gene that expresses chitin synthase, (5) a CYC1 terminator, (6) a GAL1 promoter, (7) a gene that expresses chitosanase, (8) a CYC1 terminator, (9) a GAL1 promoter, (10) a gene that expresses chitin deacetylase, and (11) a CYC1 terminator.

Aspect 115. The DNA construct of any of aspects 112-114, wherein the DNA construct has SEQ ID NO. 8 or at least 70% homology thereto.

Aspect 116. The DNA construct of any one of aspects 88-107, wherein the DNA construct comprises from 5' to 3' the following genetic components in the following order: (1) a gene that expresses lipase, (2) a gene that expresses chitosanase, (3) a gene that expresses chitin synthase, and (4) a gene that expresses chitin deacetylase.

Aspect 117. The DNA construct of any one of aspects 88-107, wherein the DNA construct comprises from 5' to 3' the following genetic components in the following order: (1) a gene that expresses lipase having SEQ ID NO. 1 or at least 70% homology thereto, (2) a gene that expresses chitosanase having SEQ ID NO. 3 or at least 70% homology thereto, (3) a gene that expresses chitin synthase having SEQ ID NO. 2 or at least 70% homology thereto, and (4) a gene that expresses chitin deacetylase having SEQ ID NO. 4 or at least 70% homology thereto.

Aspect 118. The DNA construct of any one of aspects 88-107, wherein the DNA construct comprises from 5' to 3' the following genetic components in the following order: (1) a ribosomal binding site, (2) a gene that expresses lipase, (3) a ribosomal binding site, (4) a gene that expresses chitosanase, (5) a T7 promoter, (6) a ribosomal binding site, (7) a gene that expresses chitin synthase, (8) a ribosomal binding site, and (9) a gene that expresses chitin deacetylase.

Aspect 119. The DNA construct of any of aspects 116-118, wherein the DNA construct has SEQ ID NO. 9 or at least 70% homology thereto.

Aspect 120. The DNA construct of any one of aspects 88-107, wherein the DNA construct comprises from 5' to 3' the following genetic components in the following order: (1) a gene that expresses lipase, (2) a gene that expresses chitin synthase, (3) a gene that expresses chitosanase, (4) a gene that expresses chitin deacetylase, and (5) a gene that expresses (1→3),(1→4)-β-glucan synthase.

Aspect 121. The DNA construct of any one of aspects 88-107, wherein the DNA construct comprises from 5' to 3' the following genetic components in the following order: (1) a gene that expresses lipase having SEQ ID NO. 1 or at least 70% homology thereto, (2) a gene that expresses chitin synthase having SEQ ID NO. 2 or at least 70% homology thereto, (3) a gene that expresses chitosanase having SEQ ID NO. 3 or at least 70% homology thereto, (4) a gene that expresses chitin deacetylase having SEQ ID NO. 4 or at least 70% homology thereto, and (5) a gene that expresses (1→3),(1→4)-β-glucan synthase having SEQ ID NO. 6 or at least 70% homology thereto.

Aspect 122. The DNA construct of any one of aspects 88-107, wherein the DNA construct comprises from 5' to 3' the following genetic components in the following order: (1)

a gene that expresses lipase, (2) a CYC1 terminator, (3) a GAL1 promoter, (4) a gene that expresses chitin synthase, (5) a CYC1 terminator, (6) a GAL1 promoter, (7) a gene that expresses chitosanase, (8) a CYC1 terminator, (9) a GAL1 promoter, (10) a gene that expresses chitin deacetylase, (11) a CYC1 terminator, (12) a GAL1 promoter, and (13) a gene that expresses (1→3),(1→4)-β-glucan synthase.

Aspect 123. The DNA construct of any of aspects 120-122, wherein the DNA construct has SEQ ID NO. 10 or at least 70% homology thereto.

Aspect 124. The DNA construct of any one of aspects 88-107, wherein the DNA construct comprises from 5' to 3' the following genetic components in the following order: (1) a gene that expresses chitin synthase, (2) a gene that expresses chitosanase, (3) a gene that expresses chitin deacetylase, and (4) a gene that expresses (1→3),(1→4)-β-glucan synthase.

Aspect 125. The DNA construct of any one of aspects 88-107, wherein the DNA construct comprises from 5' to 3' the following genetic components in the following order: (1) a gene that expresses chitin synthase having SEQ ID NO. 2 or at least 70% homology thereto, (2) a gene that expresses chitosanase having SEQ ID NO. 3 or at least 70% homology thereto, (3) a gene that expresses chitin deacetylase having SEQ ID NO. 4 or at least 70% homology thereto, and (4) a gene that expresses (1→3),(1→4)-β-glucan synthase having SEQ ID NO. 6 or at least 70% homology thereto.

Aspect 126. The DNA construct of any one of aspects 88-107, wherein the DNA construct comprises from 5' to 3' the following genetic components in the following order: (1) a gene that expresses chitin synthase, (2) a CYC1 terminator, (3) a GAL1 promoter, (4) a gene that expresses chitosanase, (5) a CYC1 terminator, (6) a GAL1 promoter, (7) a gene that expresses chitin deacetylase, (8) a CYC1 terminator, (9) a GAL1 promoter, and (10) a gene that expresses (1→3),(1→4)-β-glucan synthase.

Aspect 127. The DNA construct of any of aspects 88-107, wherein the DNA construct has SEQ ID NO. 10 or at least 70% homology thereto.

Aspect 128. The DNA construct of any one of aspects 88-128, wherein the construct further comprises a gene that confers resistance to an antibiotic.

Aspect 129. The DNA construct of aspect 128, wherein the antibiotic comprises tetracycline, neomycin, kanamycin, ampicillin, hygromycin, chloramphenicol, amphotericin B, bacitracin, carbapenem, cephalosporin, ethambutol, fluoroquinolones, isoniazid, methicillin, oxacillin, vancomycin, streptomycin, quinolines, rifampin, rifampicin, sulfonamides, cephalothin, erythromycin, gentamicin, penicillin, other commonly-used antibiotics, or a combination thereof.

Aspect 130. The DNA construct of any one of aspects 88-129, wherein the construct further comprises a gene for expressing a reporter protein.

Aspect 131. The DNA construct of aspect 130, wherein the reporter protein is a fluorescent protein.

Aspect 132. The DNA construct of aspect 130, wherein the reporter protein comprises a red fluorescent protein, a cyan fluorescent protein, a green fluorescent protein, a yellow fluorescent protein, or a combination thereof.

Aspect 133. The DNA construct of aspect 130, wherein the reporter protein is a yellow fluorescent protein having SEQ ID NO. 5 or at least 70% homology thereto.

Aspect 134. A vector comprising the DNA construct of any of aspects 88-133.

Aspect 135. The vector of aspect 134, wherein the vector is a plasmid.

Aspect 136. The vector of aspect 134, wherein the vector is pWLNEO, pSV2CAT, pOG44, pXTI, pSG, pSVK3, pBSK, pBR322, pYES, pYES2, pBSKII, pUC, pUC19, or pETDuet-1.

Aspect 137. The vector of aspect 136, wherein the vector is pYES2.

Aspect 138. A biological device comprising host cells transformed with the DNA construct in any one of aspects 88-133.

Aspect 139. The biological device of aspect 138, wherein the host cells comprise yeast or bacteria.

Aspect 140. The biological device of aspect 139, wherein the yeast comprise *Saccharomyces cerevisiae.*

Aspect 141. The biological device of aspect 139, wherein the bacteria comprise *Escherichia coli.*

Aspect 142. A supplemental DNA construct comprising the following genetic components: (1) a gene that expresses transglycosylase and (2) a gene that expresses chitin synthase regulatory factor CHR1.

Aspect 143. The supplemental DNA construct of aspect 142, wherein the gene that expresses transglycosylase has SEQ ID NO. 15 or at least 70% homology thereto.

Aspect 144. The supplemental DNA construct of aspect 142 or 143, wherein the gene that expresses chitin synthase regulatory factor CHR1 has SEQ ID NO. 16 or at least 70% homology thereto.

Aspect 145. The supplemental DNA construct of any of aspects 142-144, wherein the supplemental DNA construct has SEQ ID NO. 17 or at least 70% homology thereto.

Aspect 146. The supplemental DNA construct of any one of aspects 142-145, wherein the supplemental DNA construct further comprises a gene that confers resistance to an antibiotic.

Aspect 147. The supplemental DNA construct of aspect 146, wherein the antibiotic comprises tetracycline, neomycin, kanamycin, ampicillin, hygromycin, chloramphenicol, amphotericin B, bacitracin, carbapenem, cephalosporin, ethambutol, fluoroquinolones, isoniazid, methicillin, oxacillin, vancomycin, streptomycin, quinolines, rifampin, rifampicin, sulfonamides, cephalothin, erythromycin, gentamicin, penicillin, other commonly-used antibiotics, or a combination thereof.

Aspect 148. A second vector comprising the supplemental DNA construct of any of aspects 142-147.

Aspect 149. The second vector of aspect 148, wherein the second vector is a plasmid.

Aspect 150. The second vector of aspect 148, wherein the second vector is pWLNEO, pSV2CAT, pOG44, pXTI, pSG, pSVK3, pBSK, pBR322, pYES, pYES2, pBSKII, pUC, pUC19, or pETDuet-1.

Aspect 151. The second vector of aspect 150, wherein the second vector is pYES2.

Aspect 152. A second biological device comprising second host cells transformed with the supplemental DNA construct in any one of aspects 142-147.

Aspect 153. The second biological device of aspect 152, wherein the second host cells comprise yeast.

Aspect 154. The second biological device of aspect 153, wherein the yeast comprise *Saccharomyces cerevisiae.*

Aspect 155. A polyactive carbohydrate produced by the biological device of aspects 138-141.

Aspect 156. A polyactive carbohydrate produced by the biological device of aspects 138-141 and the second biological device of aspects 152-154.

Aspect 157. A polyurethane composition produced by the process comprising admixing the polyactive carbohydrate of aspect 155 or 156 and a natural oil polyol to produce a first admixture; and reacting the first admixture with a polyisocyanate to produce the polyurethane composition.

Aspect 158. The polyurethane composition of aspect 157, wherein step (a) further comprises admixing a surfactant, wherein the surfactant is a cationic surfactant, an anionic surfactant, a zwitterionic surfactant, or a nonionic surfactant.

Aspect 159. The polyurethane composition of aspect 157, wherein step (a) further comprises admixing a surfactant, wherein the surfactant is a polysorbate, a lecithin, an alcohol ethoxylate, or PEG-40 hydrogenated castor oil.

Aspect 160. The polyurethane composition of aspect 159, wherein the polysorbate is polysorbate 20 or polysorbate 80.

Aspect 161. The polyurethane composition of aspect 157, wherein the natural oil polyol comprises or is derived from soy oil, castor oil, a chemically-modified vegetable oil, a carbohydrate, lignin, cork, cashew nutshell liquid, *Lesquerella* oil, or a combination thereof.

Aspect 162. The polyurethane composition of aspect 157, wherein the natural oil polyol comprises castor oil, ricinoleic acid, or a combination thereof.

Aspect 163. The polyurethane composition of aspect 157, wherein the polyisocyanate comprises 2,4-toluenediisocyanate, 2,6-toluenediisocyanate, 4,4'-methylene diphenyl diisocyanate (MDI), 4,4'-methylenebis(cyclohexylisocyanate) (H12-MDI), 1-isocyanato-β-isocyanato-methyl-3,5,5-trimethylcyclohexane (isophorone diisocyanate), 2,4,4-trimethylhexamethylenediisocyanate, ethylidenediisocyanate, butylenediisocyanate, hexamethylenediisocyanate, cyclohexylene-1,4-diisocyanate, cyclohexylene-1,2-diisocyanate, xylylene diisocyanate, dichlorohexamethylene diisocyanate, dicyclohexyl-4,4'-diisocyanate, 1-methyl-2,4-diisocyanato-cyclohexane, 1-methyl-2,6-diisocyanato-cyclohexane, naphthalene-1,5-diisocyanate, p-phenylendiisocyanate, tetramethyl-xylylenediisocyanate (TMXDI), or any combination thereof.

Aspect 164. The polyurethane composition of aspect 157, wherein the ratio of polyisocyanate to the first admixture formed is from 1:1 to 1:8.

Aspect 165. The polyurethane composition of aspect 157, wherein the polyisocyanate comprises 2,4-toluenediisocyanate and 2,6-toluenediisocyanate.

Aspect 166. The polyurethane composition of aspect 157, wherein the polyisocyanate is 4,4'-methylene diphenyl diisocyanate.

Aspect 167. The polyurethane composition of aspect 157, wherein step (a) further comprises admixing a filler.

Aspect 168. The polyurethane composition of aspect 167, wherein the filler is a clay.

Aspect 169. The polyurethane composition of aspect 167, wherein the clay is bentonite, montmorillonite, kaolinite, or a zeolite.

Aspect 170. The polyurethane composition of aspect 167, wherein the filler is a metal or semimetal oxide or a chelated metal ion.

Aspect 171. The polyurethane composition of aspect 157, wherein the polyactive carbohydrate is from 0.1 to 1% by weight of the first admixture. 172. The polyurethane composition of aspect 157, wherein the natural oil polyol is from 20 to 80 vol % of the first admixture.

Aspect 173. The polyurethane composition of aspect 157, wherein the natural oil polyol is castor oil.

Aspect 174. A biofoam comprising the polyurethane composition of aspects 157-173.

Aspect 175. The biofoam of aspect 174, wherein the polyurethane composition is dried to remove residual solvent.

Aspect 176. The biofoam of aspect 174, wherein the polyurethane composition is dried from 20° C. to 70° C.

Aspect 177. The biofoam of aspect 174, wherein the polyurethane composition is dried in an oven from 0.5 hour to 100 hours.

Aspect 178. The biofoam of aspect 174, wherein (1) the polyurethane composition is poured into a mold, and (2) the polyurethane composition is dried to remove residual solvent.

Aspect 179. The biofoam of aspect 174, further comprising a flame retardant, a color additive, a release agent, a biocide, another additive, or a combination thereof.

Aspect 180. The biofoam of aspect 174, further comprising a blowing agent.

Aspect 181. The biofoam of aspect 180, wherein the blowing agent is a physical blowing agent.

Aspect 182. The biofoam of aspect 181, wherein the physical blowing agent is a hydrofluorocarbon, a hydrocarbon, a hydrofluoroolefin, liquid carbon dioxide, or another low boiling point liquid.

Aspect 183. The biofoam of aspect 180, wherein the blowing agent is a chemical blowing agent.

Aspect 184. The biofoam of aspect 183, wherein the chemical blowing agent is carbon dioxide produced by the reaction of isocyanate groups with water.

Aspect 185. An article comprising the biofoam in any one of aspects 174-184.

EXAMPLES

The following examples are put forth so as to provide those of ordinary skill in the art with a complete disclosure and description of how the compounds, compositions, and methods described and claimed herein are made and evaluated, and are intended to be purely exemplary and are not intended to limit the scope of what the inventors regard as their invention. Efforts have been made to ensure accuracy with respect to numbers (e.g., amounts, temperatures, etc.) but some errors and deviations should be accounted for. Unless indicated otherwise, parts are parts by weight, temperature is in ° C. or is at ambient temperature, and pressure is at or near atmospheric. Numerous variations and combinations of reaction conditions, e.g., component concentrations, desired solvents, solvent mixtures, temperatures, pressures, and other reaction ranges and conditions can be used to optimize the product purity and yield obtained from the described process. Only reasonable and routine experimentation will be required to optimize such processes and conditions.

Example 1: Preparation of DNA Construct for Production of Polyactive Carbohydrates The DNA construct was composed of the genetic components described herein and assembled in plasmid vectors (e.g., pYES2, pBSK, pETDuet-1). Sequences of genes and/or proteins with desired properties were identified in GenBank; these included a gene that expresses lipase, a gene that expresses chitin synthase, a gene that expresses chitosanase, and a gene that expresses chitin deacetylase. In some experiments, genes that express regulatory sequence CHR1, transglycosylase, dehydrogenase, and/or (1→3),(1→4)-β-glucan synthase were also identified in GenBank. These sequences were synthesized by CloneTex Systems, Inc. (Austin, TX). Other genetic parts were also obtained for inclusion in the DNA constructs including, for example, promoter genes (e.g., GAL1 promoter), reporter genes (e.g., yellow fluorescent reporter protein), and terminator sequences (e.g., CYC1 terminator). These genetic parts included restriction sites for ease of insertion into plasmid vectors. Lipase was included in some constructs and was functional at any position in the construct. However, a position 5' of the gene for expressing chitin synthase was preferable when the lipase gene was included.

The cloning of the DNA construct into the biological devices was performed as follows. Sequences of individual genes were amplified by polymerase chain reaction using primers that incorporated restriction sites at their 5' ends (in a typical experiment, the restriction sites matched enzymes HindIII and XbaI) to facilitate construction of the full sequence to be inserted into the plasmid. Genes were then ligated using standard protocols to form an insert. The plasmid was then digested with restriction enzymes according to directions and using reagents provided by the enzymes' supplier (Promega). The complete insert, containing restriction sites on each end, was then ligated into the plasmid. Successful construction of the insert and ligation of the insert into the plasmid were confirmed by gel electrophoresis.

From 5' to 3', one version of the construct includes (a) a gene that expresses chitin synthase, (b) a CYC1 terminator, (c) a GAL1 promoter, (d) a gene that expresses chitosanase, (e) a CYC1 terminator, (f) a GAL1 promoter, (g) a gene that expresses chitin deacetylase, (h) a CYC1 terminator, (i) a GAL1 promoter, and (j) a yellow fluorescent reporter protein (FIGS. 1A and 1B).

From 5' to 3', a second version of the construct includes (a) a gene that expresses lipase, (b) a CYC1 terminator, (c) a GAL1 promoter, (d) a gene that expresses chitin synthase, (e) a CYC1 terminator, (f) a GAL1 promoter, (g) a gene that expresses chitosanase, (h) a CYC1 terminator, (i) a GAL1 promoter, (j) a gene that expresses chitin deacetylase, (k) a CYC1 terminator, (1) a GAL1 promoter, and (m) a yellow fluorescent reporter protein (FIGS. 2A and 2B).

From 5' to 3', a third version of the construct includes (a) a gene that expresses lipase, (b) a ribosomal binding site, (c) a gene that expresses chitosanase, (d) a T7 promoter, (e) a LAC operon, (f) a ribosomal binding site, (g) a gene that expresses chitin synthase, (h) a ribosomal binding site, and (i) a gene that expresses chitin deacetylase (FIGS. 3A and 3B).

From 5' to 3' a fourth version of the construct includes (a) a gene that expresses lipase, (b) a CYC1 terminator, (c) a GAL1 promoter, (d) a gene that expresses chitin synthase, (e) a CYC1 terminator, (f) a GAL1 promoter, (g) a gene that expresses chitosanase, (h) a CYC1 terminator, (i) a GAL1 promoter, (j) a gene that expresses chitin deacetylase, (k) a CYC1 terminator, (1) a GAL1 promoter, (m) a yellow fluorescent reporter protein, (n) a GAL1 promoter, and (o) a gene that expresses (1→3),(1→4)-o glucan synthase (FIGS. 4A and 4B).

From 5' to 3' a fourth version of the construct includes (a) a gene that expresses chitin synthase, (b) a CYC1 terminator, (c) a GAL1 promoter, (d) a gene that expresses chitosanase, (e) a CYC1 terminator, (f) a GAL1 promoter, (g) a gene that expresses chitin deacetylase, (h) a CYC1 terminator, (i) a GAL1 promoter, (j) a yellow fluorescent reporter protein, (k) a GAL1 promoter, and (1) a gene that expresses (1→3), (1→4)-o glucan synthase (FIGS. 9A and 9B).

Figure 10A:
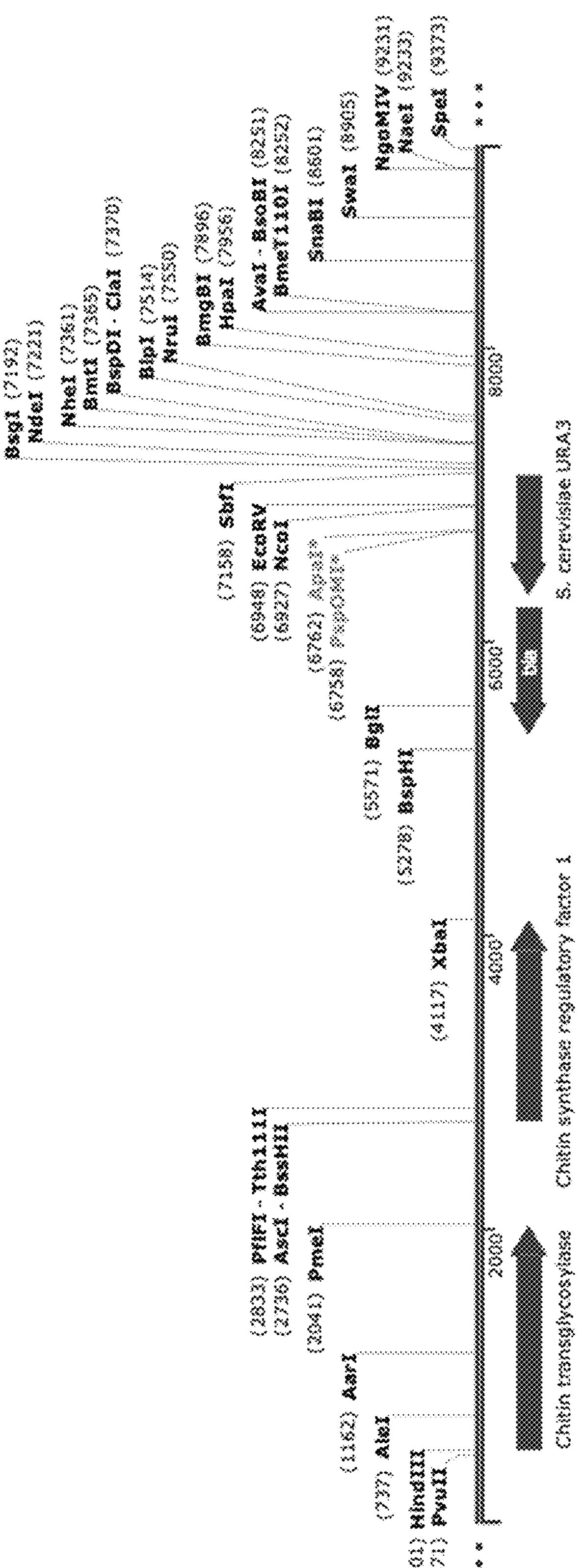
FIGS. 10A and 10B show, respectively, a linear and a circular schematic of a constructed pYES2 plasmid showing the direction, placement, and size of genetic parts of an exemplary DNA device disclosed herein.
Figure 10B:
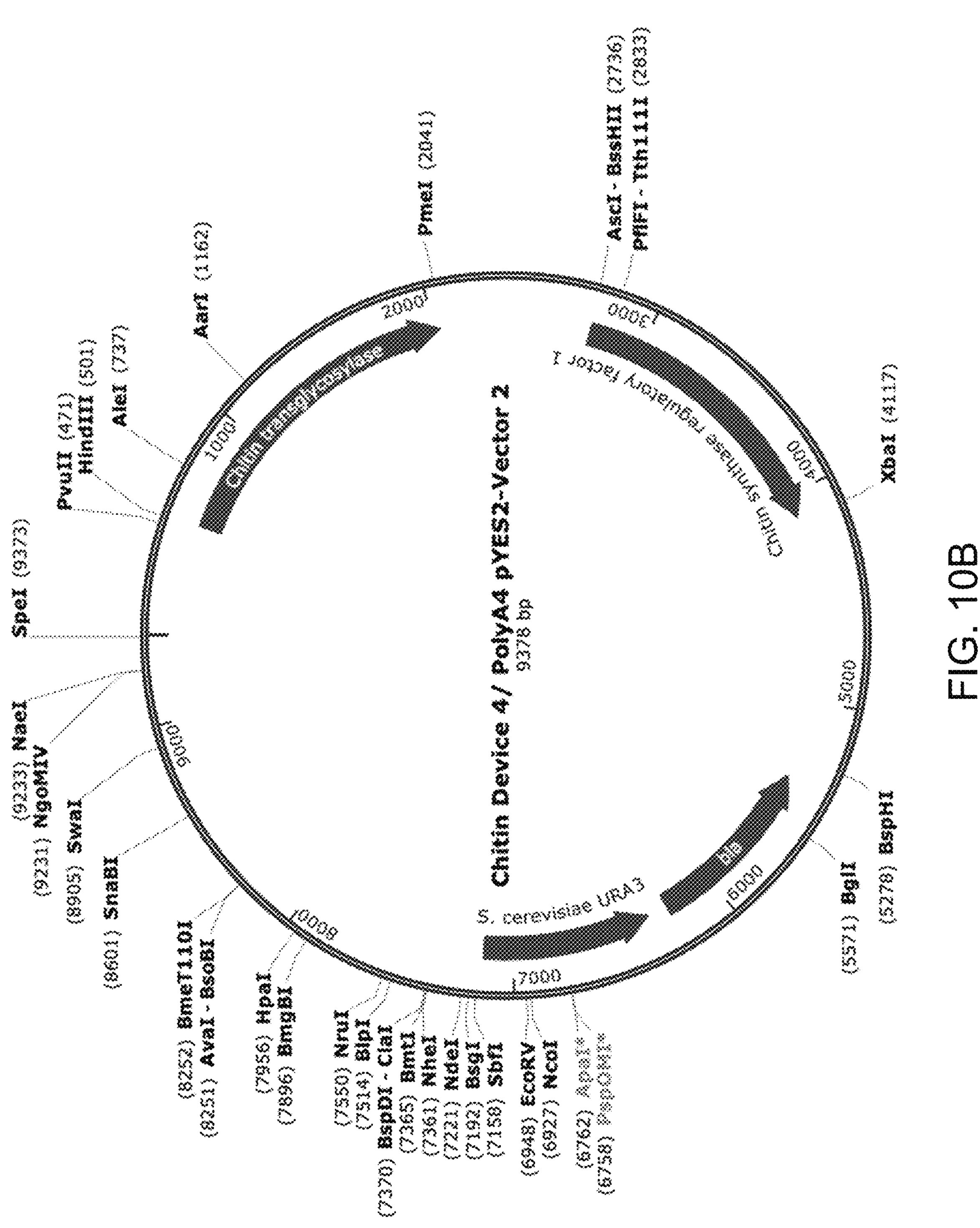

From 5' to 4' a supplemental DNA construct includes (a) a gene that expresses transglycosylase, (b) a CYC1 terminator, (c) a GAL1 promoter, and (d) a gene that expresses chitin synthase regulatory factor CHR1 (FIGS. 10A and 10B).

PCR was used to enhance DNA concentration using a Mastercycler Personal 5332 ThermoCycler (Eppendorf North America) with specific sequence primers and the standard method for amplification (Sambrook, J., E. F. Fritsch, and T. Maniatis, 1989*, Molecular Cloning: A Laboratory Manual,* $2^{nd}$ ed., Vol. 1, Cold Spring Harbor Laboratory Press: Cold Spring Harbor, NY). Digestion and ligation were used to ensure assembly of DNA synthesized parts using restriction enzymes and reagents (PCR master mix of restriction enzymes: XhoI, KpnI, XbaI, EcoRI, BamHI, and HindIII, with alkaline phosphatase and quick ligation kit, all from Promega). DNA was quantified using a NanoVue spectrophotometer (GE Life Sciences) and a standard UV/Visible spectrophotometer using the ratio of absorbances at 260 nm and 280 nm. In order to verify final ligations, DNA was visualized and purified via electrophoresis using a Thermo EC-150 power supply.

The DNA construct was made with gene parts fundamental for expression of sequences such as, for example, native and constitutive promoters, reporter genes, and transcriptional terminators or stops. Backbone plasmids and synthetic inserts can be mixed together for ligation purposes at different ratios ranging from 1:1, 1:2, 1:3, 1:4, and up to 1:5. In one aspect, the ratio of backbone plasmid to synthetic insert is 1:4. After the vector having the DNA construct has been produced, the resulting vector can be incorporated into the host cells using the method described below.

A DNA device for the production of polyactive carbohydrates was constructed by assembling a plasmid (e.g., pYES2) having the following genetic components in the following order: (a) a gene that expresses chitin synthase having SEQ ID NO. 2, (b) a CYC1 terminator, (c) a GAL1 promoter, (d) a gene that expresses chitosanase having SEQ ID NO. 3, (e) a CYC1 terminator, (f) a GAL1 promoter, (g) a gene that expresses chitin deacetylase having SEQ ID NO. 4, (h) a CYC1 terminator, (i) a GAL1 promoter, and (j) a yellow fluorescent reporter protein having SEQ ID NO. 5. The DNA construct having SEQ ID NO. 7 was transformed into cells, as described below, to produce the biological devices. Plasmids containing exemplary DNA constructs as disclosed herein are shown in FIGS. 1A, 1B, 2A, 2B, 3A, 3B, 4A, 4B, 9A, and 9B. Plasmids containing exemplary supplemental DNA constructs as disclosed herein are shown in FIGS. 10A and 10B.

Example 2: Selection of Microorganisms

The polyactive carbohydrate was produced using transfected yeasts (*Saccharomyces cerevisiae*, ATCC® 200892™).

Alternatively, bacterial devices were constructed with one of the following strains of cells: *Escherichia coli*, ONE-SHOT® Top10 competent cells from Life Technologies™, BL21 (DE3) *E. coli* from Novagen, Inc., or DH5α™ *E. coli* from Thermo Fisher Scientific.

Example 3: Development of Competent Yeast Cells

Yeast cells were made competent by subjecting them to an electrochemical process adapted from Gietz and Schiestl (*Nature Protocols,* 2007, 2:35-37). Briefly, a single yeast colony was inoculated into 100 mL YPD (yeast extract peptone dextrose) growth media. Yeast was grown overnight on a shaker at 30° C. to $OD_{600}$=1.0. (Acceptable results were obtained with $OD_{600}$ values ranging from 0.6 to 1.8.) Cells were centrifuged at 2000 rpm in a tabletop centrifuge and resuspended in 10 mL TEL buffer (10 mM Tris-HCl, 1 mM EDTA, 0.1 M LiAc, pH=7.5) and shaken vigorously overnight at room temperature. Cells were again centrifuged and resuspended in 1 mL TEL buffer. Cells prepared in this manner could be stored in the refrigerator for up to one month.

Example 4: Transformation of Microbial Cells to Produce Polyactive Carbohydrate Devices Competent cells were stored in the freezer until needed. Cells were thawed on ice and 100 μL of competent cells in TEL buffer were placed in a sterile 1.5 mL microcentrifuge tube. To this was added 5 μL of a 10 mg/mL solution of salmon sperm DNA (carrier DNA). Transforming DNA was added in various amounts. From 1 to 5 g was sufficient for plasmids from commercial sources, but more DNA was required when transforming yeast with artificial DNA constructs. 10 μL of the DNA device were added to the microcentrifuge tube containing the competent yeast cells and the contents of the tube were mixed. The DNA-yeast suspension was incubated for 30 min at room temperature.

A PLATE solution (consisting of 40% PEG-3350 in 1×TEL buffer) was prepared. 0.7 mL of PLATE solution was added to the DNA-yeast suspension and the contents were mixed thoroughly and incubated for 1 h at room temperature. The mixture was placed in an electromagnetic chamber for 30 minutes. Cells were then heated at 42° C. for 5-10 minutes and 250 μL aliquots were plated on yeast malt agar to which selective growth compounds had been added. Plates were incubated overnight at 30° C.

DNA expression and effectiveness of transformation were determined by fluorescence of the transformed cells expressed in fluorescence units (FSUs) using a 20/20 Luminometer (Promega) according to a protocol provided by the manufacturer. Plasmid DNA extraction, purification, PCR, and gel electrophoresis were also used to confirm transformation. Different transformed devices were obtained. Different types of fluorescent reporter proteins were used (e.g., yellow, red, green, and cyan) for all transformed cells and/or constructs. However, the yellow fluorescent protein was preferred. When no fluorescent reporter protein was assembled, no fluorescence was observed.

*S. cerevisiae* cells were subjected to transformation with the modified pYES2 plasmid as described above. Transformed yeast cells were incubated for 30 min at 28-30° C. Colonies of transformed yeast cells were selected, their DNA isolated and subjected to PCR amplification. Two control treatments were also carried out: (1) a negative control involving competent yeast and nuclease free water instead of a plasmid and (2) a positive control involving competent yeast with unmodified pYES2 plasmid.

Alternatively, the pETDuet-1 plasmid-based device was transformed into DH5α and BL21(DE3) *E. coli* using a standard heat shock protocol. Four clones were selected from a synthetic complete dropout plate (deficient in uracil) and processed for full-length DNA sequencing. Some clones were preserved in YPD medium containing 15% glycerol for storage at −80° C. until use. A clone with 100% DNA sequence accuracy was selected for further processing and was used to obtain a high concentration of plasmid construct at a mid-scale plasmid purification level.

The following non-limiting procedures were used to produce polyactive carbohydrates:

Method 1

1. Yeasts transformed with the device depicted in FIGS. 1A and 1B were fermented at 30° C. for 72 hours. Alternatively, the yeasts were transformed with the device depicted in FIGS. 2A and 2B. In some experiments, the yeasts were transformed with the device depicted in FIGS. 4A and 4B. In other experiments, the yeasts were transformed with the device depicted in FIGS. 9A and 9B. If used, bacteria were transformed with the device depicted in FIGS. 3A and 3B.
2. At 48 hours of fermentation, lyticase (240 μL/L) was added.
3. The culture was sterilized by autoclaving at 121° C. for 30 minutes.
4. The mixture was filtered with an 8 μm filter to produce a supernatant composed of the polyactive carbohydrate.

Method 2

1. Yeast transformed with the device depicted in FIGS. 1A and 1B were fermented at 30° C. for 72 hours.
2. The mixture was centrifuged at 9,000 rpm for 15 minutes to produce a pellet.
3. The pellet was resuspended in water (1 g/100 mL)
4. Lyticase (240 μL/L) was added to the solution.
5. The solution was sonicated two times for 30 minutes.
6. The solution was centrifuged at 9,000 rpm for 15 minutes.
7. The mixture was filtered with a 0.45 μm filter to produce a supernatant composed of the polyactive carbohydrate.

Method 3

1. Yeast transformed with the device depicted in FIGS. 1A and 1B were fermented at 30° C. for 72 hours with shaking at 150 rpm.
2. The culture was induced with 2% raffinose, 1% galactose, and 1% glucosamine.
3. The culture was then sonicated 7 times for a total of 2 minutes and 30 seconds.
4. The culture was filtered with decreasing size filter membranes (8 μm, 5 μm, 3 μm, and 1.2 μm) to remove particulate matter, cells, and cellular material.

Figure 5:
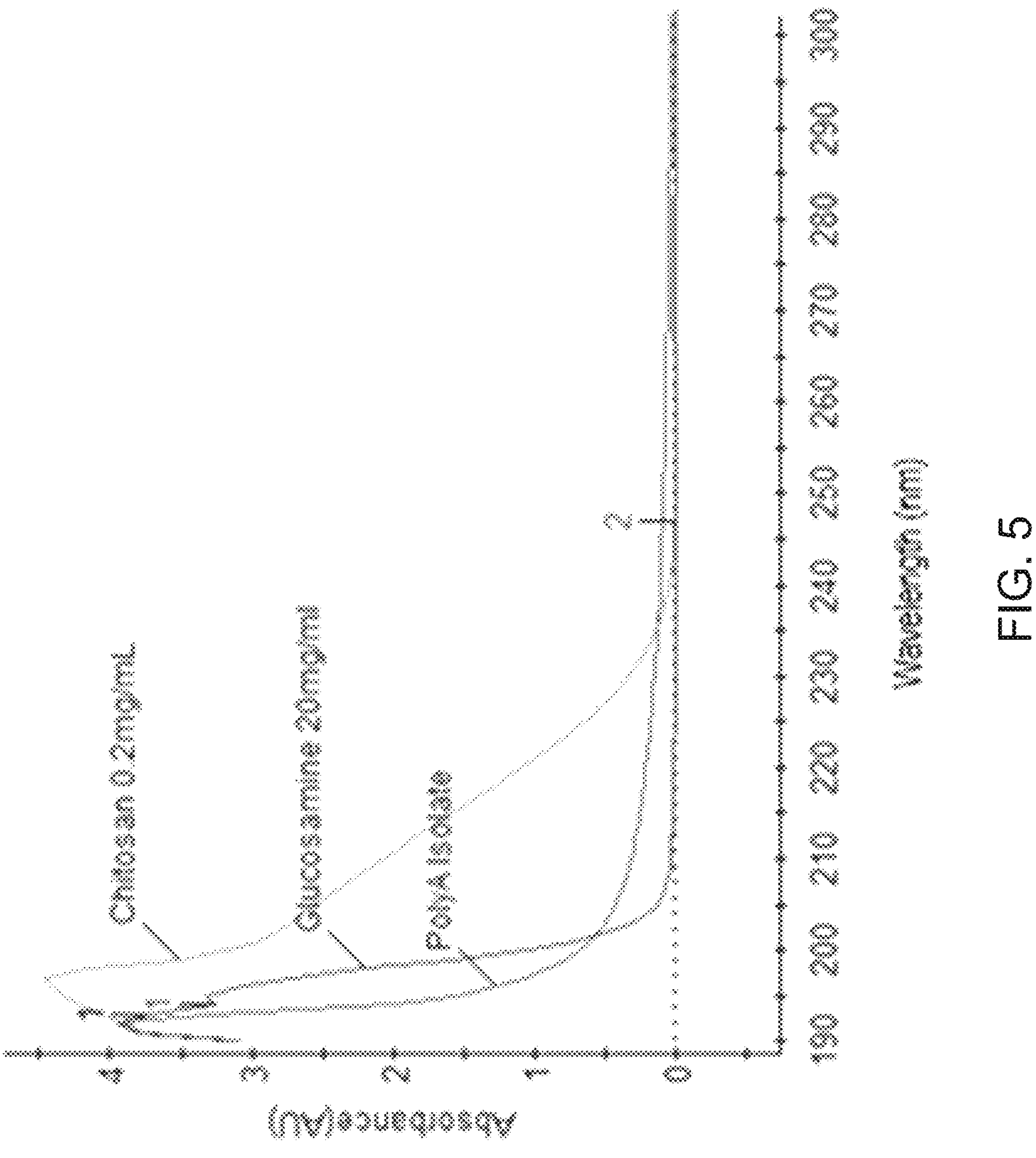
FIG. 5 shows UV-Vis spectra of solutions of glucosamine (20 mg/mL), chitosan (0.2 mg/mL) and a polyactive carbohydrate isolate as disclosed herein.

In any of the above methods, prior to inducing the cultures, in some experiments, a culture of a second biological device including a supplemental DNA construct depicted in FIGS. 10A and 10B was mixed with the transformed yeast and/or bacterial cultures to produce a mixed culture. The methods then continued as described including induction and sonication. UV-Vis spectroscopic analysis revealed that a solution of the polyactive carbohydrate produced as described above has similar structural features of chitosan and glucosamine (FIG. 5).

Example 5: Plant Treatment and Hormone Analysis

For the following experiments, a polyactive carbohydrate extract was produced using Method 3 of Example 4 and applied in different doses to Bermuda grass samples in a greenhouse as well as in a field. For experiments where a chitosan solution was used, different concentrations were studied (i.e., 0.01%, 0.02%, 0.03%) with most experiments being conducted using a 0.02% (w/v) solution of chitosan.

Bermuda grass was grown in a greenhouse for two months. Treatments were applied twice a week at 300 $mL/m^2$ for the first three week, then once a week thereafter. Treatments included 0.02% chitosan, a polyactive carbohydrate extract, and a 1:1 mixture of chitosan and polyactive carbohydrate extract. Two controls, fertilizer alone with no additional compound and water alone were also applied. Samples for each treatment were collected for hormone analysis.

Six-week old samples were collected from the field and stored at −20° C.; frozen samples were sent to an outside company for analysis in a frozen state. 250 mg of each sample were used for analysis.

A 50:50 (v/v) mixture of methanol:acetonitrile was used to extract plant hormones from each sample. After adding solvent, the samples were shaken for 25 min and centrifuged at 16,000 g for 10 min. The supernatants were removed in a speed vac. Pellets were redissolved in 15% methanol and subjected to liquid chromatography using a ZORBAX Eclipse Plus C18 column (2.1 mm×100 mm, Agilent) at 0.45 mL/min installed in a Shimadzu LC system that was interfaced with a Sciex QTRAP 6500+ mass spectrometer with a TurboIonSpray (TIS) electrospray ion source. Plant hormones were detected using MRM transitions and quantified using an external standard curve with data being normalized according to internal standards. Results are presented in Table 9 below:

TABLE 9

Plant Hormone Production for Different Treatment Groups

| Treatment | Hormone Production (ng/g) Cytokinins* | Salicylic Acid | Auxins** | Jasmonic Acid |
|---|---|---|---|---|
| Control (water) | 14.24 | 859.43 | 118.44 | 2.47 |
| 0.02% Chitosan | 14.13 | 2314.63 | 48.15 | 3.99 |
| Polyactive carbohydrate | 29.31 | 1758.04 | 80.82 | 3.81 |
| Chitosan and polyactive carbohydrate | 16.79 | 1537.82 | 87.34 | 2.27 |
| Fertilizer | 23.18 | 1528.70 | 98.07 | 3.12 |

*The presence of auxins induces cytokinins; thus, it normal to observe high cytokinins and lower auxin, or vice versa.

**Auxin numbers represent the sum or addition of the two main auxin isomers (indole-3-acetic acid or IAA, and IAA-Asp, an amino acid conjugate of IAA).

Example 6: Enhancement of Plant Root Growth and Strength

Soil was fertilized with Hou-actinite and a section of Bermuda grass sod with an overall surface area of 2025 $cm^2$ was placed on the soil. Sod roots were not yet visible. Treatments (i.e., control, chitosan, polyactive carbohydrate) were applied after the sod had been placed on the soil. Soil treated with chitosan or polyactive carbohydrate showed earlier rooting (i.e., within the first 48 hours) compared to a control treated with fertilizer alone. Sod and soil were treated twice per week in volumes of 75 or 150 mL per square meter for each treatment.

Figures 7A, 7B, 7C:
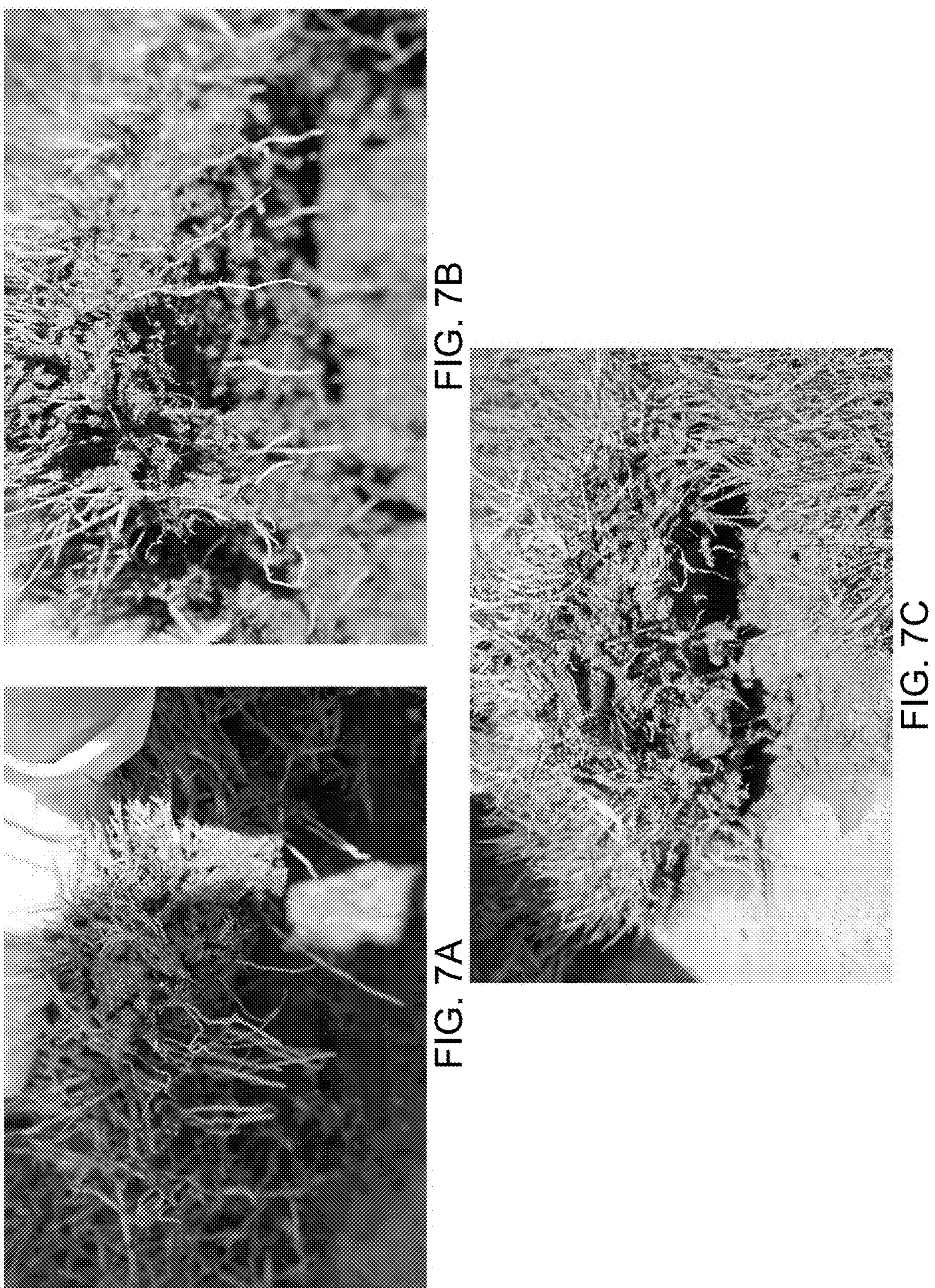
FIGS. 7A, 7B, and 7C show root length for sod treated with a 0.02% solution of chitosan, with the polyactive carbohydrate solution disclosed herein, and a control (watering only), respectively.

Three measurements were taken per treatment at each time of application and the mean of these was calculated. Root length was measured with a ruler (see FIGS. 7A-7C) and is presented in Table 10:

TABLE 10

Root Length

| Day | Control (Fertilizer Only) | 0.02% Chitosan 75 $mL/m^2$ | 0.02% Chitosan 150 $mL/m^2$ | Polyactive Carbohydrate 75 $mL/m^2$ | Polyactive Carbohydrate 150 $mL/m^2$ |
|---|---|---|---|---|---|
| 0 | NA | NA | NA | NA | NA |
| 3 | 0.2 in | 0.7 in | 1 in | 1.5 in | 0.9 in |
| 6 | 0.6 in | 1.5 in | 2.2 in | 1.6 in | 1.5 in |
| 9 | 1.5 in | 2.2 in | 2.2 in | 3 in | 2.4 in |

Figure 8:
FIG. 8 shows use of a tension meter to measure root strength as described herein.

Root anchoring experiments were carried out by determining root tension per unit area at different times; this is expressed in Newtons, with a higher tension indicating more rooting occurred per unit area. This, in turn, indicated better anchoring of the plant(s) to the soil. The tension meter (see FIG. 8) was placed on different parts of sod and a mean measurement was calculated from all measurements on one piece of sod. Tension forces were also determined for individual plants and reflect results on entire sod sections. For tension meter measurements, sod and soil were prepared and treated as described above. Forces were determined from sod and single grass plants after three weeks of treatments. In general, chitosan and polyactive carbohydrate (as used in Example 5) treatments exhibited higher tension compared to controls. Root tension measurements are presented in Table 11 below:

TABLE 11

Root Tension

| Treatment | Dose (mL) | Root Force/Sod* (N) | Root Force/Single Plant (N) |
|---|---|---|---|
| Control (water) | NA | 12.5 | 3.5 |
| Chitosan | 150 | 22 | 6.33 |
| 0.02% | 75 | NA | 4.66 |
| Polyactive | 150 | 22 | 5.33 |
| Carbohydrate | 75 | 21 | 5 |

*Sod sample was a 45 cm × 45 cm square.

Figure 6B:
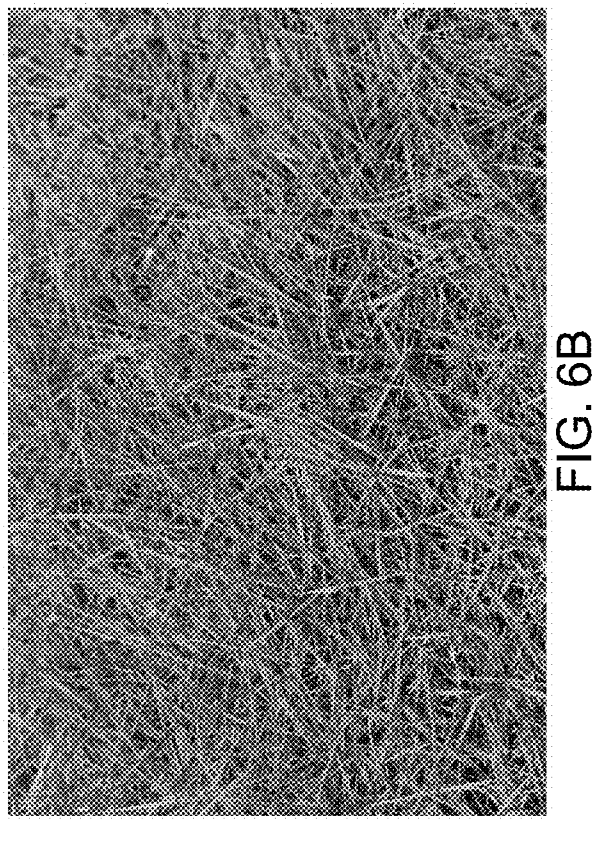
FIGS. 6A and 6B show recovery of grass to a green color after two weeks of treatments with a polyactive carbohydrate solution as disclosed herein.
Figure 6A:
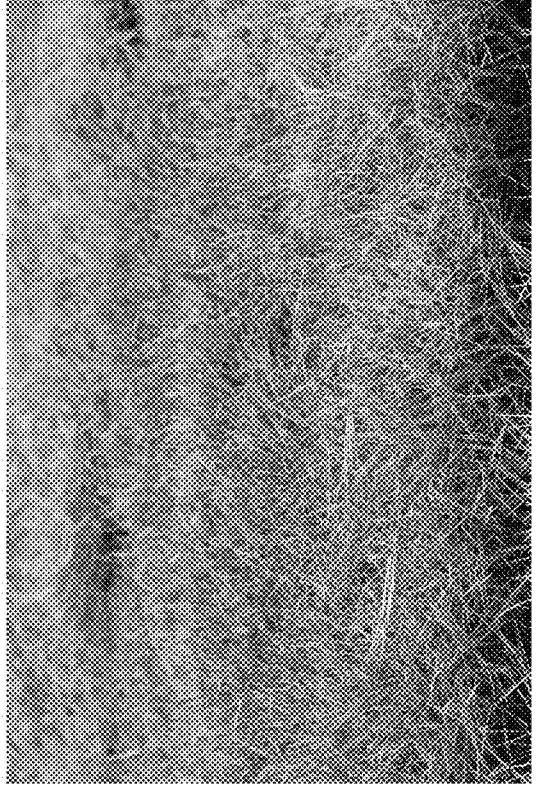

Treatments with chitosan and/or the polyactive carbohydrate were also applied to yellow or brown-colored grasses and were able to return the grasses to a natural green color (FIG. 6), indicating the suitability of the polyactive carbohydrate for therapeutic use after drought and/or to correct a mineral deficiency. Greenhouse results corroborated field results.

Example 7: Production of Soft Biofoams

Polyactive Carbohydrate Extract

The following procedure was used to produce the polyactive carbohydrate extract:

1. Fermentation of yeast transformed with the construct in FIGS. 1A, 1B, 2A, 2B, 3A, 3B, 4A, 4B, 9A, and/or 9B in yeast malt medium with 2% of raffinose, 1 mg/mL of glucosamine and induction with galactose at 30° C. for 72 hours.
2. Centrifugation at 9000 rpm for 15 minutes and pelletizing of the culture.
3. Pellet resuspension (1 g/50 mL) in sterile deionized water.
4. Sonication: 3 times for 2.5 minutes.
6. Centrifugation at 9000 rpm for 15 minutes.
7. Filtration of supernatant with 0.45 μm filter.

Preparation of Soft Biofoams

The polyactive carbohydrate extract (38 mL; optical density 2.5) was mixed with surfactant TWEEN 80 (2 ml) for 3 minutes. Castor oil (50 mL) was next added and mixed for 10 minutes.

Separately, the polyactive carbohydrate extract (10 mL) and bentonite (0.5 g) were vortexed for 5 minutes. This mixture was added to the solution above and mixed for 10 minutes. The above process was carried out at room temperature (250-28° C.) to produce the biopolyol.

Isocyanate (Geos Quimica S.A.S—Isocyanate for rigid—MDI) (20 mL) was added to the biopolyol above at a ratio of 5:1 (biopolyol:isocyanate) for 7 minutes at room temperature (25°-28° C.). Pressured air (5-15 psi) was injected during the last two (2) minutes of this process; however, in some cases there is no need to inject air. The resultant product was allowed to dry overnight at room temperature. The mixture was transferred to a mold to produce a shaped article (e.g., a cube). The biofoam was taken out of the mold and transferred to an oven to complete drying (30°-40° C.) for 30-60 minutes.

Throughout this application, various publications are referenced. The disclosures of these publications in their entireties are hereby incorporated by reference into this application in order to more fully describe the compounds, compositions, and methods described herein.

Various modifications and variations can be made to the compounds, compositions, and methods described herein. Other aspects of the compounds, compositions, and methods described herein will be apparent from consideration of the specification and practice of the compounds, compositions, and methods disclosed herein. It is intended that the specification and examples be considered as exemplary.

What is claimed:

1. A method for increasing root growth of a plant, the method comprising contacting the plant with an extract produced from a biological device, wherein the biological device comprises host cells transformed with a DNA construct comprising the following genetic components: (a) a gene that expresses chitin synthase, (b) a gene that expresses chitosanase, and (c) a gene that expresses chitin deacetylase, wherein the extract comprises a polyactive carbohydrate.

2. A method for increasing the drought-resistance of a plant, the method comprising contacting the plant with an extract produced from a biological device, wherein the biological device comprises host cells transformed with a DNA construct comprising the following genetic components: (a) a gene that expresses chitin synthase, (b) a gene that expresses chitosanase, and (c) a gene that expresses chitin deacetylase, wherein the extract comprises a polyactive carbohydrate.

3. A method for improving the physical appearance of a plant, the method comprising contacting the plant with an extract produced from a biological device, wherein the biological device comprises host cells transformed with a DNA construct comprising the following genetic components: (a) a gene that expresses chitin synthase, (b) a gene that expresses chitosanase, and (c) a gene that expresses chitin deacetylase, wherein the extract comprises a polyactive carbohydrate.

4. The method according to claim 1, wherein the extract is further applied to soil where the plant is growing.

5. The method according to claim 1, wherein the plant is further contacted with chitosan.

6. The method of claim 5, wherein the plant is contacted with a composition comprising the extract and chitosan.

7. The method according to claim 1, wherein the gene that expresses chitin synthase comprises SEQ ID NO. 2 or at least 70% homology thereof.

8. The method according to claim 1, wherein the gene that expresses chitosanase has comprises SEQ ID NO. 3 or at least 70% homology thereof.

9. The method according to claim 1, wherein the gene that expresses chitin deacetylase comprises SEQ ID NO. 4 or at least 70% homology thereof.

10. The method according to claim 1, wherein the construct further comprises a gene that expresses lipase.

11. The method of claim 10, wherein the gene that expresses lipase comprises SEQ ID NO. 1 or at least 70% homology thereof.

12. The method according to claim 1, wherein the construct further comprises a gene that expresses (1→3), (1→4)-β-glucan synthase.

13. The method of claim 12, wherein the gene that expresses (1→3), (1→4)-β-glucan synthase comprises SEQ ID NO. 6 of at least 70% homology thereof.

14. The method according to claim 1, wherein the construct further comprises a gene that expresses chitin synthase regulatory factor CHR1.

15. The method of claim 14, wherein the gene that expresses chitin synthase regulatory factor CHR1 comprises SEQ ID NO. 11 or at least 70% homology thereof or SEQ ID NO. 16 or at least 70% homology thereof.

16. The method according to claim 1, wherein the construct further comprises a gene that expresses transglycosylase.

17. The method of claim 16, wherein the gene that expresses transglycosylase comprises SEQ ID NO. 12 or at least 70% homology thereof or SEQ ID NO. 15 or at least 70% homology thereof.

18. The method according to claim 1, wherein the construct further comprises a gene that expresses a dehydrogenase.

19. The method of claim 18, wherein the gene that expresses a dehydrogenase expresses a protein comprising SEQ ID NO. 13 or at least 70% homology thereof.

20. The method according to claim 1, wherein the construct further comprises one or more ribosomal binding sites preceding the gene that expresses lipase, the gene that expresses chitin synthase, the gene that expresses chitosanase, the gene that expresses chitin deacetylase, the gene that expresses (1→3), (1→4)-β-glucan synthase, the gene that expresses chitin synthase regulatory factor CHR1, the gene that expresses transglycosylase, or any combination thereof.

21. The method according to claim 1, wherein the construct further comprises a gene that confers resistance to an antibiotic.

22. The method according to claim 1, wherein the construct further comprises a gene for expressing a reporter protein.

23. The method according to claim 1, wherein the construct comprises from 5' to 3' the following genetic components in the following order: (1) a gene that expresses chitin synthase, (2) a gene that expresses chitosanase, and (3) a gene that expresses chitin deacetylase.

24. The method according to claim 1, wherein the construct comprises from 5' to 3' the following genetic components in the following order: (1) a gene that expresses chitin synthase comprising SEQ ID NO. 2 or at least 70% homology thereto, (2) a gene that expresses chitosanase comprising SEQ ID NO. 3 or at least 70% homology thereto, and (3) a gene that expresses chitin deacetylase comprising SEQ ID NO. 4 or at least 70% homology thereto.

25. The method of to claim 23, wherein the construct comprises SEQ ID NO. 7 or at least 70% homology thereto, SEQ ID NO. 8 or at least 70% homology thereto, SEQ ID NO. 9, or at least 70% homology thereto, or SEQ ID NO. 10 or at least 70% homology thereto.

26. The method according to claim 1, wherein the construct comprises from 5' to 3' the following genetic components in the following order: (1) a gene that expresses lipase, (2) a gene that expresses chitin synthase, (3) a gene that expresses chitosanase, and (4) a gene that expresses chitin deacetylase.

27. The method according to claim 1, wherein the construct comprises from 5' to 3' the following genetic components in the following order: (1) a gene that expresses lipase comprising SEQ ID NO. 1 or at least 70% homology thereto, (2) a gene that expresses chitin synthase comprising SEQ ID NO. 2 or at least 70% homology thereto, (3) a gene that expresses chitosanase comprising SEQ ID NO. 3 or at least 70% homology thereto, and (4) a gene that expresses chitin deacetylase comprising SEQ ID NO. 4 or at least 70% homology thereto.

28. The method according to claim 1, wherein the construct comprises from 5' to 3' the following genetic components in the following order: (1) a gene that expresses lipase, (2) a gene that expresses chitosanase, (3) a gene that expresses chitin synthase, and (4) a gene that expresses chitin deacetylase.

29. The method according to claim 1, wherein the construct comprises from 5' to 3' the following genetic components in the following order: (1) a gene that expresses lipase comprising SEQ ID NO. 1 or at least 70% homology thereto, (2) a gene that expresses chitosanase comprising SEQ ID NO. 3 or at least 70% homology thereto, (3) a gene that expresses chitin synthase comprising SEQ ID NO. 2 or at least 70% homology thereto, and (4) a gene that expresses chitin deacetylase comprising SEQ ID NO. 4 or at least 70% homology thereto.

30. The method according to claim 1, wherein the construct comprises from 5' to 3' the following genetic components in the following order: (1) a ribosomal binding site, (2) a gene that expresses lipase, (3) a ribosomal binding site, (4) a gene that expresses chitosanase, (5) a T7 promoter, (6) a ribosomal binding site, (7) a gene that expresses chitin synthase, (8) a ribosomal binding site, and (9) a gene that expresses chitin deacetylase.

31. The method according to claim 1, wherein the construct comprises from 5' to 3' the following genetic components in the following order: (1) a gene that expresses lipase, (2) a gene that expresses chitin synthase, (3) a gene that expresses chitosanase, (4) a gene that expresses chitin deacetylase, and (5) a gene that expresses (1→3), (1→4)-β-glucan synthase.

32. The method according to claim 1, wherein the construct comprises from 5' to 3' the following genetic components in the following order: (1) a gene that expresses lipase comprising SEQ ID NO. 1 or at least 70% homology thereto, (2) a gene that expresses chitin synthase comprising SEQ ID NO. 2 or at least 70% homology thereto, (3) a gene that expresses chitosanase comprising SEQ ID NO. 3 or at least 70% homology thereto, (4) a gene that expresses chitin deacetylase comprising SEQ ID NO. 4 or at least 70% homology thereto, and (5) a gene that expresses (1→3), (1→4)-β-glucan synthase comprising SEQ ID NO. 6 or at least 70% homology thereto.

33. The method according to claim 1, wherein the construct comprises from 5' to 3' the following genetic components in the following order: (1) a gene that expresses chitin synthase, (2) a gene that expresses chitosanase, (3) a gene that expresses chitin deacetylase, and (4) a gene that expresses (1→3), (1→4)-β-glucan synthase.

34. The method according to claim 1, wherein the construct comprises from 5' to 3' the following genetic components in the following order: (1) a gene that expresses chitin synthase comprising SEQ ID NO. 2 or at least 70% homology thereto, (2) a gene that expresses chitosanase comprising SEQ ID NO. 3 or at least 70% homology thereto, (3) a gene that expresses chitin deacetylase comprising SEQ ID NO. 4 or at least 70% homology thereto, and (4) a gene that expresses (1→3), (1→4)-β-glucan synthase comprising SEQ ID NO. 6 or at least 70% homology thereto.

35. The method according to claim 1, wherein the construct comprises from 5' to 3' the following genetic components in the following order: (1) a gene that expresses chitin synthase, (2) a gene that expresses chitosanase, (3) a gene that expresses chitin deacetylase, (4) a gene that expresses (1→3), (1→4)-β-glucan synthase, (5) a gene that expresses transglycosylase, and (6) a gene that expresses chitin synthase regulatory factor CHR1.

36. The method of claim 1, further comprising contacting the plant with a second extract produced from a second biological device, wherein the second biological device comprises second host cells transformed with a supplemental DNA construct comprising the following genetic components: (a) a gene that expresses transglycosylase and (b) a gene that expresses chitin synthase regulatory factor CRH1.

37. The method of claim 36, wherein the supplemental DNA construct comprises from 5' to 3' the following genetic components in the following order: (1) a gene that expresses transglycosylase and (2) a gene that expresses chitin synthase regulatory factor CRH1.

* * * * *

SEQUENCE LISTING

<160> NUMBER OF SEQ ID NOS: 17

<210> SEQ ID NO 1
<211> LENGTH: 1237
<212> TYPE: DNA
<213> ORGANISM: Micrococcus sp. HL-2003

<400> SEQUENCE: 1
ggatccggta ccatggtgtt tatcgtcaat cttttctcct gcaccttatc tgaaaccacg 60
gttagctcaa taaaatctga agctacggtt agctcaacat ttactgccgt cacggccctg 120
caattggtgg ctgagggtaa gttgcagtcg gcgaagggtt tcggtggtgg tacgattcac 180
tacccaaccc tcgcggccga agcaccctgg tggacgccgg gccaaggcca tggttacgag 240
gcgatcacct acggctggct ggtcggcgaa ctgctgcgcc gcgccgatgg gcgtgggcct 300
ggtctgttag gcgctattgc cgtggttcct ggttacgttt cttacgagaa ctctatcaag 360
tggtggggac cgcgtctggc ttcttggggc tttgtcgttg cacggccgtt gggcctggac 420
tttcatgtgg gcctggcgga tgaagagttt tatcgtgttg cccatatagc gcgcagcaaa 480
gccaatgcag cactagataa cattgctgat gacaccgtcg gcagtataga tcctaagcgg 540
ttgggcgcta ttggctggtc aggtggcggc ggcgcgctta aactggcaac ggagcgcagc 600
acagtacgag ccattttgac cagtactaat aaacctgaat ggcgacgctt cgataaattc 660
ttatgtgcct gcgaggatga ccggattgct gagactaaga aatatgccaa cgcgttttat 720
aaaaatgccg acatgctcga agagttgacc cgtgaacaca gtatcgggcc ggataaaaca 780
ttattgacac aaactcggtt tggcttgggg tgcttggatc aaccgcaagc aggggttaaa 840
attcattttg aagagtacct tgatcaaacc catggattta tcaatttgac gccagtttca 900
cataaggcga gagcaaatct gattcagatg cctaatgcca cattcggcct tggcccgcgt 960
gcttttgggc atcctggtgc aggtggatcg gtaggttttg ccgaccccga acacgatgta 1020
gcgtttggtt tcgtgactaa tacattgggg ccttatgtag ttgagtttaa aagccgtcat 1080
ccctcatttt atgcatataa agatggattg gtgctgactg gaaatgacgt cgactatgtg 1140
actgattact atgcaacaaa gcatgctgta catttagatg atccacgtgc acagaagttg 1200
gtcggaatat tggccggttg tctgtaagct tctcgag 1237

<210> SEQ ID NO 2
<211> LENGTH: 3414
<212> TYPE: DNA
<213> ORGANISM: Saccharomyces cerevisiae

<400> SEQUENCE: 2

```
aagcttgcca ccatgagtga tcaaaataat cgatcgagaa atgaatatca ctcaaaccgg     60
aagaatgaac cttcctatga actccaaaat gcacatagcg ggctatttca ctcttctaat    120
gaagaattaa caaacaggaa ccaaagatat accaatcaaa atgccagcat gggttcattc    180
actccagtcc aatctttgca atttccagaa caatctcagc aaacaaatat gctttataac    240
ggtgacgatg gcaataataa tactatcaat gataacgaac gagacatata tggaggtttt    300
gtcaaccacc atcgccagcg tcccccacca gcaactgcag aatacaatga cgtttttaat    360
acgaatagtc aacagctacc gtcggaacat caatacaata acgtaccttc atatccactt    420
ccttcgataa atgtgattca aaccactcca gaactcatac ataacggctc acagactatg    480
gccaccccca tcgaaaggcc cttctttaac gaaaacgact actattataa taacaggaac    540
tctaggacgt caccgagtat tgcttctagt agcgatggtt atgcagatca ggaagctagg    600
cccattttgg agcaacccaa caataacatg aatagcggta atattcctca ataccatgac    660
caaccttttg gatacaacaa tggttaccat ggcctacagg caaaagatta ctatgacgat    720
ccggagggtg gttatattga tcagagagga gatgactatc agattaattc atatttgggt    780
agaaacggtg aaatggttga tccttacgat tatgaaaaca gtttaagaca tatgactcct    840
atggagcgta gagaatatct tcatgatgat agcagacccg taaacgatgg aaaagaagaa    900
ttagacagtg tgaaaagcgg ttactctcat agagacttgg gggaatatga caaggatgat    960
ttttcaaggg atgacgagta cgatgatctc aacactattg ataaattaca gtttcaagct   1020
aatggtgtac ctgcatcatc ctcggtgtct tctatcggat ctaaagaatc cgacataata   1080
gtaagcaatg ataacttaac cgcaaataga gcactaaaga gaagcggtac tgaaattagg   1140
aaattcaaac tttggaatgg taattttgtt ttcgattctc caatcagtaa gacgctattg   1200
gaccaatacg ctactacaac agaaaatgca aacactttac caaatgagtt taagtttatg   1260
agatatcaag cagttacttg cgaacctaat caacttgcag agaagaattt cacggtgagg   1320
cagttgaagt atttaactcc aagggaaacg gaattgatgc tagtagtcac aatgtataat   1380
gaagaccata tcctgttagg aagaactttg aaaggtatta tggacaatgt caaatatatg   1440
gtgaaaaaaa aaaattcaag cacttggggg ccggatgcat ggaaaaagat tgtcgtttgt   1500
atcatttcag atggtagatc caaaattaat gaacgctcgc tagcattact aagttcgtta   1560
ggttgttacc aggacgggtt tgctaaggat gaaattaatg aaaaaaaagt ggcaatgcat   1620
gtctacgaac atacgacaat gatcaacatc acaaatattt cggaatcaga ggtttcatta   1680
gaatgcaatc aaggtactgt tccaatacaa cttttgtttt gtttgaaaga gcaaaatcag   1740
aaaaaaatta actcacatag atgggcattt gaaggctttg cagaattact gcgtcccaat   1800
atcgttacat tgttagatgc tggtactatg ccaggtaaag attctattta ccagttatgg   1860
agagagttca ggaatccaaa tgttggtggc gcatgtggtg aaataagaac tgatttgggt   1920
aagagatttg taaagttgtt gaatccttta gttgcatcac agaatttcga atacaaaatg   1980
tccaatattt tagacaaaac aaccgagtct aactttggat ttattactgt tctaccgggg   2040
gcattctctg cgtataggtt tgaagctgtg agaggccaac cattacagaa gtacttttat   2100
ggtgaaatta tggaaaatga aggttttcat ttttttttctt ccaatatgta tcttgctgaa   2160
gatcgtattt tatgctttga agtggtcaca aaaaaaaatt gtaattggat tttgaaatac   2220
tgcagaagtt cttatgcttc aacagatgta ccggagaggg tccctgaatt tattcttcag   2280
```

```
aggaggcgtt ggttgaatgg ttcatttttt gctagtgtat attccttttg tcatttttac   2340

agagtctgga gcagtggtca taatattggt agaaaactcc ttttgacggt tgaatttttt   2400

taccttttct tcaatacatt gatttcatgg ttttcattga gttcattttt cctagtcttt   2460

aggattctca ctgtttctat tgcactggca taccattcag catttaatgt gttgtccgtc   2520

atattcctgt ggctttatgg gatttgtacc ttatcaacat tcatactgtc attgggtaat   2580

aaacctaaaa gtactgagaa attttatgtt ctaacttgcg tcatttttgc ggtgatgatg   2640

atttacatga tattctgcag tatattcatg agtgtcaaat ccttccaaaa tatattgaaa   2700

aacgatacca tcagctttga gggtttgatt accacagagg ctttcaggga tattgttatc   2760

tctctgggct ccacttattg tttgtaccta atcagttcaa ttatctattt gcagccatgg   2820

catatgttga caagttttat tcagtatatt ttattgagtc cttcttacat caatgttttg   2880

aatatctatg cattttgtaa tgtccacgac ttatcatggg gtacaaaggg tgcaatggca   2940

aatccgctgg gtaagattaa tactacagaa gatggtacgt tcaaaatgga agttctggtc   3000

tctagttcag agattcaagc aaactacgat aaatatttga aagttttaaa tgacttcgat   3060

ccaaaatcag aatctcggcc tactgagcca tcttatgatg aaaaaaagac tggctattat   3120

gcaaacgtta gatctctcgt gattatcttt tgggtcatca caaatttcat catcgttgct   3180

gttgtcttag aaaccggtgg gattgcagat tatattgcta tgaaatccat atcaactgat   3240

gacactttag aaactgcaaa gaaggcggaa attcccttaa tgaccagtaa ggcctcaatt   3300

tattttaatg taattttatg gttagttgca ttatcggcat taataaggtt cattggttgc   3360

tcaatataca tgatagtaag gtttttaaa aaggttacat ttcgctaagg tacc          3414
```

```
<210> SEQ ID NO 3
<211> LENGTH: 1712
<212> TYPE: DNA
<213> ORGANISM: Saccharomyces cerevisiae

<400> SEQUENCE: 3

gaattcaagc ttatgtcact cctttacatc attcttctat tcacacaatt cttactactg     60

ccaaccgatg cctttgatag gtctgctaac acaaatattg ctgtttattg gggtcaaaac    120

tcagcaggaa cgcaagaatc cttagctact tactgtgaat cttctgatgc tgatattttc    180

ctattatctt tcttgaacca atttccaacc cttggtttga actttgccaa cgcatgctct    240

gatacttttt ctgatggctt acttcactgc acccagattg ctgaagatat tgaaacttgc    300

cagtccctag gaaagaaagt tctattatca ttaggtggtg catctggtag ctacctcttt    360

tcagatgatt ctcaagcgga aacttttgca caaactttat gggatacttt cggtgaaggt    420

acaggtgcca gtgagagacc atttgactca gcagtcgttg atggttttga ttttgatatt    480

gaaaacaaca acgaagtagg ctatagtgcg ttagctacca agttaagaac tttgtttgcc    540

gaaggtacaa agcaatatta cctttctgcc gcaccacaat gtccataccc ggatgcttct    600

gttggtgact tgttggaaaa tgcagacatt gattttgcgt tcatccaatt ttacaataat    660

tactgcagtg tgagtggtca attcaattgg gatacttggt taacctatgc tcaaactgta    720

tccccaaata aaaatatcaa actgttctta ggtttacctg gttctgcttc tgctgctggc    780

tctggttata tttctgacac ttctttattg gaatcaacta ttgcagatat tgcctcttca    840

agttcttttg gtggtattgc gttatgggat gcatctcaag ccttttccaa cgagctaaat    900

ggtgaaccat atgttgagat tttgaagaat ttgctaacaa gtgctagcca gaccgccact    960

actacagttg ccacctcaaa aacctcagca gcctcaactt catctgcttc aacttcatct   1020
```

```
gcttcaactt ctcagaaaaa gaccacacaa tctacgacat ctacacaaag taaaagcaaa   1080

gttactttat ctccaactgc aagcagcgct atcaaaacat caattactca aactacaaaa   1140

acattgacga gtagcaccaa gacaaaatct agtctaggta ccaccacaac agagagcact   1200

ttaaattcag ttgctatcac aagtatgaaa actactctat cttcccaaat aaccagtgct   1260

gccttggtga cccctcaaac aactactact agcatagttt cttcggcccc aattcaaaca   1320

gctatcacta gtactctttc gccagcaacg aagagttctt ctgtcgtttc cctacagaca   1380

gctactacta gtacgctttc cccaacaacg accagtacaa gctcaggtag tacaagctca   1440

ggtagtacaa gctcagacag tacagctcgt acattggcta aagaattgaa tgctcaatat   1500

gcggctggta aattgaacgg taaatctacc tgtactgaag gtgaaattgc atgctctgct   1560

gatgggaagt tcgccgtttg tgatcatagc gcttgggttt acatggaatg tgcttctgga   1620

accacatgtt atgcttatga ctccggcgac tcagtctata cccaatgtaa tttctcttat   1680

ttggaaagca attactttta actcgaggat cc                                1712
```

<210> SEQ ID NO 4
<211> LENGTH: 939
<212> TYPE: DNA
<213> ORGANISM: Saccharomyces cerevisiae

<400> SEQUENCE: 4

```
atgagaatac aactaaatac aattgatttg caatgtatta ttgcactttc ctgtctgggg     60

caatttgttc acgcggaagc taatagggaa gatttaaagc agatagactt tcaatttcct    120

gtattggaaa gggcagctac aaaaaacgcct tttccggatt ggcttagtgc atttaccggg    180

ttaaaagaat ggcctgggtt agatccacct tatatacctt tagatttcat tgatttcagt    240

caaattccag attataagga atatgatcaa aaccattgcg acagtgttcc aagggactcg    300

tgctctttcg attgccatca ctgcaccgaa cacgatgatg tgtacacatg ttccaaactt    360

tcccagacat ttgacgatgg tccttctgct tccactacta aattattgga ccggttgaag    420

cataattcca ccttcttcaa tttaggtgtc aatatagttc aacatccaga tatctatcaa    480

agaatgcaaa aggagggaca cttaatcggc tcacatacct ggtctcacgt atatttgcca    540

aatgtatcga atgaaaaaat tatagctcaa attgaatggt ccatctgggc gatgaatgct    600

actggcaacc ataccccaa atggttcaga cctccatatg gcggaataga taatagagta    660

agagcaataa caaggcaatt tggcttacaa gccgtcttat gggatcacga tacttttgat    720

tggagcctcc ttctcaatga ttctgtcata actgaacaag aaattcttca aaatgtaata    780

aactggaaca agtcaggaac cggattaata ttagaacacg attcaacgga aaaaactgtc    840

gatcttgcca ttaaaataaa taagttgata ggtgatgatc aatcaacagt ttctcattgt    900

gtcggcggaa ttgattacat aaaagaattc ttgtcctaa                           939
```

<210> SEQ ID NO 5
<211> LENGTH: 890
<212> TYPE: DNA
<213> ORGANISM: Artificial sequence
<220> FEATURE:
<223> OTHER INFORMATION: Synthetic construct

<400> SEQUENCE: 5

```
ggattcaaag aggagaaata ctagatggtg agcaagggcg aggagctgtt caccggggtg     60

gtgcccatcc tggtcgagct ggacggcgac gtaaacggcc acaagttcag cgtgtccggc    120
```

```
gagggcgagg gcgatgccac ctacggcaag ctgaccctga agttcatctg caccaccggc    180

aagctgcccg tgccctggcc caccctcgtg accaccttcg gctacggcct gcaatgcttc    240

gcccgctacc ccgaccacat gaagctgcac gacttcttca agtccgccat gcccgaaggc    300

tacgtccagg agcgcaccat cttcttcaag gacgacggca actacaagac ccgcgccgag    360

gtgaagttcg agggcgacac cctggtgaac cgcatcgagc tgaagggcat cgacttcaag    420

gaggacggca acatcctggg gcacaagctg gagtacaact acaacagcca caacgtctat    480

atcatggccg acaagcagaa gaacggcatc aaggtgaact tcaagatccg ccacaacatc    540

gaggacggca gcgtgcagct cgccgaccac taccagcaga acacccccat cggcgacggc    600

cccgtgctgc tgcccgacaa ccactacctg agctaccagt ccgccctgag caaagacccc    660

aacgagaagc gcgatcacat ggtcctgctg gagttcgtga ccgccgccgg gatcactctc    720

ggcatggacg agctgtacaa gtaataatac tagagccagg catcaaataa aacgaaaggc    780

tcagtcgaaa gactgggcct ttcgttttat ctgttgtttg tcggtgaacg ctctctacta    840

gagtcacact ggctcacctt cgggtgggcc tttctgcgtt tataaagctt              890
```

```
<210> SEQ ID NO 6
<211> LENGTH: 2675
<212> TYPE: DNA
<213> ORGANISM: Zea mays

<400> SEQUENCE: 6

cgtacgccac catggcttcg ccggcaccgg cgggcgatgc cgtgtatgcg gccaatggcg     60

gcctcactga cccgcttcta gtgagcgcga acggccatgg tgccgccgcg aggaaggctg    120

gccacggcgc caggggcagg tactgggtgg cctccgacaa ggccgagagg cgcgctgcca    180

aggagtccgg cggtgaggac ggccgcgcgc tgctgttccg gaagtataag gtcaaaggcg    240

ccctcctgca cccctacagg ttgctgatca tcatccgatt agtcgctgtc ctcgccttct    300

tcgcgtggcg catcaggcac aacaaatccg acatcatgtg gttctggaca atgtccatcg    360

tcggcgacgt ctggttcggc ttctcgtggc tcctcaacca gctcccaaag ttcaaccctg    420

tgaagaccat cccagatctc gccgccctcc agcggcactt tggctaccct gacggcggcg    480

cctctaggct ccccggtatc gatgttttcg tcaccactgc cgaccccatt gatgagccca    540

tactctacac catgaactgt gtcctctcca tcctgtctgt cgattaccca gtcgatcggc    600

tagcctgcta tctctcagat gatagtgggg cgctggttct ctatgaggca ctggccgagg    660

tcggaaagtt tgcgcctcta tgggttccgt tctgccgcaa gtactccatt gagccaaggg    720

caccagaaag ctattttgag catgtggcac cgccgcaggc tggaagggtg acgcaggagt    780

tcttgaatga ttataggagg gtgcagatgg agtacgatga gttcaaggcg cgcttggaca    840

acctccctga tgccatacgc aagagatccg atgtttacaa tagcgtgaga gatgcaggag    900

gagctcaaaa ggcaacttgg atggcaaatg ggacgcagtg gcccggcaca tggattgatc    960

cagcagagaa ccataggaaa ggacaccatg ctccaattgc caaggttgtg ctgaaccatc   1020

caagccgtgg acaacaccct attactgaaa gcaatcccag cattgccacc actgatgagc   1080

gcctcccaat gcttgtttac gtctctcgtg agaagaaccc aggttatgac cacaacaaga   1140

aggcaggtgc cctgaatgca cagctgcggg cctctgctct cctctctaat gcccaactca   1200

tcatcaactt cgactgcgac cactacatca acaactctca agccctaagc tcggctgtgt   1260

gcttcatgct ggatcaacgg gacggtgata acaccgcatt tgttcagttc ccacagcgct   1320

tcgacaatgt tgaccccacg gaccgctatg gtaaccacaa tcgtgtcttc tttgatggga   1380
```

```
ccatgcttgc ccttaatggt ttgcaagggc cctcatacct cggtactggt tgcatgttcc   1440
gtcgcttagc actctatggt attgacccac cccactgtag agcagaaaac atcacggccg   1500
aagctagcag gtttggcaac tccacaatct tcctagattc agtgtcaaaa gccctgaaaa   1560
atgacaggac aatcacaccg ccaccaattg atgacacatt ccttgctgag ctagagaggg   1620
ttgtgacatg ttcttatgac aaaggtactg actggggcaa gggtgtaggg tacatctatg   1680
acatagccac tgaagatata gtaacaggat tccgcatcca cgggcagggg tggcgctcta   1740
tgtattgcac aatggagcac gatgcgttct gtggcgttgc accaatcaac ctaactgaac   1800
gcctccatca aattgtgcgc tggtctggtg ggtctttaga gatgttcttc tcccacaaca   1860
atccattcat cggtggtcgc cggattcaac cccttcagcg tgtctcctac ctcaacatga   1920
cagtctaccc agtcacatca gtcttcatcc taatctatgc tctaagcccg gtgatgtggc   1980
ttatccccga tgaagtatac atccagagac cattcactag gtatgtcgtg taccttcttg   2040
taatcatcgt gatgattcac atgattggct ggcttgagat aaagtgggcg gggtcacat    2100
ggctggacta ttggcgcaat gagcagttct ttatgatcgg ctcaacaagt gcatatccaa   2160
tggcagtgct gcacatggca gtgaacctcc tcacaaagaa gggcatacac ttcagggtca   2220
cttccaagca aacagccgcg gacgacaatg acaagttcgc cgacctttat gatttcgat    2280
gggtgccaat gctcatccca acaatggcag ttctgatctg caatgttggt gccattggtg   2340
tagccctggg caaaactgtg gtatacattg gaacatggac agcggcgaag aagatgcatg   2400
cagcactggg tctgctgttc aacatatgga tcatgtttct cctctaccca tttgcactag   2460
cgatcatggg gcggtgggcg aagaggccaa tcatccttgt agttctgctg ccggttgtct   2520
ttgcacttgt cgcgctgttg tatgtaggta tccatatcct acttgctggt ctgattccat   2580
tctaggtagt atagaaaaca ttgtaatttc ttgtgtagtt accaaggaac caattatgtt   2640
tttttagca aaaaaaaaa aaaaaaaaat ctaga                                 2675
```

<210> SEQ ID NO 7
<211> LENGTH: 14634
<212> TYPE: DNA
<213> ORGANISM: Artificial sequence
<220> FEATURE:
<223> OTHER INFORMATION: Synthetic construct

<400> SEQUENCE: 7

```
acggattaga agccgccgag cgggtgacag ccctccgaag gaagactctc ctccgtgcgt     60
cctcgtcttc accggtcgcg ttcctgaaac gcagatgtgc ctcgcgccgc actgctccga    120
acaataaaga ttctacaata ctagctttta tggttatgaa gaggaaaaat tggcagtaac    180
ctggccccac aaaccttcaa atgaacgaat caaattaaca accataggat gataatgcga    240
ttagtttttt agccttattt ctggggtaat taatcagcga agcgatgatt tttgatctat    300
taacagatat ataaatgcaa aaactgcata accactttaa ctaatacttt caacattttc    360
ggtttgtatt acttcttatt caaatgtaat aaaagtatca acaaaaaatt gttaatatac    420
ctctatactt taacgtcaag gagaaaaaac ccccggatcgg actactagca gctgtaatac    480
gactcactat agggaatatt aagcttgcca ccatgagtga tcaaaataat cgatcgagaa    540
atgaatatca ctcaaaccgg aagaatgaac cttcctatga actccaaaat gcacatagcg    600
ggctatttca ctcttctaat gaagaattaa caaacaggaa ccaaagatat accaatcaaa    660
atgccagcat gggttcattc actccagtcc aatctttgca atttccagaa caatctcagc    720
```

```
aaacaaatat gctttataac ggtgacgatg gcaataataa tactatcaat gataacgaac    780
gagacatata tggaggtttt gtcaaccacc atcgccagcg tcccccacca gcaactgcag    840
aatacaatga cgtttttaat acgaatagtc aacagctacc gtcggaacat caatacaata    900
acgtaccttc atatccactt ccttcgataa atgtgattca aaccactcca gaactcatac    960
ataacggctc acagactatg gccacccccca tcgaaaggcc cttctttaac gaaaacgact   1020
actattataa taacaggaac tctaggacgt caccgagtat tgcttctagt agcgatggtt   1080
atgcagatca ggaagctagg cccattttgg agcaacccaa caataacatg aatagcggta   1140
atattcctca ataccatgac caacctttg gatacaacaa tggttaccat ggcctacagg   1200
caaaagatta ctatgacgat ccggagggtg gttatattga tcagagagga gatgactatc   1260
agattaattc atatttgggt agaaacggtg aaatggttga tccttacgat tatgaaaaca   1320
gtttaagaca tatgactcct atggagcgta gagaatatct tcatgatgat agcagacccg   1380
taaacgatgg aaaagaagaa ttagacagtg tgaaaagcgg ttactctcat agagacttgg   1440
gggaatatga caaggatgat ttttcaaggg atgacgagta cgatgatctc aacactattg   1500
ataaattaca gtttcaagct aatggtgtac ctgcatcatc ctcggtgtct tctatcggat   1560
ctaaagaatc cgacataata gtaagcaatg ataacttaac cgcaaatag gcactaaaga   1620
gaagcggtac tgaaattagg aaattcaaac tttggaatgg taattttgtt ttcgattctc   1680
caatcagtaa gacgctattg gaccaatacg ctactacaac agaaaatgca aacactttac   1740
caaatgagtt taagtttatg agatatcaag cagttacttg cgaacctaat caacttgcag   1800
agaagaattt cacggtgagg cagttgaagt atttaactcc aagggaaacg gaattgatgc   1860
tagtagtcac aatgtataat gaagaccata tcctgttagg aagaactttg aaaggtatta   1920
tggacaatgt caaatatatg gtgaaaaaaa aaaattcaag cacttggggg ccggatgcat   1980
ggaaaaagat tgtcgtttgt atcatttcag atggtagatc caaaattaat gaacgctcgc   2040
tagcattact aagttcgtta ggttgttacc aggacgggtt tgctaaggat gaaattaatg   2100
aaaaaaaagt ggcaatgcat gtctacgaac atacgacaat gatcaacatc acaaatattt   2160
cggaatcaga ggtttcatta gaatgcaatc aaggtactgt tccaatacaa cttttgtttt   2220
gtttgaaaga gcaaaatcag aaaaaaatta actcacatag atgggcattt gaaggctttg   2280
cagaattact gcgtcccaat atcgttacat tgttagatgc tggtactatg ccaggtaaag   2340
attctattta ccagttatgg agagagttca ggaatccaaa tgttggtggc gcatgtggtg   2400
aaataagaac tgatttgggt aagagatttg taaagttgtt gaatccttta gttgcatcac   2460
agaatttcga atacaaaatg tccaatattt tagacaaaac aaccgagtct aactttggat   2520
ttattactgt tctaccgggg gcattctctg cgtataggtt tgaagctgtg agaggccaac   2580
cattacagaa gtacttttat ggtgaaatta tggaaaatga aggttttcat tttttttctt   2640
ccaatatgta tcttgctgaa gatcgtattt tatgctttga agtggtcaca aaaaaaaatt   2700
gtaattggat tttgaaatac tgcagaagtt cttatgcttc aacagatgta ccggagaggg   2760
tccctgaatt tattcttcag aggaggcgtt ggttgaatgg ttcatttttt gctagtgtat   2820
attccttttg tcatttttac agagtctgga gcagtggtca taatattggt agaaaactcc   2880
ttttgacggt tgaatttttt taccttttct tcaatacatt gatttcatgg ttttcattga   2940
gttcattttt cctagtcttt aggattctca ctgtttctat tgcactggca taccattcag   3000
catttaatgt gttgtccgtc atattcctgt ggctttatgg gatttgtacc ttatcaacat   3060
tcatactgtc attgggtaat aaacctaaaa gtactgagaa attttatgtt ctaacttgcg   3120
```

```
tcatttttgc ggtgatgatg atttacatga tattctgcag tatattcatg agtgtcaaat   3180
ccttccaaaa tatattgaaa aacgatacca tcagctttga gggtttgatt accacagagg   3240
ctttcaggga tattgttatc tctctgggct ccacttattg tttgtaccta atcagttcaa   3300
ttatctattt gcagccatgg catatgttga caagttttat tcagtatatt ttattgagtc   3360
cttcttacat caatgttttg aatatctatg cattttgtaa tgtccacgac ttatcatggg   3420
gtacaaaggg tgcaatggca aatccgctgg gtaagattaa tactacagaa gatggtacgt   3480
tcaaaatgga agttctggtc tctagttcag agattcaagc aaactacgat aaatatttga   3540
aagttttaaa tgacttcgat ccaaaatcag aatctcggcc tactgagcca tcttatgatg   3600
aaaaaaagac tggctattat gcaaacgtta gatctctcgt gattatcttt tgggtcatca   3660
caaatttcat catcgttgct gttgtcttag aaaccggtgg gattgcagat tatattgcta   3720
tgaaatccat atcaactgat gacactttag aaactgcaaa gaaggcggaa attcccttaa   3780
tgaccagtaa ggcctcaatt tattttaatg taattttatg gttagttgca ttatcggcat   3840
taataaggtt cattggttgc tcaatataca tgatagtaag gttttttaaa aaggttacat   3900
ttcgctaagg tacctcatgt aattagttat gtcacgctta cattcacgcc ctccccccac   3960
atccgctcta accgaaaagg aaggagttag acaacctgaa gtctaggtcc ctatttattt   4020
ttttatagtt atgttagtat taagaacgtt atttatattt caaatttttc ttttttttct   4080
gtacagacgc gtgtacgcat gtaacattat actgaaaacc ttgcttgaga aggttttggg   4140
acgctcgaag gctttaattt gccggattag aagccgccga gcgggtgaca gccctccgaa   4200
ggaagactct cctccgtgcg tcctcgtctt caccggtcgc gttcctgaaa cgcagatgtg   4260
cctcgcgccg cactgctccg aacaataaag attctacaat actagctttt atggttatga   4320
agaggaaaaa ttggcagtaa cctggcccca caaaccttca aatgaacgaa tcaaattaac   4380
aaccatagga tgataatgcg attagttttt tagccttatt tctggggtaa ttaatcagcg   4440
aagcgatgat ttttgatcta ttaacagata tataaatgca aaaactgcat aaccacttta   4500
actaatactt tcaacatttt cggtttgtat tacttcttat tcaaatgtaa taaaagtatc   4560
aacaaaaaat tgttaatata cctctatact ttaacgtcaa ggagggatcc gccaccatgt   4620
cactccttta catcattctt ctattcacac aattcttact actgccaacc gatgcctttg   4680
ataggtctgc taacacaaat attgctgttt attggggtca aaactcagca ggaacgcaag   4740
aatccttagc tacttactgt gaatcttctg atgctgatat tttcctatta tctttcttga   4800
accaatttcc aacccttggt ttgaactttg ccaacgcatg ctctgatact tttctgatg    4860
gcttacttca ctgcacccag attgctgaag atattgaaac ttgccagtcc ctaggaaaga   4920
aagttctatt atcattaggt ggtgcatctg gtagctacct cttttcagat gattctcaag   4980
cggaaacttt tgcacaaact ttatgggata ctttcggtga aggtacaggt gccagtgaga   5040
gaccatttga ctcagcagtc gttgatggtt ttgattttga tattgaaaac aacaacgaag   5100
taggctatag tgcgttagct accaagttaa gaactttgtt tgccgaaggt acaaagcaat   5160
attacctttc tgccgcacca caatgtccat acccggatgc ttctgttggt gacttgttgg   5220
aaaatgcaga cattgatttt gcgttcatcc aattttacaa taattactgc agtgtgagtg   5280
gtcaattcaa ttgggatact tggttaacct atgctcaaac tgtatcccca aataaaaata   5340
tcaaactgtt cttaggttta cctggttctg cttctgctgc tggctctggt tatatttctg   5400
acacttcttt attggaatca actattgcag atattgcctc ttcaagttct tttggtggta   5460
```

```
ttgcgttatg ggatgcatct caagcctttt ccaacgagct aaatggtgaa ccatatgttg   5520
agattttgaa gaatttgcta acaagtgcta gccagaccgc cactactaca gttgccacct   5580
caaaaacctc agcagcctca acttcatctg cttcaacttc atctgcttca acttctcaga   5640
aaaagaccac acaatctacg acatctacac aaagtaaaag caaagttact ttatctccaa   5700
ctgcaagcag cgctatcaaa acatcaatta ctcaaactac aaaaacattg acgagtagca   5760
ccaagacaaa atctagtcta ggtaccacca caacagagag cactttaaat tcagttgcta   5820
tcacaagtat gaaaactact ctatcttccc aaataaccag tgctgccttg gtgacccctc   5880
aaacaactac tactagcata gtttcttcgg ccccaattca aacagctatc actagtactc   5940
tttcgccagc aacgaagagt tcttctgtcg tttccctaca gacagctact actagtacgc   6000
tttccccaac aacgaccagt acaagctcag gtagtacaag ctcaggtagt acaagctcag   6060
acagtacagc tcgtacattg gctaaagaat tgaatgctca atatgcggct ggtaaattga   6120
acggtaaatc tacctgtact gaaggtgaaa ttgcatgctc tgctgatggg aagttcgccg   6180
tttgtgatca tagcgcttgg gtttacatgg aatgtgcttc tggaaccaca tgttatgctt   6240
atgactccgg cgactcagtc tatacccaat gtaatttctc ttatttggaa agcaattact   6300
tttaattaat catgtaatta gttatgtcac gcttacattc acgccctccc cccacatccg   6360
ctctaaccga aaaggaagga gttagacaac ctgaagtcta ggtccctatt tattttttta   6420
tagttatgtt agtattaaga acgttattta tatttcaaat tttttctttt tttctgtaca   6480
gacgcgtgta cgcatgtaac attatactga aaaccttgct tgagaaggtt ttgggacgct   6540
cgaaggcttt aatttgccgg attagaagcc gccgagcggg tgacagccct ccgaaggaag   6600
actctcctcc gtgcgtcctc gtcttcaccg gtcgcgttcc tgaaacgcag atgtgcctcg   6660
cgccgcactg ctccgaacaa taaagattct acaatactag cttttatggt tatgaagagg   6720
aaaaattggc agtaacctgg ccccacaaac cttcaaatga acgaatcaaa ttaacaacca   6780
taggatgata atgcgattag tttttttagcc ttatttctgg ggtaattaat cagcgaagcg   6840
atgatttttg atctattaac agatatataa atgcaaaaac tgcataacca ctttaactaa   6900
tactttcaac attttcggtt tgtattactt cttattcaaa tgtaataaaa gtatcaacaa   6960
aaaattgtta atatacctct atactttaac gtcaaggagc tcgagatgag aatacaacta   7020
aatacaattg atttgcaatg tattattgca ctttcctgtc tggggcaatt tgttcacgcg   7080
gaagctaata gggaagattt aaagcagata gactttcaat ttcctgtatt ggaaagggca   7140
gctacaaaaa cgccttttcc ggattggctt agtgcattta ccgggttaaa agaatggcct   7200
gggttagatc caccttatat acctttagat ttcattgatt tcagtcaaat tccagattat   7260
aaggaatatg atcaaaacca ttgcgacagt gttccaaggg actcgtgctc tttcgattgc   7320
catcactgca ccgaacacga tgatgtgtac acatgttcca aactttccca gacatttgac   7380
gatggtcctt ctgcttccac tactaaatta ttggaccggt tgaagcataa ttccaccttc   7440
ttcaatttag gtgtcaatat agttcaacat ccagatatct atcaaagaat gcaaaaggag   7500
ggacacttaa tcggctcaca tacctggtct cacgtatatt tgccaaatgt atcgaatgaa   7560
aaaattatag ctcaaattga atggtccatc tgggcgatga atgctactgg caaccatacc   7620
cccaaatggt tcagacctcc atatggcgga atagataata gagtaagagc aataacaagg   7680
caatttggct tacaagccgt cttatgggat cacgatactt ttgattggag cctccttctc   7740
aatgattctg tcataactga acaagaaatt cttcaaaatg taataaactg gaacaagtca   7800
ggaaccggat taatattaga acacgattca acggaaaaaa ctgtcgatct tgccattaaa   7860
```

```
ataaataagt tgataggtga tgatcaatca acagtttctc attgtgtcgg cggaattgat   7920
tacataaaag aattcttgtc ctaagaattc tcatgtaatt agttatgtca cgcttacatt   7980
cacgccctcc ccccacatcc gctctaaccg aaaaggaagg agttagacaa cctgaagtct   8040
aggtccctat ttattttttt atagttatgt tagtattaag aacgttattt atatttcaaa   8100
tttttctttt ttttctgtac agacgcgtgt acgcatgtaa cattatactg aaaaccttgc   8160
ttgagaaggt tttgggacgc tcgaaggctt taatttgccg gattagaagc cgccgagcgg   8220
gtgacagccc tccgaaggaa gactctcctc cgtgcgtcct cgtcttcacc ggtcgcgttc   8280
ctgaaacgca gatgtgcctc gcgccgcact gctccgaaca ataaagattc tacaatacta   8340
gcttttatgg ttatgaagag gaaaaattgg cagtaacctg gccccacaaa ccttcaaatg   8400
aacgaatcaa attaacaacc ataggatgat aatgcgatta gtttttttagc cttatttctg   8460
gggtaattaa tcagcgaagc gatgattttt gatctattaa cagatatata aatgcaaaaa   8520
ctgcataacc actttaacta atactttcaa cattttcggt ttgtattact tcttattcaa   8580
atgtaataaa agtatcaaca aaaaattgtt aatatacctc tatactttaa cgtcaaggag   8640
gcggccgcca tggtgagcaa gggcgaggag ctgttcaccg gggtggtgcc catcctggtc   8700
gagctggacg gcgacgtaaa cggccacaag ttcagcgtgt ccggcgaggg cgagggcgat   8760
gccacctacg gcaagctgac cctgaagttc atctgcacca ccggcaagct gcccgtgccc   8820
tggcccaccc tcgtgaccac cttcggctac ggcctgcaat gcttcgcccg ctaccccgac   8880
cacatgaagc tgcacgactt cttcaagtcc gccatgcccg aaggctacgt ccaggagcgc   8940
accatcttct tcaaggacga cggcaactac aagacccgcg ccgaggtgaa gttcgagggc   9000
gacaccctgg tgaaccgcat cgagctgaag ggcatcgact tcaaggagga cggcaacatc   9060
ctggggcaca agctggagta caactacaac agccacaacg tctatatcat ggccgacaag   9120
cagaagaacg gcatcaaggt gaacttcaag atccgccaca acatcgagga cggcagcgtg   9180
cagctcgccg accactacca gcagaacacc cccatcggcg acggccccgt gctgctgccc   9240
gacaaccact acctgagcta ccagtccgcc ctgagcaaag accccaacga gaagcgcgat   9300
cacatggtcc tgctggagtt cgtgaccgcc gccgggatca ctctcggcat ggacgagctg   9360
tacaagtaat aatctagagg gccgcatcat gtaattagtt atgtcacgct tacattcacg   9420
ccctccccccc acatccgctc taaccgaaaa ggaaggagtt agacaacctg aagtctaggt   9480
ccctatttat ttttttatag ttatgttagt attaagaacg ttatttatat ttcaaatttt   9540
tcttttttttt ctgtacagac gcgtgtacgc atgtaacatt atactgaaaa ccttgcttga   9600
gaaggttttg ggacgctcga aggctttaat ttgcggccct gcattaatga atcggccaac   9660
gcgcggggag aggcggtttg cgtattgggc gctcttccgc ttcctcgctc actgactcgc   9720
tgcgctcggt cgttcggctg cggcgagcgg tatcagctca ctcaaaggcg gtaatacggt   9780
tatccacaga atcaggggat aacgcaggaa agaacatgtg agcaaaaggc cagcaaaagc   9840
ccaggaaccg taaaaaggcc gcgttgctgg cgtttttcca taggctccgc ccccctgacg   9900
agcatcacaa aaatcgacgc tcaagtcaga ggtggcgaaa cccgacagga ctataaagat   9960
accaggcgtt tccccctgga agctccctcg tgcgctctcc tgttccgacc ctgccgctta  10020
ccggatacct gtccgccttt ctcccttcgg gaagcgtggc gctttctcat agctcacgct  10080
gtaggtatct cagttcggtg taggtcgttc gctccaagct gggctgtgtg cacgaacccc  10140
ccgttcagcc cgaccgctgc gccttatccg gtaactatcg tcttgagtcc aacccggtaa  10200
```

-continued

```
gacacgactt atcgccactg gcagcagcca ctggtaacag gattagcaga gcgaggtatg  10260
taggcggtgc tacagagttc ttgaagtggt ggcctaacta cggctacact agaaggacag  10320
tatttggtat ctgcgctctg ctgaagccag ttaccttcgg aaaaagagtt ggtagctctt  10380
gatccggcaa acaaaccacc gctggtagcg gtggtttttt tgtttgcaag cagcagatta  10440
cgcgcagaaa aaaaggatct caagaagatc ctttgatctt ttctacgggg tctgacgctc  10500
agtggaacga aaactcacgt taagggattt tggtcatgag attatcaaaa aggatcttca  10560
cctagatcct tttaaattaa aaatgaagtt ttaaatcaat ctaaagtata tatgagtaaa  10620
cttggtctga cagttaccaa tgcttaatca gtgaggcacc tatctcagcg atctgtctat  10680
ttcgttcatc catagttgcc tgactccccg tcgtgtagat aactacgata cgggagcgct  10740
taccatctgg ccccagtgct gcaatgatac cgcgagaccc acgctcaccg gctccagatt  10800
tatcagcaat aaaccagcca gccggaaggg ccgagcgcag aagtggtcct gcaactttat  10860
ccgcctccat ccagtctatt aattgttgcc gggaagctag agtaagtagt tcgccagtta  10920
atagtttgcg caacgttgtt ggcattgcta caggcatcgt ggtgtcactc tcgtcgtttg  10980
gtatggcttc attcagctcc ggttcccaac gatcaaggcg agttacatga tcccccatgt  11040
tgtgcaaaaa agcggttagc tccttcggtc ctccgatcgt tgtcagaagt aagttggccg  11100
cagtgttatc actcatggtt atggcagcac tgcataattc tcttactgtc atgccatccg  11160
taagatgctt ttctgtgact ggtgagtact caaccaagtc attctgagaa tagtgtatgc  11220
ggcgaccgag ttgctcttgc ccggcgtcaa tacgggataa tagtgtatca catagcagaa  11280
ctttaaaagt gctcatcatt ggaaaacgtt cttcggggcg aaaactctca aggatcttac  11340
cgctgttgag atccagttcg atgtaaccca ctcgtgcacc caactgatct tcagcatctt  11400
ttactttcac cagcgtttct gggtgagcaa aaacaggaag gcaaaatgcc gcaaaaaagg  11460
gaataagggc gacacggaaa tgttgaatac tcatactctt cctttttcaa tgggtaataa  11520
ctgatataat taaattgaag ctctaatttg tgagtttagt atacatgcat ttacttataa  11580
tacagttttt tagttttgct ggccgcatct tctcaaatat gcttcccagc ctgcttttct  11640
gtaacgttca ccctctacct tagcatccct tccctttgca aatagtcctc ttccaacaat  11700
aataatgtca gatcctgtag agaccacatc atccacggtt ctatactgtt gacccaatgc  11760
gtctcccttg tcatctaaac ccacaccggg tgtcataatc aaccaatcgt aaccttcatc  11820
tcttccaccc atgtctcttt gagcaataaa gccgataaca aaatctttgt cgctcttcgc  11880
aatgtcaaca gtacccttag tatattctcc agtagatagg gagcccttgc atgacaattc  11940
tgctaacatc aaaaggcctc taggttcctt tgttacttct tctgccgcct gcttcaaacc  12000
gctaacaata cctgggccca ccacaccgtg tgcattcgta atgtctgccc attctgctat  12060
tctgtataca cccgcagagt actgcaattt gactgtatta ccaatgtcag caaattttct  12120
gtcttcgaag agtaaaaaat tgtacttggc ggataatgcc tttagcggct taactgtgcc  12180
ctccatggaa aatcagtcaa agatatccac atgtgttttt agtaaacaaa ttttgggacc  12240
taatgcttca actaactcca gtaattcctt ggtggtacga acatccaatg aagcacacaa  12300
gtttgtttgc ttttcgtgca tgatattaaa tagcttggca gcaacaggac taggatgagt  12360
agcagcacgt tccttatatg tagctttcga catgatttat cttcgtttcc tgcaggtttt  12420
tgttctgtgc agttgggtta agaatactgg gcaatttcat gtttcttcaa cactacatat  12480
gcgtatatat accaatctaa gtctgtgctc cttccttcgt tcttccttct gttcggagat  12540
taccgaatca aaaaaatttc aaagaaaccg aaatcaaaaa aaagaataaa aaaaaaatga  12600
```

```
tgaattgaat tgaaaagcta gcttatcgat gataagctgt caaagatgag aattaattcc  12660
acggactata gactatacta gatactccgt ctactgtacg atacacttcc gctcaggtcc  12720
ttgtccttta acgaggcctt accactcttt tgttactcta ttgatccagc tcagcaaagg  12780
cagtgtgatc taagattcta tcttcgcgat gtagtaaaac tagctagacc gagaaagaga  12840
ctagaaatgc aaaaggcact tctacaatgg ctgccatcat tattatccga tgtgacgctg  12900
cagcttctca atgatattcg aatacgcttt gaggagatac agcctaatat ccgacaaact  12960
gttttacaga tttacgatcg tacttgttac ccatcattga attttgaaca tccgaacctg  13020
ggagttttcc ctgaaacaga tagtatattt gaacctgtat aataatatat agtctagcgc  13080
tttacggaag acaatgtatg tatttcggtt cctggagaaa ctattgcatc tattgcatag  13140
gtaatcttgc acgtcgcatc cccggttcat tttctgcgtt tccatcttgc acttcaatag  13200
catatctttg ttaacgaagc atctgtgctt cattttgtag aacaaaaatg caacgcgaga  13260
gcgctaattt ttcaaacaaa gaatctgagc tgcattttta cagaacagaa atgcaacgcg  13320
aaagcgctat tttaccaacg aagaatctgt gcttcatttt tgtaaaacaa aaatgcaacg  13380
cgacgagagc gctaattttt caaacaaaga atctgagctg catttttaca gaacagaaat  13440
gcaacgcgag agcgctattt taccaacaaa gaatctatac ttcttttttg ttctacaaaa  13500
atgcatcccg agagcgctat ttttctaaca aagcatctta gattactttt tttctccttt  13560
gtgcgctcta taatgcagtc tcttgataac tttttgcact gtaggtccgt taaggttaga  13620
agaaggctac tttggtgtct attttctctt ccataaaaaa agcctgactc cacttcccgc  13680
gtttactgat tactagcgaa gctgcgggtg catttttca agataaaggc atccccgatt  13740
atattctata ccgatgtgga ttgcgcatac tttgtgaaca gaaagtgata gcgttgatga  13800
ttcttcattg gtcagaaaat tatgaacggt ttcttctatt ttgtctctat atactacgta  13860
taggaaatgt ttacattttc gtattgtttt cgattcactc tatgaatagt tcttactaca  13920
attttttgt ctaaagagta atactagaga taaacataaa aaatgtagag gtcgagttta  13980
gatgcaagtt caaggagcga aaggtggatg ggtaggttat atagggatat agcacagaga  14040
tatatagcaa agagatactt ttgagcaatg tttgtggaag cggtattcgc aatgggaagc  14100
tccaccccgg ttgataatca gaaaagcccc aaaaacagga agattgtata agcaaatatt  14160
taaattgtaa acgttaatat tttgttaaaa ttcgcgttaa atttttgtta aatcagctca  14220
ttttttaacg aatagcccga aatcggcaaa atcccttata aatcaaaaga atagaccgag  14280
atagggttga gtgttgttcc agtttccaac aagagtccac tattaaagaa cgtggactcc  14340
aacgtcaaag ggcgaaaaag ggtctatcag ggcgatggcc cactacgtga accatcaccc  14400
taatcaagtt ttttggggtc gaggtgccgt aaagcagtaa atcggaaggg taaacggatg  14460
cccccattta gagcttgacg gggaaagccg gcgaacgtgg cgagaaagga agggaagaaa  14520
gcgaaaggag cgggggctag ggcggtggga agtgtagggg tcacgctggg cgtaaccacc  14580
acacccgccg cgcttaatgg ggcgctacag ggcgcgtggg gatgatccac tagt        14634
```

<210> SEQ ID NO 8
<211> LENGTH: 16558
<212> TYPE: DNA
<213> ORGANISM: Artificial sequence
<220> FEATURE:
<223> OTHER INFORMATION: Synthetic construct

<400> SEQUENCE: 8

```
acggattaga agccgccgag cgggtgacag ccctccgaag gaagactctc ctccgtgcgt     60
cctcgtcttc accggtcgcg ttcctgaaac gcagatgtgc ctcgcgccgc actgctccga    120
acaataaaga ttctacaata ctagctttta tggttatgaa gaggaaaaat tggcagtaac    180
ctggccccac aaaccttcaa atgaacgaat caaattaaca accataggat gataatgcga    240
ttagtttttt agccttattt ctggggtaat taatcagcga agcgatgatt tttgatctat    300
taacagatat ataaatgcaa aaactgcata accactttaa ctaatacttt caacattttc    360
ggtttgtatt acttcttatt caaatgtaat aaaagtatca acaaaaaatt gttaatatac    420
ctctatactt taacgtcaag gagaaaaaac cccggatcgg actactagca gctgtaatac    480
gactcactat agggaatatt aagcttgcca ccatggtgtt tatcgtcaat cttttctcct    540
gcaccttatc tgaaaccacg gttagctcaa taaaatctga agctacggtt agctcaacat    600
ttactgccgt cacggccctg caattggtgg ctgagggtaa gttgcagtcg gcgaagggtt    660
tcggtggtgg tacgattcac tacccaaccc tcgcggccga agcaccctgg tggacgccgg    720
gccaaggcca tggttacgag gcgatcacct acggctggct ggtcggcgaa ctgctgcgcc    780
gcgccgatgg gcgtgggcct ggtctgttag gcgctattgc cgtggttcct ggttacgttt    840
cttacgagaa ctctatcaag tggtggggac cgcgtctggc ttcttggggc tttgtcgttg    900
cacggccgtt gggcctggac tttcatgtgg gcctggcgga tgaagagttt tatcgtgttg    960
cccatatagc gcgcagcaaa gccaatgcag cactagataa cattgctgat gacaccgtcg   1020
gcagtataga tcctaagcgg ttgggcgcta ttggctggtc aggtggcggc ggcgcgctta   1080
aactggcaac ggagcgcagc acagtacgag ccattttgac cagtactaat aaacctgaat   1140
ggcgacgctt cgataaattc ttatgtgcct gcgaggatga ccggattgct gagactaaga   1200
aatatgccaa cgcgttttat aaaaatgccg acatgctcga agagttgacc cgtgaacaca   1260
gtatcgggcc ggataaaaca ttattgacac aaactcggtt tggcttgggg tgcttggatc   1320
aaccgcaagc aggggttaaa attcattttg aagagtacct tgatcaaacc catggattta   1380
tcaatttgac gccagtttca cataaggcga gagcaaatct gattcagatg cctaatgcca   1440
cattcggcct tggcccgcgt gcttttgggc atcctggtgc aggtggatcg gtaggttttg   1500
ccgaccccga acacgatgta gcgtttggtt tcgtgactaa tacattgggg ccttatgtag   1560
ttgagtttaa aagccgtcat ccctcatttt atgcatataa agatggattg gtgctgactg   1620
gaaatgacgt cgactatgtg actgattact atgcaacaaa gcatgctgta catttagatg   1680
atccacgtgc acagaagttg gtcggaatat tggccggttg tctgtaaccc gggtaatcat   1740
gtaattagtt atgtcacgct tacattcacg ccctcccccc acatccgctc taaccgaaaa   1800
ggaaggagtt agacaacctg aagtctaggt ccctatttat ttttttatag ttatgttagt   1860
attaagaacg ttatttatat ttcaaatttt tctttttttt ctgtacagac gcgtgtacgc   1920
atgtaacatt atactgaaaa ccttgcttga gaaggttttg ggacgctcga aggctttaat   1980
ttgccggatt agaagccgcc gagcgggtga cagccctccg aaggaagact ctcctccgtg   2040
cgtcctcgtc ttcaccggtc gcgttcctga aacgcagatg tgcctcgcgc cgcactgctc   2100
cgaacaataa agattctaca atactagctt ttatggttat gaagaggaaa aattggcagt   2160
aacctggccc cacaaacctt caaatgaacg aatcaaatta acaaccatag gatgataatg   2220
cgattagttt tttagcctta tttctggggt aattaatcag cgaagcgatg atttttgatc   2280
tattaacaga tatataaatg caaaaactgc ataaccactt taactaatac tttcaacatt   2340
ttcggtttgt attacttctt attcaaatgt aataaaagta tcaacaaaaa attgttaata   2400
```

```
tacctctata ctttaacgtc aaggaggcgc gccaccatga gtgatcaaaa taatcgatcg   2460
agaaatgaat atcactcaaa ccggaagaat gaaccttcct atgaactcca aaatgcacat   2520
agcgggctat ttcactcttc taatgaagaa ttaacaaaca ggaaccaaag atataccaat   2580
caaaatgcca gcatgggttc attcactcca gtccaatctt tgcaatttcc agaacaatct   2640
cagcaaacaa atatgcttta taacggtgac gatggcaata ataatactat caatgataac   2700
gaacgagaca tatatggagg ttttgtcaac caccatcgcc agcgtccccc accagcaact   2760
gcagaataca atgacgtttt taatacgaat agtcaacagc taccgtcgga acatcaatac   2820
aataacgtac cttcatatcc acttccttcg ataaatgtga ttcaaaccac tccagaactc   2880
atacataacg gctcacagac tatggccacc cccatcgaaa ggcccttctt taacgaaaac   2940
gactactatt ataataacag gaactctagg acgtcaccga gtattgcttc tagtagcgat   3000
ggttatgcag atcaggaagc taggcccatt ttggagcaac ccaacaataa catgaatagc   3060
ggtaatattc ctcaatacca tgaccaacct tttggataca acaatggtta ccatggccta   3120
caggcaaaag attactatga cgatccggag ggtggttata ttgatcagag aggagatgac   3180
tatcagatta attcatattt gggtagaaac ggtgaaatgg ttgatcctta cgattatgaa   3240
aacagtttaa gacatatgac tcctatggag cgtagagaat atcttcatga tgatagcaga   3300
cccgtaaacg atggaaaaga agaattagac agtgtgaaaa gcggttactc tcatagagac   3360
ttgggggaat atgacaagga tgatttttca agggatgacg agtacgatga tctcaacact   3420
attgataaat tacagtttca agctaatggt gtacctgcat catcctcggt gtcttctatc   3480
ggatctaaag aatccgacat aatagtaagc aatgataact taaccgcaaa tagagcacta   3540
aagagaagcg gtactgaaat taggaaattc aaactttgga atggtaattt tgttttcgat   3600
tctccaatca gtaagacgct attggaccaa tacgctacta caacagaaaa tgcaaacact   3660
ttaccaaatg agtttaagtt tatgagatat caagcagtta cttgcgaacc taatcaactt   3720
gcagagaaga atttcacggt gaggcagttg aagtatttaa ctccaaggga aacggaattg   3780
atgctagtag tcacaatgta taatgaagac catatcctgt taggaagaac tttgaaaggt   3840
attatggaca atgtcaaata tatggtgaaa aaaaaaaatt caagcacttg gggggccggat   3900
gcatggaaaa agattgtcgt ttgtatcatt tcagatggta gatccaaaat taatgaacgc   3960
tcgctagcat tactaagttc gttaggttgt taccaggacg ggtttgctaa ggatgaaatt   4020
aatgaaaaaa aagtggcaat gcatgtctac gaacatacga caatgatcaa catcacaaat   4080
atttcggaat cagaggtttc attagaatgc aatcaaggta ctgttccaat acaacttttg   4140
ttttgtttga aagagcaaaa tcagaaaaaa attaactcac atagatgggc atttgaaggc   4200
tttgcagaat tactgcgtcc caatatcgtt acattgttag atgctggtac tatgccaggt   4260
aaagattcta tttaccagtt atggagagag ttcaggaatc caaatgttgg tggcgcatgt   4320
ggtgaaataa gaactgattt gggtaagaga tttgtaaagt tgttgaatcc tttagttgca   4380
tcacagaatt tcgaatacaa aatgtccaat attttagaca aaacaaccga gtctaacttt   4440
ggatttatta ctgttctacc gggggcattc tctgcgtata ggtttgaagc tgtgagaggc   4500
caaccattac agaagtactt ttatggtgaa attatggaaa atgaaggttt tcattttttt   4560
tcttccaata tgtatcttgc tgaagatcgt attttatgct ttgaagtggt cacaaaaaaa   4620
aattgtaatt ggattttgaa atactgcaga agttcttatg cttcaacaga tgtaccggag   4680
agggtccctg aatttattct tcagaggagg cgttggttga atggttcatt ttttgctagt   4740
```

```
gtatattcct tttgtcattt ttacagagtc tggagcagtg gtcataatat tggtagaaaa   4800
ctccttttga cggttgaatt tttttacctt ttcttcaata cattgatttc atggttttca   4860
ttgagttcat ttttcctagt ctttaggatt ctcactgttt ctattgcact ggcataccat   4920
tcagcattta atgtgttgtc cgtcatattc ctgtggcttt atgggatttg taccttatca   4980
acattcatac tgtcattggg taataaacct aaaagtactg agaaatttta tgttctaact   5040
tgcgtcattt ttgcggtgat gatgatttac atgatattct gcagtatatt catgagtgtc   5100
aaatccttcc aaaatatatt gaaaaacgat accatcagct ttgagggttt gattaccaca   5160
gaggctttca gggatattgt tatctctctg ggctccactt attgtttgta cctaatcagt   5220
tcaattatct atttgcagcc atggcatatg ttgacaagtt ttattcagta tattttattg   5280
agtccttctt acatcaatgt tttgaatatc tatgcatttt gtaatgtcca cgacttatca   5340
tggggtacaa agggtgcaat ggcaaatccg ctgggtaaga ttaatactac agaagatggt   5400
acgttcaaaa tggaagttct ggtctctagt tcagagattc aagcaaacta cgataaatat   5460
ttgaaagttt taaatgactt cgatccaaaa tcagaatctc ggcctactga gccatcttat   5520
gatgaaaaaa agactggcta ttatgcaaac gttagatctc tcgtgattat cttttgggtc   5580
atcacaaatt tcatcatcgt tgctgttgtc ttagaaaccg gtgggattgc agattatatt   5640
gctatgaaat ccatatcaac tgatgacact ttagaaactg caaagaaggc ggaaattccc   5700
ttaatgacca gtaaggcctc aatttatttt aatgtaattt tatggttagt tgcattatcg   5760
gcattaataa ggttcattgg ttgctcaata tacatgatag taaggttttt taaaaaggtt   5820
acatttcgct aaggtacctc atgtaattag ttatgtcacg cttacattca cgccctcccc   5880
ccacatccgc tctaaccgaa aaggaaggag ttagacaacc tgaagtctag gtccctattt   5940
atttttttat agttatgtta gtattaagaa cgttatttat atttcaaatt tttctttttt   6000
ttctgtacag acgcgtgtac gcatgtaaca ttatactgaa aaccttgctt gagaaggttt   6060
tgggacgctc gaaggcttta atttgccgga ttagaagccg ccgagcgggt gacagccctc   6120
cgaaggaaga ctctcctccg tgcgtcctcg tcttcaccgg tcgcgttcct gaaacgcaga   6180
tgtgcctcgc gccgcactgc tccgaacaat aaagattcta caatactagc ttttatggtt   6240
atgaagagga aaaattggca gtaacctggc cccacaaacc ttcaaatgaa cgaatcaaat   6300
taacaaccat aggatgataa tgcgattagt tttttagcct tatttctggg gtaattaatc   6360
agcgaagcga tgatttttga tctattaaca gatatataaa tgcaaaaact gcataaccac   6420
tttaactaat actttcaaca ttttcggttt gtattacttc ttattcaaat gtaataaaag   6480
tatcaacaaa aaattgttaa tatacctcta tactttaacg tcaaggaggg atccgccacc   6540
atgtcactcc tttacatcat tcttctattc acacaattct tactactgcc aaccgatgcc   6600
tttgataggt ctgctaacac aaatattgct gtttattggg gtcaaaactc agcaggaacg   6660
caagaatcct tagctactta ctgtgaatct tctgatgctg atattttcct attatctttc   6720
ttgaaccaat ttccaaccct tggtttgaac tttgccaacg catgctctga tacttttttct   6780
gatggcttac ttcactgcac ccagattgct gaagatattg aaacttgcca gtccctagga   6840
aagaaagttc tattatcatt aggtggtgca tctggtagct acctcttttc agatgattct   6900
caagcggaaa cttttgcaca aactttatgg gatactttcg gtgaaggtac aggtgccagt   6960
gagagaccat ttgactcagc agtcgttgat ggttttgatt ttgatattga aaacaacaac   7020
gaagtaggct atagtgcgtt agctaccaag ttaagaactt tgtttgccga aggtacaaag   7080
caatattacc tttctgccgc accacaatgt ccatacccgg atgcttctgt tggtgacttg   7140
```

```
ttggaaaatg cagacattga ttttgcgttc atccaatttt acaataatta ctgcagtgtg   7200
agtggtcaat tcaattggga tacttggtta acctatgctc aaactgtatc cccaaataaa   7260
aatatcaaac tgttcttagg tttacctggt tctgcttctg ctgctggctc tggttatatt   7320
tctgacactt ctttattgga atcaactatt gcagatattg cctcttcaag ttcttttggt   7380
ggtattgcgt tatgggatgc atctcaagcc ttttccaacg agctaaatgg tgaaccatat   7440
gttgagattt tgaagaattt gctaacaagt gctagccaga ccgccactac tacagttgcc   7500
acctcaaaaa cctcagcagc ctcaacttca tctgcttcaa cttcatctgc ttcaacttct   7560
cagaaaaaga ccacacaatc tacgacatct acacaaagta aaagcaaagt tactttatct   7620
ccaactgcaa gcagcgctat caaaacatca attactcaaa ctacaaaaac attgacgagt   7680
agcaccaaga caaaatctag tctaggtacc accacaacag agagcacttt aaattcagtt   7740
gctatcacaa gtatgaaaac tactctatct tcccaaataa ccagtgctgc cttggtgacc   7800
cctcaaacaa ctactactag catagtttct tcggccccaa ttcaaacagc tatcactagt   7860
actctttcgc cagcaacgaa gagttcttct gtcgtttccc tacagacagc tactactagt   7920
acgctttccc caacaacgac cagtacaagc tcaggtagta caagctcagg tagtacaagc   7980
tcagacagta cagctcgtac attggctaaa gaattgaatg ctcaatatgc ggctggtaaa   8040
ttgaacggta aatctacctg tactgaaggt gaaattgcat gctctgctga tgggaagttc   8100
gccgtttgtg atcatagcgc ttgggtttac atggaatgtg cttctggaac cacatgttat   8160
gcttatgact ccggcgactc agtctatacc caatgtaatt tctcttattt ggaaagcaat   8220
tacttttaat taatcatgta attagttatg tcacgcttac attcacgccc tccccccaca   8280
tccgctctaa ccgaaaagga aggagttaga caacctgaag tctaggtccc tatttatttt   8340
tttatagtta tgttagtatt aagaacgtta tttatatttc aaatttttct tttttttctg   8400
tacagacgcg tgtacgcatg taacattata ctgaaaacct tgcttgagaa ggttttggga   8460
cgctcgaagg ctttaatttg ccggattaga agccgccgag cgggtgacag ccctccgaag   8520
gaagactctc ctccgtgcgt cctcgtcttc accggtcgcg ttcctgaaac gcagatgtgc   8580
ctcgcgccgc actgctccga acaataaaga ttctacaata ctagctttta tggttatgaa   8640
gaggaaaaat tggcagtaac ctggccccac aaaccttcaa atgaacgaat caaattaaca   8700
accataggat gataatgcga ttagtttttt agccttattt ctggggtaat taatcagcga   8760
agcgatgatt tttgatctat taacagatat ataaatgcaa aaactgcata accactttaa   8820
ctaatacttt caacattttc ggtttgtatt acttcttatt caaatgtaat aaaagtatca   8880
acaaaaaatt gttaatatac ctctatactt taacgtcaag gagctcgaga tgagaataca   8940
actaaataca attgatttgc aatgtattat tgcactttcc tgtctggggc aatttgttca   9000
cgcggaagct aatagggaag atttaaagca gatagacttt caatttcctg tattggaaag   9060
ggcagctaca aaaacgcctt ttccggattg gcttagtgca tttaccgggt taaaagaatg   9120
gcctgggtta gatccacctt atatacctta agatttcatt gatttcagtc aaattccaga   9180
ttataaggaa tatgatcaaa accattgcga cagtgttcca agggactcgt gctctttcga   9240
ttgccatcac tgcaccgaac acgatgatgt gtacacatgt tccaaacttt cccagacatt   9300
tgacgatggt ccttctgctt ccactactaa attattggac cggttgaagc ataattccac   9360
cttcttcaat ttaggtgtca atatagttca acatccagat atctatcaaa gaatgcaaaa   9420
ggagggacac ttaatcggct cacatacctg gtctcacgta tatttgccaa atgtatcgaa   9480
```

```
tgaaaaaatt atagctcaaa ttgaatggtc catctgggcg atgaatgcta ctggcaacca   9540
tacccccaaa tggttcagac ctccatatgg cggaatagat aatagagtaa gagcaataac   9600
aaggcaattt ggcttacaag ccgtcttatg ggatcacgat acttttgatt ggagcctcct   9660
tctcaatgat tctgtcataa ctgaacaaga aattcttcaa aatgtaataa actggaacaa   9720
gtcaggaacc ggattaatat tagaacacga ttcaacggaa aaaactgtcg atcttgccat   9780
taaaataaat aagttgatag gtgatgatca atcaacagtt tctcattgtg tcggcggaat   9840
tgattacata aaagaattct tgtcctaaga attctcatgt aattagttat gtcacgctta   9900
cattcacgcc ctccccccac atccgctcta accgaaaagg aaggagttag acaacctgaa   9960
gtctaggtcc ctatttattt ttttatagtt atgttagtat taagaacgtt atttatattt  10020
caaatttttc tttttttttct gtacagacgc gtgtacgcat gtaacattat actgaaaacc  10080
ttgcttgaga aggttttggg acgctcgaag gctttaattt gccggattag aagccgccga  10140
gcgggtgaca gccctccgaa ggaagactct cctccgtgcg tcctcgtctt caccggtcgc  10200
gttcctgaaa cgcagatgtg cctcgcgccg cactgctccg aacaataaag attctacaat  10260
actagctttt atggttatga agaggaaaaa ttggcagtaa cctggcccca caaaccttca  10320
aatgaacgaa tcaaattaac aaccatagga tgataatgcg attagttttt tagccttatt  10380
tctggggtaa ttaatcagcg aagcgatgat tttgatcta ttaacagata tataaatgca  10440
aaaactgcat aaccacttta actaatactt tcaacatttt cggtttgtat tacttcttat  10500
tcaaatgtaa taaaagtatc aacaaaaaat tgttaatata cctctatact ttaacgtcaa  10560
ggaggcggcc gccatggtga gcaagggcga ggagctgttc accggggtgg tgcccatcct  10620
ggtcgagctg gacggcgacg taaacggcca caagttcagc gtgtccggcg agggcgaggg  10680
cgatgccacc tacggcaagc tgaccctgaa gttcatctgc accaccggca agctgcccgt  10740
gccctggccc accctcgtga ccaccttcgg ctacggcctg caatgcttcg cccgctaccc  10800
cgaccacatg aagctgcacg acttcttcaa gtccgccatg cccgaaggct acgtccagga  10860
gcgcaccatc ttcttcaagg acgacggcaa ctacaagacc cgcgccgagg tgaagttcga  10920
gggcgacacc ctggtgaacc gcatcgagct gaagggcatc gacttcaagg aggacggcaa  10980
catcctgggg cacaagctgg agtacaacta caacagccac aacgtctata tcatggccga  11040
caagcagaag aacggcatca aggtgaactt caagatccgc cacaacatcg aggacggcag  11100
cgtgcagctc gccgaccact accagcagaa cacccccatc ggcgacggcc ccgtgctgct  11160
gcccgacaac cactacctga gctaccagtc cgccctgagc aaagacccca acgagaagcg  11220
cgatcacatg gtcctgctgg agttcgtgac cgccgccggg atcactctcg gcatggacga  11280
gctgtacaag taataatcta gagggccgca tcatgtaatt agttatgtca cgcttacatt  11340
cacgccctcc ccccacatcc gctctaaccg aaaaggaagg agttagacaa cctgaagtct  11400
aggtccctat ttattttttt atagttatgt tagtattaag aacgttattt atatttcaaa  11460
tttttctttt ttttctgtac agacgcgtgt acgcatgtaa cattatactg aaaaccttgc  11520
ttgagaaggt tttgggacgc tcgaaggctt taatttgcgg ccctgcatta atgaatcggc  11580
caacgcgcgg ggagaggcgg tttgcgtatt gggcgctctt ccgcttcctc gctcactgac  11640
tcgctgcgct cggtcgttcg gctgcggcga gcggtatcag ctcactcaaa ggcggtaata  11700
cggttatcca cagaatcagg ggataacgca ggaaagaaca tgtgagcaaa aggccagcaa  11760
aagcccagga accgtaaaaa ggccgcgttg ctggcgtttt tccataggct ccgcccccct  11820
gacgagcatc acaaaaatcg acgctcaagt cagaggtggc gaaacccgac aggactataa  11880
```

```
agataccagg cgtttccccc tggaagctcc ctcgtgcgct ctcctgttcc gaccctgccg  11940
cttaccggat acctgtccgc ctttctccct tcgggaagcg tggcgctttc tcatagctca  12000
cgctgtaggt atctcagttc ggtgtaggtc gttcgctcca agctgggctg tgtgcacgaa  12060
ccccccgttc agcccgaccg ctgcgcctta tccggtaact atcgtcttga gtccaacccg  12120
gtaagacacg acttatcgcc actggcagca gccactggta acaggattag cagagcgagg  12180
tatgtaggcg gtgctacaga gttcttgaag tggtggccta actacggcta cactagaagg  12240
acagtatttg gtatctgcgc tctgctgaag ccagttacct tcggaaaaag agttggtagc  12300
tcttgatccg gcaaacaaac caccgctggt agcggtggtt tttttgtttg caagcagcag  12360
attacgcgca gaaaaaaagg atctcaagaa gatcctttga tcttttctac ggggtctgac  12420
gctcagtgga acgaaaactc acgttaaggg attttggtca tgagattatc aaaaaggatc  12480
ttcacctaga tccttttaaa ttaaaaatga agttttaaat caatctaaag tatatatgag  12540
taaacttggt ctgacagtta ccaatgctta atcagtgagg cacctatctc agcgatctgt  12600
ctatttcgtt catccatagt tgcctgactc cccgtcgtgt agataactac gatacgggag  12660
cgcttaccat ctggccccag tgctgcaatg ataccgcgag acccacgctc accggctcca  12720
gatttatcag caataaacca gccagccgga agggccgagc gcagaagtgg tcctgcaact  12780
ttatccgcct ccatccagtc tattaattgt tgccgggaag ctagagtaag tagttcgcca  12840
gttaatagtt tgcgcaacgt tgttggcatt gctacaggca tcgtggtgtc actctcgtcg  12900
tttggtatgg cttcattcag ctccggttcc caacgatcaa ggcgagttac atgatccccc  12960
atgttgtgca aaaaagcggt tagctccttc ggtcctccga tcgttgtcag aagtaagttg  13020
gccgcagtgt tatcactcat ggttatggca gcactgcata attctcttac tgtcatgcca  13080
tccgtaagat gcttttctgt gactggtgag tactcaacca agtcattctg agaatagtgt  13140
atgcggcgac cgagttgctc ttgcccggcg tcaatacggg ataatagtgt atcacatagc  13200
agaactttaa aagtgctcat cattggaaaa cgttcttcgg ggcgaaaact ctcaaggatc  13260
ttaccgctgt tgagatccag ttcgatgtaa cccactcgtg cacccaactg atcttcagca  13320
tcttttactt tcaccagcgt ttctgggtga gcaaaaacag gaaggcaaaa tgccgcaaaa  13380
aagggaataa gggcgacacg gaaatgttga atactcatac tcttcctttt tcaatgggta  13440
ataactgata taattaaatt gaagctctaa tttgtgagtt tagtatacat gcatttactt  13500
ataatacagt tttttagttt tgctggccgc atcttctcaa atatgcttcc cagcctgctt  13560
ttctgtaacg ttcaccctct accttagcat cccttccctt tgcaaatagt cctcttccaa  13620
caataataat gtcagatcct gtagagacca catcatccac ggttctatac tgttgaccca  13680
atgcgtctcc cttgtcatct aaacccacac cgggtgtcat aatcaaccaa tcgtaacctt  13740
catctcttcc acccatgtct ctttgagcaa taaagccgat aacaaaatct ttgtcgctct  13800
tcgcaatgtc aacagtaccc ttagtatatt ctccagtaga tagggagccc ttgcatgaca  13860
attctgctaa catcaaaagg cctctaggtt cctttgttac ttcttctgcc gcctgcttca  13920
aaccgctaac aatacctggg cccaccacac cgtgtgcatt cgtaatgtct gcccattctg  13980
ctattctgta tacacccgca gagtactgca atttgactgt attaccaatg tcagcaaatt  14040
ttctgtcttc gaagagtaaa aaattgtact tggcggataa tgcctttagc ggcttaactg  14100
tgccctccat ggaaaaatca gtcaagatat ccacatgtgt ttttagtaaa caaattttgg  14160
gacctaatgc ttcaactaac tccagtaatt ccttggtggt acgaacatcc aatgaagcac  14220
```

```
acaagtttgt ttgcttttcg tgcatgatat taaatagctt ggcagcaaca ggactaggat  14280
gagtagcagc acgttcctta tatgtagctt tcgacatgat ttatcttcgt ttcctgcagg  14340
tttttgttct gtgcagttgg gttaagaata ctgggcaatt tcatgtttct tcaacactac  14400
atatgcgtat atataccaat ctaagtctgt gctccttcct tcgttcttcc ttctgttcgg  14460
agattaccga atcaaaaaaa tttcaaagaa accgaaatca aaaaaaagaa taaaaaaaaa  14520
atgatgaatt gaattgaaaa gctagcttat cgatgataag ctgtcaaaga tgagaattaa  14580
ttccacggac tatagactat actagatact ccgtctactg tacgatacac ttccgctcag  14640
gtccttgtcc tttaacgagg ccttaccact cttttgttac tctattgatc cagctcagca  14700
aaggcagtgt gatctaagat tctatcttcg cgatgtagta aaactagcta gaccgagaaa  14760
gagactagaa atgcaaaagg cacttctaca atggctgcca tcattattat ccgatgtgac  14820
gctgcagctt ctcaatgata ttcgaatacg ctttgaggag atacagccta atatccgaca  14880
aactgtttta cagatttacg atcgtacttg ttacccatca ttgaattttg aacatccgaa  14940
cctgggagtt ttccctgaaa cagatagtat atttgaacct gtataataat atatagtcta  15000
gcgctttacg gaagacaatg tatgtatttc ggttcctgga gaaactattg catctattgc  15060
ataggtaatc ttgcacgtcg catccccggt tcattttctg cgtttccatc ttgcacttca  15120
atagcatatc tttgttaacg aagcatctgt gcttcatttt gtagaacaaa aatgcaacgc  15180
gagagcgcta atttttcaaa caaagaatct gagctgcatt tttacagaac agaaatgcaa  15240
cgcgaaagcg ctattttacc aacgaagaat ctgtgcttca tttttgtaaa acaaaaatgc  15300
aacgcgacga gagcgctaat ttttcaaaca aagaatctga gctgcatttt tacagaacag  15360
aaatgcaacg cgagagcgct attttaccaa caaagaatct atacttcttt tttgttctac  15420
aaaaatgcat cccgagagcg ctatttttct aacaaagcat cttagattac tttttttctc  15480
ctttgtgcgc tctataatgc agtctcttga taactttttg cactgtaggt ccgttaaggt  15540
tagaagaagg ctactttggt gtctattttc tcttccataa aaaaagcctg actccacttc  15600
ccgcgtttac tgattactag cgaagctgcg ggtgcatttt ttcaagataa aggcatcccc  15660
gattatattc tataccgatg tggattgcgc atactttgtg aacagaaagt gatagcgttg  15720
atgattcttc attggtcaga aaattatgaa cggtttcttc tattttgtct ctatatacta  15780
cgtataggaa atgtttacat tttcgtattg ttttcgattc actctatgaa tagttcttac  15840
tacaattttt ttgtctaaag agtaatacta gagataaaca taaaaaatgt agaggtcgag  15900
tttagatgca agttcaagga gcgaaaggtg gatgggtagg ttatataggg atatagcaca  15960
gagatatata gcaaagagat acttttgagc aatgtttgtg gaagcggtat tcgcaatggg  16020
aagctccacc ccggttgata atcagaaaag ccccaaaaac aggaagattg tataagcaaa  16080
tatttaaatt gtaaacgtta atattttgtt aaaattcgcg ttaaattttt gttaaatcag  16140
ctcatttttt aacgaatagc ccgaaatcgg caaaatccct tataaatcaa aagaatagac  16200
cgagataggg ttgagtgttg ttccagtttc caacaagagt ccactattaa agaacgtgga  16260
ctccaacgtc aaagggcgaa aaagggtcta tcagggcgat ggcccactac gtgaaccatc  16320
accctaatca agttttttgg ggtcgaggtg ccgtaaagca gtaaatcgga agggtaaacg  16380
gatgccccca tttagagctt gacggggaaa gccggcgaac gtggcgagaa aggaagggaa  16440
gaaagcgaaa ggagcggggg ctagggcggt gggaagtgta ggggtcacgc tgggcgtaac  16500
caccacaccc gccgcgctta atggggcgct acagggcgcg tggggatgat ccactagt    16558
```

<210> SEQ ID NO 9
<211> LENGTH: 12544
<212> TYPE: DNA
<213> ORGANISM: Artificial sequence
<220> FEATURE:
<223> OTHER INFORMATION: Synthetic construct

<400> SEQUENCE: 9

```
ggggaattgt gagcggataa caattcccct ctagaaataa ttttgtttaa ctttaagaag      60
gagatatacc atggtgttta tcgtcaatct tttctcctgc accttatctg aaaccacggt     120
tagctcaata aaatctgaag ctacggttag ctcaacattt actgccgtca cggccctgca     180
attggtggct gagggtaagt tgcagtcggc gaagggtttc ggtggtggta cgattcacta     240
cccaaccctc gcggccgaag caccctggtg gacgccgggc caaggccatg gttacgaggc     300
gatcacctac ggctggctgg tcggcgaact gctgcgccgc gccgatgggc gtgggcctgg     360
tctgttaggc gctattgccg tggttcctgg ttacgtttct tacgagaact ctatcaagtg     420
gtggggaccg cgtctggctt cttggggctt tgtcgttgca cggccgttgg gcctggactt     480
tcatgtgggc ctggcggatg aagagtttta tcgtgttgcc catatagcgc gcagcaaagc     540
caatgcagca ctagataaca ttgctgatga caccgtcggc agtatagatc ctaagcggtt     600
gggcgctatt ggctggtcag gtggcggcgg cgcgcttaaa ctggcaacgg agcgcagcac     660
agtacgagcc attttgacca gtactaataa acctgaatgg cgacgcttcg ataaattctt     720
atgtgcctgc gaggatgacc ggattgctga gactaagaaa tatgccaacg cgttttataa     780
aaatgccgac atgctcgaag agttgacccg tgaacacagt atcgggccgg ataaaacatt     840
attgacacaa actcggtttg gcttggggtg cttggatcaa ccgcaagcag gggttaaaat     900
tcattttgaa gagtaccttg atcaaaccca tggatttatc aatttgacgc cagtttcaca     960
taaggcgaga gcaaatctga ttcagatgcc taatgccaca ttcggccttg gcccgcgtgc    1020
ttttgggcat cctggtgcag gtggatcggt aggttttgcc gaccccgaac acgatgtagc    1080
gtttggtttc gtgactaata cattggggcc ttatgtagtt gagtttaaaa gccgtcatcc    1140
ctcattttat gcatataaag atggattggt gctgactgga aatgacgtcg actatgtgac    1200
tgattactat gcaacaaagc atgctgtaca tttagatgat ccacgtgcac agaagttggt    1260
cggaatattg gccggttgtc tgtaaggatc cagaaataat tttgtttaac tttaagaagg    1320
agagaattca tgtcactcct ttacatcatt cttctattca cacaattctt actactgcca    1380
accgatgcct ttgataggtc tgctaacaca aatattgctg tttattgggg tcaaaactca    1440
gcaggaacgc aagaatcctt agctacttac tgtgaatctt ctgatgctga tattttccta    1500
ttatctttct tgaaccaatt tccaaccctt ggtttgaact ttgccaacgc atgctctgat    1560
actttttctg atggcttact tcactgcacc cagattgctg aagatattga aacttgccag    1620
tccctaggaa agaaagttct attatcatta ggtggtgcat ctggtagcta cctcttttca    1680
gatgattctc aagcggaaac ttttgcacaa actttatggg atactttcgg tgaaggtaca    1740
ggtgccagtg agagaccatt tgactcagca gtcgttgatg gttttgattt tgatattgaa    1800
aacaacaacg aagtaggcta tagtgcgtta gctaccaagt taagaacttt gtttgccgaa    1860
ggtacaaagc aatattacct ttctgccgca ccacaatgtc catacccgga tgcttctgtt    1920
ggtgacttgt tggaaaatgc agacattgat tttgcgttca tccaatttta caataattac    1980
tgcagtgtga gtggtcaatt caattgggat acttggttaa cctatgctca aactgtatcc    2040
ccaaataaaa atatcaaact gttcttaggt ttacctggtt ctgcttctgc tgctggctct    2100
```

ggttatattt ctgacacttc tttattggaa tcaactattg cagatattgc ctcttcaagt 2160
tcttttggtg gtattgcgtt atgggatgca tctcaagcct tttccaacga gctaaatggt 2220
gaaccatatg ttgagatttt gaagaatttg ctaacaagtg ctagccagac cgccactact 2280
acagttgcca cctcaaaaac ctcagcagcc tcaacttcat ctgcttcaac ttcatctgct 2340
tcaacttctc agaaaaagac cacacaatct acgacatcta cacaaagtaa aagcaaagtt 2400
actttatctc caactgcaag cagcgctatc aaaacatcaa ttactcaaac tacaaaaaca 2460
ttgacgagta gcaccaagac aaaatctagt ctaggtacca ccacaacaga gagcacttta 2520
aattcagttg ctatcacaag tatgaaaact actctatctt cccaaataac cagtgctgcc 2580
ttggtgaccc ctcaaacaac tactactagc atagtttctt cggccccaat tcaaacagct 2640
atcactagta ctctttcgcc agcaacgaag agttcttctg tcgtttccct acagacagct 2700
actactagta cgctttcccc aacaacgacc agtacaagct caggtagtac aagctcaggt 2760
agtacaagct cagacagtac agctcgtaca ttggctaaag aattgaatgc tcaatatgcg 2820
gctggtaaat tgaacggtaa atctacctgt actgaaggtg aaattgcatg ctctgctgat 2880
gggaagttcg ccgtttgtga tcatagcgct tgggtttaca tggaatgtgc ttctggaacc 2940
acatgttatg cttatgactc cggcgactca gtctataccc aatgtaattt ctcttatttg 3000
gaaagcaatt acttttaagc ggccgcataa tgcttaagtc gaacagaaag taatcgtatt 3060
gtacacggcc gcataatcga aattaatacg actcactata ggggaattgt gagcggataa 3120
caattcccca tcttagtata ttagttaagt ataagaagga gatatacata tgagtgatca 3180
aaataatcga tcgagaaatg aatatcactc aaaccggaag aatgaacctt cctatgaact 3240
ccaaaatgca catagcgggc tatttcactc ttctaatgaa gaattaacaa acaggaacca 3300
aagatatacc aatcaaaatg ccagcatggg ttcattcact ccagtccaat ctttgcaatt 3360
tccagaacaa tctcagcaaa caaatatgct ttataacggt gacgatggca ataataatac 3420
tatcaatgat aacgaacgag acatatatgg aggttttgtc aaccaccatc gccagcgtcc 3480
cccaccagca actgcagaat acaatgacgt ttttaatacg aatagtcaac agctaccgtc 3540
ggaacatcaa tacaataacg taccttcata tccacttcct tcgataaatg tgattcaaac 3600
cactccagaa ctcatacata acggctcaca gactatggcc acccccatcg aaaggccctt 3660
ctttaacgaa aacgactact attataataa caggaactct aggacgtcac cgagtattgc 3720
ttctagtagc gatggttatg cagatcagga agctaggccc attttggagc aacccaacaa 3780
taacatgaat agcggtaata ttcctcaata ccatgaccaa ccttttggat acaacaatgg 3840
ttaccatggc ctacaggcaa aagattacta tgacgatccg gagggtggtt atattgatca 3900
gagaggagat gactatcaga ttaattcata tttgggtaga aacggtgaaa tggttgatcc 3960
ttacgattat gaaaacagtt taagacatat gactcctatg gagcgtagag aatatcttca 4020
tgatgatagc agacccgtaa acgatggaaa agaagaatta gacagtgtga aaagcggtta 4080
ctctcataga gacttggggg aatatgacaa ggatgatttt tcaagggatg acgagtacga 4140
tgatctcaac actattgata aattacagtt tcaagctaat ggtgtacctg catcatcctc 4200
ggtgtcttct atcggatcta aagaatccga cataatagta agcaatgata acttaaccgc 4260
aaatagagca ctaaagagaa gcggtactga aattaggaaa ttcaaacttt ggaatggtaa 4320
ttttgttttc gattctccaa tcagtaagac gctattggac caatacgcta ctacaacaga 4380
aaatgcaaac actttaccaa atgagtttaa gtttatgaga tatcaagcag ttacttgcga 4440
acctaatcaa cttgcagaga agaatttcac ggtgaggcag ttgaagtatt taactccaag 4500

```
ggaaacggaa ttgatgctag tagtcacaat gtataatgaa gaccatatcc tgttaggaag   4560
aactttgaaa ggtattatgg acaatgtcaa atatatggtg aaaaaaaaaa attcaagcac   4620
ttgggggccg gatgcatgga aaaagattgt cgtttgtatc atttcagatg gtagatccaa   4680
aattaatgaa cgctcgctag cattactaag ttcgttaggt tgttaccagg acgggtttgc   4740
taaggatgaa attaatgaaa aaaaagtggc aatgcatgtc tacgaacata cgacaatgat   4800
caacatcaca aatatttcgg aatcagaggt ttcattagaa tgcaatcaag gtactgttcc   4860
aatacaactt ttgttttgtt tgaaagagca aaatcagaaa aaaattaact cacatagatg   4920
ggcatttgaa ggctttgcag aattactgcg tcccaatatc gttacattgt tagatgctgg   4980
tactatgcca ggtaaagatt ctatttacca gttatggaga gagttcagga atccaaatgt   5040
tggtggcgca tgtggtgaaa taagaactga tttgggtaag agatttgtaa agttgttgaa   5100
tcctttagtt gcatcacaga atttcgaata caaaatgtcc aatattttag acaaaacaac   5160
cgagtctaac tttggattta ttactgttct accgggggca ttctctgcgt ataggtttga   5220
agctgtgaga ggccaaccat tacagaagta cttttatggt gaaattatgg aaaatgaagg   5280
ttttcatttt ttttcttcca atatgtatct tgctgaagat cgtattttat gctttgaagt   5340
ggtcacaaaa aaaaattgta attggatttt gaaatactgc agaagttctt atgcttcaac   5400
agatgtaccg gagagggtcc ctgaatttat tcttcagagg aggcgttggt tgaatggttc   5460
attttttgct agtgtatatt ccttttgtca tttttacaga gtctggagca gtggtcataa   5520
tattggtaga aaactccttt tgacggttga attttttac cttttcttca atacattgat   5580
ttcatggttt tcattgagtt cattttttcct agtctttagg attctcactg tttctattgc   5640
actggcatac cattcagcat ttaatgtgtt gtccgtcata ttcctgtggc tttatgggat   5700
ttgtacctta tcaacattca tactgtcatt gggtaataaa cctaaaagta ctgagaaatt   5760
ttatgttcta acttgcgtca tttttgcggt gatgatgatt tacatgatat tctgcagtat   5820
attcatgagt gtcaaatcct tccaaaatat attgaaaaac gataccatca gctttgaggg   5880
tttgattacc acagaggctt tcagggatat tgttatctct ctgggctcca cttattgttt   5940
gtacctaatc agttcaatta tctatttgca gccatggcat atgttgacaa gttttattca   6000
gtatatttta ttgagtcctt cttacatcaa tgttttgaat atctatgcat tttgtaatgt   6060
ccacgactta tcatggggta caaagggtgc aatggcaaat ccgctgggta agattaatac   6120
tacagaagat ggtacgttca aaatggaagt tctggtctct agttcagaga ttcaagcaaa   6180
ctacgataaa tatttgaaag ttttaaatga cttcgatcca aaatcagaat ctcggcctac   6240
tgagccatct tatgatgaaa aaaagactgg ctattatgca aacgttagat ctctcgtgat   6300
tatcttttgg gtcatcacaa atttcatcat cgttgctgtt gtcttagaaa ccggtgggat   6360
tgcagattat attgctatga aatccatatc aactgatgac actttagaaa ctgcaaagaa   6420
ggcggaaatt cccttaatga ccagtaaggc ctcaatttat tttaatgtaa ttttatggtt   6480
agttgcatta tcggcattaa taaggttcat tggttgctca atatacatga tagtaaggtt   6540
ttttaaaaag gttacatttc gctaaggtac cagaaataat tttgtttaac tttaagaagg   6600
agactcgaga tgagaataca actaaataca attgatttgc aatgtattat tgcactttcc   6660
tgtctggggc aatttgttca cgcggaagct aatagggaag atttaaagca gatagacttt   6720
caatttcctg tattggaaag ggcagctaca aaaacgcctt ttccggattg gcttagtgca   6780
tttaccgggt taaaagaatg gcctgggtta gatccacctt atatacettt agatttcatt   6840
```

gatttcagtc aaattccaga ttataaggaa tatgatcaaa accattgcga cagtgttcca 6900
agggactcgt gctctttcga ttgccatcac tgcaccgaac acgatgatgt gtacacatgt 6960
tccaaacttt cccagacatt tgacgatggt ccttctgctt ccactactaa attattggac 7020
cggttgaagc ataattccac cttcttcaat ttaggtgtca atatagttca acatccagat 7080
atctatcaaa gaatgcaaaa ggagggacac ttaatcggct cacatacctg gtctcacgta 7140
tatttgccaa atgtatcgaa tgaaaaaatt atagctcaaa ttgaatggtc catctgggcg 7200
atgaatgcta ctggcaacca tacccccaaa tggttcagac ctccatatgg cggaatagat 7260
aatagagtaa gagcaataac aaggcaattt ggcttacaag ccgtcttatg ggatcacgat 7320
acttttgatt ggagcctcct tctcaatgat tctgtcataa ctgaacaaga aattcttcaa 7380
aatgtaataa actggaacaa gtcaggaacc ggattaatat tagaacacga ttcaacggaa 7440
aaaactgtcg atcttgccat taaaataaat aagttgatag gtgatgatca atcaacagtt 7500
tctcattgtg tcggcggaat tgattacata aaagaattct tgtcctaatt aattaaccta 7560
ggctgctgcc accgctgagc aataactagc ataacccctt ggggcctcta aacgggtctt 7620
gaggggtttt ttgctgaaag gaggaactat atccggattg gcgaatggga cgcgccctgt 7680
agcggcgcat taagcgcggc gggtgtggtg gttacgcgca gcgtgaccgc tacacttgcc 7740
agcgccctag cgcccgctcc tttcgctttc ttcccttcct ttctcgccac gttcgccggc 7800
tttccccgtc aagctctaaa tcgggggctc cctttagggt tccgatttag tgctttacgg 7860
cacctcgacc ccaaaaaact tgattagggt gatggttcac gtagtgggcc atcgccctga 7920
tagacggttt ttcgcccttt gacgttggag tccacgttct ttaatagtgg actcttgttc 7980
caaactggaa caacactcaa ccctatctcg gtctattctt ttgatttata agggattttg 8040
ccgatttcgg cctattggtt aaaaaatgag ctgatttaac aaaaatttaa cgcgaatttt 8100
aacaaaatat taacgtttac aatttctggc ggcacgatgg catgagatta tcaaaaagga 8160
tcttcaccta gatcctttta aattaaaaat gaagttttaa atcaatctaa agtatatatg 8220
agtaaacttg gtctgacagt taccaatgct taatcagtga ggcacctatc tcagcgatct 8280
gtctatttcg ttcatccata gttgcctgac tccccgtcgt gtagataact acgatacggg 8340
agggcttacc atctggcccc agtgctgcaa tgataccgcg agacccacgc tcaccggctc 8400
cagatttatc agcaataaac cagccagccg gaagggccga gcgcagaagt ggtcctgcaa 8460
ctttatccgc ctccatccag tctattaatt gttgccggga agctagagta agtagttcgc 8520
cagttaatag tttgcgcaac gttgttgcca ttgctacagg catcgtggtg tcacgctcgt 8580
cgtttggtat ggcttcattc agctccggtt cccaacgatc aaggcgagtt acatgatccc 8640
ccatgttgtg caaaaaagcg gttagctcct tcggtcctcc gatcgttgtc agaagtaagt 8700
tggccgcagt gttatcactc atggttatgg cagcactgca taattctctt actgtcatgc 8760
catccgtaag atgcttttct gtgactggtg agtactcaac caagtcattc tgagaatagt 8820
gtatgcggcg accgagttgc tcttgcccgg cgtcaatacg ggataatacc gcgccacata 8880
gcagaacttt aaaagtgctc atcattggaa aacgttcttc ggggcgaaaa ctctcaagga 8940
tcttaccgct gttgagatcc agttcgatgt aacccactcg tgcacccaac tgatcttcag 9000
catcttttac tttcaccagc gtttctgggt gagcaaaaac aggaaggcaa aatgccgcaa 9060
aaaagggaat aagggcgaca cggaaatgtt gaatactcat actcttcctt tttcaatcat 9120
gattgaagca tttatcaggg ttattgtctc atgagcggat acatatttga atgtatttag 9180
aaaaataaac aaataggtca tgaccaaaat cccttaacgt gagttttcgt tccactgagc 9240

```
gtcagacccc gtagaaaaga tcaaaggatc ttcttgagat cctttttttc tgcgcgtaat    9300
ctgctgcttg caaacaaaaa aaccaccgct accagcggtg gtttgtttgc cggatcaaga    9360
gctaccaact ctttttccga aggtaactgg cttcagcaga gcgcagatac caaatactgt    9420
ccttctagtg tagccgtagt taggccacca cttcaagaac tctgtagcac cgcctacata    9480
cctcgctctg ctaatcctgt taccagtggc tgctgccagt ggcgataagt cgtgtcttac    9540
cgggttggac tcaagacgat agttaccgga taaggcgcag cggtcgggct gaacgggggg    9600
ttcgtgcaca cagcccagct tggagcgaac gacctacacc gaactgagat acctacagcg    9660
tgagctatga gaaagcgcca cgcttcccga agggagaaag gcggacaggt atccggtaag    9720
cggcagggtc ggaacaggag agcgcacgag ggagcttcca gggggaaacg cctggtatct    9780
ttatagtcct gtcgggtttc gccacctctg acttgagcgt cgatttttgt gatgctcgtc    9840
aggggggcgg agcctatgga aaaacgccag caacgcggcc tttttacggt tcctggcctt    9900
ttgctggcct tttgctcaca tgttctttcc tgcgttatcc cctgattctg tggataaccg    9960
tattaccgcc tttgagtgag ctgataccgc tcgccgcagc cgaacgaccg agcgcagcga   10020
gtcagtgagc gaggaagcgg aagagcgcct gatgcggtat tttctcctta cgcatctgtg   10080
cggtatttca caccgcatat atggtgcact ctcagtacaa tctgctctga tgccgcatag   10140
ttaagccagt atacactccg ctatcgctac gtgactgggt catggctgcg ccccgacacc   10200
cgccaacacc cgctgacgcg ccctgacggg cttgtctgct cccggcatcc gcttacagac   10260
aagctgtgac cgtctccggg agctgcatgt gtcagaggtt ttcaccgtca tcaccgaaac   10320
gcgcgaggca gctgcggtaa agctcatcag cgtggtcgtg aagcgattca cagatgtctg   10380
cctgttcatc cgcgtccagc tcgttgagtt tctccagaag cgttaatgtc tggcttctga   10440
taaagcgggc catgttaagg gcggtttttt cctgtttggt cactgatgcc tccgtgtaag   10500
ggggatttct gttcatgggg gtaatgatac cgatgaaacg agagaggatg ctcacgatac   10560
gggttactga tgatgaacat gcccggttac tggaacgttg tgagggtaaa caactggcgg   10620
tatggatgcg gcgggaccag agaaaaatca ctcagggtca atgccagcgc ttcgttaata   10680
cagatgtagg tgttccacag ggtagccagc agcatcctgc gatgcagatc cggaacataa   10740
tggtgcaggg cgctgacttc cgcgtttcca gactttacga aacacggaaa ccgaagacca   10800
ttcatgttgt tgctcaggtc gcagacgttt tgcagcagca gtcgcttcac gttcgctcgc   10860
gtatcggtga ttcattctgc taaccagtaa ggcaaccccg ccagcctagc cgggtcctca   10920
acgacaggag cacgatcatg ctagtcatgc cccgcgccca ccggaaggag ctgactgggt   10980
tgaaggctct caagggcatc ggtcgagatc ccggtgccta atgagtgagc taacttacat   11040
taattgcgtt gcgctcactg cccgctttcc agtcgggaaa cctgtcgtgc cagctgcatt   11100
aatgaatcgg ccaacgcgcg gggagaggcg gtttgcgtat tgggcgccag ggtggttttt   11160
cttttcacca gtgagacggg caacagctga ttgcccttca ccgcctggcc ctgagagagt   11220
tgcagcaagc ggtccacgct ggtttgcccc agcaggcgaa aatcctgttt gatggtggtt   11280
aacggcggga tataacatga gctgtcttcg gtatcgtcgt atcccactac cgagatgtcc   11340
gcaccaacgc gcagcccgga ctcggtaatg gcgcgcattg cgcccagcgc catctgatcg   11400
ttggcaacca gcatcgcagt gggaacgatg ccctcattca gcatttgcat ggtttgttga   11460
aaaccggaca tggcactcca gtcgccttcc cgttccgcta tcggctgaat ttgattgcga   11520
gtgagatatt tatgccagcc agccagacgc agacgcgccg agacagaact taatgggccc   11580
```

```
gctaacagcg cgatttgctg gtgacccaat gcgaccagat gctccacgcc cagtcgcgta  11640

ccgtcttcat gggagaaaat aatactgttg atgggtgtct ggtcagagac atcaagaaat  11700

aacgccggaa cattagtgca ggcagcttcc acagcaatgg catcctggtc atccagcgga  11760

tagttaatga tcagcccact gacgcgttgc gcgagaagat tgtgcaccgc cgctttacag  11820

gcttcgacgc cgcttcgttc taccatcgac accaccacgc tggcacccag ttgatcggcg  11880

cgagatttaa tcgccgcgac aatttgcgac ggcgcgtgca gggccagact ggaggtggca  11940

acgccaatca gcaacgactg tttgcccgcc agttgttgtg ccacgcggtt gggaatgtaa  12000

ttcagctccg ccatcgccgc ttccactttt tcccgcgttt tcgcagaaac gtggctggcc  12060

tggttcacca cgcgggaaac ggtctgataa gagacaccgg catactctgc gacatcgtat  12120

aacgttactg gtttcacatt caccaccctg aattgactct cttccgggcg ctatcatgcc  12180

ataccgcgaa aggttttgcg ccattcgatg gtgtccggga tctcgacgct ctcccttatg  12240

cgactcctgc attaggaagc agcccagtag taggttgagg ccgttgagca ccgccgccgc  12300

aaggaatggt gcatgcaagg agatggcgcc caacagtccc ccggccacgg ggcctgccac  12360

catacccacg ccgaaacaag cgctcatgag cccgaagtgg cgagcccgat cttccccatc  12420

ggtgatgtcg gcgatatagg cgccagcaac cgcacctgtg gcgccggtga tgccggccac  12480

gatgcgtccg gcgtagagga tcgagatcga tctcgatccc gcgaaattaa tacgactcac  12540

tata                                                               12544
```

```
<210> SEQ ID NO 10
<211> LENGTH: 20014
<212> TYPE: DNA
<213> ORGANISM: Artificial sequence
<220> FEATURE:
<223> OTHER INFORMATION: Synthetic construct

<400> SEQUENCE: 10

acggattaga agccgccgag cgggtgacag ccctccgaag gaagactctc ctccgtgcgt     60

cctcgtcttc accggtcgcg ttcctgaaac gcagatgtgc ctcgcgccgc actgctccga    120

acaataaaga ttctacaata ctagctttta tggttatgaa gaggaaaaat tggcagtaac    180

ctggccccac aaaccttcaa atgaacgaat caaattaaca accataggat gataatgcga    240

ttagtttttt agccttattt ctggggtaat taatcagcga agcgatgatt tttgatctat    300

taacagatat ataaatgcaa aaactgcata accactttaa ctaatacttt caacattttc    360

ggtttgtatt acttcttatt caaatgtaat aaaagtatca acaaaaaatt gttaatatac    420

ctctatactt taacgtcaag gagaaaaaac cccggatcgg actactagca gctgtaatac    480

gactcactat agggaatatt aagcttgcca ccatgagtga tcaaaataat cgatcgagaa    540

atgaatatca ctcaaaccgg aagaatgaac cttcctatga actccaaaat gcacatagcg    600

ggctatttca ctcttctaat gaagaattaa caaacaggaa ccaaagatat accaatcaaa    660

atgccagcat gggttcattc actccagtcc aatctttgca atttccagaa caatctcagc    720

aaacaaatat gctttataac ggtgacgatg gcaataataa tactatcaat gataacgaac    780

gagacatata tggaggtttt gtcaaccacc atcgccagcg tcccccacca gcaactgcag    840

aatacaatga cgtttttaat acgaatagtc aacagctacc gtcggaacat caatacaata    900

acgtaccttc atatccactt ccttcgataa atgtgattca aaccactcca gaactcatac    960

ataacggctc acagactatg gccaccccca tcgaaaggcc cttctttaac gaaaacgact   1020

actattataa taacaggaac tctaggacgt caccgagtat tgcttctagt agcgatggtt   1080
```

```
atgcagatca ggaagctagg cccattttgg agcaacccaa caataacatg aatagcggta   1140
atattcctca ataccatgac caacctttg gatacaacaa tggttaccat ggcctacagg    1200
caaaagatta ctatgacgat ccggagggtg gttatattga tcagagagga gatgactatc   1260
agattaattc atatttgggt agaaacggtg aaatggttga tccttacgat tatgaaaaca   1320
gtttaagaca tatgactcct atggagcgta gagaatatct tcatgatgat agcagacccg   1380
taaacgatgg aaaagaagaa ttagacagtg tgaaaagcgg ttactctcat agagacttgg   1440
gggaatatga caaggatgat ttttcaaggg atgacgagta cgatgatctc aacactattg   1500
ataaattaca gtttcaagct aatggtgtac ctgcatcatc ctcggtgtct tctatcggat   1560
ctaaagaatc cgacataata gtaagcaatg ataacttaac cgcaaataga gcactaaaga   1620
gaagcggtac tgaaattagg aaattcaaac tttggaatgg taattttgtt ttcgattctc   1680
caatcagtaa gacgctattg gaccaatacg ctactacaac agaaaatgca aacactttac   1740
caaatgagtt taagtttatg agatatcaag cagttacttg cgaacctaat caacttgcag   1800
agaagaattt cacggtgagg cagttgaagt atttaactcc aagggaaacg gaattgatgc   1860
tagtagtcac aatgtataat gaagaccata tcctgttagg aagaactttg aaaggtatta   1920
tggacaatgt caaatatatg gtgaaaaaaa aaaattcaag cacttggggg ccggatgcat   1980
ggaaaaagat tgtcgtttgt atcatttcag atggtagatc caaaattaat gaacgctcgc   2040
tagcattact aagttcgtta ggttgttacc aggacgggtt tgctaaggat gaaattaatg   2100
aaaaaaaagt ggcaatgcat gtctacgaac atacgacaat gatcaacatc acaaatattt   2160
cggaatcaga ggtttcatta gaatgcaatc aaggtactgt tccaatacaa cttttgtttt   2220
gtttgaaaga gcaaaatcag aaaaaaatta actcacatag atgggcattt gaaggctttg   2280
cagaattact gcgtcccaat atcgttacat tgttagatgc tggtactatg ccaggtaaag   2340
attctattta ccagttatgg agagagttca ggaatccaaa tgttggtggc gcatgtggtg   2400
aaataagaac tgatttgggt aagagatttg taaagttgtt gaatccttta gttgcatcac   2460
agaatttcga atacaaaatg tccaatattt tagacaaaac aaccgagtct aactttggat   2520
ttattactgt tctaccgggg gcattctctg cgtataggtt tgaagctgtg agaggccaac   2580
cattacagaa gtacttttat ggtgaaatta tggaaaatga aggttttcat ttttttttctt  2640
ccaatatgta tcttgctgaa gatcgtattt tatgctttga agtggtcaca aaaaaaaatt   2700
gtaattggat tttgaaatac tgcagaagtt cttatgcttc aacagatgta ccggagaggg   2760
tccctgaatt tattcttcag aggaggcgtt ggttgaatgg ttcatttttt gctagtgtat   2820
attccttttg tcatttttac agagtctgga gcagtggtca taatattggt agaaaactcc   2880
ttttgacggt tgaatttttt taccttttct tcaatacatt gatttcatgg ttttcattga   2940
gttcattttt cctagtcttt aggattctca ctgtttctat tgcactggca taccattcag   3000
catttaatgt gttgtccgtc atattcctgt ggctttatgg gatttgtacc ttatcaacat   3060
tcatactgtc attgggtaat aaacctaaaa gtactgagaa attttatgtt ctaacttgcg   3120
tcatttttgc ggtgatgatg atttacatga tattctgcag tatattcatg agtgtcaaat   3180
ccttccaaaa tatattgaaa aacgatacca tcagctttga gggtttgatt accacagagg   3240
ctttcaggga tattgttatc tctctgggct ccacttattg tttgtaccta atcagttcaa   3300
ttatctattt gcagccatgg catatgttga caagttttat tcagtatatt ttattgagtc   3360
cttcttacat caatgttttg aatatctatg cattttgtaa tgtccacgac ttatcatggg   3420
```

-continued

```
gtacaaaggg tgcaatggca aatccgctgg gtaagattaa tactacagaa gatggtacgt   3480
tcaaaatgga agttctggtc tctagttcag agattcaagc aaactacgat aaatatttga   3540
aagttttaaa tgacttcgat ccaaaatcag aatctcggcc tactgagcca tcttatgatg   3600
aaaaaaagac tggctattat gcaaacgtta gatctctcgt gattatcttt tgggtcatca   3660
caaatttcat catcgttgct gttgtcttag aaaccggtgg gattgcagat tatattgcta   3720
tgaaatccat atcaactgat gacactttag aaactgcaaa gaaggcggaa attcccttaa   3780
tgaccagtaa ggcctcaatt tattttaatg taattttatg gttagttgca ttatcggcat   3840
taataaggtt cattggttgc tcaatataca tgatagtaag gtttttttaaa aaggttacat   3900
ttcgctaagg tacctcatgt aattagttat gtcacgctta cattcacgcc ctccccccac   3960
atccgctcta accgaaaagg aaggagttag acaacctgaa gtctaggtcc ctatttattt   4020
ttttatagtt atgttagtat taagaacgtt atttatattt caaatttttc ttttttttct   4080
gtacagacgc gtgtacgcat gtaacattat actgaaaacc ttgcttgaga aggttttggg   4140
acgctcgaag gctttaattt gccggattag aagccgccga gcgggtgaca gccctccgaa   4200
ggaagactct cctccgtgcg tcctcgtctt caccggtcgc gttcctgaaa cgcagatgtg   4260
cctcgcgccg cactgctccg aacaataaag attctacaat actagctttt atggttatga   4320
agaggaaaaa ttggcagtaa cctggcccca caaaccttca aatgaacgaa tcaaattaac   4380
aaccatagga tgataatgcg attagttttt tagccttatt tctggggtaa ttaatcagcg   4440
aagcgatgat tttgatctta ttaacagata tataaatgca aaaactgcat aaccacttta   4500
actaatactt tcaacatttt cggtttgtat tacttcttat tcaaatgtaa taaaagtatc   4560
aacaaaaaat tgttaatata cctctatact ttaacgtcaa ggagggatcc gccaccatgt   4620
cactccttta catcattctt ctattcacac aattcttact actgccaacc gatgcctttg   4680
ataggtctgc taacacaaat attgctgttt attggggtca aaactcagca ggaacgcaag   4740
aatccttagc tacttactgt gaatcttctg atgctgatat tttcctatta tctttcttga   4800
accaatttcc aacccttggt ttgaactttg ccaacgcatg ctctgatact tttctgatg    4860
gcttacttca ctgcacccag attgctgaag atattgaaac ttgccagtcc ctaggaaaga   4920
aagttctatt atcattaggt ggtgcatctg gtagctacct cttttcagat gattctcaag   4980
cggaaacttt tgcacaaact ttatgggata ctttcggtga aggtacaggt gccagtgaga   5040
gaccatttga ctcagcagtc gttgatggtt ttgattttga tattgaaaac aacaacgaag   5100
taggctatag tgcgttagct accaagttaa gaactttgtt tgccgaaggt acaaagcaat   5160
attacctttc tgccgcacca caatgtccat acccggatgc ttctgttggt gacttgttgg   5220
aaaatgcaga cattgatttt gcgttcatcc aattttacaa taattactgc agtgtgagtg   5280
gtcaattcaa ttgggatact tggttaacct atgctcaaac tgtatcccca aataaaaata   5340
tcaaactgtt cttaggttta cctggttctg cttctgctgc tggctctggt tatatttctg   5400
acacttcttt attggaatca actattgcag atattgcctc ttcaagttct tttggtggta   5460
ttgcgttatg ggatgcatct caagcctttt ccaacgagct aaatggtgaa ccatatgttg   5520
agattttgaa gaatttgcta acaagtgcta gccagaccgc cactactaca gttgccacct   5580
caaaaacctc agcagcctca acttcatctg cttcaacttc atctgcttca acttctcaga   5640
aaaagaccac acaatctacg acatctacac aaagtaaaag caaagttact ttatctccaa   5700
ctgcaagcag cgctatcaaa acatcaatta ctcaaactac aaaaacattg acgagtagca   5760
ccaagacaaa atctagtcta ggtaccacca caacagagag cactttaaat tcagttgcta   5820
```

```
tcacaagtat gaaaactact ctatcttccc aaataaccag tgctgccttg gtgacccctc   5880
aaacaactac tactagcata gtttcttcgg ccccaattca aacagctatc actagtactc   5940
tttcgccagc aacgaagagt tcttctgtcg tttccctaca gacagctact actagtacgc   6000
tttccccaac aacgaccagt acaagctcag gtagtacaag ctcaggtagt acaagctcag   6060
acagtacagc tcgtacattg gctaaagaat tgaatgctca atatgcggct ggtaaattga   6120
acggtaaatc tacctgtact gaaggtgaaa ttgcatgctc tgctgatggg aagttcgccg   6180
tttgtgatca tagcgcttgg gtttacatgg aatgtgcttc tggaaccaca tgttatgctt   6240
atgactccgg cgactcagtc tatacccaat gtaatttctc ttatttggaa agcaattact   6300
tttaattaat catgtaatta gttatgtcac gcttacattc acgccctccc cccacatccg   6360
ctctaaccga aaaggaagga gttagacaac ctgaagtcta ggtccctatt tattttttta   6420
tagttatgtt agtattaaga acgttattta tatttcaaat ttttcttttt tttctgtaca   6480
gacgcgtgta cgcatgtaac attatactga aaaccttgct tgagaaggtt ttgggacgct   6540
cgaaggcttt aatttgccgg attagaagcc gccgagcggg tgacagccct ccgaaggaag   6600
actctcctcc gtgcgtcctc gtcttcaccg gtcgcgttcc tgaaacgcag atgtgcctcg   6660
cgccgcactg ctccgaacaa taaagattct acaatactag cttttatggt tatgaagagg   6720
aaaaattggc agtaacctgg ccccacaaac cttcaaatga acgaatcaaa ttaacaacca   6780
taggatgata atgcgattag ttttttagcc ttatttctgg ggtaattaat cagcgaagcg   6840
atgatttttg atctattaac agatatataa atgcaaaaac tgcataacca ctttaactaa   6900
tactttcaac attttcggtt tgtattactt cttattcaaa tgtaataaaa gtatcaacaa   6960
aaaattgtta atatacctct atactttaac gtcaaggagc tcgagatgag aatacaacta   7020
aatacaattg atttgcaatg tattattgca ctttcctgtc tggggcaatt tgttcacgcg   7080
gaagctaata gggaagattt aaagcagata gactttcaat ttcctgtatt ggaaagggca   7140
gctacaaaaa cgccttttcc ggattggctt agtgcattta ccgggttaaa agaatggcct   7200
gggttagatc caccttatat acctttagat ttcattgatt tcagtcaaat tccagattat   7260
aaggaatatg atcaaaacca ttgcgacagt gttccaaggg actcgtgctc tttcgattgc   7320
catcactgca ccgaacacga tgatgtgtac acatgttcca aactttccca gacatttgac   7380
gatggtcctt ctgcttccac tactaaatta ttggaccggt tgaagcataa ttccaccttc   7440
ttcaatttag gtgtcaatat agttcaacat ccagatatct atcaaagaat gcaaaaggag   7500
ggacacttaa tcggctcaca tacctggtct cacgtatatt tgccaaatgt atcgaatgaa   7560
aaaattatag ctcaaattga atggtccatc tgggcgatga atgctactgg caaccatacc   7620
cccaaatggt tcagacctcc atatggcgga atagataata gagtaagagc aataacaagg   7680
caatttggct tacaagccgt cttatgggat cacgatactt ttgattggag cctccttctc   7740
aatgattctg tcataactga acaagaaatt cttcaaaatg taataaactg gaacaagtca   7800
ggaaccggat taatattaga acacgattca acggaaaaaa ctgtcgatct tgccattaaa   7860
ataaataagt tgataggtga tgatcaatca acagtttctc attgtgtcgg cggaattgat   7920
tacataaaag aattcttgtc ctaagaattc tcatgtaatt agttatgtca cgcttacatt   7980
cacgccctcc ccccacatcc gctctaaccg aaaaggaagg agttagacaa cctgaagtct   8040
aggtccctat ttattttttt atagttatgt tagtattaag aacgttattt atatttcaaa   8100
tttttctttt ttttctgtac agacgcgtgt acgcatgtaa cattatactg aaaaccttgc   8160
```

-continued

```
ttgagaaggt tttgggacgc tcgaaggctt taatttgccg gattagaagc cgccgagcgg   8220
gtgacagccc tccgaaggaa gactctcctc cgtgcgtcct cgtcttcacc ggtcgcgttc   8280
ctgaaacgca gatgtgcctc gcgccgcact gctccgaaca ataaagattc tacaatacta   8340
gcttttatgg ttatgaagag gaaaaattgg cagtaacctg gccccacaaa ccttcaaatg   8400
aacgaatcaa attaacaacc ataggatgat aatgcgatta gtttttagc cttatttctg    8460
gggtaattaa tcagcgaagc gatgattttt gatctattaa cagatatata aatgcaaaaa   8520
ctgcataacc actttaacta atactttcaa cattttcggt ttgtattact tcttattcaa   8580
atgtaataaa agtatcaaca aaaaattgtt aatatacctc tatactttaa cgtcaaggag   8640
gcggccgcca ccatggtgag caagggcgag gagctgttca ccggggtggt gcccatcctg   8700
gtcgagctgg acggcgacgt aaacggccac aagttcagcg tgtccggcga gggcgagggc   8760
gatgccacct acggcaagct gaccctgaag ttcatctgca ccaccggcaa gctgcccgtg   8820
ccctggccca ccctcgtgac caccctgacc tacggcgtgc agtgcttcag ccgctacccc   8880
gaccacatga agcagcacga cttcttcaag tccgccatgc ccgaaggcta cgtccaggag   8940
cgcaccatct tcttcaagga cgacggcaac tacaagaccc gcgccgaggt gaagttcgag   9000
ggcgacaccc tggtgaaccg catcgagctg aagggcatcg acttcaagga ggacggcaac   9060
atcctggggc acaagctgga gtacaactac aacagccaca acgtctatat catggccgac   9120
aagcagaaga acggcatcaa ggtgaacttc aagatccgcc acaacatcga ggacggcagc   9180
gtgcagctcg ccgaccacta ccagcagaac acccccatcg gcgacggccc cgtgctgctg   9240
cccgacaacc actacctgag cacccagtcc gccctgagca aagaccccaa cgagaagcgc   9300
gatcacatgg tcctgctgga gttcgtgacc gccgccggga tcactctcgg catggacgag   9360
ctgtacaagt aagtcgactc atgtaattag ttatgtcacg cttacattca cgccctcccc   9420
ccacatccgc tctaaccgaa aaggaaggag ttagacaacc tgaagtctag gtccctattt   9480
atttttttat agttatgtta gtattaagaa cgttatttat atttcaaatt tttctttttt   9540
ttctgtacag acgcgtgtac gcatgtaaca ttatactgaa aaccttgctt gagaaggttt   9600
tgggacgctc gaaggcttta atttgccgga ttagaagccg ccgagcgggt gacagccctc   9660
cgaaggaaga ctctcctccg tgcgtcctcg tcttcaccgg tcgcgttcct gaaacgcaga   9720
tgtgcctcgc gccgcactgc tccgaacaat aaagattcta caatactagc ttttatggtt   9780
atgaagagga aaaattggca gtaacctggc cccacaaacc ttcaaatgaa cgaatcaaat   9840
taacaaccat aggatgataa tgcgattagt tttttagcct tatttctggg gtaattaatc   9900
agcgaagcga tgatttttga tctattaaca gatatataaa tgcaaaaact gcataaccac   9960
tttaactaat actttcaaca ttttcggttt gtattacttc ttattcaaat gtaataaaag  10020
tatcaacaaa aaattgttaa tatacctcta tactttaacg tcaaggaggc ggccgccacc  10080
atggcgaagt ttggtagccg taataagtct ccgaagtgga tctctaacgg ctgctgcttc  10140
ctgctgggtg cctttactgc tctgctgctg ctgtggggtc tgtgctcctt tattatcccg  10200
attccgaaca ccgatccgaa gctgaactct gtagcgacct ctctgcgttc tctgaacttc  10260
ccgaagaacc cagcagctac cctgccaccg aacctgcagc atgatccacc ggatactact  10320
ttctacgacg atccggaaac ctcttatact atggataaac cgatgaagaa ctgggacgag  10380
aaacgtaagg aatggctgct gcatcacccg tccttcggcg cagctgctcg tgacaagatc  10440
ctgctggtaa ccggttccca gccgaaacgc tgtcacaacc cgattggtga tcacctgctg  10500
ctgcgtttct ttaagaacaa agtggattac tgccgtctgc ataattacga tatcatctat  10560
```

```
aacaacgcac tgctgcaccc gaaaatgaac tcctattggg ctaagtaccc agtgatccgt  10620
gctgcaatga tggctcatcc ggaagttgaa tgggtgtggt gggttgactc tgacgctgta  10680
ttcactgaca tggagtttaa actgccactg aaacgctata agaaccacaa tctggtggtg  10740
catggttggg aaggtctggt acgtctgaac cactcctgga ctggtctgaa cgcaggtgta  10800
ttcctgatcc gtaattgcca atggagcctg gagttcatgg atgtatgggt tagcatgggt  10860
ccacaaactc cagaatacga gaaatggggt gagcgtctgc gcgaaacctt caaagataaa  10920
gttctgccag actctgatga ccagactgca ctggcatacc tgatcgcaac cgataacaaa  10980
gacacctggc gtgagaaaat cttcctggaa agcgagtact acttcgaagg ctattggctg  11040
gaaatcgtaa agacttacga gaacatctcc gaacgttacg atgaagttga acgcaaagta  11100
gaaggtctgc gtcgtcgcca cgctgagaag gttagcgaga aatacggtgc aatgcgtgaa  11160
gaatacctga aagataacaa acgtcgtccg ttcatcaccc atttcactgg ttgccagccg  11220
tgcaacggtc accataaccc agcatacaat gcgaacgact gttggaatgg tatggaacgt  11280
gcactgaact ttgcagataa ccagatcctg cgtacctacg gttaccatcg tcagaatctg  11340
ctggacaagt ccgtttctcc actgccgttc ggttatccag cagcttaacc cgggtcatgt  11400
aattagttat gtcacgctta cattcacgcc ctccccccac atccgctcta accgaaaagg  11460
aaggagttag acaacctgaa gtctaggtcc ctatttattt ttttatagtt atgttagtat  11520
taagaacgtt atttatattt caaatttttc ttttttttct gtacagacgc gtgtacgcat  11580
gtaacattat actgaaaacc ttgcttgaga aggttttggg acgctcgaag gctttaattt  11640
gccggattag aagccgccga gcgggtgaca gccctccgaa ggaagactct cctccgtgcg  11700
tcctcgtctt caccggtcgc gttcctgaaa cgcagatgtg cctcgcgccg cactgctccg  11760
aacaataaag attctacaat actagctttt atggttatga agaggaaaaa ttggcagtaa  11820
cctggcccca caaaccttca aatgaacgaa tcaaattaac aaccatagga tgataatgcg  11880
attagttttt tagccttatt tctggggtaa ttaatcagcg aagcgatgat tttgatcta   11940
ttaacagata tataaatgca aaaactgcat aaccacttta actaatactt tcaacatttt  12000
cggtttgtat tacttcttat tcaaatgtaa taaaagtatc aacaaaaaat tgttaatata  12060
cctctatact ttaacgtcaa ggagcgtacg ccaccatggc ttcgccggca ccggcgggcg  12120
atgccgtgta tgcggccaat ggcggcctca ctgacccgct tctagtgagc gcgaacggcc  12180
atggtgccgc cgcgaggaag gctggccacg gcgccagggg caggtactgg gtggcctccg  12240
acaaggccga gaggcgcgct gccaaggagt ccggcggtga ggacggccgc gcgctgctgt  12300
tccggaagta taaggtcaaa ggcgccctcc tgcaccccta caggttgctg atcatcatcc  12360
gattagtcgc tgtcctcgcc ttcttcgcgt ggcgcatcag gcacaacaaa tccgacatca  12420
tgtggttctg gacaatgtcc atcgtcggcg acgtctggtt cggcttctcg tggctcctca  12480
accagctccc aaagttcaac cctgtgaaga ccatcccaga tctcgccgcc ctccagcggc  12540
actttggcta ccctgacggc ggcgcctcta ggctccccgg tatcgatgtt ttcgtcacca  12600
ctgccgaccc cattgatgag cccatactct acaccatgaa ctgtgtcctc tccatcctgt  12660
ctgtcgatta cccagtcgat cggctagcct gctatctctc agatgatagt ggggcgctgg  12720
ttctctatga ggcactggcc gaggtcggaa agtttgcgcc tctatgggtt ccgttctgcc  12780
gcaagtactc cattgagcca agggcaccag aaagctattt tgagcatgtg gcaccgccgc  12840
aggctggaag ggtgacgcag gagttcttga atgattatag gagggtgcag atggagtacg  12900
```

-continued

```
atgagttcaa ggcgcgcttg gacaacctcc ctgatgccat acgcaagaga tccgatgttt  12960
acaatagcgt gagagatgca ggaggagctc aaaaggcaac ttggatggca aatgggacgc  13020
agtggcccgg cacatggatt gatccagcag agaaccatag gaaaggacac catgctccaa  13080
ttgccaaggt tgtgctgaac catccaagcc gtggacaaca ccctattact gaaagcaatc  13140
ccagcattgc caccactgat gagcgcctcc caatgcttgt ttacgtctct cgtgagaaga  13200
acccaggtta tgaccacaac aagaaggcag gtgccctgaa tgcacagctg cgggcctctg  13260
ctctcctctc taatgcccaa ctcatcatca acttcgactg cgaccactac atcaacaact  13320
ctcaagccct aagctcggct gtgtgcttca tgctggatca acgggacggt gataacaccg  13380
catttgttca gttcccacag cgcttcgaca atgttgaccc cacggaccgc tatggtaacc  13440
acaatcgtgt cttctttgat gggaccatgc ttgcccttaa tggtttgcaa gggccctcat  13500
acctcggtac tggttgcatg ttccgtcgct tagcactcta tggtattgac ccaccccact  13560
gtagagcaga aaacatcacg gccgaagcta gcaggtttgg caactccaca atcttcctag  13620
attcagtgtc aaaagccctg aaaaatgaca ggacaatcac accgccacca attgatgaca  13680
cattccttgc tgagctagag agggttgtga catgttctta tgacaaaggt actgactggg  13740
gcaagggtgt agggtacatc tatgacatag ccactgaaga tatagtaaca ggattccgca  13800
tccacgggca ggggtggcgc tctatgtatt gcacaatgga gcacgatgcg ttctgtggcg  13860
ttgcaccaat caacctaact gaacgcctcc atcaaattgt gcgctggtct ggtgggtctt  13920
tagagatgtt cttctcccac aacaatccat tcatcggtgg tcgccggatt caaccccttc  13980
agcgtgtctc ctacctcaac atgacagtct acccagtcac atcagtcttc atcctaatct  14040
atgctctaag cccggtgatg tggcttatcc ccgatgaagt atacatccag agaccattca  14100
ctaggtatgt cgtgtacctt cttgtaatca tcgtgatgat tcacatgatt ggctggcttg  14160
agataaagtg ggcgggggtc acatggctgg actattggcg caatgagcag ttctttatga  14220
tcggctcaac aagtgcatat ccaatggcag tgctgcacat ggcagtgaac ctcctcacaa  14280
agaagggcat acacttcagg gtcacttcca agcaaacagc cgcggacgac aatgacaagt  14340
tcgccgacct ttatgatttt cgatgggtgc caatgctcat cccaacaatg gcagttctga  14400
tctgcaatgt tggtgccatt ggtgtagccc tgggcaaaac tgtggtatac attggaacat  14460
ggacagcggc gaagaagatg catgcagcac tgggtctgct gttcaacata tggatcatgt  14520
ttctcctcta cccatttgca ctagcgatca tggggcggtg ggcgaagagg ccaatcatcc  14580
ttgtagttct gctgccggtt gtctttgcac ttgtcgcgct gttgtatgta ggtatccata  14640
tcctacttgc tggtctgatt ccattctagg tagtatagaa aacattgtaa tttcttgtgt  14700
agttaccaag gaaccaatta tgtttttttt agcaaaaaaa aaaaaaaaaa aatctagagg  14760
gccgcatcat gtaattagtt atgtcacgct tacattcacg ccctcccccc acatccgctc  14820
taaccgaaaa ggaaggagtt agacaacctg aagtctaggt ccctatttat ttttttatag  14880
ttatgttagt attaagaacg ttatttatat ttcaaatttt tctttttttt ctgtacagac  14940
gcgtgtacgc atgtaacatt atactgaaaa ccttgcttga gaaggttttg ggacgctcga  15000
aggctttaat ttgcggccct gcattaatga atcggccaac gcgcggggag aggcggtttg  15060
cgtattgggc gctcttccgc ttcctcgctc actgactcgc tgcgctcggt cgttcggctg  15120
cggcgagcgg tatcagctca ctcaaaggcg gtaatacggt tatccacaga atcaggggat  15180
aacgcaggaa agaacatgtg agcaaaaggc cagcaaaagc ccaggaaccg taaaaaggcc  15240
gcgttgctgg cgtttttcca taggctccgc ccccctgacg agcatcacaa aaatcgacgc  15300
```

```
tcaagtcaga ggtggcgaaa cccgacagga ctataaagat accaggcgtt tccccctgga  15360
agctccctcg tgcgctctcc tgttccgacc ctgccgctta ccggatacct gtccgccttt  15420
ctcccttcgg gaagcgtggc gctttctcat agctcacgct gtaggtatct cagttcggtg  15480
taggtcgttc gctccaagct gggctgtgtg cacgaacccc ccgttcagcc cgaccgctgc  15540
gccttatccg gtaactatcg tcttgagtcc aacccggtaa gacacgactt atcgccactg  15600
gcagcagcca ctggtaacag gattagcaga gcgaggtatg taggcggtgc tacagagttc  15660
ttgaagtggt ggcctaacta cggctacact agaaggacag tatttggtat ctgcgctctg  15720
ctgaagccag ttaccttcgg aaaaagagtt ggtagctctt gatccggcaa acaaaccacc  15780
gctggtagcg gtggtttttt tgtttgcaag cagcagatta cgcgcagaaa aaaaggatct  15840
caagaagatc ctttgatctt ttctacgggg tctgacgctc agtggaacga aaactcacgt  15900
taagggattt tggtcatgag attatcaaaa aggatcttca cctagatcct tttaaattaa  15960
aaatgaagtt ttaaatcaat ctaaagtata tatgagtaaa cttggtctga cagttaccaa  16020
tgcttaatca gtgaggcacc tatctcagcg atctgtctat ttcgttcatc catagttgcc  16080
tgactccccg tcgtgtagat aactacgata cgggagcgct taccatctgg ccccagtgct  16140
gcaatgatac cgcgagaccc acgctcaccg gctccagatt tatcagcaat aaaccagcca  16200
gccggaaggg ccgagcgcag aagtggtcct gcaactttat ccgcctccat ccagtctatt  16260
aattgttgcc gggaagctag agtaagtagt tcgccagtta atagtttgcg caacgttgtt  16320
ggcattgcta caggcatcgt ggtgtcactc tcgtcgtttg gtatggcttc attcagctcc  16380
ggttcccaac gatcaaggcg agttacatga tcccccatgt tgtgcaaaaa agcggttagc  16440
tccttcggtc ctccgatcgt tgtcagaagt aagttggccg cagtgttatc actcatggtt  16500
atggcagcac tgcataattc tcttactgtc atgccatccg taagatgctt ttctgtgact  16560
ggtgagtact caaccaagtc attctgagaa tagtgtatgc ggcgaccgag ttgctcttgc  16620
ccggcgtcaa tacgggataa tagtgtatca catagcagaa ctttaaaagt gctcatcatt  16680
ggaaaacgtt cttcggggcg aaaactctca aggatcttac cgctgttgag atccagttcg  16740
atgtaaccca ctcgtgcacc caactgatct tcagcatctt ttactttcac cagcgtttct  16800
gggtgagcaa aaacaggaag gcaaaatgcc gcaaaaaagg gaataagggc gacacggaaa  16860
tgttgaatac tcatactctt cctttttcaa tgggtaataa ctgatataat taaattgaag  16920
ctctaatttg tgagtttagt atacatgcat ttacttataa tacagttttt tagttttgct  16980
ggccgcatct tctcaaatat gcttcccagc ctgcttttct gtaacgttca ccctctacct  17040
tagcatccct tccctttgca aatagtcctc ttccaacaat aataatgtca gatcctgtag  17100
agaccacatc atccacggtt ctatactgtt gacccaatgc gtctcccttg tcatctaaac  17160
ccacaccggg tgtcataatc aaccaatcgt aaccttcatc tcttccaccc atgtctcttt  17220
gagcaataaa gccgataaca aaatctttgt cgctcttcgc aatgtcaaca gtacccttag  17280
tatattctcc agtagatagg gagcccttgc atgacaattc tgctaacatc aaaaggcctc  17340
taggttcctt tgttacttct tctgccgcct gcttcaaacc gctaacaata cctgggccca  17400
ccacaccgtg tgcattcgta atgtctgccc attctgctat tctgtataca cccgcagagt  17460
actgcaattt gactgtatta ccaatgtcag caaattttct gtcttcgaag agtaaaaaat  17520
tgtacttggc ggataatgcc tttagcggct taactgtgcc ctccatggaa aaatcagtca  17580
agatatccac atgtgttttt agtaaacaaa ttttgggacc taatgcttca actaactcca  17640
```

```
gtaattcctt ggtggtacga acatccaatg aagcacacaa gtttgtttgc ttttcgtgca  17700
tgatattaaa tagcttggca gcaacaggac taggatgagt agcagcacgt tccttatatg  17760
tagctttcga catgatttat cttcgtttcc tgcaggtttt tgttctgtgc agttgggtta  17820
agaatactgg gcaatttcat gtttcttcaa cactacatat gcgtatatat accaatctaa  17880
gtctgtgctc cttccttcgt tcttccttct gttcggagat taccgaatca aaaaaatttc  17940
aaagaaaccg aaatcaaaaa aaagaataaa aaaaaaatga tgaattgaat tgaaaagcta  18000
gcttatcgat gataagctgt caaagatgag aattaattcc acggactata gactatacta  18060
gatactccgt ctactgtacg atacacttcc gctcaggtcc ttgtccttta acgaggcctt  18120
accactcttt tgttactcta ttgatccagc tcagcaaagg cagtgtgatc taagattcta  18180
tcttcgcgat gtagtaaaac tagctagacc gagaaagaga ctagaaatgc aaaaggcact  18240
tctacaatgg ctgccatcat tattatccga tgtgacgctg cagcttctca atgatattcg  18300
aatacgcttt gaggagatac agcctaatat ccgacaaact gttttacaga tttacgatcg  18360
tacttgttac ccatcattga attttgaaca tccgaacctg ggagttttcc ctgaaacaga  18420
tagtatattt gaacctgtat aataatatat agtctagcgc tttacggaag acaatgtatg  18480
tatttcggtt cctggagaaa ctattgcatc tattgcatag gtaatcttgc acgtcgcatc  18540
cccggttcat ttctgcgtt tccatcttgc acttcaatag catatctttg ttaacgaagc  18600
atctgtgctt cattttgtag aacaaaaatg caacgcgaga gcgctaattt ttcaaacaaa  18660
gaatctgagc tgcattttta cagaacagaa atgcaacgcg aaagcgctat tttaccaacg  18720
aagaatctgt gcttcatttt tgtaaaacaa aaatgcaacg cgacgagagc gctaattttt  18780
caaacaaaga atctgagctg catttttaca gaacagaaat gcaacgcgag agcgctattt  18840
taccaacaaa gaatctatac ttcttttttg ttctacaaaa atgcatcccg agagcgctat  18900
ttttctaaca aagcatctta gattactttt tttctccttt gtgcgctcta taatgcagtc  18960
tcttgataac tttttgcact gtaggtccgt taaggttaga agaaggctac tttggtgtct  19020
attttctctt ccataaaaaa agcctgactc cacttcccgc gtttactgat tactagcgaa  19080
gctgcgggtg catttttttca agataaaggc atccccgatt atattctata ccgatgtgga  19140
ttgcgcatac tttgtgaaca gaaagtgata gcgttgatga ttcttcattg gtcagaaaat  19200
tatgaacggt ttcttctatt ttgtctctat atactacgta taggaaatgt ttacattttc  19260
gtattgtttt cgattcactc tatgaatagt tcttactaca attttttttgt ctaaagagta  19320
atactagaga taaacataaa aaatgtagag gtcgagttta gatgcaagtt caaggagcga  19380
aaggtggatg ggtaggttat atagggatat agcacagaga tatatagcaa agagatactt  19440
ttgagcaatg tttgtggaag cggtattcgc aatgggaagc tccacccccgg ttgataatca  19500
gaaaagcccc aaaaacagga agattgtata agcaaatatt taaattgtaa acgttaatat  19560
tttgttaaaa ttcgcgttaa atttttgtta aatcagctca ttttttaacg aatagcccga  19620
aatcggcaaa atcccttata aatcaaaaga atagaccgag atagggttga gtgttgttcc  19680
agtttccaac aagagtccac tattaaagaa cgtggactcc aacgtcaaag ggcgaaaaag  19740
ggtctatcag ggcgatggcc cactacgtga accatcaccc taatcaagtt ttttggggtc  19800
gaggtgccgt aaagcagtaa atcggaaggg taaacggatg cccccattta gagcttgacg  19860
gggaaagccg gcgaacgtgg cgagaaagga agggaagaaa gcgaaaggag cgggggctag  19920
ggcggtggga agtgtagggg tcacgctggg cgtaaccacc acacccgccg cgcttaatgg  19980
ggcgctacag ggcgcgtggg gatgatccac tagt                              20014
```

<210> SEQ ID NO 11
<211> LENGTH: 1903
<212> TYPE: DNA
<213> ORGANISM: Schizosaccharomyces pombe

<400> SEQUENCE: 11

```
ggttttaccg aaacctgttt atgtggctgg ataaaggatg tcaaaggtac ctgatgtacg     60
agaagtattt atattcgaag attgcacatt ttctgggtaa tgagcagttt gaaggtaagg    120
taataacgac tctgtgactt ccatgcctgc atccacgtcc atccccgaaa ctccttcgaa    180
gttaccagac gcattgctgg ttaattcaga tcctgcttct aaagttgata atgtttctgt    240
taaaattgaa caagaaagcc ctttagctct tgaaggaagt ccgttaccta cagtaagcga    300
tgttcttcca gagactaata atgcacatga agaggtctct tctagcagct ggtcactttc    360
gtcctctgat tctataatga gctatgattc tttgtccgac gatgtttcag ttttatcgtt    420
tctagattgt ccccttacaa cttttgagac tgcaccttcc atagcaagct tttcgaacag    480
tgcagctgat gttagttcac actctcgttc ttctagcagc tggagtgcaa agctctctcg    540
gtttacaaag catgcttcta aaccttcact ctcttcaaac tcttctgatt cctcattttc    600
caaatctggt tcggagtcaa acgctctttc ttctagagga agttttgaac ttgaacctca    660
tggtatccat agacatgtta gtcgagcgaa gcgtttactt agcaaatttt attcgaaatt    720
tcaccataaa aaggaagatt ctagtttcga tcccttagct cctcttgttt ttgcgccaaa    780
cacttctcgg gttcttcgtg ttactaatga agcaaatgct agtgccatca gtcttgaaaa    840
ggcaactagc ctttcttctc aggaacaacc cggcagcgaa attaagaaag agctttcact    900
ctatgatcat gaatttgatc aaattttgga cttagctata aaggctaaga aggatggtaa    960
cttggaaaat gcaattgaat ttttagaata cataatgccg gaggtagcat ctcagcaaaa   1020
ttttgtaccc tatgaacttg ccgaattgta taaacagcga ggaactagtc aagatctgaa   1080
gagcattctt cccttgtaca tgttggctgc ctctttaggg catgacagaa gttccttcct   1140
tgttggagaa gcatttttct atggaacata tggggcgcga gagaataagc tacgtgcttt   1200
gcagtactat catttggcca atgacaaggg taatgcggac gctatgcttg ctttatgtaa   1260
actatattta cgaggtttac ccggtcatat atttcctagt tcgcgtcgtg catttgaata   1320
tgcacaccgt gctgcgatgc ttggccatgc tcctgcttgt tatgtcctcg ggaagtttta   1380
tgaaactggg gtaggttgtg ttaaagacct agctaaatcg gaagcgggct ttcgtgccgg   1440
tcttatcaat gattcgccaa ttactgatgc tgatgccctt caaattgcta gtaccttggt   1500
tctcctccag tgaaagaaga ataagctcgt aaacggagcg ttttcctttc gcaatgtata   1560
atatataaac cctttgtctt attattttca tttaatcgta tttggcaccc aattattgat   1620
ggttataatt ggtttcattt acggcgtctt cctggaaacc ttcgcctgct gaatctgtag   1680
ttttatcctt gatatcaact gcaattctcg acgatatatg ctctcattca aaggtttcga   1740
aagtacccat accagcattt gtttagtata aggtatatca tttatcatgc atcagttgca   1800
ctagaaagtc gcaaatttg ttcttatttt taataccaat tcatctgtca tatctcattt    1860
atatttaatt tttttaataa tgactctttt ttaaaattcc aaa                     1903
```

<210> SEQ ID NO 12
<211> LENGTH: 1524
<212> TYPE: DNA
<213> ORGANISM: Saccharomyces cerevisiae

<400> SEQUENCE: 12

```
atgaaagtgc ttgacctact aacggtactc agtgcctctt cattattatc tacattcgcg     60
gctgccgaaa gtactgctac tgcagacagt acaactgcag cttctagcac tgcttcgtgt    120
aacccgttaa aaactacagg ttgtacgccg gatacagctt tggcaactag ttttagcgaa    180
gatttctcat cttcatccaa atggtttacc gacttgaagc acgcaggtga aatcaagtac    240
ggttcagacg gtttgtcaat gacactggcg aaaagatacg ataatccaag tttgaagtct    300
aacttttata tcatgtatgg taaattggaa gttatcttaa aagctgccaa tggtaccggt    360
attgtttcat cattctattt acaaagtgat gatttggatg aaattgatat tgaatgggtg    420
ggtggtgaca acactcagtt ccaatctaac ttcttttcta aaggtgatac cacaacatac    480
gacagaggcg aatttcacgg tgtcgacact cctaccgaca aatttcataa ctacacttta    540
gattgggcga tggacaagac gacttggtac ctcgatggag agtctgtcag agtattatca    600
aacacatcaa gtgagggtta cccacaatct cctatgtacc taatgatggg tatctgggcc    660
ggtggtgacc cagacaatgc tgctggtacc attgaatggg ctggtggtga aaccaactac    720
aatgacgctc cattcactat gtacattgaa aaggtcattg taactgatta ttctaccggt    780
aaaaagtaca catatggtga ccaatctggt tcttgggaat ctattgaagc tgacggtggt    840
tctatttacg gcaggtatga ccaagcccaa gaagatttcg cagttttagc caacggtggt    900
agtatttcca gcagctctac atcctcttct actgtatctt cctcggcgtc ttccactgta    960
tcttcctcgg tttcttccac tgtgtcctcc tcggcttctt ccactgtgtc ttcctcggtt   1020
tcttccactg tatcttcttc gtcttctgta tcttcctctt catccacatc tccatcttct   1080
tcgaccgcta cttcatctaa aacacttgct tcctcatcag tcaccacatc tagttccatt   1140
agttcattcg aaaagcaatc ctcctcttca tccaagaaaa cagtggcttc ctcttctaca   1200
agtgagtcca ttatttcctc cactaagacc ccagccactg tttcctctac cactaggtct   1260
acagttgccc caactactca acaatcttcc gtatcatcgg acagtcctgt acaagataag   1320
ggtggtgtcg caacatcaag taatgacgtg accagttcta ctacccagat atcaagcaaa   1380
tacacatcta caatccaaag ttcttcctcc gaagccagct cgacaaactc tgttcaaatt   1440
tctaacggtg ctgatttagc tcagagttta ccaagagagg gaaaactttt ttccgtactc   1500
gtagctttac tagccttgct ataa                                          1524
```

<210> SEQ ID NO 13
<211> LENGTH: 395
<212> TYPE: PRT
<213> ORGANISM: Acidithiobacillus ferrooxidans

<400> SEQUENCE: 13

```
Met Arg Phe Arg Leu Asn Ile Val Leu Ala Thr Met Ile Phe Ser Ser
1               5                   10                  15

Leu Ala Val Ser Thr Ala Met Ala Gly Val Pro Val Gln Trp Ser Val
            20                  25                  30

Asp Val His Ala Pro Ile Tyr Asn Pro Pro Arg Val Ala Asp Gly Val
        35                  40                  45

Ala Tyr Phe Asp Thr Ala Gln Ser Lys Gly Pro Asn Val Phe Ser Ala
    50                  55                  60

Lys Asn Gly Lys Ile Leu Trp Arg Phe Thr Thr Gly Gly Thr Ile Leu
65                  70                  75                  80

Met Pro Leu Thr Val Gly His Gly Gln Val Trp Val Ala Ser Asp Val
                85                  90                  95
```

```
Gly Ser Thr His Tyr Leu Arg Ala Ile Glu Ala Lys Thr Gly Lys Leu
            100                 105                 110

Ile Trp Asp Tyr Thr Arg His Glu Pro Pro Glu Cys Met Cys Ser His
        115                 120                 125

Leu Thr His Tyr Glu His His Leu Leu Phe Ala Gln Thr Asp Gly His
    130                 135                 140

Ser Leu Tyr Ala Phe Tyr Pro Val Gly Asn Ile Pro Asn Arg Arg Leu
145                 150                 155                 160

Trp Ala Phe Thr Gly Asp Gly Ala Lys Leu Thr Ala Pro Val Val Val
                165                 170                 175

Asp His Thr Val Ile Phe Gly Ser Ala Asp His Gly Val Tyr Gly Leu
            180                 185                 190

Phe Asp Lys Thr Gly Lys Ile Arg Trp Gln Gln Lys Thr Gly Tyr Gly
        195                 200                 205

Phe Met Ala Gln Pro Ala Val Trp Lys His Glu Val Ile Ile Gly Asn
    210                 215                 220

Arg Gly Gly Thr Val His Ala Tyr Ser Thr Thr Thr Gly Thr Ser Leu
225                 230                 235                 240

Trp Asn Phe Thr Thr Asn Gly Pro Ile Asn Thr Thr Ala Leu Ile Trp
                245                 250                 255

His Asp Ser Ala Phe Ile Ala Ser Gly Ala Gly Asp Arg Gly Val Tyr
            260                 265                 270

Ala Leu Ser Ala Lys Thr Gly Lys Gln Leu Trp Tyr Thr Arg Met Ala
        275                 280                 285

Asp Tyr Thr Ala Tyr Ala Pro Val Met Ala Lys Gln Ile Val Val Val
    290                 295                 300

Ala Ser Gln Asp Gly Asn Met Leu Gly Leu Ser Ala Thr Thr Gly Lys
305                 310                 315                 320

Val Leu Trp Arg Ser Glu Leu His Gly Ile Pro Lys Ser Gln Pro Ala
                325                 330                 335

Leu Trp Lys Gly Asp Ala Val Leu Lys Val Asn Asp His Lys Ile Met
            340                 345                 350

Ala Phe Asn Ala Gln Ser Gly Gly Leu Val Trp Thr Tyr His Ser Lys
        355                 360                 365

Asn Val Val Thr Ser Pro Val Pro Lys Gly Asp Ser Val Tyr Val Gly
    370                 375                 380

Thr Ser Gly Gly Thr Leu Val Ala Ile Gly Gln
385                 390                 395
```

<210> SEQ ID NO 14
<211> LENGTH: 20014
<212> TYPE: DNA
<213> ORGANISM: Artificial sequence
<220> FEATURE:
<223> OTHER INFORMATION: Synthetic construct

<400> SEQUENCE: 14

```
acggattaga agccgccgag cgggtgacag ccctccgaag gaagactctc ctccgtgcgt      60

cctcgtcttc accggtcgcg ttcctgaaac gcagatgtgc ctcgcgccgc actgctccga     120

acaataaaga ttctacaata ctagctttta tggttatgaa gaggaaaaat tggcagtaac     180

ctggccccac aaaccttcaa atgaacgaat caaattaaca accataggat gataatgcga     240

ttagtttttt agccttattt ctggggtaat taatcagcga agcgatgatt tttgatctat     300

taacagatat ataaatgcaa aaactgcata accactttaa ctaatacttt caacattttc     360
```

```
ggtttgtatt acttcttatt caaatgtaat aaaagtatca acaaaaaatt gttaatatac    420
ctctatactt taacgtcaag gagaaaaaac cccggatcgg actactagca gctgtaatac    480
gactcactat agggaatatt aagcttgcca ccatgagtga tcaaaataat cgatcgagaa    540
atgaatatca ctcaaaccgg aagaatgaac cttcctatga actccaaaat gcacatagcg    600
ggctatttca ctcttctaat gaagaattaa caaacaggaa ccaaagatat accaatcaaa    660
atgccagcat gggttcattc actccagtcc aatctttgca atttccagaa caatctcagc    720
aaacaaatat gctttataac ggtgacgatg gcaataataa tactatcaat gataacgaac    780
gagacatata tggaggtttt gtcaaccacc atcgccagcg tcccccacca gcaactgcag    840
aatacaatga cgtttttaat acgaatagtc aacagctacc gtcggaacat caatacaata    900
acgtaccttc atatccactt ccttcgataa atgtgattca aaccactcca gaactcatac    960
ataacggctc acagactatg gccaccccca tcgaaaggcc cttctttaac gaaaacgact   1020
actattataa taacaggaac tctaggacgt caccgagtat tgcttctagt agcgatggtt   1080
atgcagatca ggaagctagg cccattttgg agcaacccaa caataacatg aatagcggta   1140
atattcctca ataccatgac caaccttttg gatacaacaa tggttaccat ggcctacagg   1200
caaaagatta ctatgacgat ccggagggtg gttatattga tcagagagga gatgactatc   1260
agattaattc atatttgggt agaaacggtg aaatggttga tccttacgat tatgaaaaca   1320
gtttaagaca tatgactcct atggagcgta gagaatatct tcatgatgat agcagacccg   1380
taaacgatgg aaaagaagaa ttagacagtg tgaaaagcgg ttactctcat agagacttgg   1440
gggaatatga caaggatgat ttttcaaggg atgacgagta cgatgatctc aacactattg   1500
ataaattaca gtttcaagct aatggtgtac ctgcatcatc ctcggtgtct tctatcggat   1560
ctaaagaatc cgacataata gtaagcaatg ataacttaac cgcaaataga gcactaaaga   1620
gaagcggtac tgaaattagg aaattcaaac tttggaatgg taattttgtt ttcgattctc   1680
caatcagtaa gacgctattg gaccaatacg ctactacaac agaaaatgca aacactttac   1740
caaatgagtt taagtttatg agatatcaag cagttacttg cgaacctaat caacttgcag   1800
agaagaattt cacggtgagg cagttgaagt atttaactcc aagggaaacg gaattgatgc   1860
tagtagtcac aatgtataat gaagaccata tcctgttagg aagaactttg aaaggtatta   1920
tggacaatgt caaatatatg gtgaaaaaaa aaaattcaag cacttggggg ccggatgcat   1980
ggaaaaagat tgtcgtttgt atcatttcag atggtagatc caaaattaat gaacgctcgc   2040
tagcattact aagttcgtta ggttgttacc aggacgggtt tgctaaggat gaaattaatg   2100
aaaaaaaagt ggcaatgcat gtctacgaac atacgacaat gatcaacatc acaaatattt   2160
cggaatcaga ggtttcatta gaatgcaatc aaggtactgt tccaatacaa cttttgtttt   2220
gtttgaaaga gcaaaatcag aaaaaaatta actcacatag atgggcattt gaaggctttg   2280
cagaattact gcgtcccaat atcgttacat tgttagatgc tggtactatg ccaggtaaag   2340
attctattta ccagttatgg agagagttca ggaatccaaa tgttggtggc gcatgtggtg   2400
aaataagaac tgatttgggt aagagatttg taaagttgtt gaatccttta gttgcatcac   2460
agaatttcga atacaaaatg tccaatattt tagacaaaac aaccgagtct aactttggat   2520
ttattactgt tctaccgggg gcattctctg cgtataggtt tgaagctgtg agaggccaac   2580
cattacagaa gtacttttat ggtgaaatta tggaaaatga aggttttcat tttttttctt   2640
ccaatatgta tcttgctgaa gatcgtattt tatgctttga agtggtcaca aaaaaaaatt   2700
```

```
gtaattggat tttgaaatac tgcagaagtt cttatgcttc aacagatgta ccggagaggg   2760
tccctgaatt tattcttcag aggaggcgtt ggttgaatgg ttcatttttt gctagtgtat   2820
attccttttg tcatttttac agagtctgga gcagtggtca taatattggt agaaaactcc   2880
ttttgacggt tgaatttttt taccttttct tcaatacatt gatttcatgg ttttcattga   2940
gttcattttt cctagtcttt aggattctca ctgtttctat tgcactggca taccattcag   3000
catttaatgt gttgtccgtc atattcctgt ggctttatgg gatttgtacc ttatcaacat   3060
tcatactgtc attgggtaat aaacctaaaa gtactgagaa attttatgtt ctaacttgcg   3120
tcatttttgc ggtgatgatg atttacatga tattctgcag tatattcatg agtgtcaaat   3180
ccttccaaaa tatattgaaa aacgatacca tcagctttga gggtttgatt accacagagg   3240
ctttcaggga tattgttatc tctctgggct ccacttattg tttgtaccta atcagttcaa   3300
ttatctattt gcagccatgg catatgttga caagttttat tcagtatatt ttattgagtc   3360
cttcttacat caatgttttg aatatctatg catttttgtaa tgtccacgac ttatcatggg   3420
gtacaaaggg tgcaatggca aatccgctgg gtaagattaa tactacagaa gatggtacgt   3480
tcaaaatgga agttctggtc tctagttcag agattcaagc aaactacgat aaatatttga   3540
aagttttaaa tgacttcgat ccaaaatcag aatctcggcc tactgagcca tcttatgatg   3600
aaaaaaagac tggctattat gcaaacgtta gatctctcgt gattatcttt tgggtcatca   3660
caaatttcat catcgttgct gttgtcttag aaaccggtgg gattgcagat tatattgcta   3720
tgaaatccat atcaactgat gacactttag aaactgcaaa gaaggcggaa attcccttaa   3780
tgaccagtaa ggcctcaatt tattttaatg taattttatg gttagttgca ttatcggcat   3840
taataaggtt cattggttgc tcaatataca tgatagtaag gttttttaaa aaggttacat   3900
ttcgctaagg tacctcatgt aattagttat gtcacgctta cattcacgcc ctcccccac   3960
atccgctcta accgaaaagg aaggagttag acaacctgaa gtctaggtcc ctatttattt   4020
ttttatagtt atgttagtat taagaacgtt atttatattt caaatttttc ttttttttct   4080
gtacagacgc gtgtacgcat gtaacattat actgaaaacc ttgcttgaga aggttttggg   4140
acgctcgaag gctttaattt gccggattag aagccgccga gcgggtgaca gccctccgaa   4200
ggaagactct cctccgtgcg tcctcgtctt caccggtcgc gttcctgaaa cgcagatgtg   4260
cctcgcgccg cactgctccg aacaataaag attctacaat actagctttt atggttatga   4320
agaggaaaaa ttggcagtaa cctggcccca caaaccttca aatgaacgaa tcaaattaac   4380
aaccatagga tgataatgcg attagttttt tagccttatt tctggggtaa ttaatcagcg   4440
aagcgatgat tttgatcta ttaacagata tataaatgca aaaactgcat aaccacttta   4500
actaatactt tcaacatttt cggtttgtat tacttcttat tcaaatgtaa taaaagtatc   4560
aacaaaaaat tgttaatata cctctatact ttaacgtcaa ggagggatcc gccaccatgt   4620
cactccttta catcattctt ctattcacac aattcttact actgccaacc gatgcctttg   4680
ataggtctgc taacacaaat attgctgttt attggggtca aaactcagca ggaacgcaag   4740
aatccttagc tacttactgt gaatcttctg atgctgatat tttcctatta tctttcttga   4800
accaatttcc aacccttggt ttgaactttg ccaacgcatg ctctgatact ttttctgatg   4860
gcttacttca ctgcacccag attgctgaag atattgaaac ttgccagtcc ctaggaaaga   4920
aagttctatt atcattaggt ggtgcatctg gtagctacct cttttcagat gattctcaag   4980
cggaaacttt tgcacaaact ttatgggata ctttcggtga aggtacaggt gccagtgaga   5040
gaccatttga ctcagcagtc gttgatggtt ttgattttga tattgaaaac aacaacgaag   5100
```

```
taggctatag tgcgttagct accaagttaa gaactttgtt tgccgaaggt acaaagcaat   5160
attacctttc tgccgcacca caatgtccat acccggatgc ttctgttggt gacttgttgg   5220
aaaatgcaga cattgatttt gcgttcatcc aattttacaa taattactgc agtgtgagtg   5280
gtcaattcaa ttgggatact tggttaacct atgctcaaac tgtatcccca aataaaaata   5340
tcaaactgtt cttaggttta cctggttctg cttctgctgc tggctctggt tatatttctg   5400
acacttcttt attggaatca actattgcag atattgcctc ttcaagttct tttggtggta   5460
ttgcgttatg ggatgcatct caagcctttt ccaacgagct aaatggtgaa ccatatgttg   5520
agattttgaa gaatttgcta acaagtgcta gccagaccgc cactactaca gttgccacct   5580
caaaaacctc agcagcctca acttcatctg cttcaacttc atctgcttca acttctcaga   5640
aaaagaccac acaatctacg acatctacac aaagtaaaag caaagttact ttatctccaa   5700
ctgcaagcag cgctatcaaa acatcaatta ctcaaactac aaaaacattg acgagtagca   5760
ccaagacaaa atctagtcta ggtaccacca caacagagag cactttaaat tcagttgcta   5820
tcacaagtat gaaaactact ctatcttccc aaataaccag tgctgccttg gtgacccctc   5880
aaacaactac tactagcata gtttcttcgg ccccaattca aacagctatc actagtactc   5940
tttcgccagc aacgaagagt tcttctgtcg tttccctaca gacagctact actagtacgc   6000
tttccccaac aacgaccagt acaagctcag gtagtacaag ctcaggtagt acaagctcag   6060
acagtacagc tcgtacattg gctaaagaat tgaatgctca atatgcggct ggtaaattga   6120
acggtaaatc tacctgtact gaaggtgaaa ttgcatgctc tgctgatggg aagttcgccg   6180
tttgtgatca tagcgcttgg gtttacatgg aatgtgcttc tggaaccaca tgttatgctt   6240
atgactccgg cgactcagtc tatacccaat gtaatttctc ttatttggaa agcaattact   6300
tttaattaat catgtaatta gttatgtcac gcttacattc acgccctccc cccacatccg   6360
ctctaaccga aaaggaagga gttagacaac ctgaagtcta ggtccctatt tattttttta   6420
tagttatgtt agtattaaga acgttattta tatttcaaat ttttcttttt tttctgtaca   6480
gacgcgtgta cgcatgtaac attatactga aaaccttgct tgagaaggtt ttgggacgct   6540
cgaaggcttt aatttgccgg attagaagcc gccgagcggg tgacagccct ccgaaggaag   6600
actctcctcc gtgcgtcctc gtcttcaccg gtcgcgttcc tgaaacgcag atgtgcctcg   6660
cgccgcactg ctccgaacaa taaagattct acaatactag cttttatggt tatgaagagg   6720
aaaaattggc agtaacctgg ccccacaaac cttcaaatga acgaatcaaa ttaacaacca   6780
taggatgata atgcgattag ttttttagcc ttatttctgg ggtaattaat cagcgaagcg   6840
atgatttttg atctattaac agatatataa atgcaaaaac tgcataacca ctttaactaa   6900
tactttcaac attttcggtt tgtattactt cttattcaaa tgtaataaaa gtatcaacaa   6960
aaaattgtta atatacctct atactttaac gtcaaggagc tcgagatgag aatacaacta   7020
aatacaattg atttgcaatg tattattgca ctttcctgtc tggggcaatt tgttcacgcg   7080
gaagctaata gggaagattt aaagcagata gactttcaat ttcctgtatt ggaaagggca   7140
gctacaaaaa cgccttttcc ggattggctt agtgcattta ccgggttaaa agaatggcct   7200
gggttagatc caccttatat acctttagat ttcattgatt tcagtcaaat tccagattat   7260
aaggaatatg atcaaaacca ttgcgacagt gttccaaggg actcgtgctc tttcgattgc   7320
catcactgca ccgaacacga tgatgtgtac acatgttcca aactttccca gacatttgac   7380
gatggtcctt ctgcttccac tactaaatta ttggaccggt tgaagcataa ttccaccttc   7440
```

```
ttcaatttag gtgtcaatat agttcaacat ccagatatct atcaaagaat gcaaaaggag   7500
ggacacttaa tcggctcaca tacctggtct cacgtatatt tgccaaatgt atcgaatgaa   7560
aaaattatag ctcaaattga atggtccatc tgggcgatga atgctactgg caaccatacc   7620
cccaaatggt tcagacctcc atatggcgga atagataata gagtaagagc aataacaagg   7680
caatttggct tacaagccgt cttatgggat cacgatactt ttgattggag cctccttctc   7740
aatgattctg tcataactga acaagaaatt cttcaaaatg taataaactg gaacaagtca   7800
ggaaccggat taatattaga acacgattca acggaaaaaa ctgtcgatct tgccattaaa   7860
ataaataagt tgataggtga tgatcaatca acagtttctc attgtgtcgg cggaattgat   7920
tacataaaag aattcttgtc ctaagaattc tcatgtaatt agttatgtca cgcttacatt   7980
cacgccctcc ccccacatcc gctctaaccg aaaaggaagg agttagacaa cctgaagtct   8040
aggtccctat ttattttttt atagttatgt tagtattaag aacgttattt atatttcaaa   8100
tttttctttt ttttctgtac agacgcgtgt acgcatgtaa cattatactg aaaaccttgc   8160
ttgagaaggt tttgggacgc tcgaaggctt taatttgccg gattagaagc cgccgagcgg   8220
gtgacagccc tccgaaggaa gactctcctc cgtgcgtcct cgtcttcacc ggtcgcgttc   8280
ctgaaacgca gatgtgcctc gcgccgcact gctccgaaca ataaagattc tacaatacta   8340
gcttttatgg ttatgaagag gaaaaattgg cagtaacctg gccccacaaa ccttcaaatg   8400
aacgaatcaa attaacaacc ataggatgat aatgcgatta gtttttttagc cttatttctg   8460
gggtaattaa tcagcgaagc gatgattttt gatctattaa cagatatata aatgcaaaaa   8520
ctgcataacc actttaacta atactttcaa cattttcggt ttgtattact tcttattcaa   8580
atgtaataaa agtatcaaca aaaaattgtt aatatacctc tatactttaa cgtcaaggag   8640
gcggccgcca ccatggtgag caagggcgag gagctgttca ccggggtggt gcccatcctg   8700
gtcgagctgg acggcgacgt aaacggccac aagttcagcg tgtccggcga gggcgagggc   8760
gatgccacct acggcaagct gaccctgaag ttcatctgca ccaccggcaa gctgcccgtg   8820
ccctggccca ccctcgtgac caccctgacc tacggcgtgc agtgcttcag ccgctacccc   8880
gaccacatga agcagcacga cttcttcaag tccgccatgc ccgaaggcta cgtccaggag   8940
cgcaccatct tcttcaagga cgacggcaac tacaagaccc gcgccgaggt gaagttcgag   9000
ggcgacaccc tggtgaaccg catcgagctg aagggcatcg acttcaagga ggacggcaac   9060
atcctggggc acaagctgga gtacaactac aacagccaca acgtctatat catggccgac   9120
aagcagaaga acggcatcaa ggtgaacttc aagatccgcc acaacatcga ggacggcagc   9180
gtgcagctcg ccgaccacta ccagcagaac acccccatcg gcgacggccc cgtgctgctg   9240
cccgacaacc actacctgag cacccagtcc gccctgagca aagaccccaa cgagaagcgc   9300
gatcacatgg tcctgctgga gttcgtgacc gccgccggga tcactctcgg catggacgag   9360
ctgtacaagt aagtcgactc atgtaattag ttatgtcacg cttacattca cgccctcccc   9420
ccacatccgc tctaaccgaa aaggaaggag ttagacaacc tgaagtctag gtccctattt   9480
atttttttat agttatgtta gtattaagaa cgttatttat atttcaaatt tttctttttt   9540
ttctgtacag acgcgtgtac gcatgtaaca ttatactgaa aaccttgctt gagaaggttt   9600
tgggacgctc gaaggcttta atttgccgga ttagaagccg ccgagcgggt gacagccctc   9660
cgaaggaaga ctctcctccg tgcgtcctcg tcttcaccgg tcgcgttcct gaaacgcaga   9720
tgtgcctcgc gccgcactgc tccgaacaat aaagattcta caatactagc ttttatggtt   9780
atgaagagga aaaattggca gtaacctggc cccacaaacc ttcaaatgaa cgaatcaaat   9840
```

```
taacaaccat aggatgataa tgcgattagt tttttagcct tatttctggg gtaattaatc   9900
agcgaagcga tgatttttga tctattaaca gatatataaa tgcaaaaact gcataaccac   9960
tttaactaat actttcaaca ttttcggttt gtattacttc ttattcaaat gtaataaaag  10020
tatcaacaaa aaattgttaa tatacctcta tactttaacg tcaaggaggc ggccgccacc  10080
atggcgaagt ttggtagccg taataagtct ccgaagtgga tctctaacgg ctgctgcttc  10140
ctgctgggtg cctttactgc tctgctgctg ctgtggggtc tgtgctcctt tattatcccg  10200
attccgaaca ccgatccgaa gctgaactct gtagcgacct ctctgcgttc tctgaacttc  10260
ccgaagaacc cagcagctac cctgccaccg aacctgcagc atgatccacc ggatactact  10320
ttctacgacg atccggaaac ctcttatact atggataaac cgatgaagaa ctgggacgag  10380
aaacgtaagg aatggctgct gcatcacccg tccttcggcg cagctgctcg tgacaagatc  10440
ctgctggtaa ccggttccca gccgaaacgc tgtcacaacc cgattggtga tcacctgctg  10500
ctgcgtttct ttaagaacaa agtggattac tgccgtctgc ataattacga tatcatctat  10560
aacaacgcac tgctgcaccc gaaaatgaac tcctattggg ctaagtaccc agtgatccgt  10620
gctgcaatga tggctcatcc ggaagttgaa tgggtgtggt gggttgactc tgacgctgta  10680
ttcactgaca tggagtttaa actgccactg aaacgctata agaaccacaa tctggtggtg  10740
catggttggg aaggtctggt acgtctgaac cactcctgga ctggtctgaa cgcaggtgta  10800
ttcctgatcc gtaattgcca atggagcctg gagttcatgg atgtatgggt tagcatgggt  10860
ccacaaactc cagaatacga gaaatggggt gagcgtctgc gcgaaacctt caaagataaa  10920
gttctgccag actctgatga ccagactgca ctggcatacc tgatcgcaac cgataacaaa  10980
gacacctggc gtgagaaaat cttcctggaa agcgagtact acttcgaagg ctattggctg  11040
gaaatcgtaa agacttacga gaacatctcc gaacgttacg atgaagttga acgcaaagta  11100
gaaggtctgc gtcgtcgcca cgctgagaag gttagcgaga aatacggtgc aatgcgtgaa  11160
gaatacctga aagataacaa acgtcgtccg ttcatcaccc atttcactgg ttgccagccg  11220
tgcaacggtc accataaccc agcatacaat gcgaacgact gttggaatgg tatggaacgt  11280
gcactgaact ttgcagataa ccagatcctg cgtacctacg gttaccatcg tcagaatctg  11340
ctggacaagt ccgtttctcc actgccgttc ggttatccag cagcttaacc cgggtcatgt  11400
aattagttat gtcacgctta cattcacgcc ctccccccac atccgctcta accgaaaagg  11460
aaggagttag acaacctgaa gtctaggtcc ctatttattt ttttatagtt atgttagtat  11520
taagaacgtt atttatattt caaatttttc ttttttttct gtacagacgc gtgtacgcat  11580
gtaacattat actgaaaacc ttgcttgaga aggttttggg acgctcgaag gctttaattt  11640
gccggattag aagccgccga gcgggtgaca gccctccgaa ggaagactct cctccgtgcg  11700
tcctcgtctt caccggtcgc gttcctgaaa cgcagatgtg cctcgcgccg cactgctccg  11760
aacaataaag attctacaat actagctttt atggttatga agaggaaaaa ttggcagtaa  11820
cctggcccca caaaccttca aatgaacgaa tcaaattaac aaccatagga tgataatgcg  11880
attagttttt tagccttatt tctggggtaa ttaatcagcg aagcgatgat ttttgatcta  11940
ttaacagata tataaatgca aaaactgcat aaccacttta actaatactt tcaacatttt  12000
cggtttgtat tacttcttat tcaaatgtaa taaaagtatc aacaaaaaat tgttaatata  12060
cctctatact ttaacgtcaa ggagcgtacg ccaccatggc ttcgccggca ccggcgggcg  12120
atgccgtgta tgcggccaat ggcggcctca ctgacccgct tctagtgagc gcgaacggcc  12180
```

```
atggtgccgc cgcgaggaag gctggccacg gcgccagggg caggtactgg gtggcctccg  12240
acaaggccga gaggcgcgct gccaaggagt ccggcggtga ggacggccgc gcgctgctgt  12300
tccggaagta taaggtcaaa ggcgccctcc tgcaccccta caggttgctg atcatcatcc  12360
gattagtcgc tgtcctcgcc ttcttcgcgt ggcgcatcag gcacaacaaa tccgacatca  12420
tgtggttctg gacaatgtcc atcgtcggcg acgtctggtt cggcttctcg tggctcctca  12480
accagctccc aaagttcaac cctgtgaaga ccatcccaga tctcgccgcc ctccagcggc  12540
actttggcta ccctgacggc ggcgcctcta ggctccccgg tatcgatgtt ttcgtcacca  12600
ctgccgaccc cattgatgag cccatactct acaccatgaa ctgtgtcctc tccatcctgt  12660
ctgtcgatta cccagtcgat cggctagcct gctatctctc agatgatagt ggggcgctgg  12720
ttctctatga ggcactggcc gaggtcggaa agtttgcgcc tctatgggtt ccgttctgcc  12780
gcaagtactc cattgagcca agggcaccag aaagctattt tgagcatgtg gcaccgccgc  12840
aggctggaag ggtgacgcag gagttcttga atgattatag gagggtgcag atggagtacg  12900
atgagttcaa ggcgcgcttg gacaacctcc ctgatgccat acgcaagaga tccgatgttt  12960
acaatagcgt gagagatgca ggaggagctc aaaaggcaac ttggatggca aatgggacgc  13020
agtggcccgg cacatggatt gatccagcag agaaccatag gaaaggacac catgctccaa  13080
ttgccaaggt tgtgctgaac catccaagcc gtggacaaca ccctattact gaaagcaatc  13140
ccagcattgc caccactgat gagcgcctcc caatgcttgt ttacgtctct cgtgagaaga  13200
acccaggtta tgaccacaac aagaaggcag gtgccctgaa tgcacagctg cgggcctctg  13260
ctctcctctc taatgcccaa ctcatcatca acttcgactg cgaccactac atcaacaact  13320
ctcaagccct aagctcggct gtgtgcttca tgctggatca acgggacggt gataacaccg  13380
catttgttca gttcccacag cgcttcgaca atgttgaccc cacggaccgc tatggtaacc  13440
acaatcgtgt cttctttgat gggaccatgc ttgcccttaa tggtttgcaa gggccctcat  13500
acctcggtac tggttgcatg ttccgtcgct tagcactcta tggtattgac ccaccccact  13560
gtagagcaga aaacatcacg gccgaagcta gcaggtttgg caactccaca atcttcctag  13620
attcagtgtc aaaagccctg aaaaatgaca ggacaatcac accgccacca attgatgaca  13680
cattccttgc tgagctagag agggttgtga catgttctta tgacaaaggt actgactggg  13740
gcaagggtgt agggtacatc tatgacatag ccactgaaga tatagtaaca ggattccgca  13800
tccacgggca ggggtggcgc tctatgtatt gcacaatgga gcacgatgcg ttctgtggcg  13860
ttgcaccaat caacctaact gaacgcctcc atcaaattgt gcgctggtct ggtgggtctt  13920
tagagatgtt cttctcccac aacaatccat tcatcggtgg tcgccggatt caaccccttc  13980
agcgtgtctc ctacctcaac atgacagtct acccagtcac atcagtcttc atcctaatct  14040
atgctctaag cccggtgatg tggcttatcc ccgatgaagt atacatccag agaccattca  14100
ctaggtatgt cgtgtacctt cttgtaatca tcgtgatgat tcacatgatt ggctggcttg  14160
agataaagtg ggcgggggtc acatggctgg actattggcg caatgagcag ttctttatga  14220
tcggctcaac aagtgcatat ccaatggcag tgctgcacat ggcagtgaac ctcctcacaa  14280
agaagggcat acacttcagg gtcacttcca agcaaacagc cgcggacgac aatgacaagt  14340
tcgccgacct ttatgatttt cgatgggtgc caatgctcat cccaacaatg gcagttctga  14400
tctgcaatgt tggtgccatt ggtgtagccc tgggcaaaac tgtggtatac attggaacat  14460
ggacagcggc gaagaagatg catgcagcac tgggtctgct gttcaacata tggatcatgt  14520
ttctcctcta cccatttgca ctagcgatca tggggcggtg ggcgaagagg ccaatcatcc  14580
```

```
ttgtagttct gctgccggtt gtctttgcac ttgtcgcgct gttgtatgta ggtatccata  14640
tcctacttgc tggtctgatt ccattctagg tagtatagaa aacattgtaa tttcttgtgt  14700
agttaccaag gaaccaatta tgtttttttt agcaaaaaaa aaaaaaaaaa aatctagagg  14760
gccgcatcat gtaattagtt atgtcacgct tacattcacg ccctccccccc acatccgctc  14820
taaccgaaaa ggaaggagtt agacaacctg aagtctaggt ccctatttat ttttttatag  14880
ttatgttagt attaagaacg ttatttatat ttcaaatttt tcttttttttt ctgtacagac  14940
gcgtgtacgc atgtaacatt atactgaaaa ccttgcttga gaaggttttg ggacgctcga  15000
aggctttaat ttgcggccct gcattaatga atcggccaac gcgcggggag aggcggtttg  15060
cgtattgggc gctcttccgc ttcctcgctc actgactcgc tgcgctcggt cgttcggctg  15120
cggcgagcgg tatcagctca ctcaaaggcg gtaatacggt tatccacaga atcaggggat  15180
aacgcaggaa agaacatgtg agcaaaaggc cagcaaaagc ccaggaaccg taaaaaggcc  15240
gcgttgctgg cgtttttcca taggctccgc ccccctgacg agcatcacaa aaatcgacgc  15300
tcaagtcaga ggtggcgaaa cccgacagga ctataaagat accaggcgtt tccccctgga  15360
agctccctcg tgcgctctcc tgttccgacc ctgccgctta ccggatacct gtccgccttt  15420
ctcccttcgg gaagcgtggc gctttctcat agctcacgct gtaggtatct cagttcggtg  15480
taggtcgttc gctccaagct gggctgtgtg cacgaacccc ccgttcagcc cgaccgctgc  15540
gccttatccg gtaactatcg tcttgagtcc aacccggtaa gacacgactt atcgccactg  15600
gcagcagcca ctggtaacag gattagcaga gcgaggtatg taggcggtgc tacagagttc  15660
ttgaagtggt ggcctaacta cggctacact agaaggacag tatttggtat ctgcgctctg  15720
ctgaagccag ttaccttcgg aaaaagagtt ggtagctctt gatccggcaa acaaaccacc  15780
gctggtagcg gtggtttttt tgtttgcaag cagcagatta cgcgcagaaa aaaaggatct  15840
caagaagatc ctttgatctt ttctacgggg tctgacgctc agtggaacga aaactcacgt  15900
taagggattt tggtcatgag attatcaaaa aggatcttca cctagatcct tttaaattaa  15960
aaatgaagtt ttaaatcaat ctaaagtata tatgagtaaa cttggtctga cagttaccaa  16020
tgcttaatca gtgaggcacc tatctcagcg atctgtctat ttcgttcatc catagttgcc  16080
tgactccccg tcgtgtagat aactacgata cgggagcgct taccatctgg ccccagtgct  16140
gcaatgatac cgcgagaccc acgctcaccg gctccagatt tatcagcaat aaaccagcca  16200
gccggaaggg ccgagcgcag aagtggtcct gcaactttat ccgcctccat ccagtctatt  16260
aattgttgcc gggaagctag agtaagtagt tcgccagtta atagtttgcg caacgttgtt  16320
ggcattgcta caggcatcgt ggtgtcactc tcgtcgtttg gtatggcttc attcagctcc  16380
ggttcccaac gatcaaggcg agttacatga tcccccatgt tgtgcaaaaa agcggttagc  16440
tccttcggtc ctccgatcgt tgtcagaagt aagttggccg cagtgttatc actcatggtt  16500
atggcagcac tgcataattc tcttactgtc atgccatccg taagatgctt ttctgtgact  16560
ggtgagtact caaccaagtc attctgagaa tagtgtatgc ggcgaccgag ttgctcttgc  16620
ccggcgtcaa tacgggataa tagtgtatca catagcagaa ctttaaaagt gctcatcatt  16680
ggaaaacgtt cttcggggcg aaaactctca aggatcttac cgctgttgag atccagttcg  16740
atgtaaccca ctcgtgcacc caactgatct tcagcatctt ttactttcac cagcgtttct  16800
gggtgagcaa aaacaggaag gcaaaatgcc gcaaaaaagg gaataagggc gacacggaaa  16860
tgttgaatac tcatactctt cctttttcaa tgggtaataa ctgatataat taaattgaag  16920
```

```
ctctaatttg tgagtttagt atacatgcat ttacttataa tacagttttt tagttttgct  16980
ggccgcatct tctcaaatat gcttcccagc ctgcttttct gtaacgttca ccctctacct  17040
tagcatccct tccctttgca aatagtcctc ttccaacaat aataatgtca gatcctgtag  17100
agaccacatc atccacggtt ctatactgtt gacccaatgc gtctcccttg tcatctaaac  17160
ccacaccggg tgtcataatc aaccaatcgt aaccttcatc tcttccaccc atgtctcttt  17220
gagcaataaa gccgataaca aaatctttgt cgctcttcgc aatgtcaaca gtacccttag  17280
tatattctcc agtagatagg gagcccttgc atgacaattc tgctaacatc aaaaggcctc  17340
taggttcctt tgttacttct tctgccgcct gcttcaaacc gctaacaata cctgggccca  17400
ccacaccgtg tgcattcgta atgtctgccc attctgctat tctgtataca cccgcagagt  17460
actgcaattt gactgtatta ccaatgtcag caaattttct gtcttcgaag agtaaaaaat  17520
tgtacttggc ggataatgcc tttagcggct taactgtgcc ctccatggaa aaatcagtca  17580
agatatccac atgtgttttt agtaaacaaa ttttgggacc taatgcttca actaactcca  17640
gtaattcctt ggtggtacga acatccaatg aagcacacaa gtttgtttgc ttttcgtgca  17700
tgatattaaa tagcttggca gcaacaggac taggatgagt agcagcacgt tccttatatg  17760
tagctttcga catgatttat cttcgtttcc tgcaggtttt tgttctgtgc agttgggtta  17820
agaatactgg gcaatttcat gtttcttcaa cactacatat gcgtatatat accaatctaa  17880
gtctgtgctc cttccttcgt tcttccttct gttcggagat taccgaatca aaaaaatttc  17940
aaagaaaccg aaatcaaaaa aaagaataaa aaaaaaatga tgaattgaat tgaaaagcta  18000
gcttatcgat gataagctgt caaagatgag aattaattcc acggactata gactatacta  18060
gatactccgt ctactgtacg atacacttcc gctcaggtcc ttgtccttta acgaggcctt  18120
accactcttt tgttactcta ttgatccagc tcagcaaagg cagtgtgatc taagattcta  18180
tcttcgcgat gtagtaaaac tagctagacc gagaaagaga ctagaaatgc aaaaggcact  18240
tctacaatgg ctgccatcat tattatccga tgtgacgctg cagcttctca atgatattcg  18300
aatacgcttt gaggagatac agcctaatat ccgacaaact gttttacaga tttacgatcg  18360
tacttgttac ccatcattga attttgaaca tccgaacctg ggagttttcc ctgaaacaga  18420
tagtatattt gaacctgtat aataatatat agtctagcgc tttacggaag acaatgtatg  18480
tatttcggtt cctggagaaa ctattgcatc tattgcatag gtaatcttgc acgtcgcatc  18540
cccggttcat tttctgcgtt tccatcttgc acttcaatag catatctttg ttaacgaagc  18600
atctgtgctt cattttgtag aacaaaaatg caacgcgaga gcgctaattt ttcaaacaaa  18660
gaatctgagc tgcattttta cagaacagaa atgcaacgcg aaagcgctat tttaccaacg  18720
aagaatctgt gcttcatttt tgtaaaacaa aaatgcaacg cgacgagagc gctaattttt  18780
caaacaaaga atctgagctg catttttaca gaacagaaat gcaacgcgag agcgctattt  18840
taccaacaaa gaatctatac ttcttttttg ttctacaaaa atgcatcccg agagcgctat  18900
ttttctaaca aagcatctta gattactttt tttctccttt gtgcgctcta taatgcagtc  18960
tcttgataac tttttgcact gtaggtccgt taaggttaga agaaggctac tttggtgtct  19020
attttctctt ccataaaaaa agcctgactc cacttcccgc gtttactgat tactagcgaa  19080
gctgcgggtg catttttca agataaaggc atccccgatt atattctata ccgatgtgga  19140
ttgcgcatac tttgtgaaca gaaagtgata gcgttgatga ttcttcattg gtcagaaaat  19200
tatgaacggt ttcttctatt ttgtctctat atactacgta taggaaatgt ttacattttc  19260
gtattgtttt cgattcactc tatgaatagt tcttactaca attttttgt ctaaagagta  19320
```

```
atactagaga taaacataaa aaatgtagag gtcgagttta gatgcaagtt caaggagcga  19380

aaggtggatg ggtaggttat atagggatat agcacagaga tatatagcaa agagatactt  19440

ttgagcaatg tttgtggaag cggtattcgc aatgggaagc tccaccccgg ttgataatca  19500

gaaaagcccc aaaaacagga agattgtata agcaaatatt taaattgtaa acgttaatat  19560

tttgttaaaa ttcgcgttaa atttttgtta aatcagctca tttttaacg aatagcccga  19620

aatcggcaaa atcccttata aatcaaaaga atagaccgag atagggttga gtgttgttcc  19680

agtttccaac aagagtccac tattaaagaa cgtggactcc aacgtcaaag ggcgaaaaag  19740

ggtctatcag ggcgatggcc cactacgtga accatcaccc taatcaagtt ttttggggtc  19800

gaggtgccgt aaagcagtaa atcggaaggg taaacggatg cccccattta gagcttgacg  19860

gggaaagccg gcgaacgtgg cgagaaagga agggaagaaa gcgaaaggag cgggggctag  19920

ggcggtggga agtgtagggg tcacgctggg cgtaaccacc acacccgccg cgcttaatgg  19980

ggcgctacag ggcgcgtggg gatgatccac tagt                              20014
```

<210> SEQ ID NO 15
<211> LENGTH: 1521
<212> TYPE: DNA
<213> ORGANISM: Saccharomyces cerevisiae

<400> SEQUENCE: 15

```
atgaaagtct tggatttgtt gactgtattg tctgcatcta gtttgttgtc cacctttgca    60

gcagccgaat ctaccgcaac tgctgactca acaaccgctg catcttccac agcttcttgc   120

aatccattga agaccactgg ctgtactccc gacacagctt tagctacttc tttctctgaa   180

gatttctcca gttctagtaa gtggtttact gatttgaagc acgctggtga gattaagtac   240

ggctctgatg gattatcaat gactttagcc aagagatatg ataacccatc tttgaaatct   300

aacttctaca taatgtatgg taagttggaa gtgatattga aagctgcaaa tggaactggc   360

atcgtgtctt cattctattt gcaaagtgat gatttggatg agatagatat tgagtgggtt   420

ggtggcgaca acacccaatt ccaatccaat ttcttctcca aaggtgacac tacaacttat   480

gatagaggag aatttcacgg tgtggacaca ccaactgaca aattccataa ctacacatta   540

gactgggcta tggataagac aacctggtac ttagacggtg aatctgtgag agtcttgagt   600

aatacttcat cagagggtta tccacaatca cctatgtatt tgatgatggg tatttgggca   660

ggtggcgatc cagataatgc tgctggtact atagagtggg ctggtggaga aactaactac   720

aatgatgctc cctttacaat gtacatagag aaggtgattg tgactgatta ctctaccggt   780

aagaagtata catacggaga tcaatctggt tcttgggagt caattgaagc cgatggtgga   840

tctatctatg gcagatatga tcaggcacaa gaagacttcg ctgtgttagc aaacggtggc   900

tcaatttcat catcatctac ttcctcttct actgtatcct cttctgcttc atctacagtc   960

tccagttccg taagttctac tgtgagttca tctgcctcct ccacagtttc atcttccgtg  1020

tccagtacag taagttcctc atcttctgtc tctagttcaa gttccacatc tccaagttct  1080

tccactgcta catcttcaaa gacattggca tcatcatcag tcacaacctc aagttccatt  1140

tccagtttcg agaagcaaag ttcttcatct tctaagaaga ccgttgcttc cagttcaacc  1200

agtgaatcca tcatctcctc aaccaagact cctgctaccg taagttcaac cactagatca  1260

actgtagctc caactactca gcagtcatca gtctcttcag attcaccagt tcaagataaa  1320

ggtggcgttg ccacttccag taacgatgtt acatcatcaa ctacacaaat ctcaagtaag  1380
```

tacacctcta caattcaaag ttcttccagt gaagcctcca gtaccaattc agttcagatt 1440
tccaacggag cagatttggc acagagtttg cccagagaag gcaaattgtt ctcagtatta 1500
gtagcattgt tggctttatt g 1521

<210> SEQ ID NO 16
<211> LENGTH: 1368
<212> TYPE: DNA
<213> ORGANISM: Schizosaccharomyces pombe

<400> SEQUENCE: 16
atgcctgcat ctacatccat acccgaaaca ccatctaagt taccagacgc cttgttagtg 60
aactctgatc cagcctctaa ggttgacaac gtctccgtca agatagaaca ggaaagtcct 120
ttagctttag agggatcacc tttgcccaca gtttctgatg tgttgccaga aaccaataac 180
gcacatgaag aagtgtcttc atcttcctgg agtttgtctt cttccgactc tatcatgtct 240
tatgatagtt taagtgacga tgtgtccgtc ttatcattct tggattgtcc tttaactacc 300
tttgaaaccg caccatcaat tgcttctttc tctaattccg ctgccgatgt ctcatctcat 360
tctaggtcat cttcctcttg gtctgctaag ttatcaaggt ttaccaaaca tgctagtaag 420
ccatcattgt ctagtaattc ttccgattca tctttctcca agtcaggaag tgagtctaat 480
gccttatcct caagaggctc ctttgaatta gaacctcatg gcatccacag acatgttagt 540
agggctaaga ggttattgtc taagttctac agtaagtttc atcacaagaa ggaagactct 600
tcctttgatc cattagctcc attagtgttt gcaccaaaca catctcgtgt gttaagggtt 660
actaacgagg caaatgcttc tgcaatttct ttagagaaag caacttcatt gtcttcacaa 720
gaacaacctg gttcagaaat caagaaagaa ttgtctttgt atgaccatga gttcgatcaa 780
atcttggact tagctatcaa ggccaagaag gatggtaact tggagaatgc aattgagttc 840
ttggagtaca ttatgccaga agttgcatcc caacagaact ttgttcctta cgaattggct 900
gaattgtata agcagagagg tacttcacaa gacttgaaga gtatcttgcc tttgtatatg 960
ttggctgcca gtttaggaca tgatagatca tctttcttag tgggagaagc cttcttctat 1020
ggtacatacg gagccaggga gaataagttg agagctttac agtactacca cttggccaac 1080
gacaaaggca acgcagatgc catgttagct ttgtgcaagt tgtacttgag aggcttgcct 1140
ggacatatct tcccttctag tagaagagcc tttgaatacg cacacagagc tgctatgttg 1200
ggtcatgctc cagcatgtta cgtgttaggt aagttctatg aaactggagt tggttgcgtt 1260
aaagatttgg caaagtcaga agctggcttc agagcaggct tgatcaacga tagtccaata 1320
actgatgccg atgcattgca aattgcctca acattagtct tgttgcag 1368

<210> SEQ ID NO 17
<211> LENGTH: 9378
<212> TYPE: DNA
<213> ORGANISM: Artificial sequence
<220> FEATURE:
<223> OTHER INFORMATION: Synthetic construct

<400> SEQUENCE: 17
acggattaga agccgccgag cgggtgacag ccctccgaag gaagactctc ctccgtgcgt 60
cctcgtcttc accggtcgcg ttcctgaaac gcagatgtgc ctcgcgccgc actgctccga 120
acaataaaga ttctacaata ctagctttta tggttatgaa gaggaaaaat tggcagtaac 180
ctggccccac aaaccttcaa atgaacgaat caaattaaca accataggat gataatgcga 240
ttagtttttt agccttattt ctggggtaat taatcagcga agcgatgatt tttgatctat 300

```
taacagatat ataaatgcaa aaactgcata accactttaa ctaatacttt caacattttc    360
ggtttgtatt acttcttatt caaatgtaat aaaagtatca acaaaaaatt gttaatatac    420
ctctatactt taacgtcaag gagaaaaaac cccggatcgg actactagca gctgtaatac    480
gactcactat agggaatatt aagcttggcc accatgaaag tcttggattt gttgactgta    540
ttgtctgcat ctagtttgtt gtccaccttt gcagcagccg aatctaccgc aactgctgac    600
tcaacaaccg ctgcatcttc cacagcttct tgcaatccat tgaagaccac tggctgtact    660
cccgacacag ctttagctac ttctttctct gaagatttct ccagttctag taagtggttt    720
actgatttga agcacgctgg tgagattaag tacggctctg atggattatc aatgacttta    780
gccaagagat atgataaccc atctttgaaa tctaacttct acataatgta tggtaagttg    840
gaagtgatat tgaaagctgc aaatggaact ggcatcgtgt cttcattcta tttgcaaagt    900
gatgatttgg atgagataga tattgagtgg gttggtggcg acaacaccca attccaatcc    960
aatttcttct ccaaaggtga cactacaact tatgatagag gagaatttca cggtgtggac   1020
acaccaactg acaaattcca taactacaca ttagactggg ctatggataa gacaacctgg   1080
tacttagacg gtgaatctgt gagagtcttg agtaatactt catcagaggg ttatccacaa   1140
tcacctatgt atttgatgat gggtatttgg gcaggtggcg atccagataa tgctgctggt   1200
actatagagt gggctggtgg agaaactaac tacaatgatg ctccctttac aatgtacata   1260
gagaaggtga ttgtgactga ttactctacc ggtaagaagt atacatacgg agatcaatct   1320
ggttcttggg agtcaattga agccgatggt ggatctatct atggcagata tgatcaggca   1380
caagaagact tcgctgtgtt agcaaacggt ggctcaattt catcatcatc tacttcctct   1440
tctactgtat cctcttctgc ttcatctaca gtctccagtt ccgtaagttc tactgtgagt   1500
tcatctgcct cctccacagt ttcatcttcc gtgtccagta cagtaagttc ctcatcttct   1560
gtctctagtt caagttccac atctccaagt tcttccactg ctacatcttc aaagacattg   1620
gcatcatcat cagtcacaac ctcaagttcc atttccagtt tcgagaagca aagttcttca   1680
tcttctaaga agaccgttgc ttccagttca accagtgaat ccatcatctc ctcaaccaag   1740
actcctgcta ccgtaagttc aaccactaga tcaactgtag ctccaactac tcagcagtca   1800
tcagtctctt cagattcacc agttcaagat aaaggtggcg ttgccacttc cagtaacgat   1860
gttacatcat caactacaca aatctcaagt aagtacacct ctacaattca aagttcttcc   1920
agtgaagcct ccagtaccaa ttcagttcag atttccaacg gagcagattt ggcacagagt   1980
ttgcccagag aaggcaaatt gttctcagta ttagtagcat tgttggcttt attgtaagtt   2040
taaactcatg taattagtta tgtcacgctt acattcacgc cctcccccca catccgctct   2100
aaccgaaaag gaaggagtta gacaacctga agtctaggtc cctatttatt tttttatagt   2160
tatgttagta ttaagaacgt tatttatatt tcaaattttt cttttttttc tgtacagacg   2220
cgtgtacgca tgtaacatta tactgaaaac cttgcttgag aaggttttgg gacgctcgaa   2280
ggctttaatt tgccggatta gaagccgccg agcgggtgac agccctccga aggaagactc   2340
tcctccgtgc gtcctcgtct tcaccggtcg cgttcctgaa acgcagatgt gcctcgcgcc   2400
gcactgctcc gaacaataaa gattctacaa tactagcttt tatggttatg aagaggaaaa   2460
attggcagta acctggcccc acaaaccttc aaatgaacga atcaaattaa caaccatagg   2520
atgataatgc gattagtttt ttagccttat ttctggggta attaatcagc gaagcgatga   2580
tttttgatct attaacagat atataaatgc aaaaactgca taaccacttt aactaatact   2640
```

```
ttcaacattt tcggtttgta ttacttctta ttcaaatgta ataaaagtat caacaaaaaa   2700
ttgttaatat acctctatac tttaacgtca aggaggcgcg ccaccatgcc tgcatctaca   2760
tccatacccg aaacaccatc taagttacca gacgccttgt tagtgaactc tgatccagcc   2820
tctaaggttg acaacgtctc cgtcaagata gaacaggaaa gtcctttagc tttagaggga   2880
tcacctttgc ccacagtttc tgatgtgttg ccagaaacca ataacgcaca tgaagaagtg   2940
tcttcatctt cctggagttt gtcttcttcc gactctatca tgtcttatga tagtttaagt   3000
gacgatgtgt ccgtcttatc attcttggat tgtcctttaa ctacctttga aaccgcacca   3060
tcaattgctt ctttctctaa ttccgctgcc gatgtctcat ctcattctag gtcatcttcc   3120
tcttggtctg ctaagttatc aaggtttacc aaacatgcta gtaagccatc attgtctagt   3180
aattcttccg attcatcttt ctccaagtca ggaagtgagt ctaatgcctt atcctcaaga   3240
ggctcctttg aattagaacc tcatggcatc cacagacatg ttagtagggc taagaggtta   3300
ttgtctaagt tctacagtaa gtttcatcac aagaaggaag actcttcctt tgatccatta   3360
gctccattag tgtttgcacc aaacacatct cgtgtgttaa gggttactaa cgaggcaaat   3420
gcttctgcaa tttctttaga gaaagcaact tcattgtctt cacaagaaca acctggttca   3480
gaaatcaaga aagaattgtc tttgtatgac catgagttcg atcaaatctt ggacttagct   3540
atcaaggcca agaaggatgg taacttggag aatgcaattg agttcttgga gtacattatg   3600
ccagaagttg catcccaaca gaactttgtt ccttacgaat tggctgaatt gtataagcag   3660
agaggtactt cacaagactt gaagagtatc ttgcctttgt atatgttggc tgccagttta   3720
ggacatgata gatcatcttt cttagtggga gaagccttct tctatggtac atacggagcc   3780
agggagaata agttgagagc tttacagtac taccacttgg ccaacgacaa aggcaacgca   3840
gatgccatgt tagctttgtg caagttgtac ttgagaggct tgcctggaca tatcttccct   3900
tctagtagaa gagcctttga atacgcacac agagctgcta tgttgggtca tgctccagca   3960
tgttacgtgt taggtaagtt ctatgaaact ggagttggtt gcgttaaaga tttggcaaag   4020
tcagaagctg gcttcagagc aggcttgatc aacgatagtc caataactga tgccgatgca   4080
ttgcaaattg cctcaacatt agtcttgttg cagtaatcta gagggccgca tcatgtaatt   4140
agttatgtca cgcttacatt cacgccctcc ccccacatcc gctctaaccg aaaaggaagg   4200
agttagacaa cctgaagtct aggtccctat ttattttttt atagttatgt tagtattaag   4260
aacgttattt atatttcaaa tttttctttt ttttctgtac agacgcgtgt acgcatgtaa   4320
cattatactg aaaaccttgc ttgagaaggt tttgggacgc tcgaaggctt taatttgcgg   4380
ccctgcatta atgaatcggc caacgcgcgg ggagaggcgg tttgcgtatt gggcgctctt   4440
ccgcttcctc gctcactgac tcgctgcgct cggtcgttcg gctgcggcga gcggtatcag   4500
ctcactcaaa ggcggtaata cggttatcca cagaatcagg ggataacgca ggaaagaaca   4560
tgtgagcaaa aggccagcaa aagcccagga accgtaaaaa ggccgcgttg ctggcgtttt   4620
tccataggct ccgcccccct gacgagcatc acaaaaatcg acgctcaagt cagaggtggc   4680
gaaacccgac aggactataa agataccagg cgtttccccc tggaagctcc ctcgtgcgct   4740
ctcctgttcc gaccctgccg cttaccggat acctgtccgc ctttctccct tcgggaagcg   4800
tggcgctttc tcatagctca cgctgtaggt atctcagttc ggtgtaggtc gttcgctcca   4860
agctgggctg tgtgcacgaa ccccccgttc agcccgaccg ctgcgcctta tccggtaact   4920
atcgtcttga gtccaacccg gtaagacacg acttatcgcc actggcagca gccactggta   4980
acaggattag cagagcgagg tatgtaggcg gtgctacaga gttcttgaag tggtggccta   5040
```

actacggcta cactagaagg acagtatttg gtatctgcgc tctgctgaag ccagttacct 5100
tcggaaaaag agttggtagc tcttgatccg gcaaacaaac caccgctggt agcggtggtt 5160
tttttgtttg caagcagcag attacgcgca gaaaaaaagg atctcaagaa gatcctttga 5220
tcttttctac ggggtctgac gctcagtgga acgaaaactc acgttaaggg attttggtca 5280
tgagattatc aaaaaggatc ttcacctaga tccttttaaa ttaaaaatga agttttaaat 5340
caatctaaag tatatatgag taaacttggt ctgacagtta ccaatgctta atcagtgagg 5400
cacctatctc agcgatctgt ctatttcgtt catccatagt tgcctgactc cccgtcgtgt 5460
agataactac gatacgggag cgcttaccat ctggccccag tgctgcaatg ataccgcgag 5520
acccacgctc accggctcca gatttatcag caataaacca gccagccgga agggccgagc 5580
gcagaagtgg tcctgcaact ttatccgcct ccatccagtc tattaattgt tgccgggaag 5640
ctagagtaag tagttcgcca gttaatagtt tgcgcaacgt tgttggcatt gctacaggca 5700
tcgtggtgtc actctcgtcg tttggtatgg cttcattcag ctccggttcc caacgatcaa 5760
ggcgagttac atgatccccc atgttgtgca aaaaagcggt tagctccttc ggtcctccga 5820
tcgttgtcag aagtaagttg gccgcagtgt tatcactcat ggttatggca gcactgcata 5880
attctcttac tgtcatgcca tccgtaagat gcttttctgt gactggtgag tactcaacca 5940
agtcattctg agaatagtgt atgcggcgac cgagttgctc ttgcccggcg tcaatacggg 6000
ataatagtgt atcacatagc agaactttaa aagtgctcat cattggaaaa cgttcttcgg 6060
ggcgaaaact ctcaaggatc ttaccgctgt tgagatccag ttcgatgtaa cccactcgtg 6120
cacccaactg atcttcagca tcttttactt tcaccagcgt ttctgggtga gcaaaaacag 6180
gaaggcaaaa tgccgcaaaa aagggaataa gggcgacacg gaaatgttga atactcatac 6240
tcttcctttt tcaatgggta ataactgata taattaaatt gaagctctaa tttgtgagtt 6300
tagtatacat gcatttactt ataatacagt tttttagttt tgctggccgc atcttctcaa 6360
atatgcttcc cagcctgctt ttctgtaacg ttcaccctct accttagcat cccttccctt 6420
tgcaaatagt cctcttccaa caataataat gtcagatcct gtagagacca catcatccac 6480
ggttctatac tgttgaccca atgcgtctcc cttgtcatct aaacccacac cgggtgtcat 6540
aatcaaccaa tcgtaacctt catctcttcc acccatgtct ctttgagcaa taaagccgat 6600
aacaaaatct ttgtcgctct tcgcaatgtc aacagtaccc ttagtatatt ctccagtaga 6660
tagggagccc ttgcatgaca attctgctaa catcaaaagg cctctaggtt cctttgttac 6720
ttcttctgcc gcctgcttca aaccgctaac aatacctggg cccaccacac cgtgtgcatt 6780
cgtaatgtct gcccattctg ctattctgta tacacccgca gagtactgca atttgactgt 6840
attaccaatg tcagcaaatt ttctgtcttc gaagagtaaa aaattgtact tggcggataa 6900
tgcctttagc ggcttaactg tgccctccat ggaaaaatca gtcaagatat ccacatgtgt 6960
ttttagtaaa caaattttgg gacctaatgc ttcaactaac tccagtaatt ccttggtggt 7020
acgaacatcc aatgaagcac acaagtttgt ttgcttttcg tgcatgatat taaatagctt 7080
ggcagcaaca ggactaggat gagtagcagc acgttcctta tatgtagctt tcgacatgat 7140
ttatcttcgt ttcctgcagg tttttgttct gtgcagttgg gttaagaata ctgggcaatt 7200
tcatgtttct tcaacactac atatgcgtat atataccaat ctaagtctgt gctccttcct 7260
tcgttcttcc ttctgttcgg agattaccga atcaaaaaaa tttcaaagaa accgaaatca 7320
aaaaaaagaa taaaaaaaaa atgatgaatt gaattgaaaa gctagcttat cgatgataag 7380

-continued

```
ctgtcaaaga tgagaattaa ttccacggac tatagactat actagatact ccgtctactg   7440

tacgatacac ttccgctcag gtccttgtcc tttaacgagg ccttaccact cttttgttac   7500

tctattgatc cagctcagca aaggcagtgt gatctaagat tctatcttcg cgatgtagta   7560

aaactagcta gaccgagaaa gagactagaa atgcaaaagg cacttctaca atggctgcca   7620

tcattattat ccgatgtgac gctgcagctt ctcaatgata ttcgaatacg ctttgaggag   7680

atacagccta atatccgaca aactgtttta cagatttacg atcgtacttg ttacccatca   7740

ttgaattttg aacatccgaa cctgggagtt ttccctgaaa cagatagtat atttgaacct   7800

gtataataat atatagtcta gcgctttacg gaagacaatg tatgtatttc ggttcctgga   7860

gaaactattg catctattgc ataggtaatc ttgcacgtcg catccccggt tcattttctg   7920

cgtttccatc ttgcacttca atagcatatc tttgttaacg aagcatctgt gcttcatttt   7980

gtagaacaaa aatgcaacgc gagagcgcta atttttcaaa caaagaatct gagctgcatt   8040

tttacagaac agaaatgcaa cgcgaaagcg ctattttacc aacgaagaat ctgtgcttca   8100

tttttgtaaa acaaaaatgc aacgcgacga gagcgctaat tttcaaaca aagaatctga   8160

gctgcatttt tacagaacag aaatgcaacg cgagagcgct attttaccaa caaagaatct   8220

atacttcttt tttgttctac aaaaatgcat cccgagagcg ctatttttct aacaaagcat   8280

cttagattac ttttttctc ctttgtgcgc tctataatgc agtctcttga taacttttg   8340

cactgtaggt ccgttaaggt tagaagaagg ctactttggt gtctattttc tcttccataa   8400

aaaaagcctg actccacttc ccgcgtttac tgattactag cgaagctgcg ggtgcatttt   8460

ttcaagataa aggcatcccc gattatattc tataccgatg tggattgcgc atactttgtg   8520

aacagaaagt gatagcgttg atgattcttc attggtcaga aaattatgaa cggtttcttc   8580

tattttgtct ctatatacta cgtataggaa atgtttacat tttcgtattg ttttcgattc   8640

actctatgaa tagttcttac tacaattttt ttgtctaaag agtaatacta gagataaaca   8700

taaaaaatgt agaggtcgag tttagatgca agttcaagga gcgaaaggtg gatgggtagg   8760

ttatataggg atatagcaca gagatatata gcaaagagat acttttgagc aatgtttgtg   8820

gaagcggtat tcgcaatggg aagctccacc ccggttgata atcagaaaag ccccaaaaac   8880

aggaagattg tataagcaaa tatttaaatt gtaaacgtta atattttgtt aaaattcgcg   8940

ttaaattttt gttaaatcag ctcatttttt aacgaatagc ccgaaatcgg caaaatccct   9000

tataaatcaa aagaatagac cgagataggg ttgagtgttg ttccagtttc caacaagagt   9060

ccactattaa agaacgtgga ctccaacgtc aaagggcgaa aaagggtcta tcagggcgat   9120

ggcccactac gtgaaccatc accctaatca agtttttgg ggtcgaggtg ccgtaaagca   9180

gtaaatcgga agggtaaacg gatgccccca tttagagctt gacggggaaa gccggcgaac   9240

gtggcgagaa aggaagggaa gaaagcgaaa ggagcggggg ctagggcggt gggaagtgta   9300

ggggtcacgc tgggcgtaac caccacaccc gccgcgctta atggggcgct acagggcgcg   9360

tggggatgat ccactagt                                                 9378
```